(12) United States Patent
Shreder et al.

(10) Patent No.: US 7,879,846 B2
(45) Date of Patent: Feb. 1, 2011

(54) SERINE HYDROLASE INHIBITORS

(75) Inventors: Kevin Shreder, Del Mar, CA (US); Yi Hu, San Diego, CA (US); Allister Fraser, Encinitas, CA (US); Yasushi Kohno, Shimotsuga-gun (JP); Akihiko Kojima, Shimotsuga-gun (JP); Junichi Ishiyama, Shimotsuga-gun (JP)

(73) Assignee: Kyorin Pharmaceutical Co.., Ltd., Tokyo (JP)

( * ) Notice: Subject to any disclaimer, the term of this patent is extended or adjusted under 35 U.S.C. 154(b) by 604 days.

(21) Appl. No.: 11/903,483

(22) Filed: Sep. 20, 2007

(65) Prior Publication Data

US 2008/0161290 A1 Jul. 3, 2008

Related U.S. Application Data

(60) Provisional application No. 60/846,545, filed on Sep. 21, 2006.

(51) Int. Cl.
*C07D 413/04* (2006.01)
*A61K 31/536* (2006.01)

(52) U.S. Cl. ..................................... 514/230.5; 544/90
(58) Field of Classification Search .................. 544/90; 514/230.5
See application file for complete search history.

(56) References Cited

U.S. PATENT DOCUMENTS

| | | | |
|---|---|---|---|
| 3,598,123 A | 8/1971 | Zaffaroni et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,044,126 A | 8/1977 | Cook et al. |
| 4,315,766 A | 2/1982 | Hamprecht et al. |
| 4,328,245 A | 5/1982 | Yu et al. |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,446,262 A | 5/1984 | Okumura et al. |
| 4,522,811 A | 6/1985 | Eppstein et al. |
| 4,523,942 A | 6/1985 | Hamprecht et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,651,926 A | 7/1997 | Kido et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,001,811 A | 12/1999 | Gyorkos et al. |
| 6,001,813 A | 12/1999 | Gyorkos et al. |
| 6,001,814 A | 12/1999 | Gyorkos et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |

(Continued)

FOREIGN PATENT DOCUMENTS

EP 0 769 498 A1 4/1997

(Continued)

OTHER PUBLICATIONS

Arcadi, A. et al., Synthesis and in vitro and in vivo evaluation of the 2-(6'methoxy-3',4'-dihydro-1'-naphtyl)- 4H-3,1-benzoxazin-4- one as a new potent substrate inhibitor of human leukocyte elastase. *Bioorg. Med. Chem. Lett.* 1999, 9, 1291.

(Continued)

*Primary Examiner*—Kahsay T Habte
(74) *Attorney, Agent, or Firm*—Jones Day

(57) ABSTRACT

Provided herein are benzoxazinone compounds of formula I and compositions containing the compounds. The compounds and compositions are useful in the methods of inhibiting the action of serine hydrolase, including neutrophil elastase. In certain embodiments, the compounds and compositions are useful in the prevention, amelioration or treatment of serine hydrolase-mediated diseases.

50 Claims, No Drawings

U.S. PATENT DOCUMENTS

| | | | |
|---|---|---|---|
| 6,139,865 | A | 10/2000 | Friend et al. |
| 6,150,334 | A | 11/2000 | Gyorkos et al. |
| 6,180,625 | B1 | 1/2001 | Persson et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 6,774,232 | B2 | 8/2004 | Sarkar |
| 7,232,836 | B2 * | 6/2007 | Lahm et al. ............. 514/341 |
| 7,276,601 | B2 | 10/2007 | Taylor |
| 7,339,057 | B2 | 3/2008 | Taylor |
| 2003/0203851 | A1 | 10/2003 | Gyorkos et al. |
| 2005/0075372 | A1* | 4/2005 | Lahm et al. ............. 514/341 |
| 2005/0215785 | A1 | 9/2005 | Taylor |
| 2006/0241304 | A1 | 10/2006 | Taylor |
| 2006/0258651 | A1 | 11/2006 | Linschoten |
| 2008/0275022 | A1 | 11/2008 | Aquila |
| 2008/0275065 | A1 | 11/2008 | O'Sullivan et al. |

FOREIGN PATENT DOCUMENTS

| | | |
|---|---|---|
| EP | 1174430 | 1/2002 |
| JP | 07-309851 | 11/1995 |
| JP | 11-322611 | 11/1999 |
| JP | 2001-250689 | 9/2001 |
| WO | WO 03015518 A1 * | 2/2003 |
| WO | WO 2004/108139 | 12/2004 |
| WO | WO2005/018532 | 3/2005 |

OTHER PUBLICATIONS

Buchwald, et al., Long-term, continuous intravenous heparin administration by an implantable infusion pump in ambulatory patients with recurrent venous thrombosis, Surgery 88:507-516 (1980).

Colson, E. et al., Synthesis and anti-elastase properties of 6-amino-2-phenyl-4$H$-3,1-benzoxazin-4-one aminoacyl and dipeptidyl derivatives Biochimie. 2005, 87, 223.

Crane et al., 2-(Adamantan-1-yl)-5-methylbenzo[$d$]-[1,3]oxazin-4-one, Acta Crystallographica, Section E: Structure Reports Online, E60, 0669-0670 (2004).

Deshpande et al., Synthesis of austroeorticinic acid, Indian Journal of Chemistry, vol. 35B, pp. 790-793 (1996).

Di Cesare et al., Fluoronaphthyridines and -quinolones as Antibacterial Agents. 5. Synthesis and antimicrobial Activity of Chiral 1-$tert$-Butyl-6-fluoro-7-substituted-naphthyridones, J. Med. Chen 35, 4205-4213 (1992).

Fletcher et al., A Comparison of Proteinase Inhibitor Methoxysuccinyl-Ala-Ala-Pro-Val-Chloromethylketone and Specific B-Lactam Inhibitors in an Acute Model of Human Polymorphonuclear Leukocyte Elastase-induced Lung Hemorrhage in the Hamster, AARD, vol. 141, No. 3, pp. 672-677 (1990).

Gilmore et al., Synthesis and evaluation of 2-Aryl-4H-3,1-Benzoxazin-4-Ones as C1r Serine Protease Inhibitors, Bioorganic & Midincinal Chemistry Letters, Vo. 6, No. 6, pp. 679-682, (1996).

Gordeev, Mikhail F., Combinatorial approaches to Pharmacophoric Heterocycles: A Solid-Phase Syntheses of 3,1-Benzoxazine-4-Ones, Biotechnology and BioEngineering (Combinatorial Chemistry), vol. 61, No. 1, pp. 13-16, (1998).

Gütschow, M. et al., 2-(diethylamino)thieno1,3oxazin-4-ones as stable inhibitors of human leukocyte elastase. J Med Chem. 1999, 42, 5437.

Gütschow, M. et al., Novel thieno[2,3-d][1,3]oxazin-4-ones as inhibitors of human leukocyte elastase. J Med Chem. 1998, 41, 1729.

Gütschow, Michael, One-Pot Reactions of N-(Mesyloxy)phthalimides with Secondary Amines to 2-Ureidobenzamides, 2-Ureidobenzoic Acids, Ethyl 1-Ureidobenzoates, or Isatoic Anhydrides, J. Org. Chem, 64, pp. 5109-5115 (1999).

Hoffmann et al., Effect of Recombinant Hirudin, a Specific Inhibitor of Thrombin, on Endotoxin-induced Intravascular Coagulation and Acute Lung Injury in Pigs, AARD, vol. 142, No. 4, pp. 782-788 (1990).

Ishiyama et al., Pharmacological characterization of AX-9657, a potent and selective neutrophil elastase inhibitor with good lung distribution, ACS 237$^{th}$ Spring National Meeting and Exposition Mar. 22-26, 2009, Abstract 198.

Katritzky et al., Facile Syntheses of 2,2-Dimethyl-6-(2-oxoalkyl)-1,3-dioxin-4-ones and the Corresponding 6-Substituted 4-Hydroxy-2-pyrones, J. Org. Chem., 70: 4854-4856 (2005).

Krantz et al., Design and Synthesis of 4IHI-3,1-Benzoxazin-4-ones as Potent Alternate Substrate Inhibitors of Human Leukocyte Elastase, J. Med. Chem 33, 464-479 (1990).

Langer, Robert, New Methods of Drug Delivery, Science 249: 1527-1533 (1990).

Lin et al., Development of a cellular assay for evaluating the permeability of novel neutrophil elastase inhibitors, ACS 237$^{th}$ Spring National Meeting and Exposition Mar. 22-26, 2009, Abstract 266.

Lygo, Barry, N-Acyl-2-methylaziridines: Synthesis and Utility in the C-Acylation of B-Ketoester Derived Dianions, Tetrahedron, 51, pp. 12859-12868 (1995).

Mitsuhashi et al., British J. of Pharmacology, 126(5), 1147-1152, (1999).

Neumann et al., Inhibition of Human Chymase by 2-Amin-3,1-benzoxazin-4-ones, Bioorganic & Medicinal Chemistry 9, pp. 947-954 (2001).

Palanki et al., The Design and Synthesis of Novel Orally Active Inhibitors of AP-1 and NF-kB Mediated Transcriptional Activation. SAR of In Vitro and In Vivo Studies, Bioorganic & Medicinal Chemistry Letters 13, pp. 4077-4080 (2003).

Parlow, et al., Solution-Phase Parallel Synthesis of a Benzoxazinone Library Using Complementary Molecular Reactivity and Molecular Recognition (CMR/R) Purification Technology, Tetrahedron 54, pp. 4013-4031 (1998).

Radhakrishnan, R. et al., Crystal structures of the complex of porcine pancreatic elastase with two valine-derived benzoxazinone inhibitors. J. Mol. Biol. 1987, 198, 417.

Saudek et al, A Preliminary Trial of the Programmable Implantable Medication System for Insulin Delivery, New England Journal of Medicine, vol. 321, No. 9, pp. 574-579 )1089), (1989).

Sefton, Michael, Implantable Pumps, Biomedical Engineering, vol. 14, 3, pp. 201-240 (1987).

Shcherbakova et al., 3$H$-Quinazolin-4-ones as a new calcilytic template for the potential treatment of osteoporosis, Bioorganic & Medicinal Chemistry Letters 15, pp. 1557-1560 (2005).

Shreder et al., Synthesis and optimization of 2-pyridin-3-yl-benzo[d][1,3]oxazin-4-one based inhibitors of human neutrophil elastase, ACS 237$^{th}$ Spring National Meeting and Exposition Mar. 22-26, 2009, Abstract 199.

Simpson et al., Reduction of Experimental Canine Myocardial Reperfuson Injury by a Monoclonal Antibody (Anti_Mol, Anti-CD11b) That Inhibits Leukocyte Adhesion, J. Clin, Invest., 81: 624-629 (1988).

Uejima, Y. et al., Inhibition of human sputum elastase by 7-substituted 5-methyl-2-isopropylamino-4H-3,1-benzoxazin-4-ones. Biochem. Pharmacol. 1994, 48, 426.

* cited by examiner

SERINE HYDROLASE INHIBITORS

This application claims priority to U.S. Provisional Application No. 60/846,545, filed Sep. 21, 2006, the entirety of which is incorporated herein by reference.

1. FIELD

Compounds, compositions and methods for treating, preventing or ameliorating serine hydrolase-mediated diseases, including, but not limited to, neutrophil elastase-mediated diseases are provided. The compounds provided herein are benzoxazinones that are serine hydrolase inhibitors.

2. BACKGROUND

Serine hydrolases represent one of the largest and most diverse families of enzymes in higher eukaryotes, comprising numerous serine proteases, lipases, esterases, and amidases. Human neutrophil elastase is a kind of serine hydrolase released from the granules of neutrophil, which appear in the cases of infections or inflammatory diseases. Neutrophil elastase is an enzyme hydrolyzing proteins such as elastin, collagen, proteoglycan, fibronectin and others which constitute the interstitum of intravital connective tissues such as lung, cartilage, vascular wall and skin. In addition, it has been clarified that neutrophil elastase acts on other proteins or cells as well.

In the living body, serine hydrolases, such as neutrophil elastase keeps the homeostasis of the living body while the activities thereof are controlled by endogenous inhibitor proteins such as $\alpha_1$-protease inhibitor, $\alpha_2$-macrogloblin and secretory leukocyte protease inhibitor. However, when a balance between neutrophil elastase and the endogenous inhibitors is lost by the excessive release of neutrophil elastase in the inflammation site or by the lowering in the inhibitor level, the control of neutrophil elastase activities cannot be kept, by which tissues are injured.

Diseases in which serine hydrolase, including neutrophil elastase may participate are, for example, pulmonary emphysema, acute respiratory distress syndrome, adult respiratory distress syndrome (ARDS), idiopathic interstitial pneumonia (IIP), cystic pulmonary fibrosis, chronic interstitial pneumonia, chronic bronchitis, chronic sinopulmonary infection, diffuse panbronchiolitis, bronchiectasis, asthma, pancreatitis, nephritis, hepatic failure, chronic rheumatoid arthritis, joint scleroma, osteoarthritis, psoriasis, periodontitis, atherosclerosis, rejection against organ transplant, premature amniorrhexis, bullous dermatosis, shock, sepsis, systemic lupus erythematosus (SLE), Crohn's disease, disseminated intracapillary coagulation (DIC), tissue injury after ischemia-reperfusion, formation of cornea cicatricial tissue, myelitis and others.

Therefore, there is a need for effective serine hydrolase inhibitors as therapeutics for treatment of serine hydrolase-mediated diseases.

3. SUMMARY

Provided herein are compounds that are serine hydrolase inhibitors, pharmaceutical compositions containing the compounds and methods of use thereof. In one embodiment, the compounds are neutrophil elastase, including human neutrophil elastase inhibitors. The compounds are benzoxazinones and pharmaceutically acceptable derivatives thereof. In certain embodiments, the compounds for use in the compositions and methods provided herein are of Formula I:

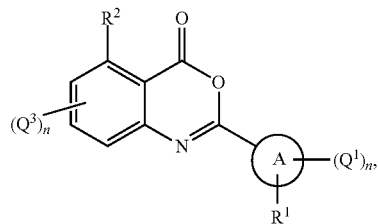

or a pharmaceutically acceptable derivative thereof, wherein the variables are chosen such that the resulting compounds show activity as elastase inhibitors.

Pharmaceutical compositions containing a compound of Formula I and a pharmaceutically acceptable carrier are provided herein. Also provided are methods for treating, preventing, or ameliorating one or more symptoms of serine hydrolase-mediated diseases by administering the compounds and compositions provided herein. In certain embodiments, the serine hydrolase is a neutrophil elastase, such as human neutrophil elastase.

In certain embodiments, provided herein are methods for inhibiting an action of a serine hydrolase, including but not limited to neutrophil elastase, by administering compounds and compositions provided herein. In other embodiments, provided herein are methods for treatment, prevention, or amelioration of one or more symptoms of diseases or conditions including, but not limited to conditions associated with pulmonary emphysema, acute respiratory distress syndrome, adult respiratory distress syndrome, idiopathic interstitial pneumonia, cystic pulmonary fibrosis, chronic interstitial pneumonia, chronic bronchitis, chronic sinopulmonary infection, diffuse panbronchiolitis, bronchiectasis, asthma, pancreatitis, nephritis, hepatic failure, chronic rheumatoid arthritis, joint scleroma, osteoarthritis, psoriasis, periodontitis, atherosclerosis, rejection against organ transplant, premature amniorrhexis, bullous dermatosis, shock, sepsis, systemic lupus erythematosus, Crohn's disease, disseminated intracapillary coagulation, tissue injury after ischemia-reperfusion, formation of cornea cicatricial tissue and myelitis by administering compounds and compositions provided herein.

4. DETAILED DESCRIPTION

Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein "subject" is an animal, such as a mammal, including human, such as a patient.

The terms "serine hydrolase-mediated disease, or "serine hydrolase-mediated condition", as used herein, mean any disease or other deleterious condition or state in which a serine hydrolase, including neutrophil elastase or proteinase-3 is known to play a role. Exemplary diseases or conditions include, without limitation, pulmonary emphysema, acute respiratory distress syndrome, adult respiratory distress syndrome, idiopathic interstitial pneumonia, cystic pulmonary fibrosis, chronic interstitial pneumonia, chronic bronchitis, chronic sinopulmonary infection, diffuse panbronchiolitis, bronchiectasis, asthma, pancreatitis, nephritis, hepatic failure, chronic rheumatoid arthritis, joint scleroma, osteoarthritis, psoriasis, periodontitis, atherosclerosis, rejection against organ transplant, premature amniorrhexis, bullous dermatosis, shock, sepsis, systemic lupus erythematosus, Crohn's disease, disseminated intracapillary coagulation, tissue injury after ischemia-reperfusion, formation of cornea cicatricial tissue and myelitis.

As used herein, biological activity refers to the in vivo activities of a compound or physiological responses that result upon in vivo administration of a compound, composition or other mixture. Biological activity, thus, encompasses therapeutic effects and pharmacokinetic behaviour of such compounds, compositions and mixtures. Biological activities can be observed in in vitro systems designed to test for such activities.

As used herein, pharmaceutically acceptable derivatives of a compound include salts, esters, enol ethers, enol esters, acetals, ketals, orthoesters, hemiacetals, hemiketals, acids, bases, solvates, hydrates, N-oxides or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, aralkyl and cycloalkyl. Pharmaceutically acceptable enol esters include, but are not limited to, derivatives of formula C=C(OC(O)R) where R is hydrogen, alkyl, alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating a respiratory disease.

As used herein, amelioration of the symptoms of a particular disorder by administration of a particular compound or pharmaceutical composition refers to any lessening, whether permanent or temporary, lasting or transient that can be attributed to or associated with administration of the compound or composition.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, the $IC_{50}$ refers to an amount, concentration or dosage of a particular test compound that achieves a 50% inhibition of a maximal response in an assay that measures such response.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, ethene, propene, butene, pentene, acetylene and hexyne. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "heteroalkyl" refers to a straight, branched or cyclic, in certain embodiments straight or branched, aliphatic hydrocarbon group having, inserted in the hydrocarbon chain one or more oxygen, sulfur, including S(=O) and S(=O)$_2$ groups, or substituted or unsubstituted nitrogen atoms, including NR and N$^+$RR groups, where the nitrogen substituent(s) is(are) alkyl, aryl, aralkyl, heteroaryl, heteroaralkyl or COR', where R' is alkyl, aryl, aralkyl, heteroaryl, heteroaralkyl, OY or —NYY', where Y and Y' are each independently hydrogen, alkyl, aryl, heteroaryl, cycloalkyl or heterocyclyl, in one embodiment having from 1 to about 20 atoms, in another embodiment having from 1 to 12 atoms in the chain.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein, generally selected from $Q^1$.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl, wherein the substituents, when present, are one or more substituents as defined herein, generally selected from $Q^1$.

As used herein, "heteroaryl" refers to a monocyclic or multicyclic aromatic ring system, in certain embodiments, of about 5 to about 15 members where one or more, in one embodiment, 1 to 3 of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-ring aromatic ring system, in one embodiment of 3 to 10 members, in another embodiment of 4 to 7 members, in a further embodiment of 5 to 6 members, where one or more, in certain embodiments, 1 to 3 of the atoms in the ring system is a heteroatom, that is, an element other the carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein, generally selected from $Q^1$.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyano, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1 chloro 2 fluoroethyl.

As used herein, "haloalkoxy" refers to RO in which R is a haloalkyl group.

As used herein, "carboxy" refers to a divalent radical, —C(O)O—.

As used herein, "aminocarbonyl" refers to $C(O)NH_2$.

As used herein, "alkylaminocarbonyl" refers to C(O)NHR in which R is alkyl, including lower alkyl. As used herein, "dialkylaminocarbonyl" refers to C(O)NR'R in which R' are independently alkyl, including lower alkyl; "carboxamide" refers to groups of formula —NR'COR in which R' and R are independently alkyl, including lower alkyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to COOH.

As used herein, "alkoxycarbonyl" refers to C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO and RS, in which R is alkyl, including lower alkyl.

As used herein, "aryloxy" and "arylthio" refer to RO— and RS—, in which R is aryl, including lower aryl, such as phenyl.

Where the number of any given substituent is not specified (e.g., "haloalkyl"), there may be one or more substituents present. For example, "haloalkyl" may include one or more of the same or different halogens.

As another example, "$C_{1-3}$alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:942-944).

Compounds

In certain embodiments, the compounds for use in the compositions and methods provided herein are of formula I:

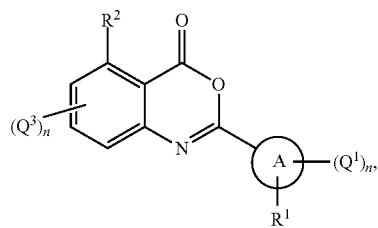

or a pharmaceutically acceptable derivative thereof, wherein A is a 5-10 membered heterocyclyl or heteroaryl ring connected to the benzoxazine core by a carbon atom of the heterocyclyl or heteroaryl ring;

$R^2$ is halo, pseudohalo, alkyl, alkenyl, alkynyl, haloalkyl, cycloalkyl, $NR^aR^b$, —$OR^c$, —$C(O)R^c$ or —$S(O)_mR^c$;

$R^a$, $R^b$ and $R^c$ are each independently selected from hydrogen, alkyl, alkenyl, alkynyl, haloalkyl, cycloalkyl, aryl, heterocyclyl and heteroaryl;

$R^1$ is hydrogen, halo, alkyl, —$OR^3$, —$SR^3$; —$NO_2$ or $NR^4R^5$;

each $R^3$ is independently selected from alkyl, alkenyl, alkynyl, haloalkyl, heteroalkyl, cycloalkyl, aryl, heterocyclyl and heteroaryl;

$R^4$ and $R^5$ are selected as follows:
i) $R^4$ and $R^5$ are each independently selected from hydrogen, alkyl, alkenyl, alkynyl, haloalkyl, cycloalkyl, aryl, heterocyclyl and heteroaryl, provided that at least one of $R^4$ or $R^5$ is not hydrogen; or
ii) $R^4$ and $R^5$ together with the nitrogen atom on which they are substituted form a 5-10 membered substituted or unsubstituted heterocyclyl or heteroaryl ring; wherein the substituents when present are selected from one or more $Q^1$;

m is 0-2;

each n is independently 0 to 6;

$R^1$, $R^2$, $R^3$, $R^4$ and $R^5$ are optionally substituted with 1, 2, 3 or 4 substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, heteroalkyl, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, heterocyclylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, alkynoxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})_2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1, 2 or 1, 3 arrangement, together form alkylenedioxy (i.e., —O—$(CH_2)_y$—O—), thioalkylenoxy (i.e., —S—$(CH_2)_y$—O—) or alkylenedithioxy (i.e., —S—$(CH_2)_y$—S—) where y is 1 or 2; or two $Q^1$ groups, which substitute the same atom, together form alkylene; and each $Q^1$ is independently unsubstituted or substituted with one, two or three substituents, each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, heteroalkyl, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, heterocyclylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, alkynylalkoxycarbonyl, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N', N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})_2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1, 2 or 1, 3 arrangement, together form alkylenedioxy (i.e., —O—(CH$_2$)$_y$—O—), thioalkylenoxy (i.e., —S—(CH$_2$)$_y$—O—) or alkylenedithioxy (i.e., —S—(CH$_2$)$_y$—S—) where y is 1 or 2; or two $Q^2$ groups, which substitute the same atom, together form alkylene;

each $Q^3$ is independently selected from halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, heteroalkyl, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, heterocyclylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, alkynoxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{51}$R$^{52}$R$^{53}$, P(R$^{50}$)$_2$, P(=O)(R$^{50}$)$_2$, OP(=O)(R$^{50}$)$_2$, —NR$^{60}$C(=O)R$^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1, 2 or 1, 3 arrangement, together form alkylenedioxy (i.e., —O—(CH$_2$)$_y$—O—), thioalkylenoxy (i.e., —S—(CH$_2$)$_y$—O—) or alkylenedithioxy (i.e., —S—(CH$_2$)$_y$—S—) where y is 1 or 2; or two $Q^3$ groups, which substitute the same atom, together form alkylene; and each $Q^3$ is independently unsubstituted or substituted with one, two or three substituents, each independently selected from $Q^2$;

$R^{50}$ is hydroxy, alkoxy, aralkoxy, alkyl, heteroaryl, heterocyclyl, aryl or —NR$^{70}$R$^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or —NR$^{70}$R$^{71}$.

In certain embodiments, the compounds of formula I are selected with a proviso that when A is 3-pyridinyl and $R^2$ is halo or methyl, then $R^1$ is not 2-phenoxy. In one embodiment, the compounds of formula I are selected with a proviso that when A is 3-pyridinyl and $R^2$ is halo or alkoxy, then $R^1$ is not 2-phenoxy. In one embodiment, the compounds of formula I are selected with a proviso that when A is 3-pyridinyl and $R^2$ is halo or alkoxy, then $R^1$ is not 2-aryloxy. In one embodiment, the compounds of formula I are selected with a proviso that when A is pyridinyl and $R^2$ is halo or alkoxy, then $R^1$ is not 2-aryloxy.

In one embodiment, the compounds of Formula I are selected such that A is a 5-10 membered heterocyclyl or heteroaryl ring connected to the benzoxazine core by a carbon atom of the heterocyclyl or heteroaryl ring;

$R^2$ is halo, pseudohalo, alkyl, alkenyl, alkynyl, haloalkyl, cycloalkyl, NR$^a$R$^b$, —OR$^c$, —C(O)R$^c$ or —S(O)$_m$R$^c$;

$R^a$, $R^b$ and $R^c$ are each independently selected from hydrogen, alkyl, alkenyl, alkynyl, haloalkyl, cycloalkyl, aryl, heterocyclyl and heteroaryl;

$R^1$ is alkyl, —OR$^3$, —SR$^3$ or NR$^4$R$^5$;

each $R^3$ is independently selected from alkyl, alkenyl, alkynyl, haloalkyl, heteroalkyl, cycloalkyl, aryl, heterocyclyl and heteroaryl;

$R^4$ and $R^5$ are selected as follows:

$R^4$ and $R^5$ are each independently selected from hydrogen, alkyl, alkenyl, alkynyl, haloalkyl, cycloalkyl, aryl, heterocyclyl and heteroaryl, provided that at least one of $R^4$ or $R^5$ is not hydrogen; or ii) $R^4$ and $R^5$ together with the nitrogen atom on which they are substituted form a 5-10 membered substituted or unsubstituted heterocyclyl or heteroaryl ring; wherein the substituents when present are selected from one or more $Q^1$;

m is 0-2; and each n is independently 0 to 6 and the other variavles are as described elsewhere herein.

In one embodiment, ring A is a 5-10 or 5-7 membered heterocyclyl or heteroaryl ring. Exemplary heterocyclyl and heteroaryl rings include, but are not limited to pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyrazinyl, tetrazolyl, pyrazolyl, indolyl, benzofuranyl, benzothienyl, dihydrobenzofuranyl, dihydrobenzothienyl, benzimidazolyl, benzothiazolyl, benzisoxazolyl, benzisothiazolyl, quinolinyl, tetrahydroquinolinyl, isoquinolinyl and others known to one of skill in the art. In one embodiment, ring A is a 5-7 membered heterocyclyl ring such as pyrrolidinyl or tetrahydrofuryl. In another embodiment, ring A is a 5-7 membered heteroaryl ring, such as pyridinyl, thienyl or pyrrolyl. In one embodiment, ring A is pyridinyl. In one embodiment, A is 3-pyridinyl. In one embodiment, A is 2-pyridinyl. In one embodiment, A is 4-pyridinyl. In another embodiment, A is 2-thienyl.

In one embodiment, $R^2$ is halo, alkyl, haloalkyl or alkoxy. In one embodiment, $R^2$ is chloro, fluoro, bromo, methyl, ethyl, trifluoromethyl or methoxy. In one embodiment, $R^2$ is butyl, propyl, isobutyl or cyclopropyl.

In one embodiment, $R^1$ is alkyl, such as methyl. In one embodiment, $R^1$ is —$OR^3$ or —$NR^4R^5$.

In one embodiment, $R^3$ is alkyl, haloalkyl, heteroalkyl, aryl, haloaryl, alkoxyalkyl, alkylaryl or arylsulfonylalkyl. In another embodiment, $R^3$ is methyl, ethyl, phenyl, 4-chlorophenyl, 4-fluorophenyl, 4-tolyl, phenylsulfonylethyl, 3,4-methylenedioxybenzyl or dimethoxyaminoethyl.

In one embodiment, $R^4$ is hydrogen, lower alkyl or alkoxyalkyl. In one embodiment, $R^4$ is hydrogen, methyl or methoxyethyl.

In one embodiment, $R^5$ is aralkyloxycarbonylalkyl, dialkylaminoalkyl, heterocyclylalkyl, alkylheterocyclyl or alkoxyalkyl. In one embodiment, $R^5$ is benzyloxycarbonylmethyl, dimethylaminoethyl, 4-morpholinoethyl, N-methylpyrrolidin-3-yl or methoxyethyl.

In one embodiment, $R^4$ and $R^5$ together with the nitrogen atom on which they are substituted form a 5 or 6 membered heterocyclyl or heteroaryl ring. In one embodiment, $R^4$ and $R^5$ together with the nitrogen atom on which they are substituted form a 5 membered heterocyclyl or heteroaryl ring. In certain embodiments, the ring is pyrrolyl or pyrrolidinyl.

In certain embodiments, $R^1$ is:

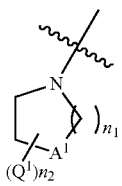

wherein $A^1$ is $CR^6R^7$ or $NR^6$; $R^6$ is hydrogen, alkyl, alkenyl, alkynyl, phenyl, heteroaryl, alkoxyalkyl, cycloalkylalkyl, hydroxyalkyl, cyanoalkyl, aralkyl, heteroarylalkyl, heterocyclylalkyl, aminocarbonylalkyl, dialkylaminoalkyl, alkoxycarbonylalkyl, hydroxycarbonylalkyl, heterocyclylcarbonylalkyl, hydroxyalkoxyalkyl, alkoxycarbonylaminoalkyl, alkynoxycarbonylaminoalkyl, or imidamidyl; $R^7$ is hydrogen or alkyl; $Q^1$ is alkyl, alkoxycarbonyl, phenyl, dialkylamino, alkoxycarbonyl, dialkylaminoalkyl, aralkyl, hydroxycarbonyl, hydroxyalkyl, hydroxyalkoxyalkyl, hydroxycarbonylalkyl, heterocyclyl, heterocyclylalkyl, —$N^+R^{51}R^{52}R^{53}$, alkylsulfinylalkylcarbonyl, cycloalkylaminoalkyl, halo, di(hydroxyalkyl)amino, dialkylaminoalkylcarbonyl, heterocyclylcarbonyl, —$SO_3H$ or alkylsulfonate; $n_1$ is 1 or 2; and $n_2$ is 0-5.

In certain embodiments, $R^6$ is hydrogen, methyl, ethyl, isopropyl, 2-propenyl, 2-propynyl, 3-butynyl, phenyl, cyclopropylmethyl, 2-hydroxyethyl, hydroxycarbonylethyl, hydroxycarbonylpropyl, ethoxycarbonylethyl, methoxymethyl, ethoxymethyl, cyanoethyl, 3-cyanopropyl, dimethylaminomethyl, dimethylaminoethyl, 4-morpholinoethyl, 2-pyrimidinyl, 3-pyrimidinyl, 4-pyrimidinyl, 2-thiazolyl, 4-fluorophenylmethyl, 4-methoxyphenylmethyl, pyrrolidin-1-ylmethyl, tetrahydrofunan-2-ylmethyl, 1,3-dioxolan-2-ylmethyl, N-methylpiperidin-4-yl, ethoxycarbonylmethyl, hydroxycarbonylmethyl, morpholin-4-ylcarbonylmethyl, t-butlyoxycarbonylaminoethyl, hydroxyethoxyethyl, aminocarbonylmethyl, 2-propynyloxycarbonylaminoethyl, or —$C(NH)NH_2$.

In certain embodiments, $Q^1$ is methyl, ethyl, propyl, isopropyl, phenyl, dimethylamino, diethylamino, dimethylaminomethyl, dimethylaminoethyl, diethylaminomethyl, hydroxy, hydroxycarbonyl, methoxycarbonyl, ethoxycarbonyl, phenylmethyl, hydroxycarbonylpropyl, hydroxyalkyl, hydroxyalkoxyalkyl, 1-imidazolyl, 4-morpholino, morpholin-4-ylmethyl, morpholin-4-ylethyl, —$N(CH_3)_3^+$, methylsulfinylmethylcarbonyl, cycloalkylaminoalkyl, fluoro, di(hydroxyethyl)amino, dialkylaminoalkylcarbonyl, pyrrolidin-1-ylmethyl, pyrrolidin-1-ylethyl, cyclopropylaminomethyl, 2-oxo-piperazin-4-yl, 1,1-dioxo-thiomorpholin-4-yl, N-methyl-N-(methoxyethyl)amino, N-methyl-piperazin-4-ylcarbonyl, N,N-dimethylaminoethylamino(methyl)carbonyl, —$SO_3H$ or —$(CH_2)_3SO_3H$.

In certain embodiments, $R^1$ is:

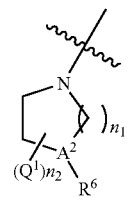

wherein $A^2$ is CH or N; and $R^6$, $Q^1$, $n_1$, and $n_2$ are as described elsewhere herein.

In one embodiment, $R^6$ is hydrogen, methyl, methoxymethyl or cyclopropylmethyl; $R^7$ is hydrogen; $Q^1$ is methyl, dimethylamino, tert-butyloxycarbonyl or methoxycarbonyl; n1 is 1 or 2; and $n_2$ is 1 or 2.

In certain embodiments, $R^1$ is

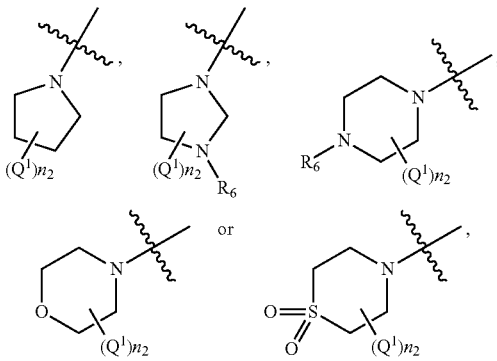

wherein $R^6$ is hydrogen, alkyl, alkoxyalkyl or cycloalkylalkyl; $Q^1$ is alkyl, dialkylamino or alkoxycarbonyl; and $n_2$ is 0-5.

In another embodiment, $R^6$ is hydrogen, methyl, methoxyethyl or cyclopropylmethyl. In another embodiment, $n_2$ is 1 and $Q^1$ is methyl, dimethylamino, tert-butyloxycarbonyl or methoxycarbonyl.

In certain embodiments, $R^1$ is

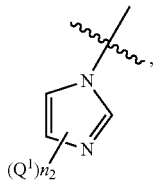

wherein $Q^1$ is alkyl, dialkylamino or alkoxycarbonyl; and $n_2$ is 0-3.

In certain embodiments, the compound is:

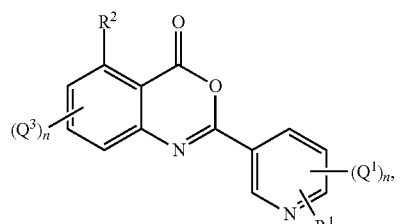

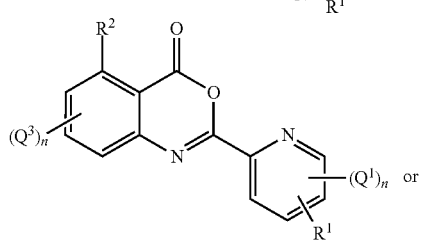

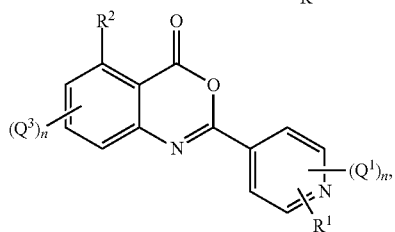

or a pharmaceutically acceptable salt thereof, wherein the variables are as defined elsewhere herein.

In certain embodiments, the compound is:

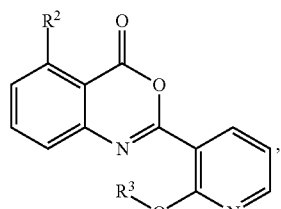

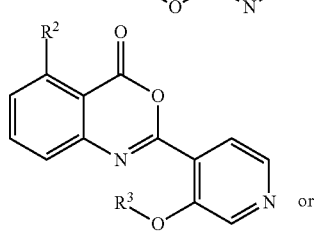

or

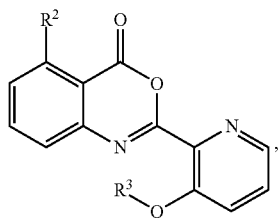

or a pharmaceutically acceptable salt thereof, wherein the variables are as defined elsewhere herein.

In certain embodiments, the compound is:

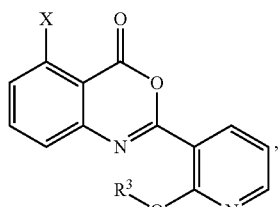

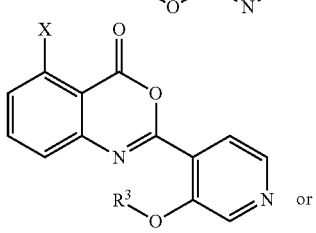

or

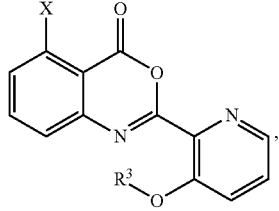

or a pharmaceutically acceptable salt thereof, wherein X is a halogen and the other variables are as defined elsewhere herein. In one embodiment, X is fluoro or chloro.

In certain embodiments, the compound is:

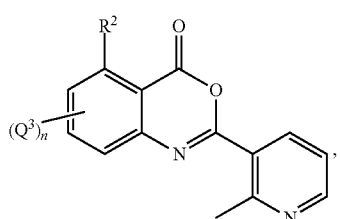

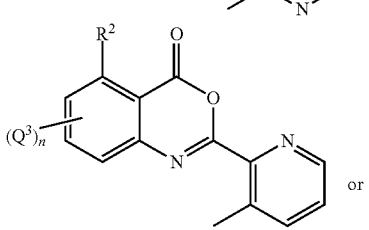

or

-continued

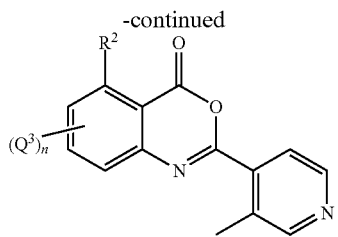

or a pharmaceutically acceptable salt thereof, wherein the variables are as defined elsewhere herein.

In certain embodiments, the compound is:

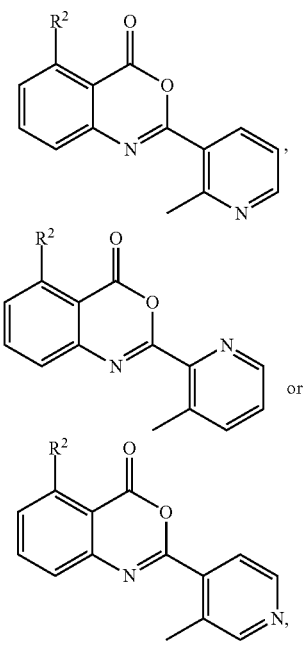

where R² is alkyl or halo.

In certain embodiments, the compound is

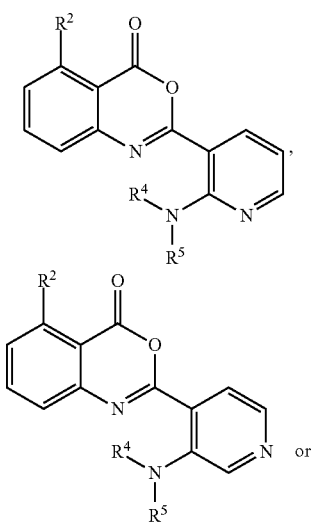

-continued

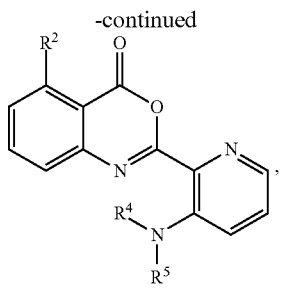

or a pharmaceutically acceptable salt thereof, wherein the variables are as defined elsewhere herein.

In certain embodiments, the compound is:

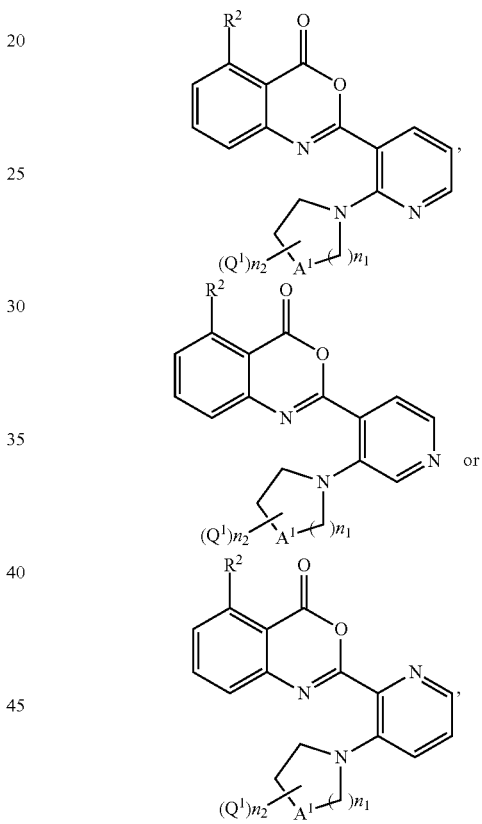

or a pharmaceutically acceptable salt thereof, wherein the variables are as defined elsewhere herein.

In certain embodiments, the compound is:

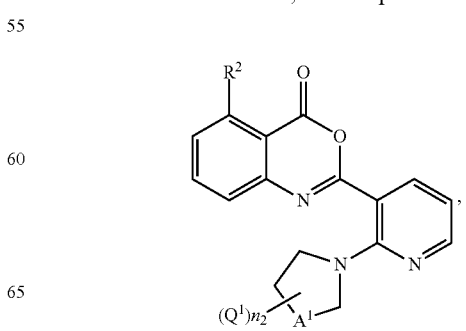

-continued

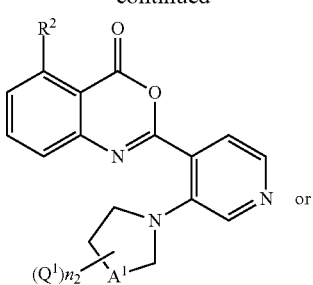

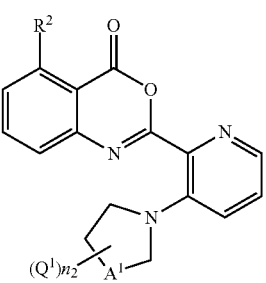

or a pharmaceutically acceptable salt thereof, wherein the variables are as defined elsewhere herein.

In certain embodiments, the compound is:

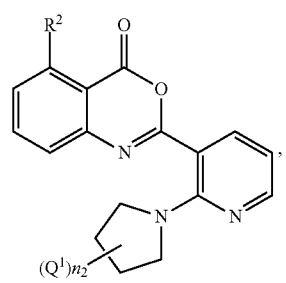

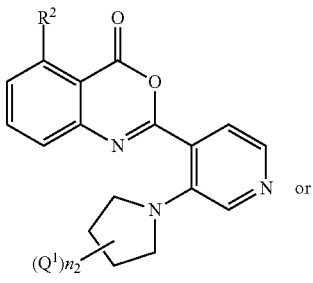

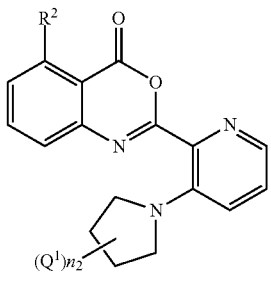

or a pharmaceutically acceptable salt thereof, wherein the variables are as defined elsewhere herein.

In certain embodiments, the compound is:

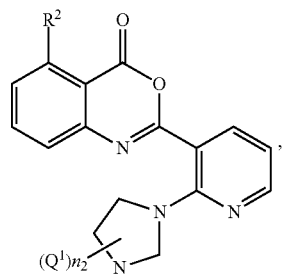

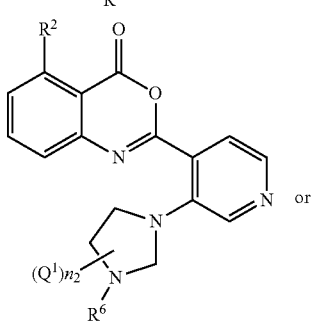

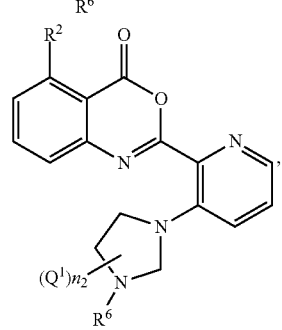

or a pharmaceutically acceptable salt thereof, wherein the variables are as defined elsewhere herein.

In certain embodiments, the compound is:

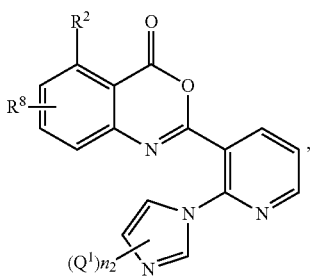

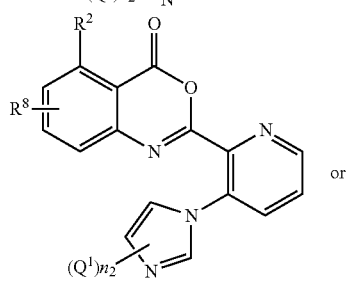

-continued

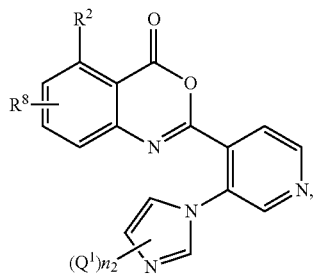

or a pharmaceutically acceptable salt thereof, wherein the variables are as defined elsewhere herein.

In certain embodiments, the compound is:

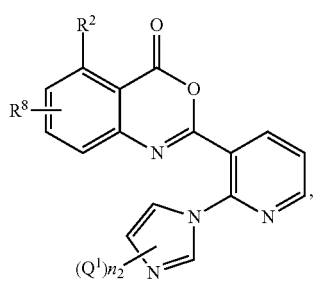

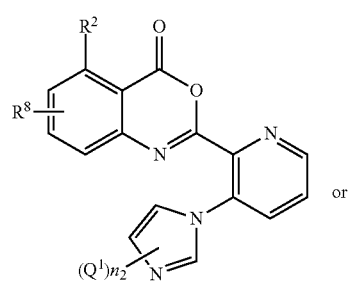

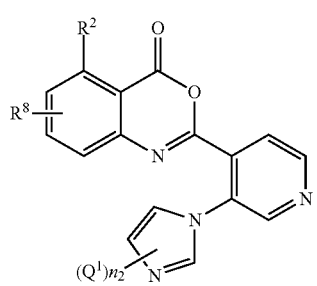

or a pharmaceutically acceptable salt thereof, wherein the variables are as defined elsewhere herein.

In certain embodiments, the compound is:

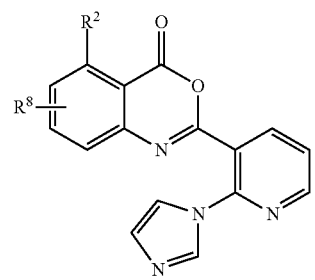

or a pharmaceutically acceptable salt thereof, wherein the variables are as defined elsewhere herein. In one embodiment, $R^2$ is alkyl, haloalkyl, alkoxy, amino, halo, alkylcarbonyl or alkylsulfenyl. In one embodiment, $R^2$ is methyl, isopropyl, trifluoromethyl, methoxy, hydroxy, amino, chloro, acyl or methylsulfenyl. In one embodiment, $R^8$ is alkoxy, pyrrolyl, pyrrolidinyl, pyrazolyl, imidazolyl, triazolyl or tetrazolyl.

In one embodiment, the compound has formula:

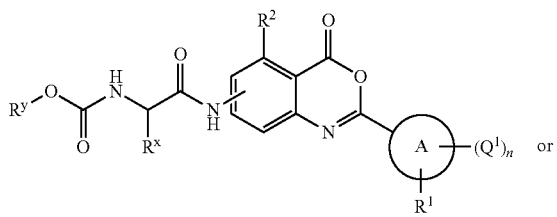

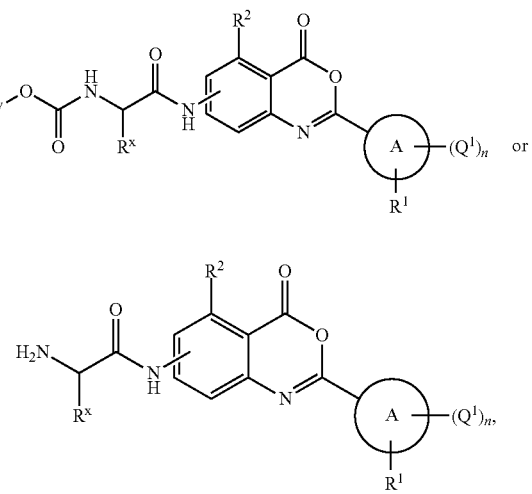

or a pharmaceutically acceptable salt thereof, wherein $R^x$ and $R^y$ are each independently selected from hydrogen, alkyl, alkenyl, alkynyl, haloalkyl, cycloalkyl, aryl, heterocyclyl and heteroaryl; and the other variables are as defined elsewhere herein. In certain embodiments, $R^x$ and $R^y$ are each independently selected from hydrogen and lower alkyl.

In one embodiment, the compound has formula:

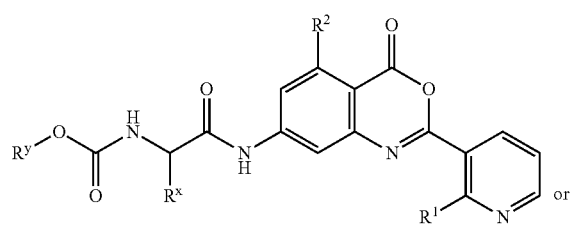

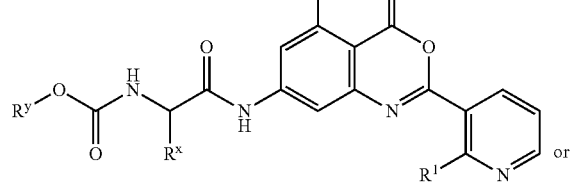

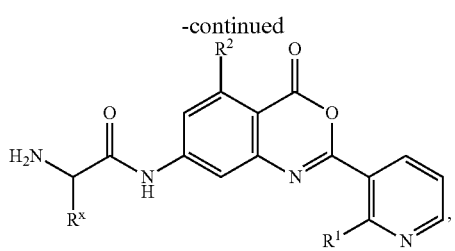

or a pharmaceutically acceptable salt thereof, wherein the variables are as defined elsewhere herein.

In one embodiment, the compound has formula:

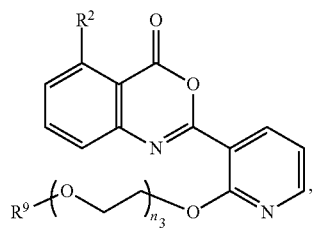

or a pharmaceutically acceptable salt thereof, wherein $R^9$ is hydrogen or unsubstituted or substituted alkyl, alkenyl, alkynyl, haloalkyl, cycloalkyl, aryl, heterocyclyl or heteroaryl and $n_3$ is 1-20. In one embodiment, $n_3$ is 3 or 4. In one embodiment, $R^9$ is hydrogen, methyl, phenyl or 3-carboxypyridin-2-yl.

In certain embodiments, the compound is:

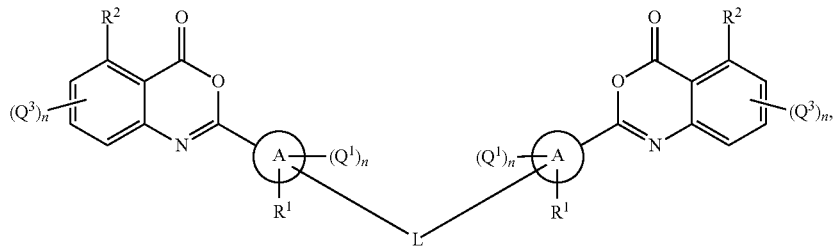

or a pharmaceutically acceptable salt thereof, wherein L is a linker and the other variables are as defined elsewhere herein.

In certain embodiments, the linker is characterized by a first covalent bond or a chemical functional group that connects one benzoxazinone moiety to a first end of the linker and a second covalent bond or chemical functional group that connects the second end of the linker to a second benzoxazinone moiety. The first and second functionality, may or may not be independently present.

The linker, L can include linear or acyclic portions, cyclic portions, aromatic rings or combinations thereof. In certain embodiments, the linker can have from 1 to 100 main chain atoms other than hydrogen atoms, selected from C, N, O, S, P and Si. In certain embodiments the linker contains up to 50 main chain atoms other than hydrogen, up to 40, up to 30, up to 20, up to 15, up to 10, up to 5, up to 2 main chain atoms other than hydrogen. In certain embodiments the linker is acyclic.

In certain embodiments, the linker contains oligomers of ethylene glycol or alkylene chains or mixtures thereof. In certain embodiments, the two benzoxazinone moieties are attached to the linker via an amide, sulfonamide, or ether connection.

In other embodiment, the linker in the conjugates provided herein contains a polyethylene glycol (PEG) chain. The PEGs for use herein can contain up to 50 main chain atoms other than hydrogen. In certain embodiments, the PEG contains 5, 11, 13, 14, 22 or 29 main chain atoms other than hydrogen. In certain embodiments, the PEG contains 5, 11, 13 or 29 main chain atoms other than hydrogen.

In certain embodiments, the compound is:

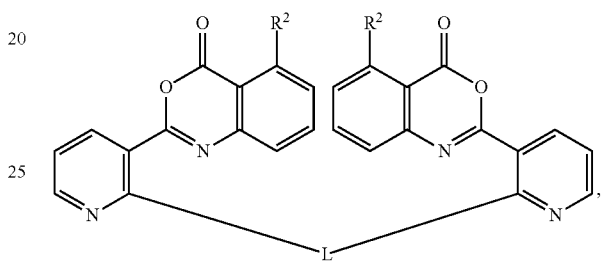

or a pharmaceutically acceptable salt thereof, wherein the variables are as defined elsewhere herein.

In certain embodiments, the compound is:

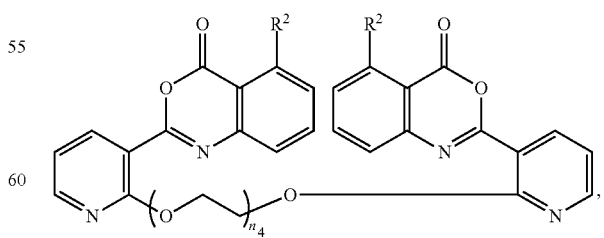

or a pharmaceutically acceptable salt thereof, wherein $n_4$ is 1-20 and the other variables are as defined elsewhere herein. In one embodiment, $n_4$ is 4.

In certain embodiments, the compound is selected from:
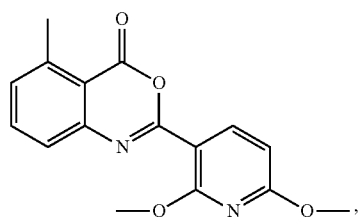
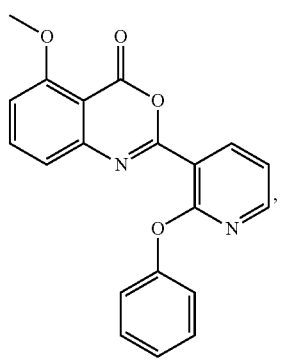
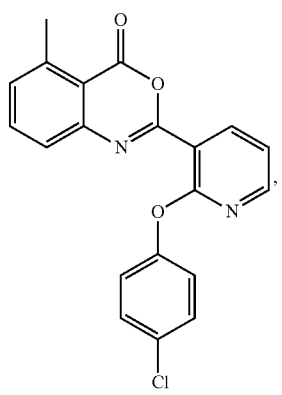
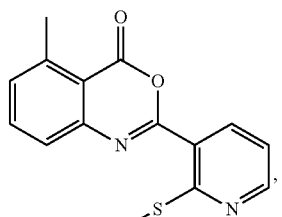
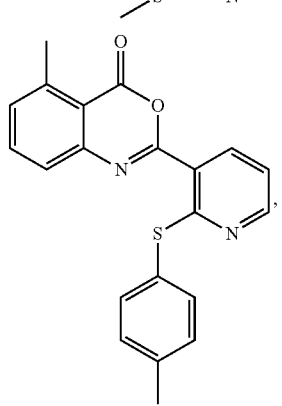
-continued
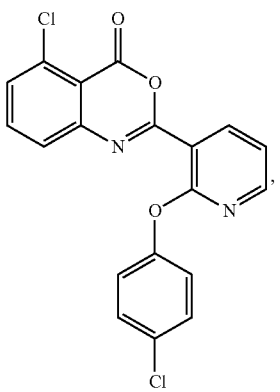
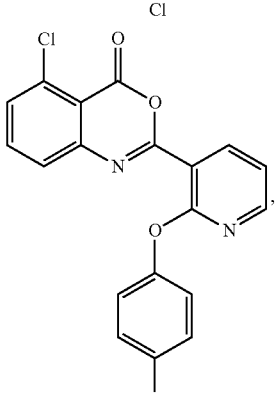
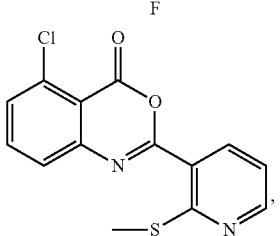
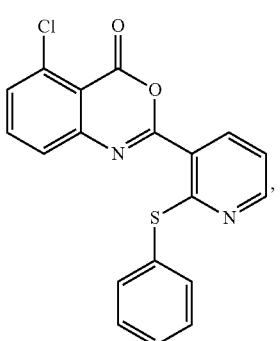
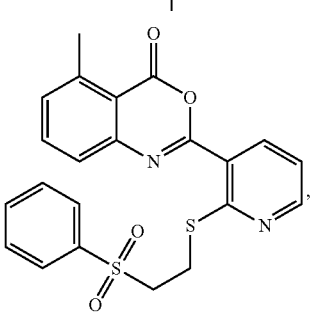

-continued
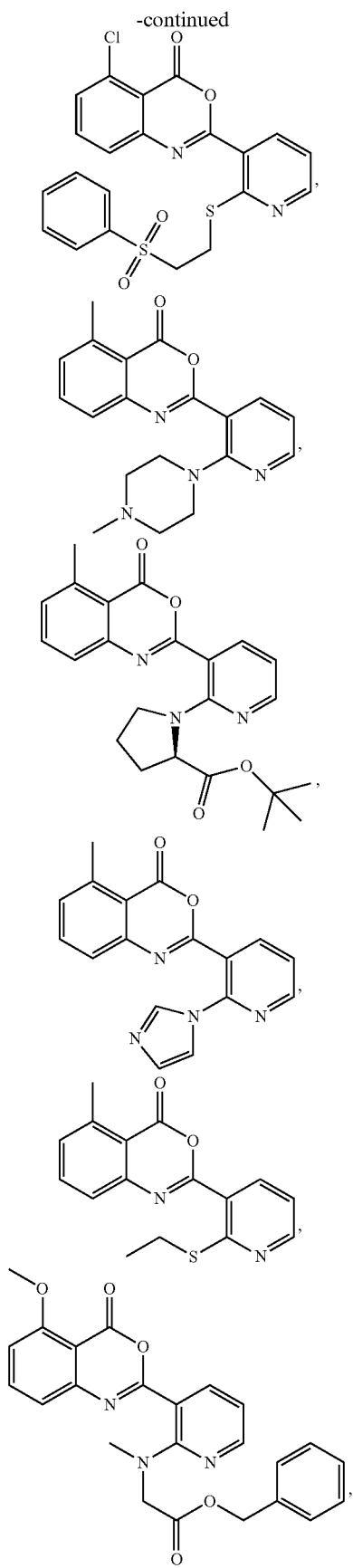
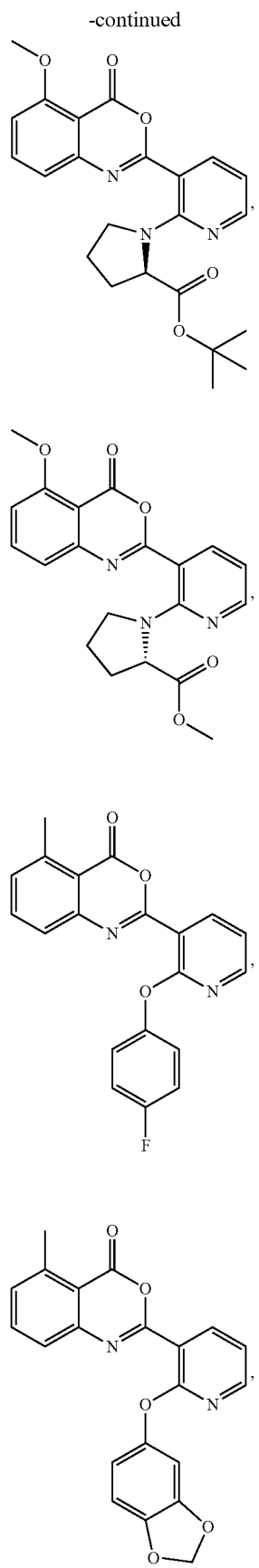

-continued
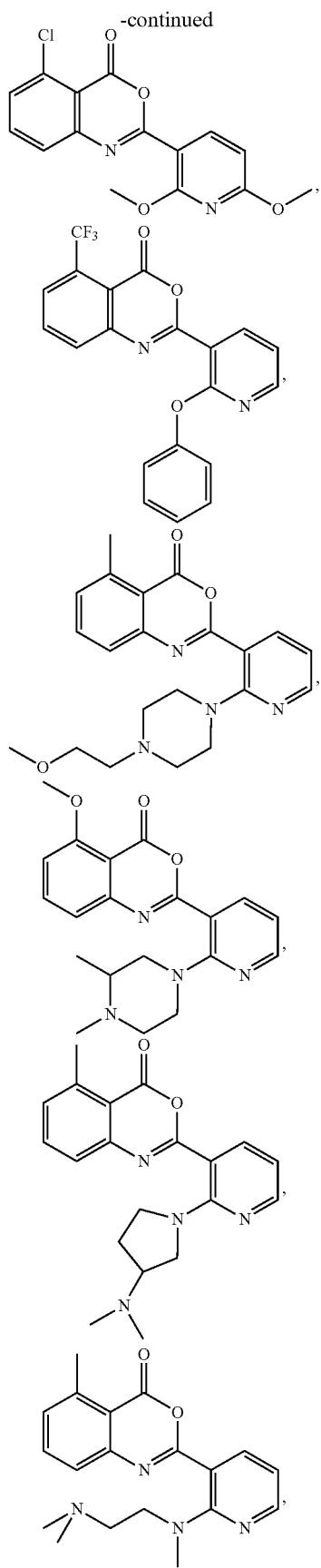
-continued
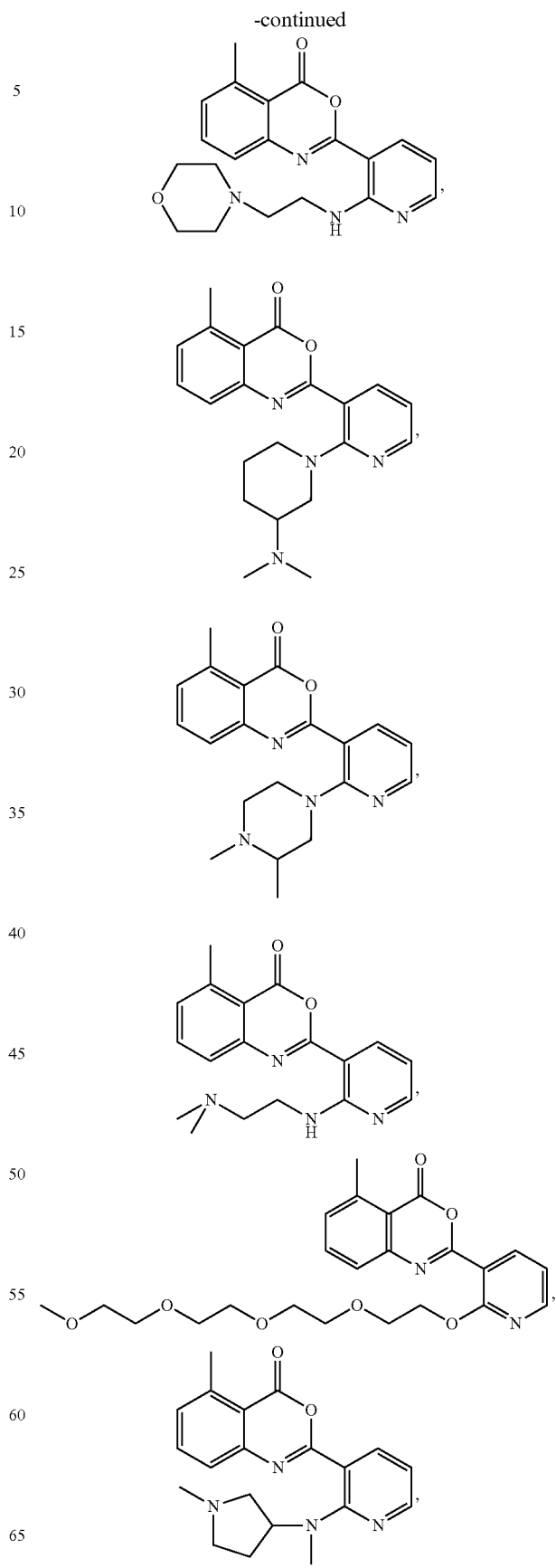

-continued
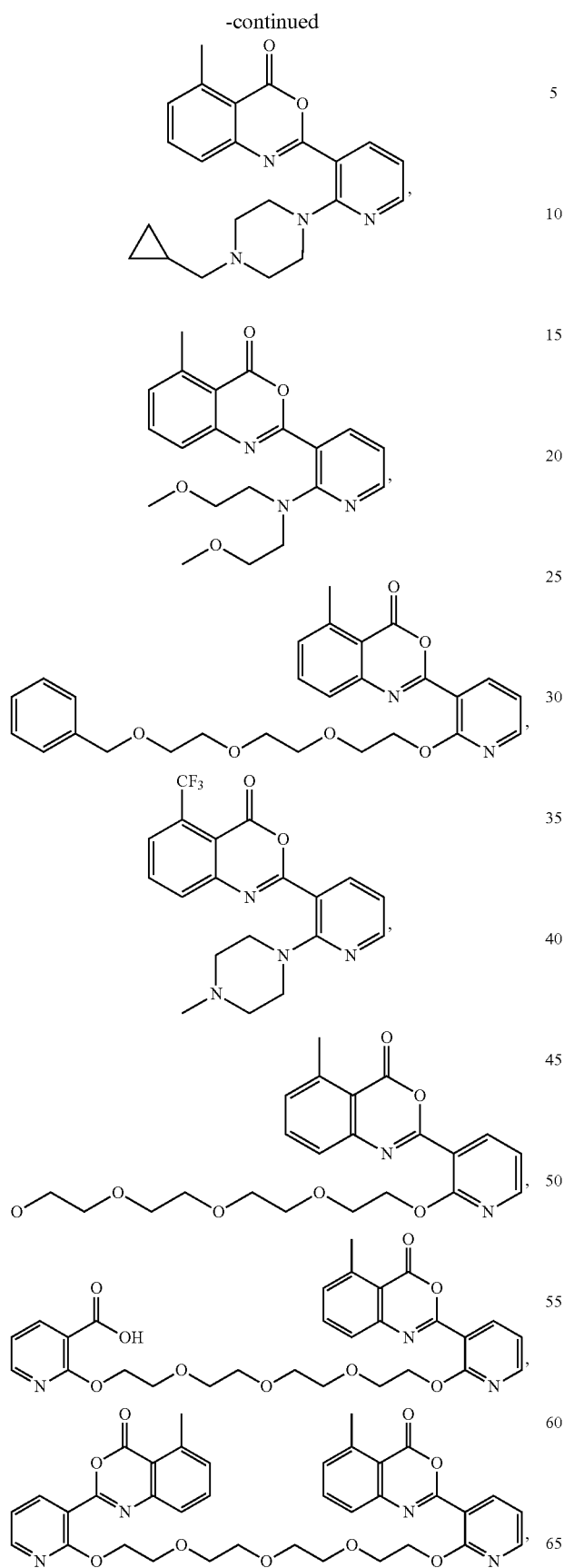
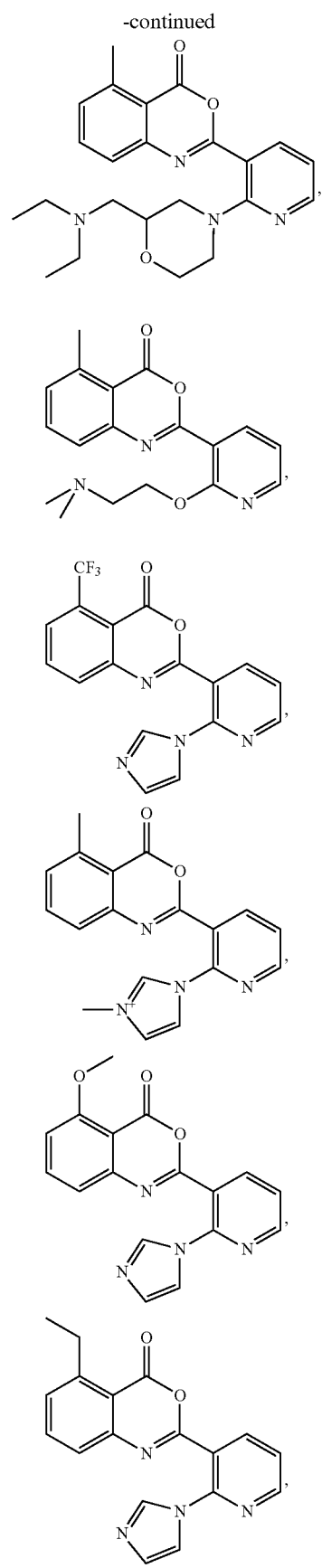

-continued
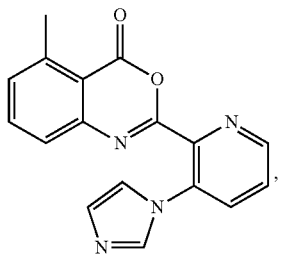
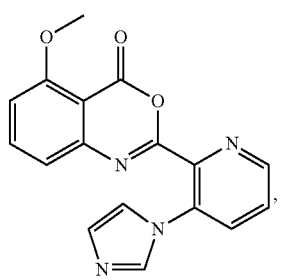
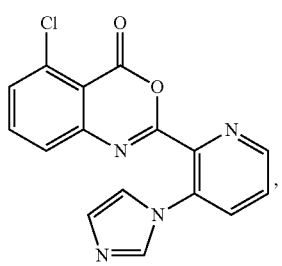
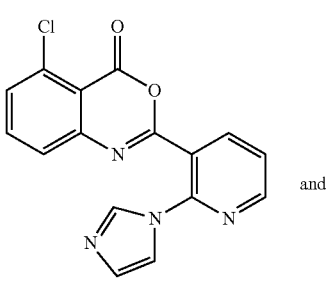 and
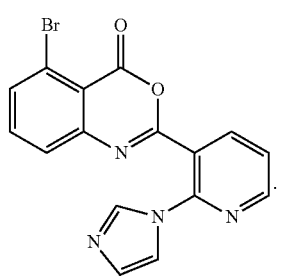
or a pharmaceutically acceptable salt thereof.
In certain embodiments, the compound is selected from:
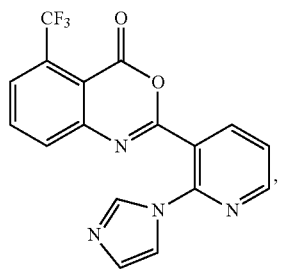
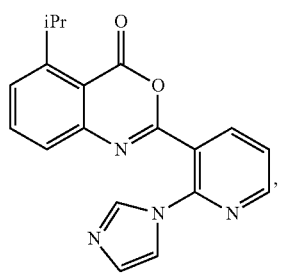
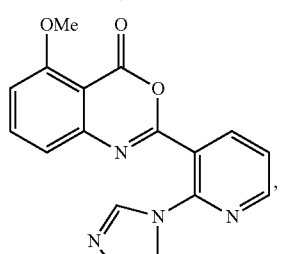
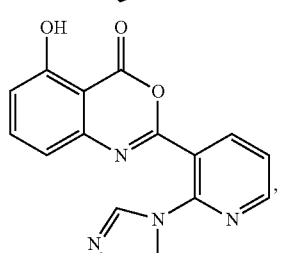
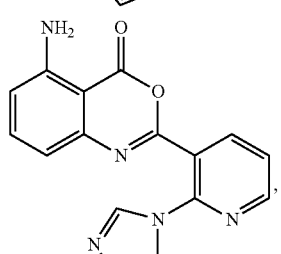
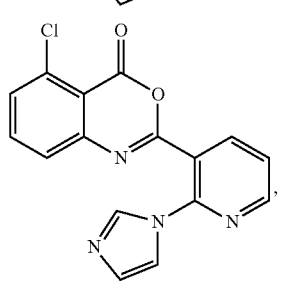

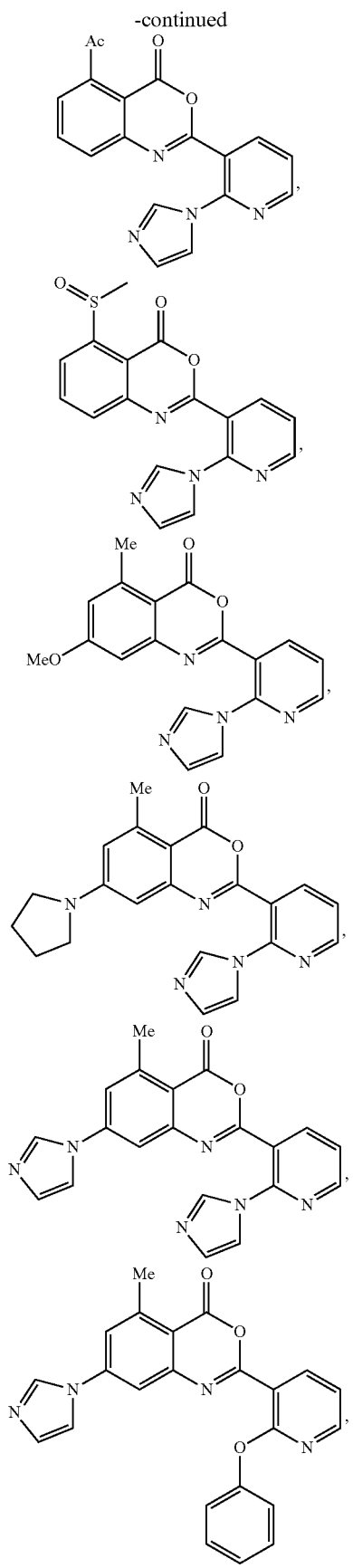
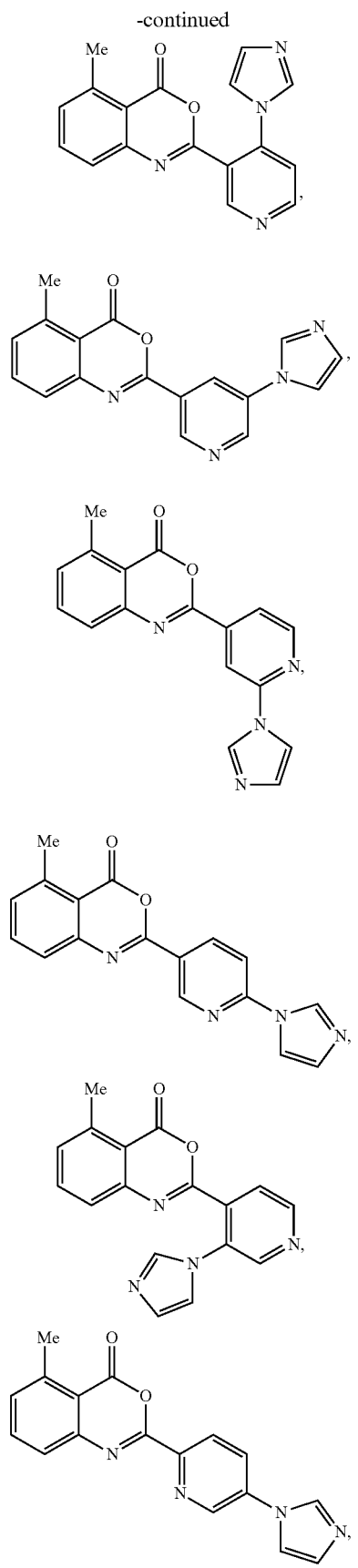

-continued

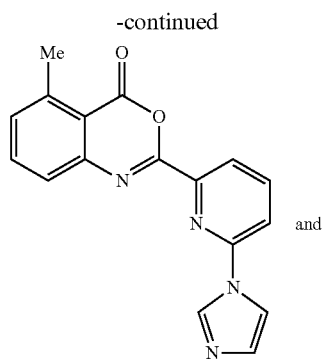

and

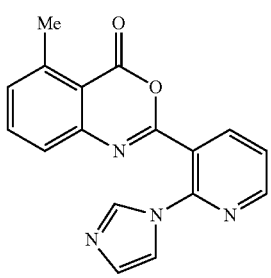

or a pharmaceutically acceptable salt thereof.

Preparation of Compounds

The compounds provided herein can be prepared by methods known to one of skill in the art and following procedures similar to those described in the Examples section herein and routine modifications thereof.

Certain exemplary reaction schemes for the preparation of compounds are illustrated below:

Scheme 1:

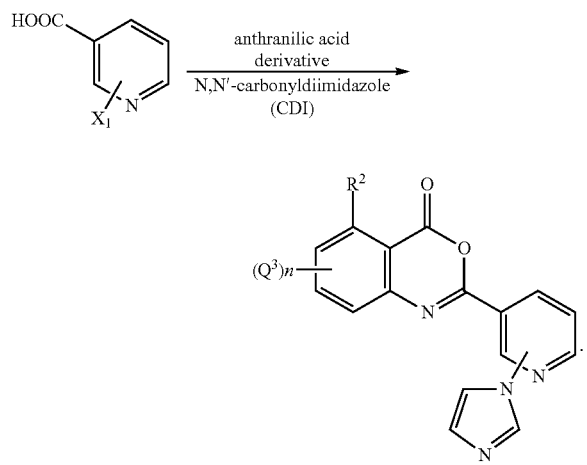

$X_1$ = leaving group

The leaving group could be any leaving group known to one of skill in the art, such as Br, Cl and F.

Scheme 2

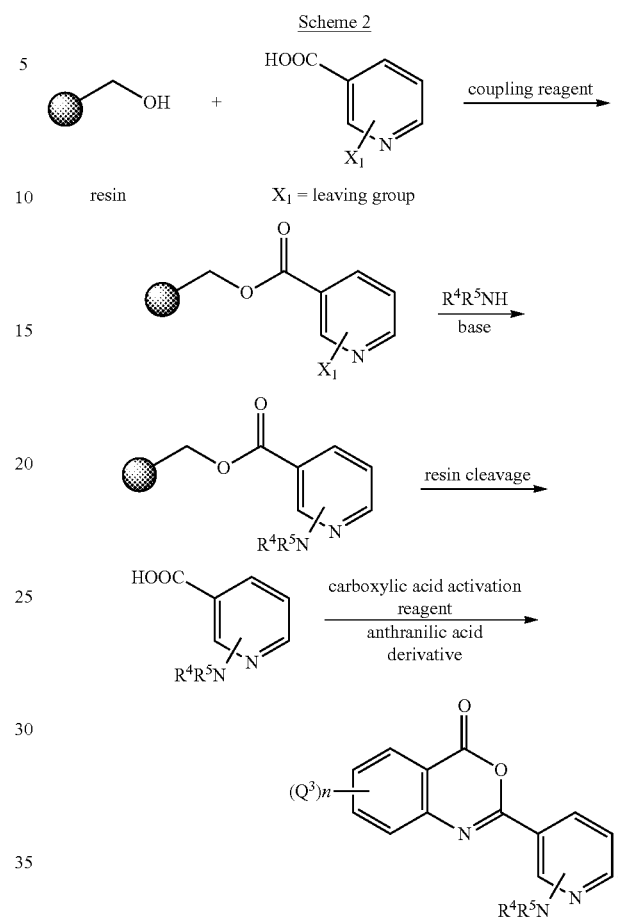

Exemplary coupling agent for use in the reaction include, but are not limited to HBTU (2-(1H-Benzotriazole-1-yl)-1,1,3,3-tetramethylaminium hexafluorophosphate), DCC (N,N'-dicyclohexylcarbodiimide), BOP (Benzotriazole-1-yl-oxy-tris-(dimethylamino)-phosphoniumhexafluorophosphate) and others known to one of skill in the art. Any base known to known to one of skill in the art can be used, exemplary bases are DBU (diazabicyclo[5.4.0]undec-7-ene), DIEA (diisopropylethylamine), TBAF (tetrabutylammonium fluoride), DIEA (N-ethyl-N,N-di-isopropylamine) and piperidine. Cataylsts known to one of skill in the art may also be used, such as HOBt (N-Hydroxybenzotriazole).

Scheme 3

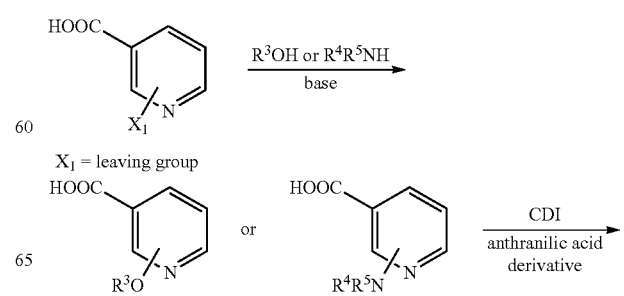

-continued

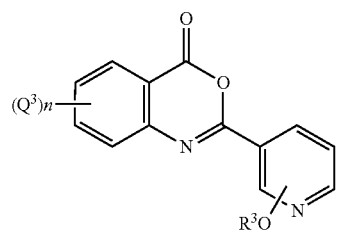

or

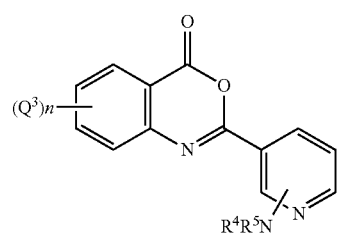

In another embodiment, the benzoxazinone compounds provided herein can be prepared by the following methods.

Scheme 4

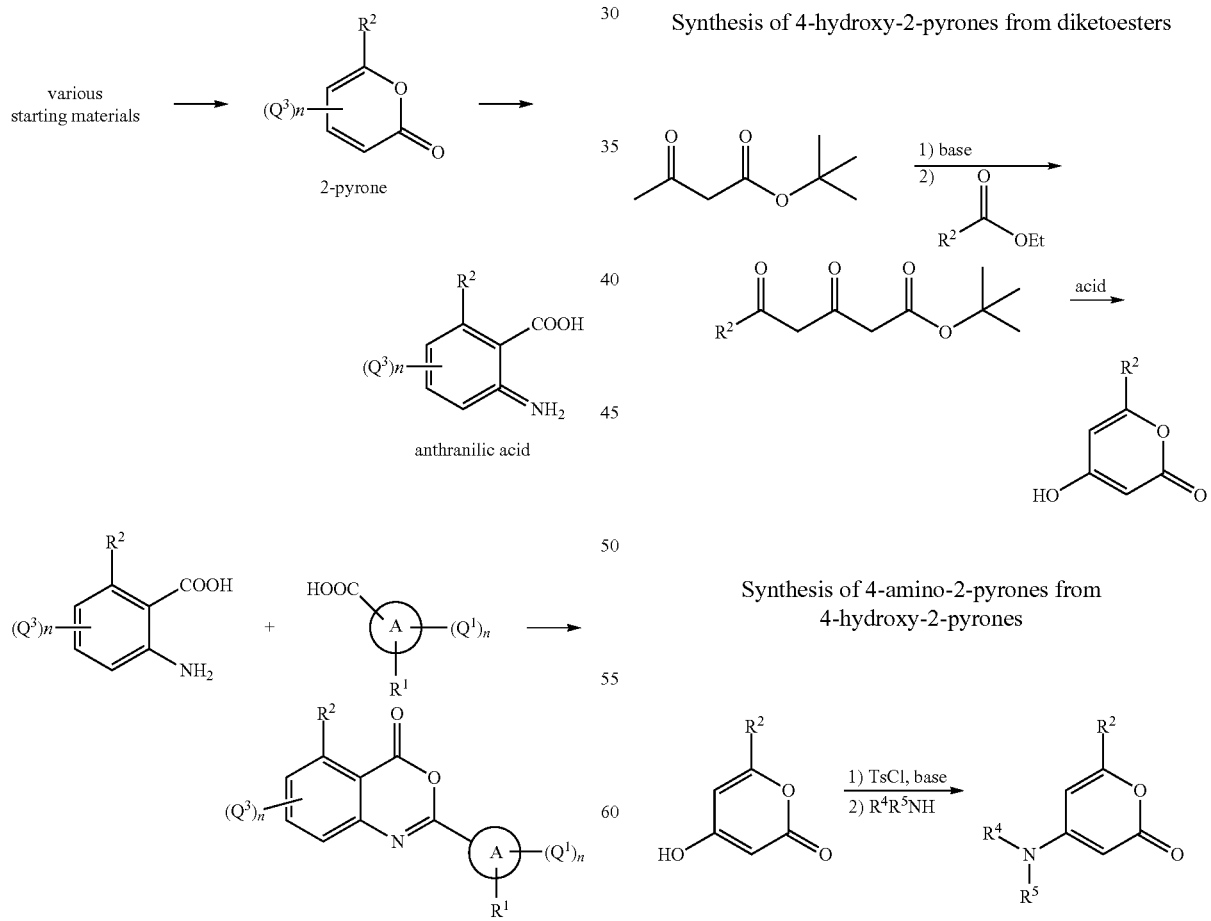

A = heterocyclic or heteroaromatic ring

The 2-pyrones of the method of scheme 4 may be purchased or prepared by methods known to one of skill in the art. Certain exemplary syntheses for the preparation of 2-pyrones are illustrated below.

Synthesis of 4-hydroxy-2-pyrones from dioxanones



This procedure may be found, for example, in *J. Org. Chem.*, 70: 4854 (2005).

Synthesis of 4-hydroxy-2-pyrones from diketoesters

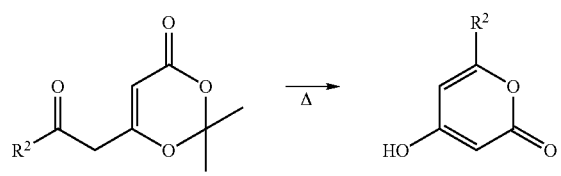

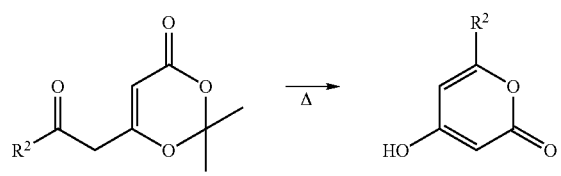

Synthesis of 4-amino-2-pyrones from 4-hydroxy-2-pyrones

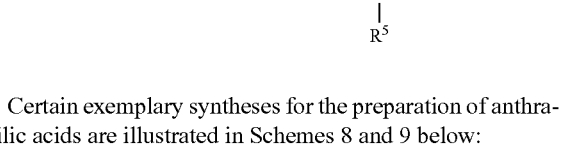

Certain exemplary syntheses for the preparation of anthranilic acids are illustrated in Schemes 8 and 9 below:

Scheme 5
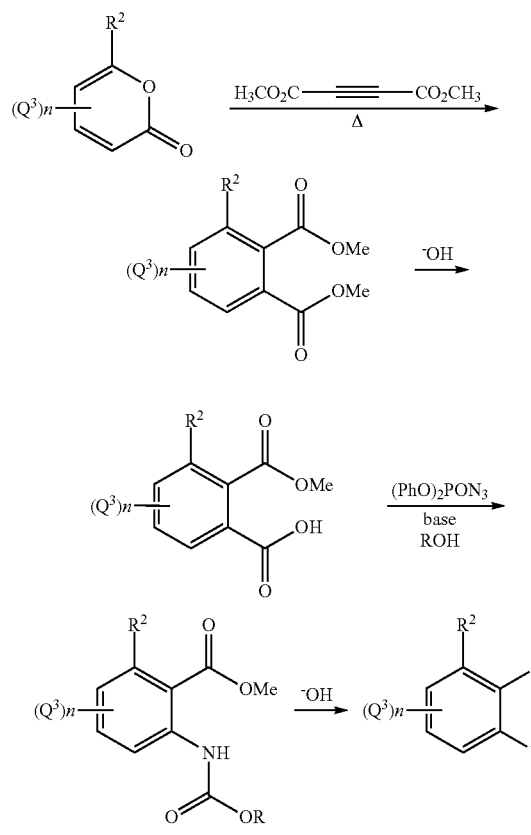
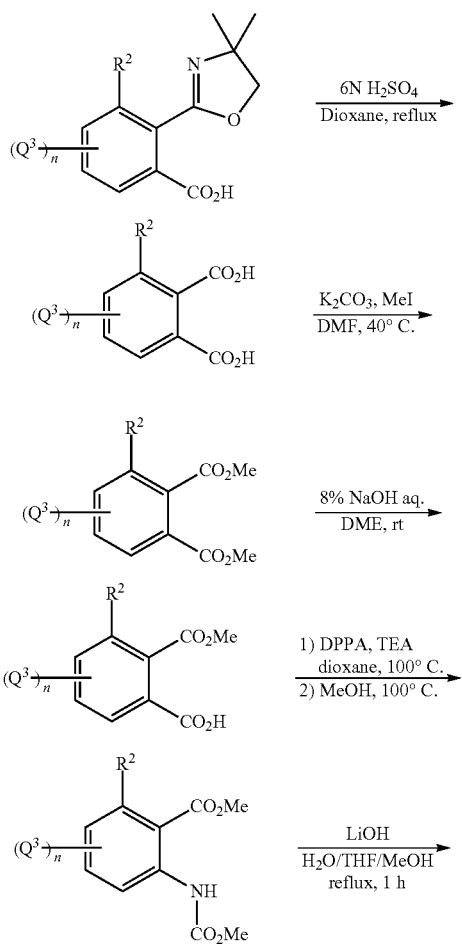
Certain benzoxazinone compounds provided herein may be prepared from anthranilic acids according to the following methods:
Scheme 6
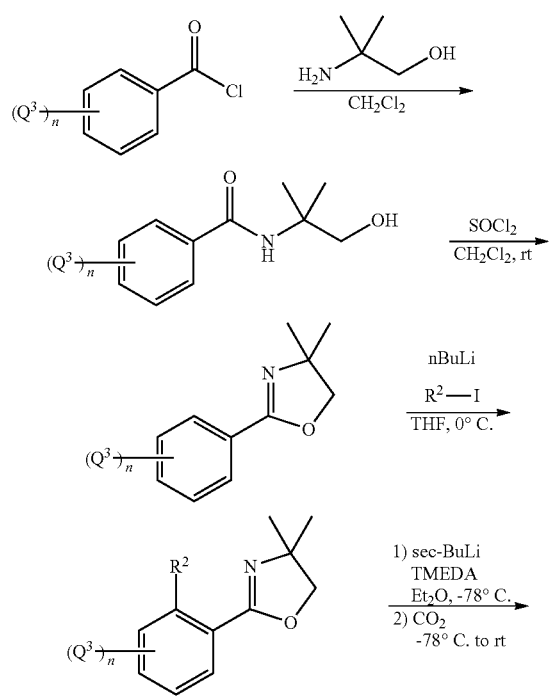
Scheme 7
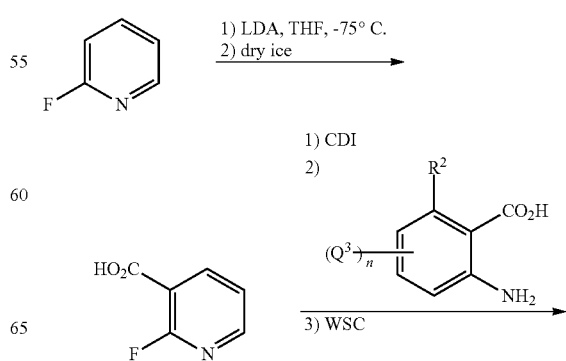

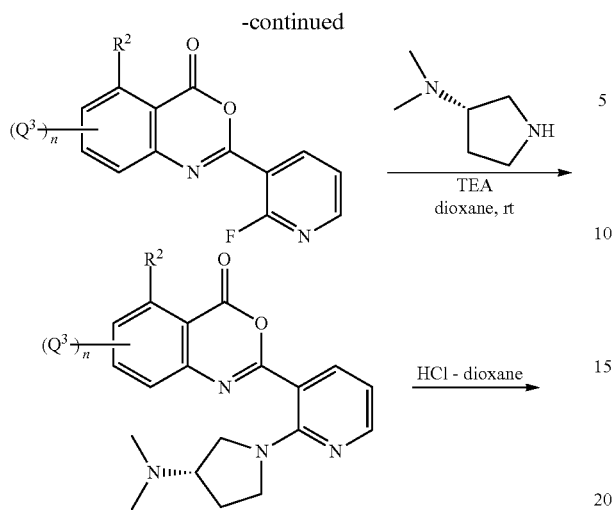
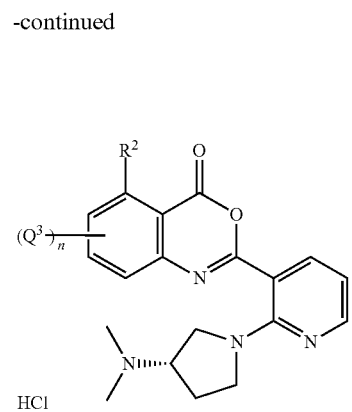
Scheme 8
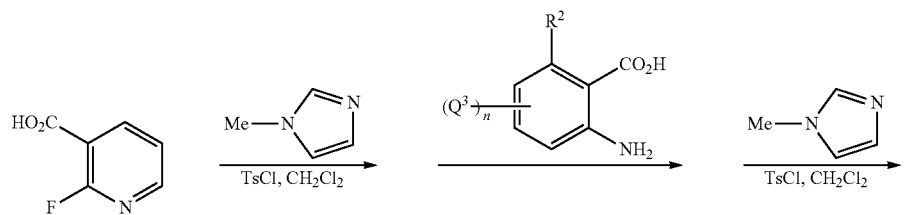
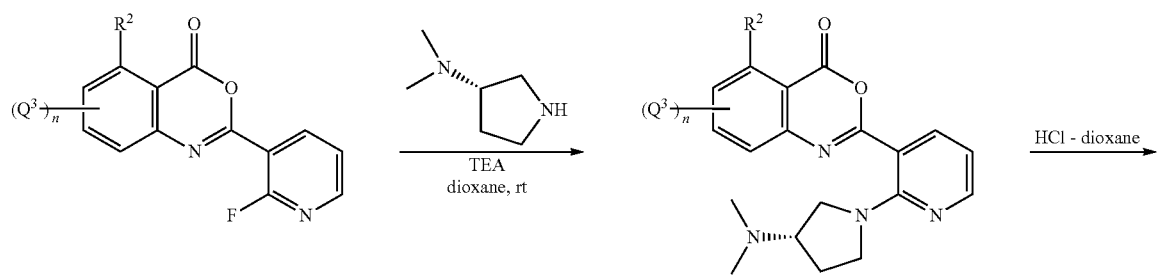
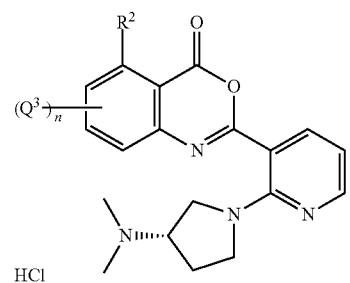

Scheme 9

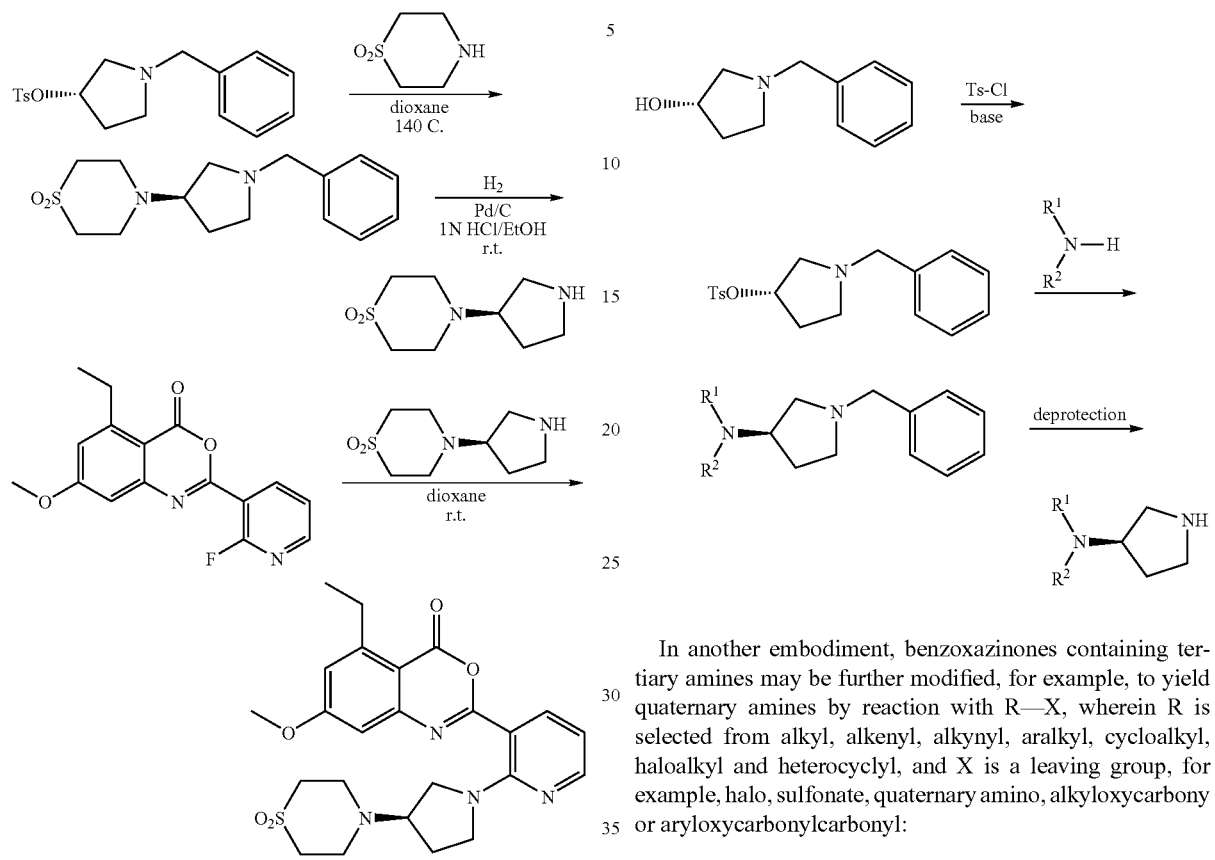

Chiral amino pyrrolidines to be used in Schemes 7, 8 and 9 may be prepared by the following method, adapted from *J. Med. Chem.* 35: 4205 (1992):

In another embodiment, benzoxazinones containing tertiary amines may be further modified, for example, to yield quaternary amines by reaction with R—X, wherein R is selected from alkyl, alkenyl, alkynyl, aralkyl, cycloalkyl, haloalkyl and heterocyclyl, and X is a leaving group, for example, halo, sulfonate, quaternary amino, alkyloxycarbony or aryloxycarbonylcarbonyl:

Scheme 10

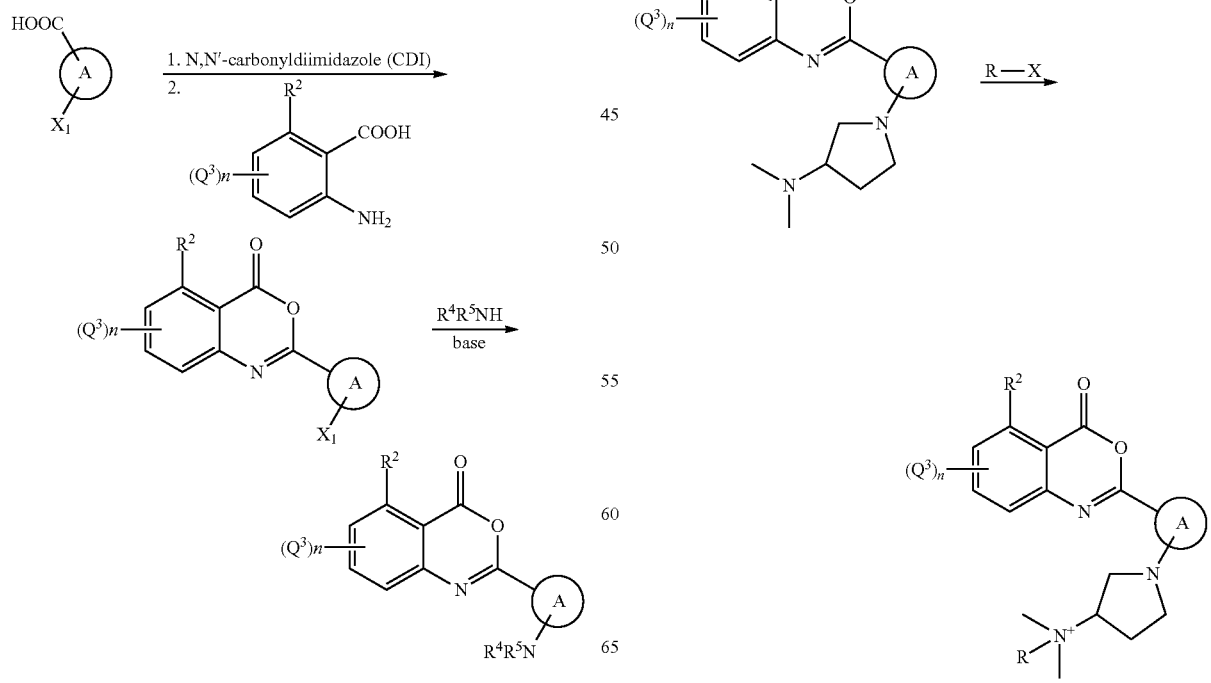

-continued
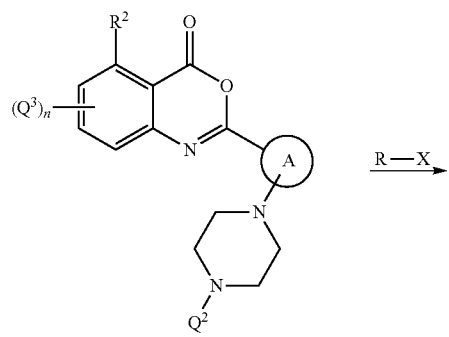
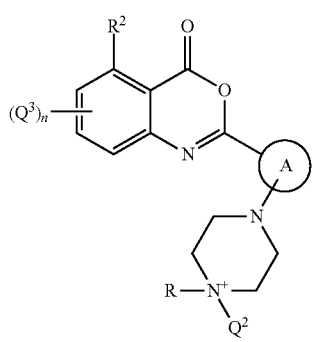
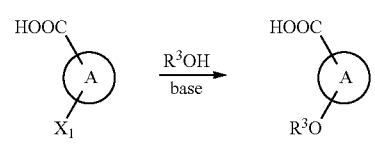
In another embodiment, certain benzoxazinone compounds provided herein may be prepared according to the following "one-pot" method:
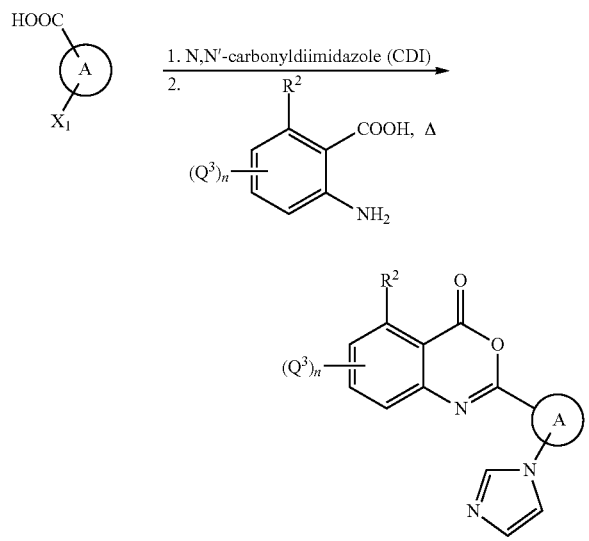
In another embodiment, alkoxy-substituted benzoxazinones may be prepared by the following method:
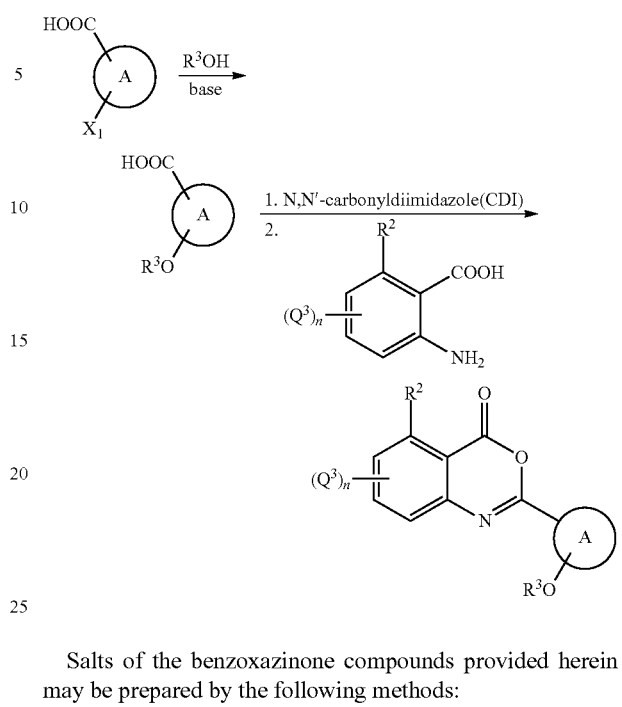
Salts of the benzoxazinone compounds provided herein may be prepared by the following methods:
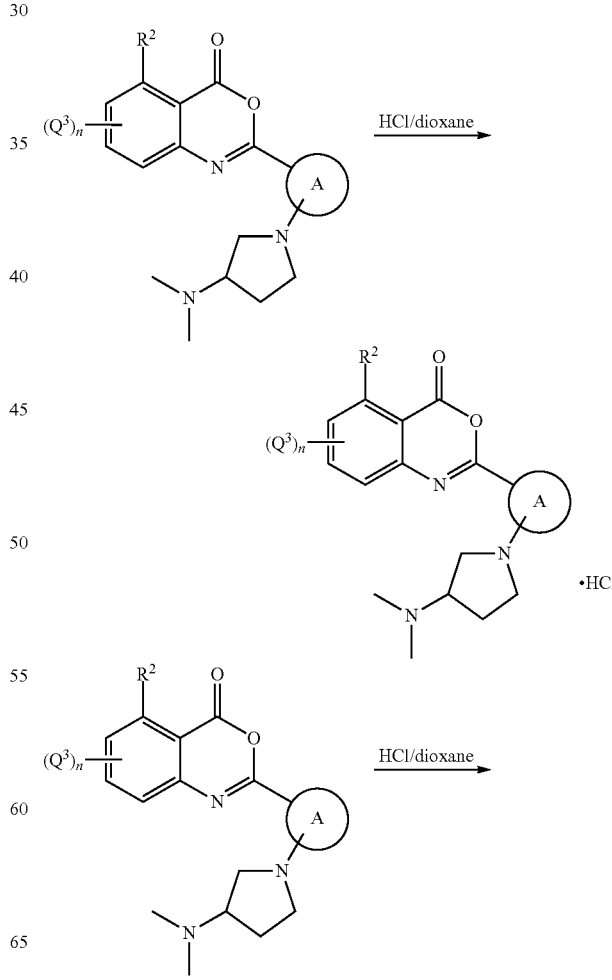

-continued

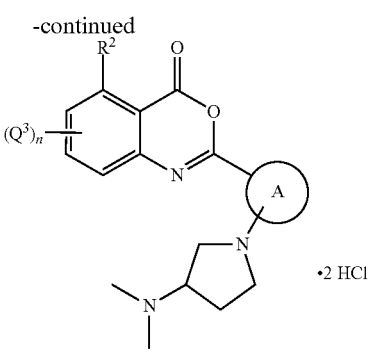

In another embodiment, methanesulfonate, trifluoroacetate, tartrate, and other salts may be prepared by similar methods.

Formulation of Pharmaceutical Compositions

The pharmaceutical compositions provided herein contain therapeutically effective amounts of one or more of compounds provided herein that are useful in the prevention, treatment, or amelioration of one or more of the symptoms of serine hydrolase-mediated diseases, including, but not limited to, neutrophil elastase-mediated diseases.

The compositions contain one or more compounds provided herein. The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of serine hydrolase-mediated diseases, including, but not limited to, neutrophil elastase-mediated diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of serine hydrolase-mediated diseases, including, but not limited to, neutrophil elastase-mediated diseases.

In certain embodiments, a therapeutically effective dosage should produce a serum concentration of active ingredient of from about 0.1 ng/ml to about 50-100 µg/ml. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing serine hydrolase-mediated diseases, including, but not limited to, neutrophil elastase-mediated diseases. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including but not limited to orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable derivatives thereof. The pharmaceutically therapeutically active compounds and derivatives thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1 85% or about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as serine hydrolase-mediated diseases, including, but not limited to, neutrophil elastase-mediated diseases. It is to be understood that such combination therapy constitutes a further aspect of the compositions and methods of treatment provided herein.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs and strip

4.1.1 Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

4.1.2 Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

4.1.3 Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

4.1.4 Topical Administration

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

4.1.5 Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point.

Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

4.1.6 Sustained Release Compositions

Active ingredients provided herein can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, CRC Crit. Ref Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249: 1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

4.1.7 Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Articles of Manufacture

The compounds or pharmaceutically acceptable derivatives can be packaged as articles of manufacture containing packaging material, a compound or pharmaceutically acceptable derivative thereof provided herein, which is used for treatment, prevention or amelioration of one or more symptoms associated with serine hydrolase, including, but not limited to, neutrophil elastase activity, and a label that indicates that the compound or pharmaceutically acceptable derivative thereof is used for treatment, prevention or amelioration of one or more symptoms of serine hydrolase-mediated diseases, including, but not limited to, neutrophil elastase-mediated diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated.

Evaluation of the Activity of the Compounds

Standard physiological, pharmacological and biochemical procedures are available for testing the compounds to identify those that possess a desired biological activity. Serine hydrolase, including, but not limited to, neutrophil elastase activity of the compounds provided herein can be readily detected using the assays described herein, as well as assays generally known to those of ordinary skill in the art. The following are noted as examples for human neutrophil elastase-mediated conditions:

For acute respiratory distress syndrome or adult respiratory distress syndrome, the method according to human neutrophil elastase (HNE) model (AARD, 141:227-677 (1990)); the endotoxin induced acute lung injury model in minipigs (AARD, 142:782-788 (1990)); or the method according to human polymorphonuclear elastase-induced lung hemorrhage model in hamsters (European Patent Publication No. 0769498) may be used; in ischemia/reperfusion, the method according to the canine model of reperfusion injury (J. Clin. Invest., 81: 624-629 (1988)) may be used.

Methods of Use of the Compounds and Compositions

Methods of use of the compounds and compositions are also provided. The methods involve both in vitro and in vivo uses of the compounds and compositions.

In certain embodiments, provided herein are methods for inhibiting an action of a serine hydrolase, including but not limited to neutrophil elastase, by administering compounds and compositions provided herein. In one embodiment, the methods involve contacting the serine hydrolase, including but not limited to neutrophil elastase with a compound provided herein.

In other embodiments, provided herein are methods for treatment, prevention, or amelioration of one or more symptoms of diseases or conditions including, but not limited to conditions associated with acute respiratory distress syndrome, adult respiratory distress syndrome (ARDS), cystic fibrosis, pulmonary emphysema, chronic obstructive pulmonary disease (COPD) and ischaemic-reperfusion injury. The compounds may also be useful in the modulation of endogenous and/or exogenous biological irritants which cause and/or propagate atherosclerosis, diabetes, myocardial infarction; hepatic disorders including but not limited to cirrhosis, systemic lupus erythematous, inflammatory disease of lymphoid origin, including but not limited to T lymphocytes, B lymphocytes, thymocytes; autoimmune diseases, bone marrow; inflammation of the joint (especially rheumatoid arthritis, osteoarthritis and gout); inflammation of the gastrointestinal tract (especially inflammatory bowel disease, ulcerative colitis, pancreatitis and gastritis); inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); age related illness such as dementia, inflammatory diseases of cardiovascular origins; granulomatous diseases; renal diseases including but not limited to nephritis and polyarteritis; cancer; pulmonary hypertension, ingested poisons, skin contacts, stings, bites; asthma; rhinitis; HIV disease progression; for minimising the effects of organ rejection in organ transplantation including but not limited to human organs; and replacement therapy of proteinase inhibitors by administering compounds and compositions provided herein.

In other embodiments, provided herein are methods for treatment, prevention, or amelioration of one or more symptoms of diseases or conditions selected from pulmonary emphysema, acute respiratory distress syndrome, adult respiratory distress syndrome, idiopathic interstitial pneumonia, cystic pulmonary fibrosis, chronic interstitial pneumonia, chronic bronchitis, chronic sinopulmonary infection, diffuse panbronchiolitis, bronchiectasis, asthma, pancreatitis, nephritis, hepatic failure, chronic rheumatoid arthritis, joint scleroma, osteoarthritis, psoriasis, periodontitis, atherosclerosis, rejection against organ transplant, premature amniorrhexis, bullous dermatosis, shock, sepsis, systemic lupus erythematosus, Crohn's disease, disseminated intracapillary coagulation, tissue injury after ischemia-reperfusion, formation of cornea cicatricial tissue and myelitis by administering compounds and compositions provided herein.

Combination Therapy

The compounds provided herein may be administered as the sole active ingredient or in combination with other active ingredients. Other active ingredients that may be used in combination with the compounds provided herein include but are not limited to, compounds known to treat serine hydrolase-mediated diseases. In one embodiment, the second active agent used in combination with a compound provided herein used for treatment, prevention or amelioration of neutrophil, such as human neutrophil elastase-mediated diseases. In certain embodiments, the second active agent has an activity as serine hydrolase inhibitor. Several inhibitors of serine hydrolases in general and neutrophil elastase in particular are known in the art. Exemplary inhibitors of serine hydrolases are disclosed in U.S. Pat. No. 6,001,814; U.S. Pat. No. 6,001,813; U.S. Pat. No. 6,150,334; U.S. Pat. No. 6,001,811 and U.S. App. Pub. No. 20030203851.

It will be appreciated that every suitable combination of the compounds provided herein with one or more of the aforementioned compounds and optionally one or more further pharmacologically active substances is contemplated herein.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

5. EXAMPLES

The compounds provided herein are prepared by the synthetic procedures known in the art and described herein. Synthetic procedures for exemplary compounds are described in Examples 1-3. Table 1 provides further examples prepared using similar procedures and routine modifications thereof. The electrospray mass spectrometry characterization data for several compounds is provided in Table 1.

All reagents and solvents were obtained from commercial sources, e.g., the Aldrich Chemical Company (Milwaukee, Wis.), unless otherwise indicated. Wang resin and HOBt were obtained from Novabiochem. CDI and 6-methyl-anthranilic acid were obtained from Alfa Aesar. 2-Fluoronicotinic acid was obtained from Matrix Scientific. Compounds were characterized using 1H NMR spectroscopy and/or electrospray ionization mass spectrometry: Proton nuclear magnetic resonance ($^1$H NMR) spectra were recorded on a Bruker 400 MHz NMR spectrometer in deuterated chloroform (CDCl$_3$) or water (D$_2$O) using the residual $^1$H solvent peak as the internal standard. LC/(ES)MS analysis was performed on an Agilent 1100 Series LC/MSD using ChemStation software. Analytical LC/MS was carried out on a C18 reverse phase column (Onyx, monolithic column, 50×4.6 mm; Phenomenex; Torrance, Calif.) using a binary system of water and acetonitrile with 0.1% trifluoroacetic acid as a modifier. Preparative HPLC was carried out using a C18 reverse phase column (Polaris, 5µ column, 150×21.2 mm; Varian; Torrance, Calif.). Preparative HPLC analysis was performed on the Hitachi D-7000 Series using a binary system of water and acetonitrile with 0.1% acetic acid as a modifier. Flash silica gel column chromatography was carried out on manually packed columns or a SP-4 automated purification system using pre-packed silica gel cartridges (Biotage; Charlottesville, Va.). Blood is collected from subjects into heparin-coated tubes containing 5000 kallikrein inhibitor units of aprotonin. Plasma is separated immediately by centrifugation at 4° C. and then stored at −70° C. until it is analyzed.

Example 1

Preparation of 2-(2-Imidazol-1-yl-pyridin-3-yl)-5-methyl-4H-benz[d][1,3]oxazin-4-one (A)

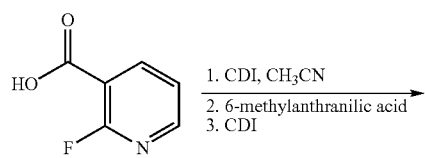

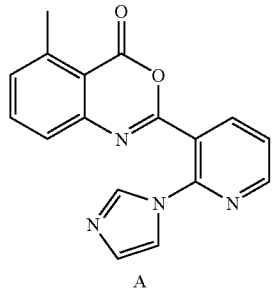

A

A solution of 2-fluoro-nicotinic acid (2.4 g, 17 mmol) and N,N'-carbonyldiimidazole (CDI, 2.76 g, 17.0 mmol) in anhydrous acetonitrile (12 mL) was stirred for 30 minutes at ambient temperature and then heated at 65° C. for 1 hour. 2-Amino-6-methyl-benzoic acid (2.57 g, 17 mmol) was added to the reaction mixture and then stirred at 65° C. for 1 hour. Additional CDI (2.76 g, 17 mmol) was added to the stirred reaction mixture, and the heat was increased to 100° C. for 1 hour. The reaction mixture was concentrated using a rotary evaporator. The crude material was loaded onto a silica gel column. The impurities were removed using a 0-60% EtOAc/hexanes gradient, and compound 2 was eluted from the column with 100% EtOAc with 5% triethylamine as a modifier. Rotary evaporation afforded compound A as a yellow powder (2.28 g, 44% yield). $^1$H-NMR δ (CDCl$_3$): 8.70 (dd, 1H, J=4.8 Hz, J=2.0 Hz), 8.40 (dd, 1H, J=8.0 Hz, J=1.6 Hz), 7.94 (s, 1H), 7.67 (t, 1H, J=15.6 Hz, J=8 Hz), 7.51 (dd, 1H, J=7.6 Hz, J=4.8 Hz), 7.33-7.38 (m, 3H), 7.16 (s, 1H), 2.83 (s, 3H). ESMS: 305.1 [M+H]$^+$, 327.1 [M+Na]$^+$.

Example 2

Preparation of 2-[2-(3-Dimethylamino-pyrrolidin-1-yl)-pyridin-3-yl]-5-methyl-4H-benz[d][1,3]oxazin-4-one (46)

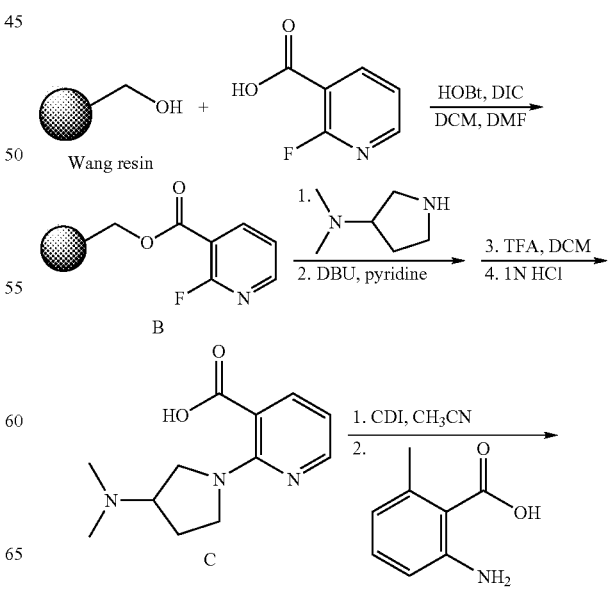

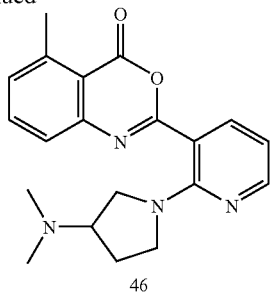

46

Preparation of 2-Fluoronicotinic acid esterified Wang resin (B): To a suspension of Wang resin (1.2 mmol/g, 15 g, 18 mmol) in dichloromethane (DCM, 150 mL) was added a solution of 2-fluoro-nicotinic acid (3.3 g, 23.4 mmol) and 1-hydroxy-4H-benztriazole (HOBt, 3.58 g, 23.4 mmol) in DCM (30 mL) and N,N'-dimethylformamide (DMF, 15 mL) followed by 4-dimethylaminopyridine (DMAP, 286 mg, 2.34 mmol) and N,N'-diisopropylcarbodiimide (DIC, 3.65 g, 23.4 mmol) at room temperature. The mixture was agitated at room temperature for 12 hours. The resin was washed with DCM then MeOH, and dried under vacuum to yield resin B (17.54 g, 100%).

Preparation of 2-(3-Dimethylamino-pyrrolidin-1-yl)-nicotinic acid (C): To a suspension of resin B (1.2 mmol/g, 5.0 g, 8.0 mmol) in pyridine (12 mL) was added dimethyl-pyrrolidin-3-yl-amine (1.37 mL, 12 mmol) and 1,8-diazabicyclo[5.4.0]undec-7-ene (DBU, 2.2 mL, 14.4 mmol) at room temperature. The mixture was agitated at 100° C. for 12 hours under a nitrogen atmosphere. The resin was washed with DCM then MeOH (3×), and dried under vacuum. Compound C was cleaved off the resin with the addition of 50% trifluoroacetic acid in DCM. The mixture was agitated at room temperature for 30 minutes. The resin was washed with DCM (3×), and the filtrate was concentrated using a rotary evaporator. 1 N HCl aqueous solution (2 mL) was added and then lyophilized to yield compound C as a light pink gum (2.2 g). The compound was taken onto the next step without further purification. $^1$H-NMR δ (CDCl$_3$): 10.85 (s, 1H), 8.26 (dd, 1H, J=4.8 Hz, J=1.6 Hz), 7.96 (dd, 1H, J=7.2 Hz, J=2.0 Hz), 6.81 (dd, 1H, J=7.6 Hz, J=4.8 Hz), 3.92-3.94 (m, 1H), 3.70-3.80 (m, 2H), 3.52-3.54 (m, 1H), 3.43 (m, 1H), 2.80 (m, 6H), 2.20 (m, 1H), 2.17 (m, 1H). ESMS: 236.0 [M+H]$^+$.

Preparation of 2-[2-(3-Dimethylamino-pyrrolidin-1-yl)-pyridin-3-yl]-5-methyl-4H-benz[d][1,3]oxazin-4-one (46). A solution of compound C (133 mg, 0.56 mmol) and CDI (91 mg, 0.56 mmol) in anhydrous acetonitrile (1.0 mL) was stirred for 1 hour at ambient temperature. 2-Amino-6-methyl-benzoic acid (41 mg, 0.27 mmol) was added, and the mixture was stirred at 60° C. overnight. The reaction solution was diluted with water (2 mL) and DMF (2 mL), filtered, then purified by C$_{18}$ reverse phase chromatography to afford compound 46 as an off-white powder (11 mg, 35% yield). $^1$H-NMR δ (CDCl$_3$): 8.32 (dd, 1H, J=4.8 Hz, J=2.0 Hz), 8.09 (dd, 1H, J=8.0 Hz, J=1.6 Hz), 7.68 (t, 1H, J=15.6 Hz, J=0.8 Hz), 7.52 (t, 1H, J=4.0 Hz, J=7.6 Hz), 7.33 (d, 1H, J=7.2 Hz), 6.82 (dd, 1H, J=8 Hz, J=4.8 Hz), 3.95 (br s, 1H), 3.81 (br s, 1H), 3.57-3.64 (m, 2H), 3.48-3.53 (m, 2H), 2.83 (s, 3H), 2.64 (br s, 6H), 2.30 (br s, 1H). ESMS: 351.1 [M+H]$^+$.

Example 3

Preparation of 2-[2-(2-{2-[2-(2-Methoxy-ethoxy)-ethoxy]-ethoxy}-ethoxy)-pyridin-3-yl]-5-methyl-4H-benz[d][1,3]oxazin-4-one (52)

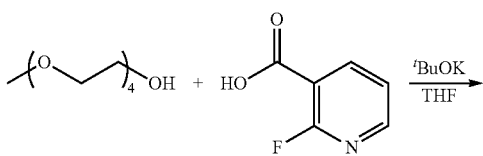

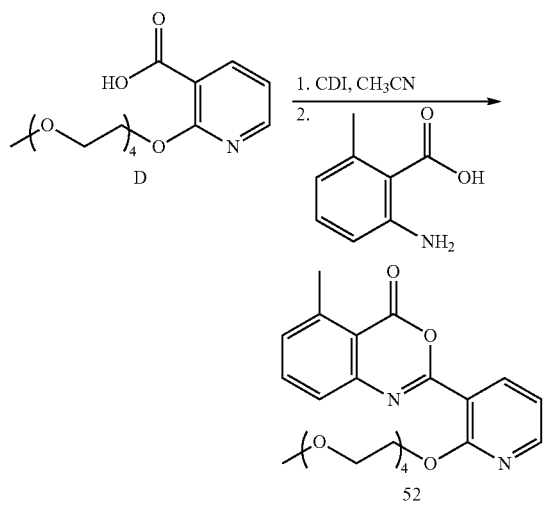

Preparation of 2-(2-{2-[2-(2-Methoxy-ethoxy)-ethoxy]-ethoxy}-ethoxy)-nicotinic acid (D). A solution of $^t$BuOK in THF (20% wt, 561.0 uL, 1.0 mmol) was added to a mixture of 2-fluoronicotinic acid (70.6 mg, 0.50 mmol) and tetraethyleneglycol monomethyl ether (105.5 μL, 0.50 mmol) in THF (2.0 mL) at ambient temperature under N$_2$. The mixture was heated at 100° C. for 3 h. The reaction mixture was diluted with EtOAc. The organic phase was acidified with 1 N HCl solution, washed with saturated NaCl solution, then dried over Na$_2$SO$_4$. Filtration and concentration in vacuo provided compound D as light yellow liquid (148.1 mg, 90%) for next step without further purification. ESMS: 330.0 [M+H]$^+$, 352.0 [M+Na]$^+$, 368.0 [M+K]$^+$.

Preparation of 2-[2-(2-{2-[2-(2-Methoxy-ethoxy)-ethoxy]-ethoxy}-ethoxy)-pyridin-3-yl]-5-methyl-4H-benz[d][1,3]oxazin-4-one (52). A solution of compound D (164.7 mg, 0.50 mmol) in CH$_3$CN (2.0 mL) was treated with N,N'-carbonyldiimidazole (CDI, 81.1 mg, 0.50 mmol) at 65° C. under N$_2$ for 1 h. 6-Methylanthranilic acid (75.6 mg, 0.50 mmol) was added at 25° C., and the mixture was heated at 65° C. overnight. Additional CDI (81.1 mg, 0.50 mmol) was added and the mixture was heated at 65° C. for 8 h. The crude mixture was purified by C$_{18}$ reverse phase chromatography to provide compound 52 as colorless gum (120.0 mg, 54%). $^1$H-NMR (400 mHz, CDCl$_3$) δ 8.29 (dd, 1H, J=5.2 Hz, J=2.0 Hz), 8.25 (dd, 1H, J=7.6 Hz, J=2.0 Hz), 7.66 (t, 1H, J=7.8 Hz), 7.50 (d, 1H, J=7.6 Hz), 7.31 (d, 1H, J=7.6 Hz), 7.01 (dd, 1H, J=7.4 Hz, J=5.0 Hz), 4.62 (m, 2H), 3.94 (m, 2H), 3.78 (m, 2H), 3.62 (m, 8H), 3.51 (m, 2H), 3.34 (s, 3H), 2.82 (s, 3H). ESMS: 445.0 [M+H]$^+$, 467.0 [M+Na]$^+$.

Example 4

Preparation of Dimethyl 3-ethyl-5-methoxyphthalate (I)

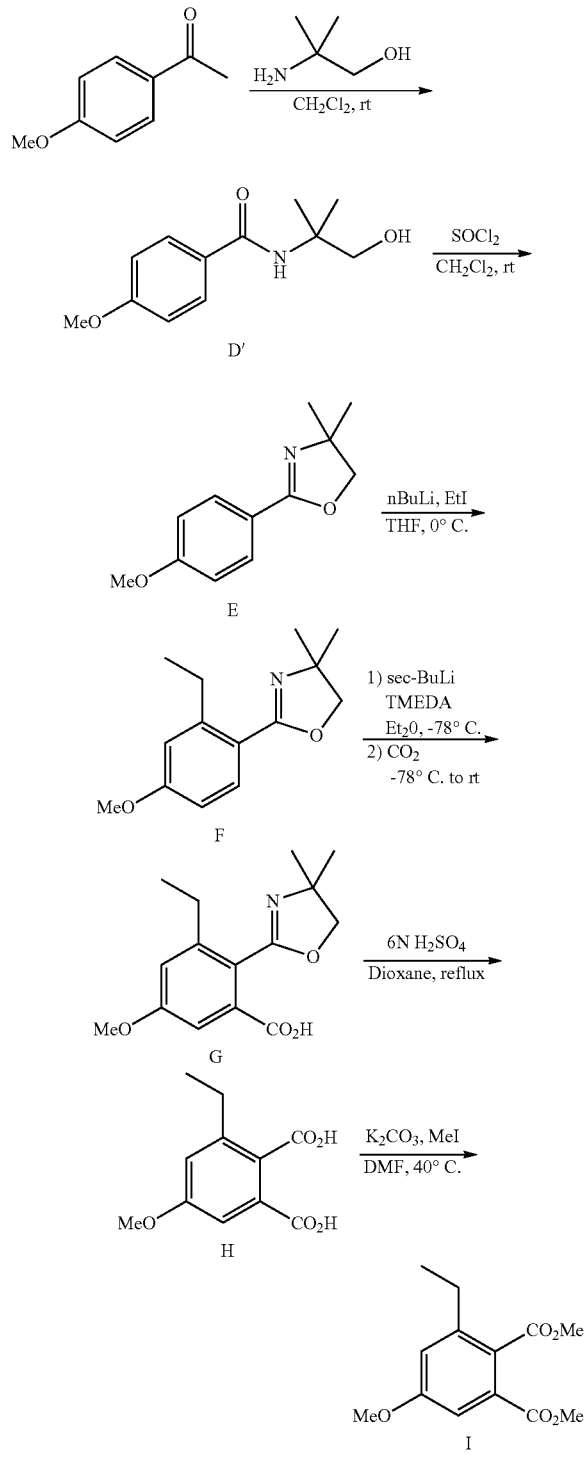

Compounds D', E and F are commercially available, or may be prepared by methods known in the art, for example, in Meyers, A. I. et al., Journal of Organic Chemistry, 1372 (1978).

Preparation of 2-(4,4-Dimethyl-4,5-dihydrooxazol-2-yl)-3-ethyl-5-methoxy-benzoic acid (G). sec-BuLi (400 mL, 1.04 mol/L in Hexane/cyclohexane) was added dropwise (over 30 min) to a solution of compound F (80.0 g, 343 mmol) and TMEDA (480 mL, 3.18 mmol) in dry Et$_2$O (1.70 L) at −78° C. (inside temperature −70~−68° C.) under Ar atmosphere. After being stirred for 1 h at this temperature, the reaction was treated with CO$_2$ gas (bubbling over 20 min, inside temperature −70~−55° C.). After being warmed gradually to room temperature over 1.5 h, the reaction mixture was poured into ice water (1.0 L). The aqueous layer was washed once with ethyl acetate and acidified (pH 2~3) with concentrated HCl (aq.) at 0° C. The precipitate was filtered and rinsed with a small amount of water to give the desired compound G (55.7 g, 201 mmol) as an off-white solid. The filtrate was extracted 15 times with ethyl acetate/methanol (10/1), and the combined organic phases were dried over Na$_2$SO$_4$ and concentrated in vacuo to afford the desired crude compound G (18.0 g) as an off-white solid. $^1$H NMR (DMSO-d$_6$, 400 MHz): δ 1.13 (3H, t, J=7.6 Hz), 1.26 (6H, s), 2.65 (2H, q, J=7.6 Hz), 3.80 (3H, s), 3.96 (2H, s), 7.04 (1H, d, J=2.4 Hz), 7.15 (1H, d, J=2.4 Hz). CIMS (+): 278 [M+H]$^+$ Preparation of 3-Ethyl-5-methoxyphthalic acid (H). A solution of 6.00 mol/L H$_2$SO$_4$ (aq.) (700 mL) was added to a solution of compound G (65.7 g, 237 mmol) in 1,4-dioxane (700 mL) at room temperature. The mixture was heated at 130° C. (oil bath temperature) and stirred. After 64 h the mixture was concentrated in vacuo, and cooled to 0° C. The precipitate was filtered and rinsed with a small amount of water to give the desired compound H (23.8 g, 106 mmol) as an off-white solid. The filtrate was extracted twice with ethyl acetate and the combined organic phases were dried over Na$_2$SO$_4$, filtered, and concentrated in vacuo to give the desired compound H (10.8 g, 48.2 mmol) as an off-white solid. The aqueous phase (after salting with NaCl) was extracted with CHCl$_3$/MeOH (4/1), and the combined organic phases were dried over Na$_2$SO$_4$ and concentrated in vacuo to recover the starting material G (26%). $^1$H NMR (DMSO-d$_6$ 400 MHz): δ 1.14 (3H, t, J=7.6 Hz), 2.60 (2H, q, J=7.6 Hz), 3.80 (3H, s), 7.04 (1H, d, J=2.4 Hz), 7.16 (1H, d, J=2.4 Hz). EIMS (+): 224 [M]$^+$ Preparation of Dimethyl 3-ethyl-5-methoxyphthalate (I). K$_2$CO$_3$ (63.9 g, 462 mmol) and MeI (28.8 mL, 462 mmol) were added to a solution of compound H (34.6 g, 154 mmol) in DMF (500 mL) at 0° C. The mixture was warmed to room temperature and stirred for 2 h, and at 40° C. for 1 h. MeI (28.8 mL, 462 mmol) was added and the mixture was stirred for 14 h. Additional MeI (28.8 mL, 462 mmol) was then added to the reaction mixture. After being stirred for 8 h, the mixture was concentrated in vacuo and water was added to the residue. The aqueous phase was extracted 3 times with ethyl acetate and the combined organic phases were washed with H$_2$O, then brine, and dried over Na$_2$SO$_4$. The organic phase was then concentrated in vacuo and purified by silica gel column chromatography (ethyl acetate:hexane=1:6), yielding the desired compound I (36.0 g, 143 mmol) as a pale-yellow oil.

Example 5

Synthesis of protected anthranilic acid, methyl 2-ethyl-4-methoxy-6-(methoxycarbonylamino)benzoate (O)

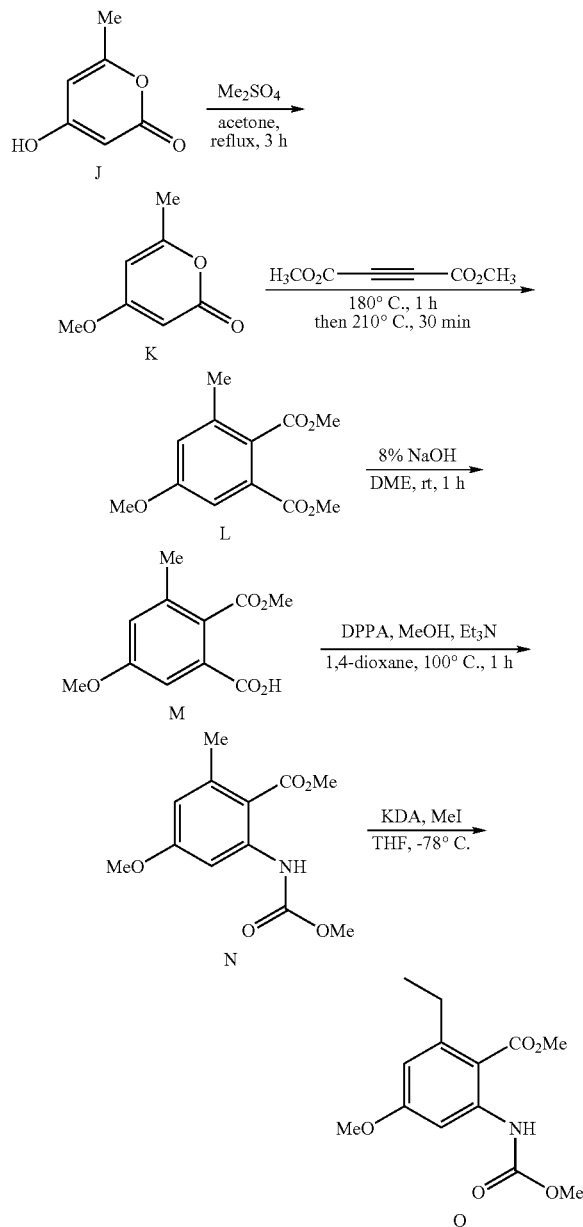

Preparation of 4-Methoxy-6-methyl-2H-pyran-2-one (K). Potassium carbonate (71.2 g, 515 mmol) and dimethylsulfate (48.7 mL, 515 mmol) was added to a solution of compound J (50.0 g, 396 mmol) in dry acetone (1.45 L). The mixture was heated to reflux for 3 hours and cooled to room temperature. The solids were removed by filtration and the filtrate was concentrated. The oily residue was purified by silica gel chromatography (ethyl acetate:hexane=1:1) to give an oily solid. The oily solid was washed with diisopropylether to afford compound K (42.3 g, 76%) as a yellow powder. $^1$H NMR (CDCl$_3$, 400 MHz): δ 2.21 (3H, s), 3.79 (3H, s), 5.41 (1H, d, J=1.8 Hz), 5.77-5.78 (1H, m). EIMS (+): 140 [M]$^+$ Preparation of Dimethyl 5-methoxy-3-methylphthalate (L). A mixture of compound K (41.4 g, 295 mmol) and dimethyl but-2-ynedioate (47.2 mL, 384 mmol) was stirred at 180° C. for 1 hour, then at 210° C. for 30 minutes. The mixture was cooled to room temperature and purified by silica gel chromatography (ethyl acetate:hexane=20:1-4:1) to give compound L (53.4 g, 76%) as a pale-yellow oil. $^1$H NMR (CDCl$_3$, 400 MHz): δ 2.34 (3H, s), 3.84 (3H, s), 3.88 (3H, s), 3.90 (3H, s), 6.91 (1H, d, J=2.4 Hz), 7.29 (1H, d, J=2.4 Hz). EIMS (+): 238 [M]$^+$ Preparation of 5-Methoxy-2-(methoxycarbonyl)-3-methyl-benzoic acid (M). To a solution of compound L (50.0 g, 210 mmol) in 1,2-dimethoxyethane (260 mL) was added 8% aqueous NaOH (262 mL) at 0° C. The mixture was stirred at room temperature for 1 hour, washed with ethyl acetate and acidified to pH 2 using 3 mol/L HCl. The precipitate was filtered and washed with water to give compound M (40.0 g). The filtrate was extracted with ethyl acetate 3 times. The combined organic layers were washed with saturated brine and dried over anhydrous Na$_2$SO$_4$. Filtration and evaporation of the solvent gave compound M (5.47, 96% total yield) as a white powder. $^1$H NMR (CDCl$_3$, 400 MHz): δ 2.35 (3H, s), 3.86 (3H, s), 3.90 (3H, s), 6.97 (1H, d, J=2.4 Hz), 7.39 (1H, d, J=2.4 Hz). EIMS (+): 224 [M]$^+$ Preparation of Methyl 4-methoxy-2-(methoxycarbonylamino)-6-methylbenzoate (N). To a suspension of compound M (45.4 g, 202 mmol) in 1,4-dioxane (420 mL) was added MeOH (40.9 mL, 1010 mmol) and triethylamine (56.3 mL, 404 mmol). The mixture was heated at 100° C. and diphenylphosphonic azide (65.3 mL, 303 mmol) was dropped into the mixture over 15 minutes. The mixture was stirred at 100° C. for 1 hour and concentrated. The residue was diluted with saturated aqueous NaHCO$_3$ and extracted with ethyl acetate 3 times. The combined organic layers were washed with saturated brine and dried over anhydrous Na$_2$SO$_4$. The combined organic layers were then filtered and evaporated. The resulting residue was crystallized from iPrOH to give a white solid. The solid was dissolved in ethyl acetate and the resulting solution was washed with water and saturated brine and dried over anhydrous Na$_2$SO$_4$. Filtration and evaporation of the solvent gave compound N (33.0 g). In addition, the mother liquid was diluted with ethyl acetate and washed with water and saturated brine, dried over anhydrous Na$_2$SO$_4$, filtered, and evaporated. The resulting residue was recrysatallized from iPrOH to give compound N (4.29 g, 73% total yield) as a white powder. $^1$H NMR (CDCl$_3$, 400 MHz): δ 2.45 (3H, s), 3.77 (3H, s), 3.84 (3H, s), 3.90 (3H, s), 6.45 (1H, d, J=2.4 Hz), 7.84 (1H, d, J=2.4 Hz), 9.97 (1H, s). EIMS (+): 253 [M]$^+$ Preparation of Methyl 2-ethyl-4-methoxy-6-(methoxycarbonylamino) benzoate (O). A solution of potassium tert-butoxide (50.7 g, 452 mmol) and diisopropylamine (63.3 mL, 452 mmol) in THF (600 mL) was cooled to −78° C. under argon. n-butyllithium in hexane (1.6 mol/L, 226 mL, 361 mmol) was added to the solution over 25 minutes. After 15 minutes of stirring at −78° C., a solution of compound N (30.5 g, 120 mmol) in THF (120 ml) was added to the mixture over 15 minutes at −78° C. The mixture was stirred an additional 20 minutes at −78° C. Methyl iodide (22.5 mL, 361 mL) was added in one portion at −78° C. After 10 minutes of stirring at −78° C., the mixture was poured into saturated aqueous NH$_4$Cl. THF was removed from the mixture in vacuo, extracted with ethyl acetate 3 times. The combined organic layers was washed with saturated brine and dried over anhydrous Na$_2$SO$_4$. Filtration and evaporation of the solvent gave compound O (32.9 g, quant.) as a yellow oil.

Example 6

Alternative synthesis of protected anthranilic acid, methyl 2-ethyl-4-methoxy-6-(methoxycarbonylamino)benzoate (O)

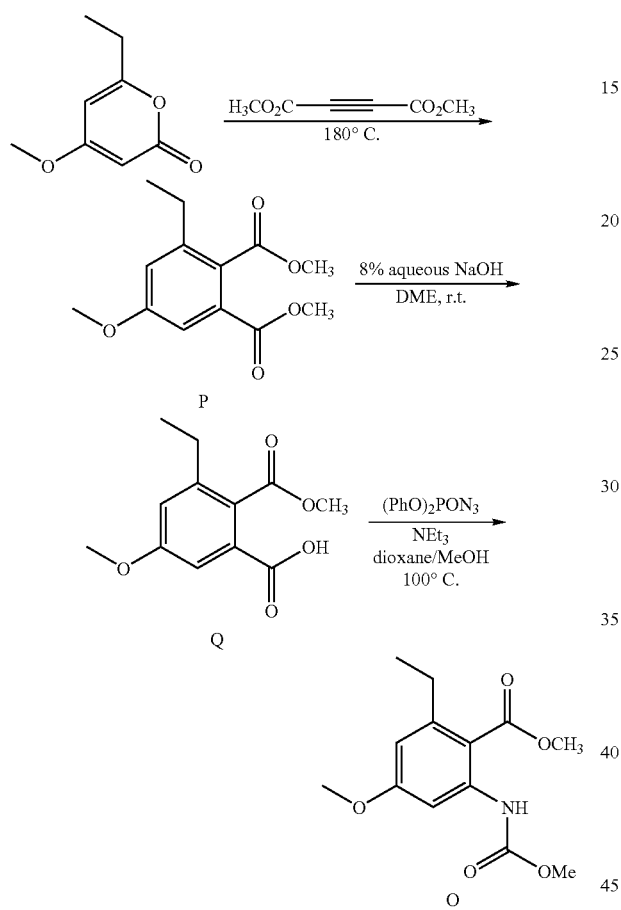

Preparation of 3-Ethyl-5-methoxyphthalic acid dimethylester (P). The following is based on the procedure described in Tam, T. F. and Coles P., Synthesis, 383 (1988). 6-ethyl-4-methoxy-2H-pyran-2-one (40.5 g, 263 mmol) was placed in a 500 mL round bottom flask and dimethylacetylenedicarboxylate (42 mL, 342 mmol) was added. This mixture was stirred until the solid completely dissolved. The flask was fitted with a water condenser and placed in a preheated oil bath at 180° C. for 3 hours. The reaction was allowed to cool to room temperature, diluted with dichloromethane (75 mL), and was purified by silica gel chromatography using a gradient of 5-20% ethyl acetate in hexanes. The appropriate fractions were collected and concentrated by rotary evaporation to yield compound P (44.16 g, 67%) as a clear oil. $^1$H NMR CDCl$_3$ δ: 7.30 (d, 1H, J=3 Hz), 6.95 (s, 1H, J=3 Hz), 3.90 (s, 3H), 3.88 (s, 3H), 3.85 (s, 3H), 2.64 (q, 2H, J=8.0 Hz), 1.21 (t, 3H, J=8.0 Hz). ESMS m/z: 221 [M−OCH$_3$]$^+$, 275 [M+Na$^+$].

Preparation of 3-Ethyl-5-methoxy-2-methoxycarbonyl-benzoic acid (O). An aqueous solution of NaOH (17.46 g in 218.0 mL H$_2$O, 436.6 mmol) was added dropwise to a solution of compound P (44.06 g, 174.7 mmol) in 1,2-dimethoxyethane (218.0 mL) at 0° C. The reaction mixture was stirred at room temperature for 1 hour. The aqueous phase was then washed with dichloromethane (100 mL) and acidified to pH 2 with 3 N HCl. The acidified aqueous layer was extracted with ethyl acetate (3×400 mL) and the combined organic layers were washed with brine then dried over anhydrous Na$_2$SO$_4$. Filtration and concentration by rotary evaporation afforded compound Q (40.15 g, 96%) as a white powder. $^1$H NMR (CDCl$_3$, 400 MHz) δ 7.41 (d, 1H, J=2.0 Hz), 7.01 (d, 1H, J=3.0 Hz), 3.90 (s, 3H), 3.87 (s, 3H), 2.65 (q, 2H, J=7.5 Hz), 1.23 (t, 3H, J=7.5 Hz). ESMS m/z 261.0 [M+Na$^+$], 207.0 [M−OMe]$^+$.

Preparation of 2-Ethyl-4-methoxy-6-methoxycarbony-lamino-benzoic acid methyl ester (O). To a suspension of compound Q (40.15 g, 168.5 mmol) in 1,4-dioxane (360 mL) was added MeOH (34 mL, 840 mmol) and triethylamine (47 mL, 340 mmol) under N$_2$. The clear solution was heated at 100° C. and diphenylphosphonic azide (54.48 mL, 252.8 mmol) was added dropwise into the reaction. The mixture was further stirred at 100° C. for 1 hour. The reaction mixture was then concentrated and the resulting residue was diluted with saturated aqueous sodium bicarbonate solution (200 mL). The aqueous layer was extracted with ethyl acetate (1×600 mL and 3×300 mL) and the combined organic layers were washed with H$_2$O (75 mL), then concentrated by rotary evaporation. Flash column chromatography using a gradient of 10-15% ethyl acetate in hexanes provided compound O (34.9 g, 78%) as a yellow oil. $^1$H NMR (CDCl$_3$, 400 MHz) δ: 9.54 (bs, 1H), 7.78 (d, 1H, J=3.0 Hz), 6.48 (d, 1H, J=3.0 Hz), 3.90 (s, 3H), 3.84 (s, 3H), 3.76 (s, 3H), 2.78 (q, 2H, J=7.0 Hz), 1.18 (t, 3H, J=7.5 Hz). ESMS m/z: 290.0 [M+Na$^+$], 236.0 [M−OMe]$^+$.

Example 7

Synthesis of 2-[2-((S)-3-Dimethylamino-pyrrolidin-1-yl)-pyridin-3-yl]-5-ethyl-7-methoxy-4H-benz[d][1,3]oxazin-4-one (132)

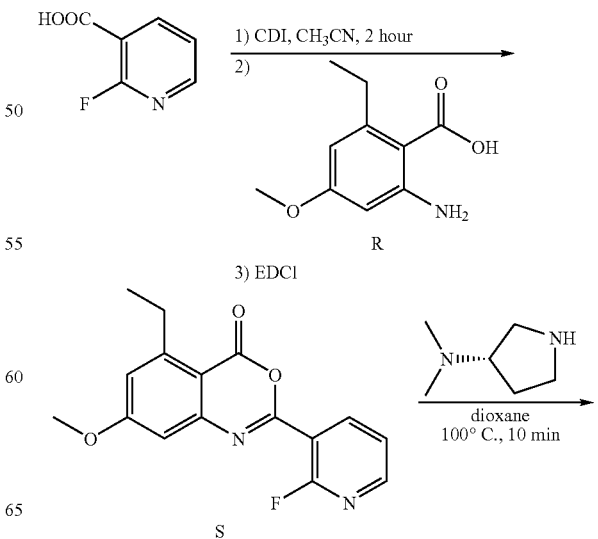

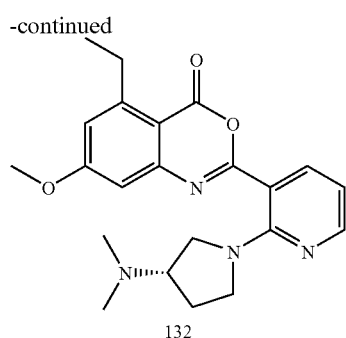

132

Preparation of 5-Ethyl-2-(2-fluoro-pyridin-3-yl)-7-methoxy-4H-benz[d][1,3]oxazin-4-one (S). To a suspension of 2-fluoro-nicotinic acid (13.6 g, 96.6 mmol) in anhydrous acetonitrile (400 mL) was added 1,1'-carbonyldiimidazole (15.7 g, 96.6 mmol), and the mixture was stirred at room temperature under $N_2$ for 2 hours. Compound R (15.7 g, 80.5 mmol) was added, and the mixture was stirred at room temperature overnight. 1-(3-dimethyl-aminopropyl)-3-ethylcarbodiimide hydrochloride (30.86 g, 161.0 mmol) was added in two portions within 30 minutes. The mixture was stirred at room temperature for one hour. A precipitate formed during stirring, was filtered off, washed with cold acetonitrile, then dried under high vacuum to afford compound S (13.94 g) as a white powder. In addition, the filtrate was concentrated and purified by silica gel chromatography using a gradient of 10-15% ethyl acetate/hexanes to afford an additional quantity of compound S (6.78 g, 86% total yield). $^1$H NMR (CDCl$_3$, 400 MHz), δ: 8.57 (t, 1H, J=1.5 Hz), 8.40 (q, 1H, J=1.5 Hz), 7.37 (m, 1H), 7.02 (d, 1H, J=3.0 Hz), 6.94 (d, 1H, J=3.0 Hz), 3.95 (s, 3H), 3.22 (q, 2H, J=7.5 Hz), 1.30 (t, 3H, J=7.5 Hz). ESMS m/z: 301.0 [M+H$^+$], 323.0 [M+Na$^+$].

Preparation of 2-[2-((S)-3-Dimethylamino-pyrrolidin-1-yl)-pyridin-3-yl]-5-ethyl-7-methoxy-4H-benz[d][1,3]oxazin-4-one (132). A solution of compound S (13.9 g, 46.4 mmol) in anhydrous 1,4-dioxane (232 mL) was treated with (S)-(−)-3-(dimethylamino)-pyrrolidine (7.50 mL, 60.3 mmol) at 100° C. under $N_2$ for 10 minutes. The solution was concentrated, and the residue was purified using a Biotage 40M amine column using a gradient of 20-50% ethyl acetate/hexanes. The fractions containing compound 132 were combined and concentrated by rotary evaporation, dissolved in acetonitrile:water (1:1, 50 mL), and then lyophilized to afford compound 132 as a pale yellow powder (12.81 g, 70% yield). $^1$H NMR (CDCl$_3$, 400 MHz) d: 8.30 (dd, 1H, J=1.5 Hz), 8.00 (dd, 1H, J=1.5 Hz), 6.95 (d, 1H, J=2.0 Hz), 6.88 (d, 1H, J=3.0 Hz), 6.72 (q, 1H, J=4.5 Hz), 3.92 (s, 3H), 3.66 (q, 1H, J=4.0 Hz), 3.48 (m, 3H), 3.21 (m, 2H), 2.78 (s, 1H), 2.26 (s, 6H), 2.12 (q, 1H, J=6.0 Hz), 1.84 (m, 1H), 1.29 (t, 3H, J=7.0 Hz); $^{13}$C NMR (CDCl$_3$, 400 MHz) d: 165.5, 158.8, 158.1, 155.7, 151.1, 151.0, 150.6, 140.3, 117.9, 112.2, 110.6, 107.3, 107.1, 65.4, 55.9, 54.4, 49.1, 44.5, 30.3, 28.6, 15.2; ESMS m/z: 395.1 [M+H$^+$]; Calculated for $C_{22}H_{26}N_4O_3$: C, 66.99; H, 6.64; N, 14.20. found: C, 66.81; H, 6.66; N, 14.14.

Example 8

Synthesis of 2-[2-((S)-3-Dimethylamino-pyrrolidin-1-yl)-pyridin-3-yl]-5-ethyl-7-methoxy-4H-benz[d][1,3]oxazin-4-one.HCl (132a)

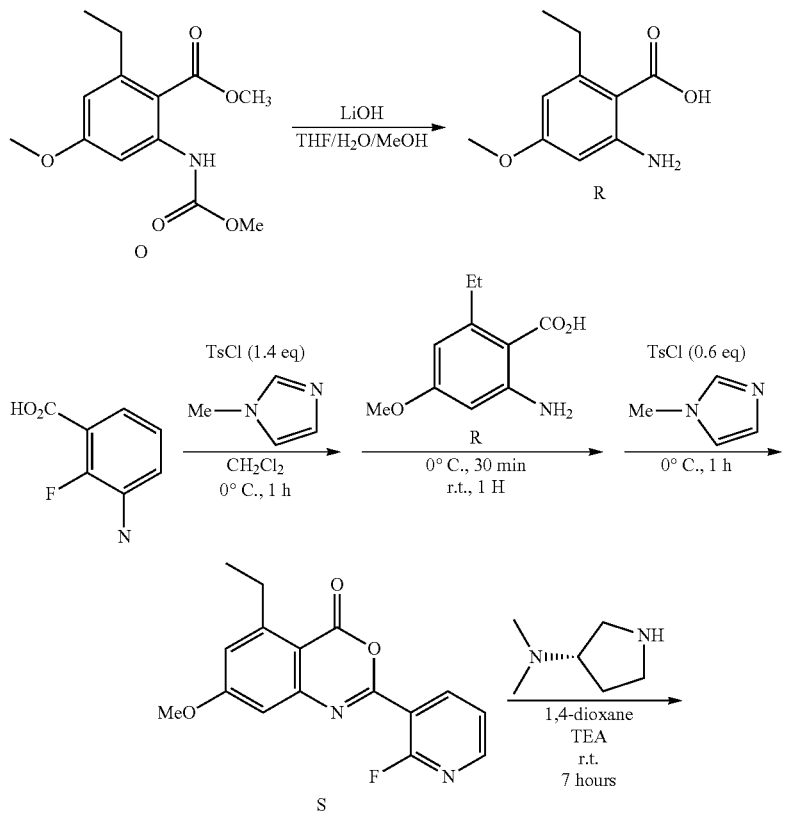

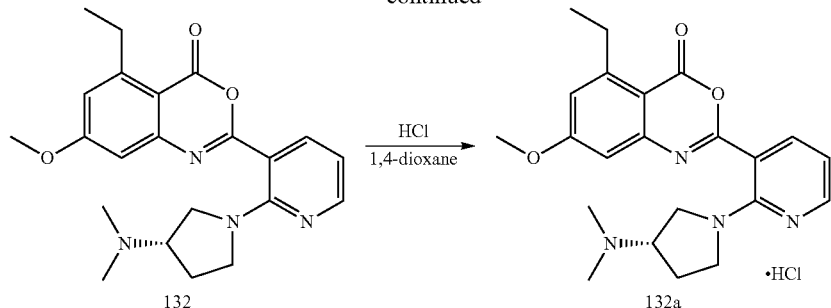

Preparation of 2-Amino-6-ethyl-4-methoxy-benzoic acid (R). Compound O (21.9 g, 82.0 mmol) in H$_2$O, THF, and MeOH (3:1:1, 255 mL) was treated with lithium hydroxide (9.80 g, 410 mmol) at 100° C. for 2 hours under N$_2$. The reaction mixture was partially concentrated and the remaining aqueous phase was washed with dichloromethane (50 mL). The aqueous phase was acidified to pH 4-5 with 3 N HCl and then extracted with ethyl acetate (3×400 mL). The combined organic solutions were washed with saturated NaCl solution and dried over anhydrous Na$_2$SO$_4$. Filtration and concentration by rotary evaporation provided compound R (15.71 g, 98%) as an off-white powder. $^1$H NMR (CDCl$_3$, 400 MHz) δ: 6.18 (d, 1H, J=2.0 Hz), 6.01 (d, 1H, J=2.0 Hz), 3.79 (s, 3H), 2.93 (q, 2H, J=7.0 Hz), 1.23 (t, 3H, J=7.5 Hz). ESMS m/z: 196.0 [M+H]$^+$, 178.0 [M−OH]$^+$.

Preparation of 5-ethyl-2-(2-fluoro-pyridin-3-yl)-7-methoxy-4H-benz[d][1,3]oxazin-4-one (S). TsCl (275 mg, 1.44 mmol) and N-methylimidazole (285 uL, 3.60 mmol) were added at 0° C. to a suspension of 2-fluoro-nicotinic acid (169 mg, 1.20 mmol) in CH$_2$Cl$_2$ (3 mL) under Ar atmosphere. The mixture was stirred at 0° C. for 1 hour. Compound R (195 mg, 1.00 mmol) was added to the mixture at 0° C. over 5 minutes and the mixture was stirred at 0° C. for 30 minutes and at room temperature for 1 hour. N-methylimidazole (47.5 uL, 0.60 mmol) and TsCl (114 mg, 0.60 mmol) were added at 0° C. to the mixture, and the mixture was stirred at 0° C. for 1 hour. The reaction mixture was poured into ice water and extracted with EtOAc. The organic layer was washed with saturated NaHCO$_3$ (aq.), water (5 times) and brine. The organic phase was then dried over anhydrous Na$_2$SO$_4$ and concentrated in vacuo to afford compound S (300 mg, 1.00 mmol) as a white powder.

Preparation of 2-[2-((S)-3-Dimethylamino-pyrrolidin-1-yl)-pyridin-3-yl]-5-ethyl-7-methoxy-4H-benz[d][1,3]oxazin-4-one (132). To a solution of compound S (37.60 g, 125 mmol) and triethylamine (42 mL, 301 mmol) in anhydrous 1,4-dioxane (800 mL) was added dropwise (S)-(−)-3-(dimethylamino)-pyrrolidine (17.1 g, 150 mmol) at room temperature under Ar. The resulting mixture was stirred for 8 hours. The solution was concentrated, and diluted with water (200 mL) and EtOAc (50 mL). The resulting solution was basified to pH 9 with saturated sodium bicarbonate and then extracted with ethyl acetate (3×300 mL). The organic layers were combined and washed with water, brine, and dried over anhydrous Na$_2$SO$_4$ followed by the removal of EtOAc in vacuo. The crude product was purified by column chromatography (Chromatrex NH-DM2035, Fuji Sislysia Chemical Co. Ltd.) using a gradient of 20-25% ethyl acetate/hexanes to yield compound 132 (37.03 g, 73%) as a yellow amorphous solid.

Preparation of 2-[2-((S)-3-Dimethylamino-pyrrolidin-1-yl)-pyridin-3-yl]-5-ethyl-7-methoxy-4H-benz[d][1,3]oxazin-4-one.HCl (132a). To a solution of compound 132 (120 mg, 0.304 mmol) in diethyl ether (2.0 mL) was added hydrogen chloride (4 M in dioxane, 0.0722 mL, 0.289 mmol) at ambient temperature. After stirring for 30 minutes, a solid formed which was filtered off, washed with diethyl ether, and dried in vacuo at ambient temperature to give compound 132a (114 mg) as a pale yellow solid. m.p.: 173-180° C. $[\alpha]_D^{24}$: −308 (c 0.53, MeOH). $^1$H NMR (DMSO-d$_6$, 400 MHz): δ: 1.21 (3H, t, J=7.3 Hz), 2.14-2.21 (1H, m), 2.28-2.36 (1H, m), 2.72 (3H, d, J=4.9 Hz), 2.78 (3H, d, J=4.9 Hz), 3.08-3.17 (2H, m), 3.36-3.49 (3H, m), 3.68-3.96 (2H, m), 3.92 (3H, s), 6.89 (1H, dd, J=7.4, 4.3 Hz), 7.01 (1H, d, J=2.4 Hz), 7.06 (1H, d, J=2.4 Hz), 8.05 (1H, dd, J=7.4, 1.8 Hz), 8.32 (1H, dd, J=4.3, 1.8 Hz), 10.72 (1H, s). anal. C, 58.45%; H, 6.56%; N, 12.35%. Calcd for C$_{22}$H$_{26}$N$_4$O$_3$.HCl.H$_2$O, C, 58.86%; H, 6.51%; N, 12.48%.

Example 9

Synthesis of salts of 2-[2-((S)-3-Dimethylamino-pyrrolidin-1-yl)-pyridin-3-yl]-5-ethyl-7-methoxy-4H-benz[d][1,3]oxazin-4-one Additional salts of 2-[2-((S)-3-Dimethylamino-pyrrolidin-1-yl)-pyridin-3-yl]-5-ethyl-7-methoxy-4H-benz[d][1,3]oxazin-4-one (compound 132) were prepared according to the following methods.

Preparation of 2-[2-((S)-3-Dimethylamino-pyrrolidin-1-yl)-pyridin-3-yl]-5-ethyl-7-methoxy-4H-benz[d][1,3]oxazin-4-one.HCl.H$_2$O. To a solution of compound 132 (120 mg, 0.304 mmol) in diethyl ether (2.0 mL) was added hydrogen chloride (4 M in dioxane, 0.0722 mL, 0.289 mmol) at room temperature. After stirring for 30 min, the resulting solid was filtered, washed with diethyl ether, and dried in vacuo at room temperature to give 2-[2-((S)-3-Dimethylamino-pyrrolidin-1-yl)-pyridin-3-yl]-5-ethyl-7-methoxy-4H-benz[d][1,3]oxazin-4-one.HCl.H$_2$O (114 mg) as a pale yellow solid. Mp 173-180° C. $[\alpha]_D^{24}$ −308 (c 0.53, MeOH). $^1$H NMR (DMSO-d$_6$, 400 MHz): δ 1.21 (3H, t, J=7.3 Hz), 2.14-2.21 (1H, m), 2.28-2.36 (1H, m), 2.72 (3H, d, J=4.9 Hz), 2.78 (3H, d, J=4.9 Hz), 3.08-3.17 (2H, m), 3.36-3.49 (3H, m), 3.68-3.96 (2H, m), 3.92 (3H, s), 6.89 (1H, dd, J=7.4, 4.3 Hz), 7.01 (1H, d, J=2.4 Hz), 7.06 (1H, d, J=2.4 Hz), 8.05 (1H, dd, J=7.4, 1.8 Hz), 8.32 (1H, dd, J=4.3, 1.8 Hz), 10.72 (1H, s). Anal. C, 58.45%; H, 6.56%; N, 12.35%. Calcd for C$_{22}$H$_{26}$N$_4$O$_3$.HCl.H$_2$O, C, 58.86%; H, 6.51%; N, 12.48%.

Preparation of 2-[2-((S)-3-Dimethylamino-pyrrolidin-1-yl)-pyridin-3-yl]-5-ethyl-7-methoxy-4H-benz[d][1,3]oxazin-4-one.2HCl.2H$_2$O. To a solution of compound 132 (120 mg, 0.304 mmol) in 1,4-dioxane (2.0 mL) was added hydrogen chloride (4 M in dioxane, 0.228 mL, 0.913 mmol) at room temperature. After stirring for 30 min, the resulting solid was filtered, washed with diethyl ether, and dried in vacuo at room temperature to give 2-[2-((S)-3-Dimethylamino-pyrrolidin-1-yl)-pyridin-3-yl]-5-ethyl-7-methoxy-4H-benz[d][1,3]oxazin-4-one.2HCl.2H$_2$O (120 mg) as a pale yellow solid. Mp 150-159° C. $[\alpha]_D^{26}$ −272 (c 0.52, MeOH). $^1$H NMR (DMSO-d$_6$, 400 MHz): δ 1.21 (3H, t, J=7.3 Hz), 2.21-2.36 (2H, m), 2.68 (3H, d, J=4.3 Hz), 2.75 (3H, d, J=4.3 Hz), 3.06-3.16 (2H, m), 3.50-3.55 (2H, m), 3.67-3.72 (1H, m), 3.84-3.96 (2H, m), 3.93 (3H, s), 6.92 (1H, dd, J=7.4, 4.3 Hz), 7.00 (1H, d, J=2.4 Hz), 7.10 (1H, d, J=2.4 Hz), 8.10 (1H, dd, J=7.4, 1.8 Hz), 8.32 (1H, dd, J=4.3, 1.8 Hz), 11.34 (1H, s). Anal. C, 52.33%; H, 6.53%; N, 11.11%. Calcd for C$_{22}$H$_{26}$N$_4$O$_3$.2HCl.2H$_2$O, C, 52.49%; H, 6.41%; N, 11.13%.

Preparation of 2-[2-((S)-3-Dimethylamino-pyrrolidin-1-yl)-pyridin-3-yl]-5-ethyl-7-methoxy-4H-benz[d][1,3]oxazin-4-one methanesulfonate monohydrate. To a solution of compound 132 (120 mg, 0.304 mmol) in diethyl ether (3.0 mL) was added methanesulfonic acid (0.0394 mL, 0.608 mmol) in diethyl ether (1.0 mL) at room temperature. After stirring for 30 min, the resulting solid was filtered, washed with diethyl ether, and dried in vacuo at room temperature, to give 2-[2-((S)-3-Dimethylamino-pyrrolidin-1-yl)-pyridin-3-yl]-5-ethyl-7-methoxy-4H-benz[d][1,3]oxazin-4-one methanesulfonate monohydrate (141 mg) as a white solid. Mp 43-49° C. $[\alpha]_D^{25}$-205 (c 0.34, MeOH). $^1$H NMR (DMSO-d$_6$, 400 MHz): δ 1.21 (3H, t, J=7.3 Hz), 2.07-2.12 (1H, m), 2.31-2.35 (1H, m), 2.33 (6H, s), 2.79 (3H, d, J=4.9 Hz), 2.82 (3H, d, J=4.3 Hz), 3.07-3.15 (2H, m), 3.48 (2H, dd, J=8.6, 5.5 Hz), 3.68-3.80 (2H, m), 3.89-3.96 (1H, m), 3.91 (3H, s), 6.27 (1H, brs), 6.91 (1H, dd, J=7.9, 4.9 Hz), 7.01 (1H, d, J=2.4 Hz), 7.03 (1H, d, J=2.4 Hz), 8.05 (1H, dd, J=7.9, 1.8 Hz), 8.32 (1H, dd, J=4.9, 1.8 Hz), 9.77 (1H, brs). Anal. C, 47.64%; H, 6.01%, N, 9.21%. Calcd for C$_{22}$H$_{26}$N$_4$O$_3$.2CH$_3$SO$_3$H.H$_2$O, C, 47.67%; H, 6.00%; N, 9.27%.

Preparation of 2-[2-((S)-3-Dimethylamino-pyrrolidin-1-yl)-pyridin-3-yl]-5-ethyl-7-methoxy-4H-benz[d][1,3]oxazin-4-one trifluoroacetate. To a solution of compound 132 (120 mg, 0.304 mmol) in diethyl ether (2.0 mL) was added trifluoroacetic acid (0.0215 mL, 0.289 mmol) at room temperature. After stirring for 30 min, the resulting solid was filtered, washed with diethyl ether, and dried in vacuo at room temperature to give 2-[2-((S)-3-Dimethylamino-pyrrolidin-1-yl)-pyridin-3-yl]-5-ethyl-7-methoxy-4H-benz[d][1,3]oxazin-4-one trifluoroacetate (112 mg) as a pale yellow solid. Mp 117-119° C. $[\alpha]_D^{25}$-258 (c 0.56, MeOH). $^1$H NMR (DMSO-d$_6$, 400 MHz): δ 1.21 (3H, t, J=7.3 Hz), 2.02-2.12 (1H, m), 2.28-2.36 (1H, m), 2.79 (6H, s), 3.08-3.17 (2H, m), 3.47 (1H, dd, J=8.0, 5.5 Hz), 3.67-3.79 (2H, m), 3.86-3.91 (1H, m), 3.91 (3H, s), 6.90 (1H, dd, J=7.9, 4.3 Hz), 7.00 (1H, d, J=2.4 Hz), 7.02 (1H, d, J=2.4 Hz), 8.03 (1H, dd, J=7.4, 1.8 Hz), 8.33 (1H, dd, J=4.3, 1.8 Hz), 9.85 (1H, s). Anal. C, 56.05%; H, 5.21%; N, 10.91%. Calcd for C$_{22}$H$_{26}$N$_4$O$_3$.CF$_3$CO$_2$H, C, 56.69%; H, 5.35%; N, 11.02%.

Preparation of 2-[2-((S)-3-Dimethylamino-pyrrolidin-1-yl)-pyridin-3-yl]-5-ethyl-7-methoxy-4H-benz[d][1,3]oxazin-4-one.1.5 trifluoroacetate. To a solution of compound 132 (120 mg, 0.304 mmol) in diethyl ether (2.0 mL) was added trifluoroacetic acid (0.0678 mL, 0.913 mmol) at room temperature. After stirring for 1 hour, the resulting solid was filtered, washed with diethyl ether, and dried in vacuo at room temperature to give 2-[2-((S)-3-Dimethylamino-pyrrolidin-1-yl)-pyridin-3-yl]-5-ethyl-7-methoxy-4H-benz[d][1,3]oxazin-4-one-1.5 trifluoroacetate (131 mg) as a colorless solid. Mp 124-125° C. $[\alpha]_D^2$ −235 (c 0.58, MeOH). $^1$H NMR (DMSO-d$_6$, 400 MHz): δ 1.21 (3H, t, J=7.3 Hz), 2.03-2.12 (1H, m), 2.30-2.36 (1H, m), 2.78 (3H, d, J=4.3 Hz), 2.81 (3H, d, J=4.3 Hz), 3.08-3.18 (2H, m), 3.47 (1H, dd, J=8.6, 5.5 Hz), 3.69 (1H, dd, J=12.2, 7.3 Hz), 3.77 (1H, dd, J=11.6, 6.7 Hz), 3.91 (3H, s), 3.91-3.95 (1H, m), 6.89 (1H, dd, J=7.4, 4.3 Hz), 7.00 (1H, d, J=2.4 Hz), 7.03 (1H, d, J=2.4 Hz), 8.03 (1H, dd, J=7.4, 1.8 Hz), 8.32 (1H, dd, J=4.3, 1.8 Hz), 9.86 (1H, s), 9.94 (0.5H, s). Anal. C, 53.04%; H, 4.89%; N, 9.98%. Calcd for C$_{22}$H$_{26}$N$_4$O$_3$.1.5CF$_3$CO$_2$H, C, 53.10%; H, 4.90%; N, 9.91%.

Preparation of 2-[2-((S)-3-Dimethylamino-pyrrolidin-1-yl)-pyridin-3-yl]-5-ethyl-7-methoxy-4H-benz[d][1,3]oxazin-4-one.0.5 D-tartrate.H$_2$O. To a solution of compound 132 (100 mg, 0.254 mmol) in methanol (2.0 mL) was added D-tartaric acid (19.0 mg, 0.127 mmol) at room temperature. After stirring for 1 hour, the resulting solid was filtered, washed with methanol, and dried in vacuo at room temperature, to give 2-[2-((S)-3-Dimethylamino-pyrrolidin-1-yl)-pyridin-3-yl]-5-ethyl-7-methoxy-4H-benz[d][1,3]oxazin-4-one hemi-D-tartrate monohydrate (49.3 mg) as a pale yellow solid. Mp 144-145° C. $[\alpha]_D^{25}$-386 (c 0.22, MeOH). $^1$H NMR (DMSO-d$_6$, 400 MHz): δ 1.20 (3H, t, J=7.3 Hz), 1.69-1.79 (1H, m), 2.06-2.12 (1H, m), 2.20 (6H, s), 2.82-2.90 (1H, m), 3.09-3.16 (2H, m), 3.21-3.31 (2H, m), 3.44-3.51 (2H, m), 3.90 (3H, s), 4.13 (1H, s), 6.80 (1H, dd, J=8.0, 4.9 Hz), 7.01 (1H, d, J=3.0 Hz), 7.03 (1H, d, J=3.0 Hz), 7.96 (1H, dd, J=8.0, 1.8 Hz), 8.28 (1H, dd, J=4.9, 1.8 Hz). Anal. C, 59.22%; H, 6.56%; N, 11.42%. Calcd for C$_{22}$H$_{26}$N$_4$O$_3$.0.5C$_4$H$_6$O$_6$H$_2$O, C, 59.13%; H, 6.41%; N, 11.49%.

Preparation of 2-[2-((S)-3-Dimethylamino-pyrrolidin-1-yl)-pyridin-3-yl]-5-ethyl-7-methoxy-4H-benz[d][1,3]oxazin-4-one.0.75 L-tartrate.H$_2$O. To a solution of compound 132 (100 mg, 0.254 mmol) in methanol (2.0 mL) was added L-tartaric acid (19.0 mg, 0.127 mmol) at room temperature. After stirring for 1 hour, the resulting solid was filtered, washed with methanol, and dried in vacuo at room temperature, to give 2-[2-((S)-3-Dimethylamino-pyrrolidin-1-yl)-pyridin-3-yl]-5-ethyl-7-methoxy-4H-benz[d][1,3]oxazin-4-one.0.75 L-tartrate H$_2$O (86.3 mg) as a pale yellow solid. Mp 148-155° C. $[\alpha]_D^{25}$ −345 (c 0.052, MeOH). $^1$H NMR (DMSO-d$_6$, 400 MHz): δ 1.20 (3H, t, J=7.3 Hz), 1.71-1.81 (1H, m), 2.06-2.14 (1H, m), 2.23 (6H, s), 2.88-2.94 (1H, m), 3.07-3.14 (2H, m), 3.33-3.40 (2H, m), 3.44-3.50 (2H, m), 3.90 (3H, s), 4.16 (1.5H, s), 6.80 (1H, dd, J=8.0, 4.9 Hz), 7.00 (1H, d, J=3.0 Hz), 7.02 (1H, d, J=3.0 Hz), 7.76 (1H, dd, J=8.0, 1.8 Hz), 8.28 (1H, dd, J=4.9, 1.8 Hz). Anal. C, 57.59%; H, 6.29%; N, 10.53%. Calcd for C$_{22}$H$_{26}$N$_4$O$_3$.0.75C$_4$H$_6$O$_6$H$_2$O, C, 57.19%; H, 6.24%; N, 10.67%.

Example 10

Synthesis of a Quaternary Amine Bearing HNE Inhibitor

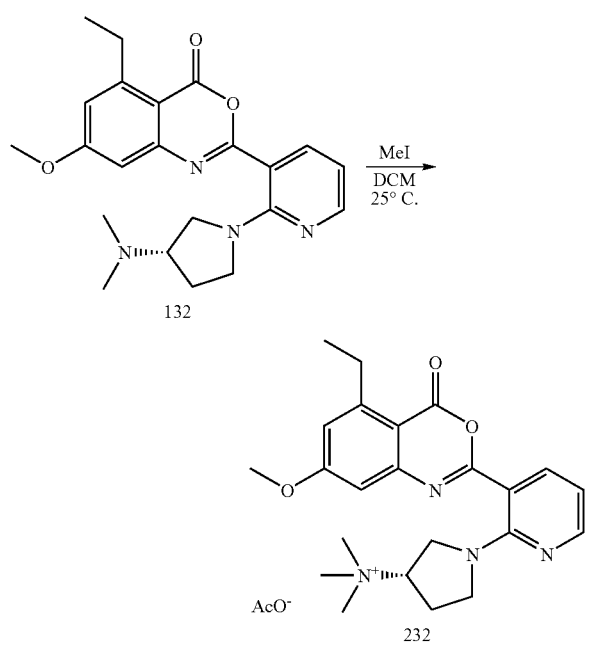

Preparation of {1-[3-(5-Ethyl-7-methoxy-4-oxo-4H-benz[d][1,3]oxazin-2-yl)-pyridin-2-yl]-pyrrolidin-3-yl}-trimethyl-ammonium acetate (232). To a solution of compound 132 (30 mg, 0.076 mmol) in dichloromethane (380 µL) was added methyl iodide (14.2 µL, 0.228 mmol) and the resulting mixture was stirred at ambient temperature for 2 hours. The solution was concentrated, and the residue was purified using preparative HPLC. The fractions containing the desired compound were lyophilized to yield compound 232 (27.8 mg, 89%) as a yellow powder. $^1$H NMR (CDCl$_3$, 400 MHz) δ: 8.30 (dd, 1H, J=4.5 Hz), 8.11 (dd, 1H, J=1.6 Hz), 6.95 (d, 1H, J=2.4 Hz), 6.89 (m, 2H), 4.74 (m, 1H), 4.13 (m, 1H), 3.94 (s, 3H), 3.91 (m, 1H), 3.52 (m, 2H), 3.43 (s, 9H), 3.19 (m, 2H), 2.52 (m, 1H), 2.33 (m, 1H), 1.92 (s, 3H), 1.29 (t, 3H, J=7.5 Hz). ESMS m/z: 409.1 [M$^+$]

Example 11

Synthesis of Pyrones

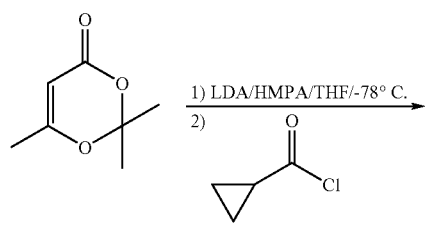

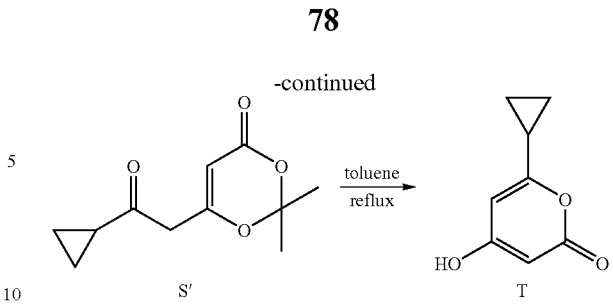

Preparation of 6-(2-Cyclopropyl-2-oxo-ethyl)-2,2-dimethyl-[1,3]dioxin-4-one (S'). To a stirred solution of THF (500 mL) and diisopropylamine (32.45 mL, 227 mmol) at −78° C. was added 2 M n-butyllithium (126 mL, 250 mmol). The reaction was then stirred for 30 minutes at −78° C. HMPA (66.58 mL, 383 mmol) was added to the mixture at −78° C. and the reaction stirred for another 30 minutes. To this cooled mixture was added dropwise 2,2,6-trimethyl-1,3-dioxin-4-one (25.3 mL, 191 mmol) and the reaction was allowed to stir for another 30 minutes at −78° C. Cyclopropanecarbonyl chloride (8.76 mL, 95.7 mmol) was added dropwise to the reaction. The mixture was allowed to warm to ambient temperature while stirring over night. The reaction was cooled in an ice bath and 1 N HCl was added until pH 6 was obtained. The reaction was extracted with diethylether (3×100 mL). The organic layers were combined, washed with brine (3×50 mL), dried with sodium sulfate, filtered, and concentrated using rotary evaporation to dark brown oil. Purification of compound S' was achieved using silica gel chromatography and a gradient of 2.5-5% EtOAc/hexanes followed by 2.5% EtOAc/dichloromethane. Fractions containing the product were pooled and concentrated using rotary evaporation to obtain compound S' as a clear oil (6.21 g, 28%). $^1$H-NMR CDCl$_3$ δ: 5.40 (s, 1H), 3.50 (s, 2H), 2.02 (m, 2H), 1.74 (s, 6H), 1.15 (m, 2H), 1.02 (m, 2H). ESMS m/z: 211 [M+H]$^+$, 233 [M+Na]$^+$, 153 [M−acetone]$^+$.

Preparation of 6-Cyclopropyl-4-hydroxy-2-pyrone (T). Compound S' (6.21 g, 29.5 mmol) was dissolved in toluene (35 mL) and refluxed for 45 minutes. As the reaction mixture cooled to ambient temperature, the title compound precipitated out, was filtered off, and dried under high vacuum to yield compound T (3.21 g. 71%) as a yellow solid. $^1$H-NMR CDCl$_3$ δ: 6.07 (s, 1H), 5.14 (s, 1H), 1.88 (m, 1H), 0.90 (m, 4H). ESMS m/z: 153 [M+H]$^+$, 175 [M+Na]$^+$.

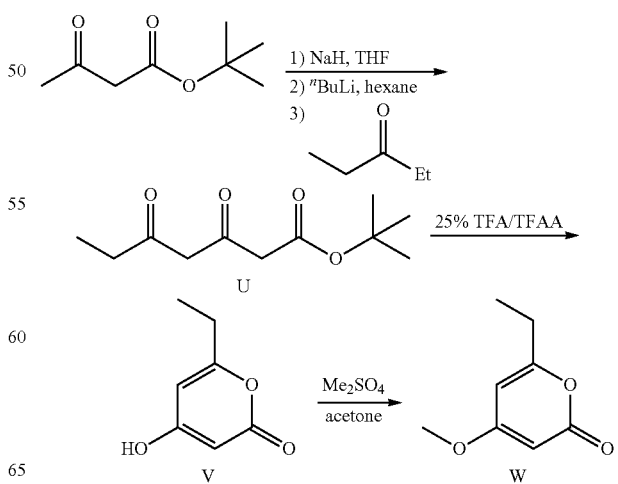

Preparation of 3,5-Dioxoheptanoic acid-t-butyl ester (U). The following is based on the procedure disclosed in B. Lygo, Tetrahedron, 51, pp. 12859-12868 (1995). To an oven dried 5 liter flask was added sodium hydride (60% dispersion in mineral oil, 1.21 mmoles, 48.55 g) under nitrogen gas. The hydride was washed with hexanes (4×250 mL). The hydride was then suspended in dry tetrahydrofuran (THF) (2000 mL) and the mixture cooled to 0° C. in an ice bath. To this solution was added t-butylacetoacetate (160 g, 1.01 mmol) via an addition funnel dropwise over 2 hours at 0° C. with a constant flow of nitrogen gas. After the addition was complete the reaction was allowed to stir at 0° C. under nitrogen for an additional 30 minutes. To this mixture was added n-butyllithium (2 M in cyclohexane, 556 mL, 1.11 mmol) via addition funnel dropwise over 3 hours. After the addition was complete the reaction mixture was allowed to stir at 0° C. for an additional 30 minutes. Ethylpropionate (85.94 mL, 1.01 mmol) was loaded into an addition funnel and added to reaction slowly over 1.5 hours. At this point the reaction was allowed to warm up to room temperature while stirring overnight. The reaction was once again cooled to 0° C. in an ice bath and 2 N HCl (1.15 liters, cooled to 0° C. before addition) was added dropwise via an addition funnel over 2 hours. The reaction pH was checked to ensure neutralization. If needed, more 2 N HCl was added by pipette to adjust the solution to pH 7. At this point the major portion of THF/cyclohexane was decanted away from the aqueous layer and the organic solvent was reduced by ~75% using rotary evaporation. The aqueous layer was extracted with ethyl acetate (3×200 mL). The residue obtained from volume reduction was diluted with ethyl acetate (500 mL) and combined with the organic pool from aqueous extraction. This organic pool was washed with saturated sodium chloride (3×250 mL), dried over anhydrous sodium sulfate, filtered, and concentrated by rotary evaporation. The residue was then subjected to high vacuum distillation (140 microns, short path distillation head) to yield 131 g of crude compound U as a clear oil. $^1$H NMR CDCl$_3$ δ: 15.16 (bs, 1H), 5.59 (s, 1H), 3.24 (s, 2H), 3.22 (q, 2H, J=8.0 Hz), 1.46 (s, 9H), 1.14 (t, 3H, J=8.0 Hz). ESMS m/z: 237 [M+Na$^+$], 159 [M-t-butyl]$^+$.

Preparation of 6-Ethyl-4-hydroxypyran-2-one (V). A solution of 25% (v/v) trifluoroacetic acid (TFA) in trifluoroacetic anhydride (TFAA, 1117 mL) was placed in a 2 liter round bottom flask and cooled in an ice bath for 40 minutes. Crude compound U was loaded into an addition funnel and slowly added to the stirred mixture over 2 hours. The reaction was allowed to warm up to room temperature overnight. The TFA/TFAA solution was removed by rotary evaporation. Residual TFA could be removed azeotropically with toluene. The residue was then purified by silica gel chromatography eluting with a gradient of 10-50% ethyl acetate in dichloromethane. The appropriate fractions were collected and concentrated by rotary evaporation to yield compound V (63.15 g, 45%) as a yellow solid. $^1$H NMR CDCl$_3$ δ: 11.08 (bs, 1H), 6.00 (s, 1H), 5.59 (s, 1H), 2.52 (q, 2H, J=8.0 Hz), 1.22 (t, 3H, J=8.0 Hz). ESMS m/z: 141.0 [M+H$^+$].

Preparation of 6-Ethyl-4-methoxypyran-2-one (W). The following is based on the procedure disclosed in Deshpande, V. H. et al. Indian Journal of Chemistry, 35, pp. 790-793 (1996). Compound V (57.65 g, 411 mmol) was placed in an oven dried 2000 mL three-neck flask and dissolved in dry acetone (1500 ml). To this solution was added potassium carbonate (74 g, 540 mmoles) and dimethylsulfate (51 ml, 540 mmoles). The flask was equipped with a water condenser and mechanical stirrer. The mixture was heated to reflux for 3.5 hours. Analysis by LCMS showed reaction to be complete. Therefore the reaction was cooled to room temperature and the solids removed by filtration. The solvent of the filtrate was removed by rotary evaporation. The yellow oily residue left behind was purified by silica gel chromatography eluting with a gradient of 10% to 50% ethyl acetate in hexanes. The appropriate fractions were collected and concentrated by rotary evaporation to yield compound W (40.55 g, 61%) as a yellow solid. $^1$H NMR CDCl$_3$ δ: 5.78 (s, 1H), 5.42 (s, 1H), 3.80 (s, 3H), 2.51 (q, 2H, J=8.0 Hz), 1.22 (t, 3H, J=8.0 Hz). ESMS m/z: 155 [M+H$^+$].

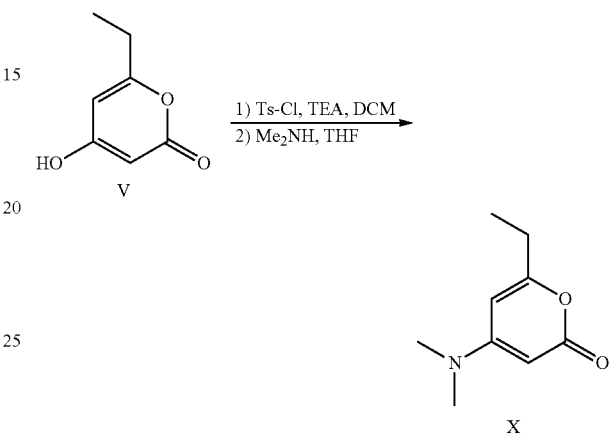

Preparation of 4-Dimethylamino-6-ethyl-2-pyrone (X). Compound V (4.9 g, 35 mmol) was dissolved in dichloromethane (50 mL) and triethylamine was added (12.2 mL, 87.5 mmol). To the resulting solution, tosyl chloride (6.7 g, 35 mmol) was added and the reaction stirred at 0° C. under nitrogen. After 1 hour, dimethylamine (2.0 M in tetrahydrofuran, 19.25 mL, 38.5 mmol) was added and the reaction was stirred an additional 2 hours at 0° C. The reaction mixture was washed with saturated aqueous sodium bicarbonate solution, brine, and then concentrated using rotary evaporation. The residue was purified by silica gel chromatography eluting with a gradient of 0-10% methanol in dichloromethane. The fractions containing the desired product were collected and concentrated by rotary evaporation to yield compound X (3.6 g, 62% yield) as a light yellow solid. $^1$H NMR CDCl$_3$ δ: 5.74 (s, 1H), 4.92 (s, 1H), 2.95 (s, 6H), 2.43 (q, 2H, J=20 Hz), 1.18 (t, 3H, J=12 Hz). ESMS m/z: 168.1 [M+H$^+$].

Example 12

Synthesis of Chiral Pyrrolidine Compounds

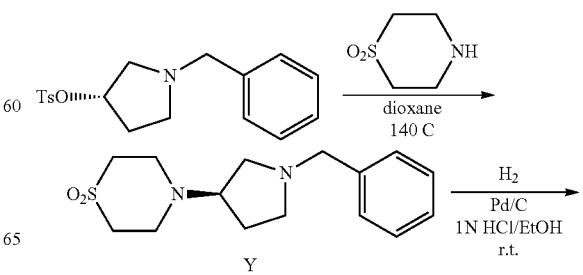

-continued

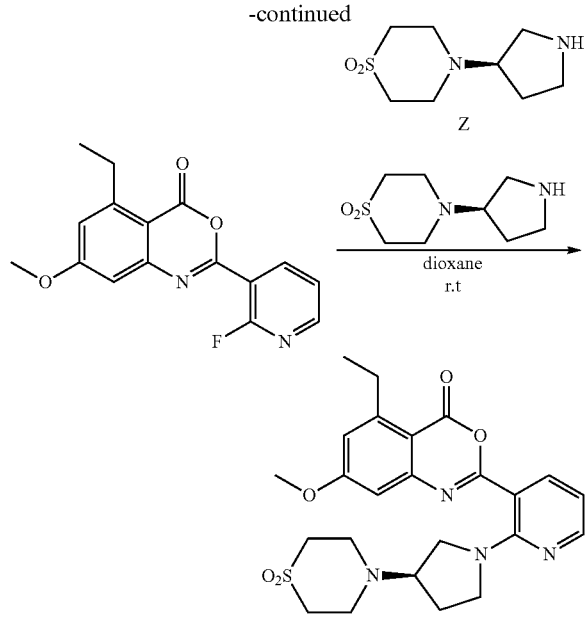

Preparation of (R)-4-(1-Benzyl-pyrrolidin-3-yl)-thiomorpholine 1,1-dioxide (Y). (S)-Toluene-4-sulfonic acid 1-benzyl-pyrrolidin-3-yl ester was prepared as described in J. Med. Chem. 1992, 35, 4205. (S)-Toluene-4-sulfonic acid 1-benzyl-pyrrolidin-3-yl ester (400 mg, 1.208 mmol, 1 eq) and 1,1-dioxo-thiomorpholine (817 mg, 6.042 mmol, 5 eq) were taken up in dioxane and heated at 140° C. for 20 hours. The reaction mixture was cooled and the dioxane was removed using rotary evaporation. The resulting residue was purified on a Biotage 40M amine column using a gradient of 0-50% ethyl acetate/hexanes to obtain the title compound (88 mg, 25%) as a yellow oil. $^{1}$H NMR (400 MHz) CDCl$_3$ δ 7.30-7.20 (m, 5H), 3.55-3.54 (s, 2H), 3.19-3.17 (m, 1H), 3.01-2.91 (m, 6H), 2.62-2.58 (m, 2H), 2.51-2.43 (m, 2H), 2.00-1.97 (m, 2H), 1.71-1.67 (m, 2H). ESMS m/z: 295.2 [M+H]$^{+}$.

Preparation of (R)-4-Pyrrolidin-3-yl-thiomorpholine 1,1-dioxide (Z). Compound Y (88 mg, 0.2989 mmol, 1 eq) was dissolved in EtOH (2.0 ml) and 1N HCl was added (300 μl). Degassed solution 3 times with N$_2$ and the Palladium catalyst (10 mg, 5% mmol) was added. Degassed with H$_2$ (g) 3 times and hydrogenated for 90 minutes. The catalyst was filtered off and 1N HCl was added (300 μl). The solvent was removed in vacuo and taken up in water and lyophilized to obtain the desired compound as a yellow oil (59 mg, 82%). $^{1}$H NMR (400 MHz) D$_2$O δ 3.88-3.68 (dm, 2H), 3.57-3.45 (m, 10H), 3.37-3.29 (m, 2H), 2.45 (m, 1H), 2.10 (m, 1H). 205.1 [M+H]$^{+}$.

Preparation of 5-ethyl-2-{2-[3-(1,1-dioxo-thiomorpholin-4-yl)pyrrolidin-1-yl]pyridin-3-yl}-7-methoxy-4H-benz[d][1,3]oxazin-4-one. To 5-ethyl-2-(2-fluoropyridin-3-yl)-7-methoxy-4H-benz[d][1,3]oxazin-4-one (50.0 mg, 0.17 mmol) in anhydrous 1,4-dioxane (850 μL) was added compound Z (52.9 mg, 0.22 mmol) and diisopropylethyl amine (120 μL, 0.85 mmol) at room temperature under N$_2$ overnight. The solution was concentrated, and the resulting residue was purified on a Biotage 40M amine column using a gradient of 20-75% ethyl acetate/hexanes to obtain the title compound. The fractions containing the title compound were combined and concentrated by speedvac to afford the title compound as a yellow oil (19.2 mg, 23% yield). $^{1}$H NMR (CDCl$_3$, 400 MHz) δ: 8.33 (dd, 1H, J=1.0 Hz), 8.1 (d, 1H, J=7.0 Hz), 6.92 (dd, 2H, J=2.5 Hz), 6.83 (m, 1H), 3.93 (s, 3H), 3.83 (m, 1H), 3.62 (m, 2H), 3.39 (m, 1H), 3.26 (m, 1H), 3.22 (m, 4H), 3.17 (m, 6H), 2.16 (m, 1H), 1.94 (m, 1H), 1.29 (t, 3H, J=7.5 Hz); ESMS m/z 485.2 [M+H]$^{+}$.

Example 13

Determination of Inhibitor IC$_{50}$ Values Against Human Neutrophil Elastase

Human sputum neutrophil elastase (Elastin Products Co.) was diluted into Assay Buffer A (200 mM Tris pH 7.4, 1 mg/ml BSA) to a working concentration of 0.55 U/ml. Inhibitors dissolved and diluted in DMSO at 50× were added to the elastase in Assay Buffer A at final concentrations ranging from $1 \times 10^{-4}$ M to $6.95 \times 10^{-12}$ M and preincubated for 20 minutes at room temperature. DMSO alone was used as the negative control. MeOSuc-AAPV-AMC (Bachem) substrate was dissolved in DMSO to 20 mM and further diluted to 1 mM in Assay Buffer A immediately before use. Substrate was added to the elastase assay at a final concentration of $1 \times 10^{-4}$ M. The reaction was allowed to proceed for 20 minutes at room temperature and then quenched with acetic acid at a final concentration of 3% (v/v). A background fluorescence control was prepared by adding substrate to elastase that had been prequenched. The AMC fluorescence was measured using a Wallac (Perkin Elmer) Victor2 plate reader equipped with excitation/emission filters of 355/460 nm. Fluorescence intensity versus inhibitor concentration was plotted and fit to the Hill equation to quantify IC$_{50}$ values. The IC$_{50}$ values for exemplary compounds are represented in Table 1.

TABLE 1

Exemplary compounds and their activity

| Compound | Structure | Electrospray mass spectrometry characterization data | HNE IC$_{50}$ (nM) |
| --- | --- | --- | --- |
| 1 | 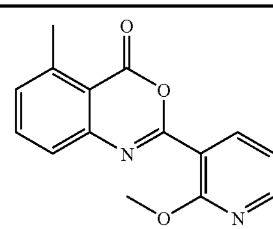 | 269.1 [M + H]$^{+}$ | C |

TABLE 1-continued

Exemplary compounds and their activity

| Compound | Structure | Electrospray mass spectrometry characterization data | HNE IC$_{50}$ (nM) |
|---|---|---|---|
| 2 | 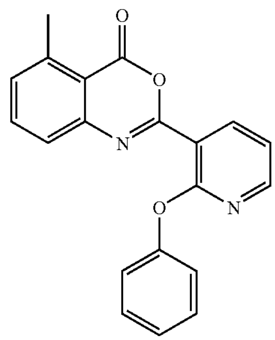 | 331.1 [M + H]$^+$<br>353.1 [M + Na]$^+$<br>369.0 [M + K]$^+$ | B |
| 3 | 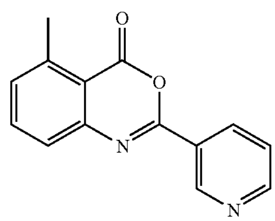 | 239.1 [M + H]$^+$ | D |
| 4 | 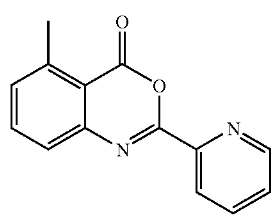 | 239.1 [M + H]$^+$<br>261.1 [M + Na]$^+$<br>279.1 [M + K]$^+$ | D |
| 5 | 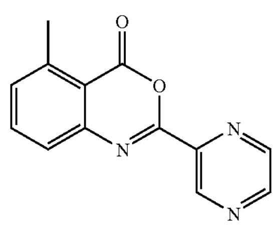 | 240.1 [M + H]$^+$<br>262.1 [M + Na]$^+$ | C |
| 6 | 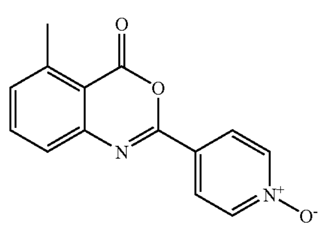 | 253.1 [M]$^+$ | D |
| 7 | 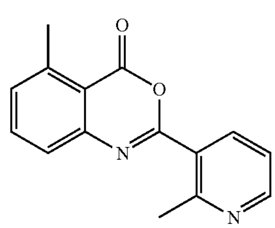 | 253.1 [M + H]$^+$ | C |

TABLE 1-continued

Exemplary compounds and their activity

| Compound | Structure | Electrospray mass spectrometry characterization data | HNE IC$_{50}$ (nM) |
|---|---|---|---|
| 8 | 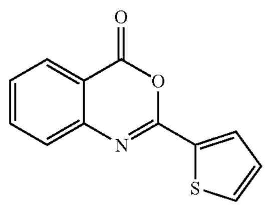 | 230.1 [M + H]$^+$ | D |
| 9 | 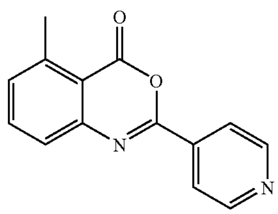 | 239.1 [M + H]$^+$ | D |
| 10 | 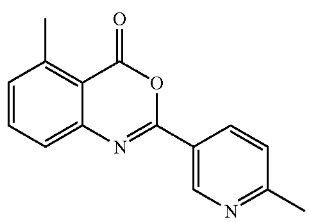 | 253.1 [M + H]$^+$ | D |
| 11 | 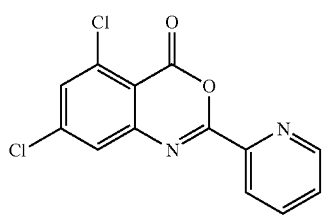 | 293.0 [M + H]$^+$<br>295.0 [M + H]$^+$,<br>315.0 [M + Na]$^+$ | D |
| 12 | 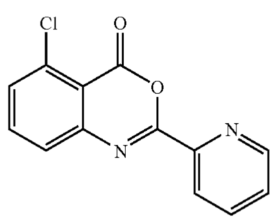 | 259.1 [M + H]$^+$<br>261.0 [M + H]$^+$<br>281.0 [M + Na]$^+$ | C |
| 13 | 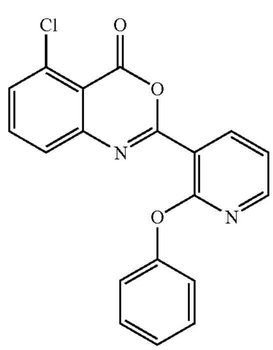 | 351.1 [M + H]$^+$<br>353.1 [M + H]$^+$<br>373.1 [M + Na]$^+$<br>389.0 [M + K]+ | C |

TABLE 1-continued

Exemplary compounds and their activity

| Compound | Structure | Electrospray mass spectrometry characterization data | HNE IC$_{50}$ (nM) |
|---|---|---|---|
| 14 | 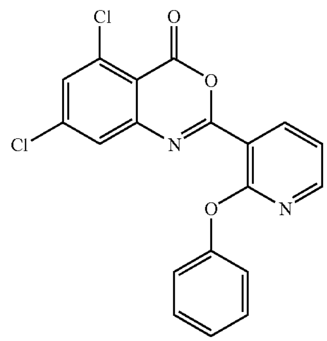 | 385.0 [M + H]$^+$<br>387.0 [M + H]$^+$<br>409.0 [M + Na]$^+$ | D |
| 15 | 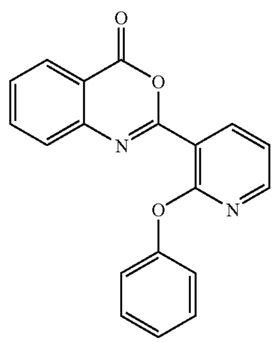 | 317.1 [M + H]$^+$<br>339.1 [M + Na]$^+$ | D |
| 16 | 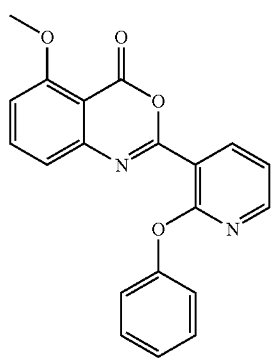 | 347.1 [M + H]$^+$<br>369.1 [M + Na]$^+$<br>385.1 [M + K]$^+$ | D |
| 17 | 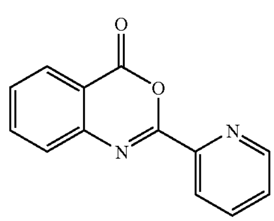 | 225.1 [M + H]$^+$ | D |
| 18 | 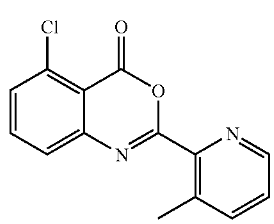 | 273.0 [M + H]$^+$<br>274.1 [M + H]$^+$<br>295.0 [M + Na]$^+$ | B |

TABLE 1-continued

Exemplary compounds and their activity

| Compound | Structure | Electrospray mass spectrometry characterization data | HNE IC$_{50}$ (nM) |
|---|---|---|---|
| 19 | 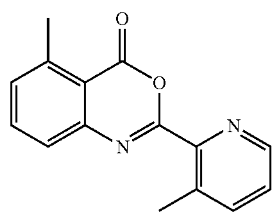 | 253.1 [M + H]$^+$<br>275.1 [M + Na]$^+$ | D |
| 20 | 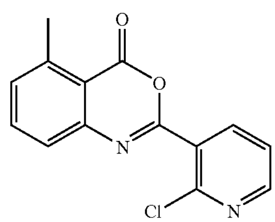 | 273.1 [M + H]$^+$<br>274.0 [M + H]$^+$<br>297.1 [M + Na]$^+$ | B |
| 21 | 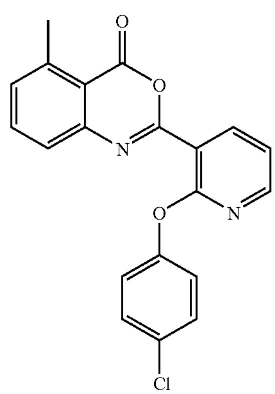 | 365.1 [M + H]$^+$<br>367.1 [M + H]$^+$<br>387.1 [M + Na]$^+$ | B |
| 22 | 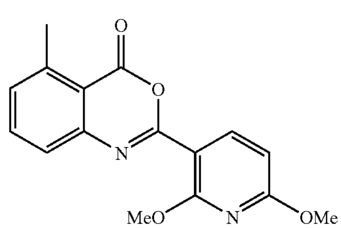 | 299.1 [M + H]$^+$<br>321.1 [M + Na]$^+$ | A |
| 23 | 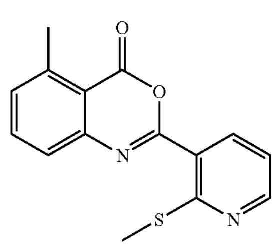 | 285.1 [M + H],<br>307.1 [M + Na]$^+$ | C |

TABLE 1-continued

Exemplary compounds and their activity

| Compound | Structure | Electrospray mass spectrometry characterization data | HNE IC$_{50}$ (nM) |
| --- | --- | --- | --- |
| 24 | 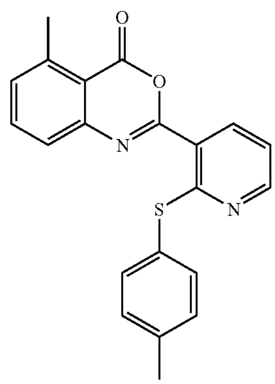 | 361.1 [M + H]$^+$<br>383.1 [M + Na]$^+$ | D |
| 25 | 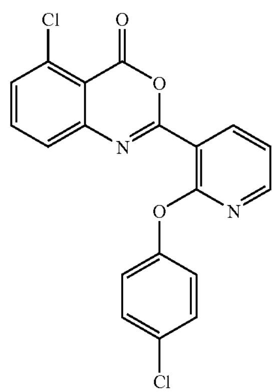 | 385.0 [M + H]$^+$<br>387.0 [M + H]$^+$<br>407.0 [M + Na]$^+$<br>422.9 [M + K]$^+$ | B |
| 26 | 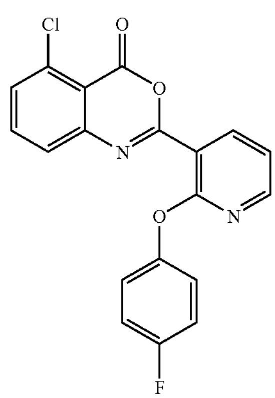 | 369.1 [M + H]$^+$<br>371.1 [M + H]$^+$<br>391.0 [M + Na]$^+$<br>407.0 [M + K]$^+$ | C |
| 27 | 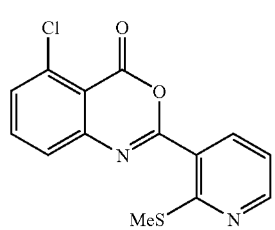 | 305.0 [M + H]$^+$<br>307.0 [M + H]$^+$<br>329.0 [M + Na]$^+$ | C |

TABLE 1-continued

Exemplary compounds and their activity

| Compound | Structure | Electrospray mass spectrometry characterization data | HNE IC$_{50}$ (nM) |
|---|---|---|---|
| 28 | 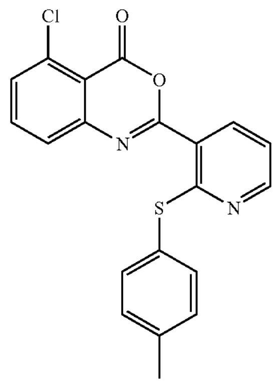 | 381.1 [M + H]$^+$<br>383.1 [M + H]$^+$<br>403.0 [M + Na]$^+$<br>405.0 [M + Na]$^+$ | C |
| 29 | 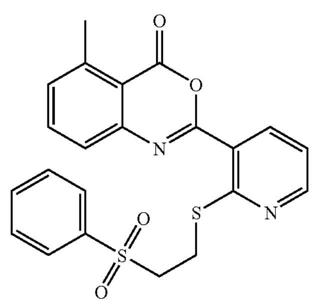 | 439.1 [M + H]$^+$<br>461.1 [M + Na]$^+$<br>477.0 [M + K]$^+$ | B |
| 30 | 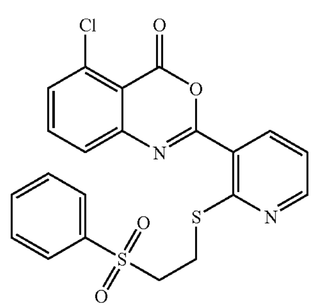 | 459.0 [M + H]$^+$<br>481.0 [M + Na]$^+$<br>497.0 [M + K]$^+$ | B |
| 31 | 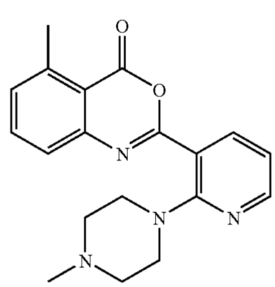 | 337.2 [M + H]$^+$ | C |

TABLE 1-continued

Exemplary compounds and their activity

| Compound | Structure | Electrospray mass spectrometry characterization data | HNE IC$_{50}$ (nM) |
|---|---|---|---|
| 32 | 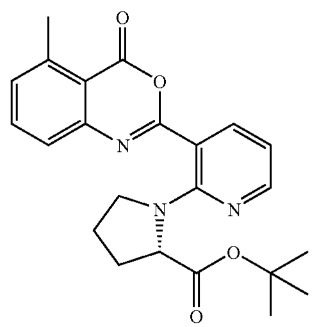 | 408.2 [M + H]$^+$<br>430.2 [M + Na]$^+$<br>837.4 [2M + H − Na]$^+$ | B |
| 33 | 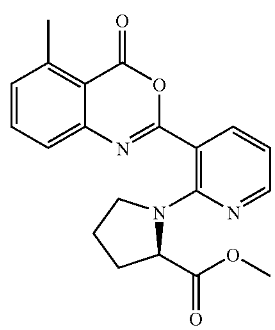 | 366.2 [M + H]$^+$<br>388.1 [M + Na]$^+$<br>404.1 [M + K]$^+$ | B |
| 34 | 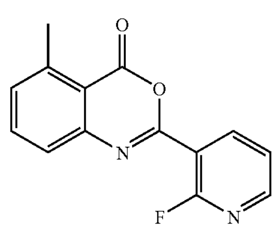 | 257.1 [M + H]$^+$ | C |
| 35 | 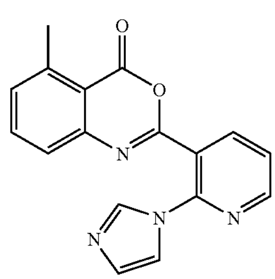 | 305.0 [M + H]$^+$<br>327.0 [M + Na]$^+$ | B |

TABLE 1-continued

Exemplary compounds and their activity

| Compound | Structure | Electrospray mass spectrometry characterization data | HNE IC$_{50}$ (nM) |
|---|---|---|---|
| 36 | 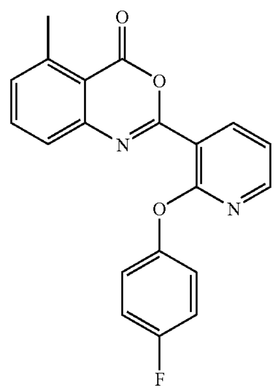 | 349.1 [M + H]$^+$<br>371.1 [M + Na]$^+$<br>387.0 [M + K]$^+$ | B |
| 37 | 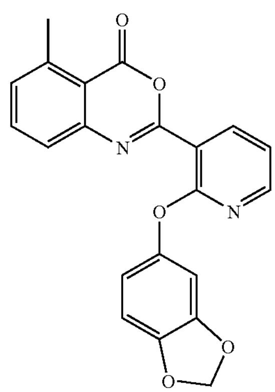 | 375.1 [M + H]$^+$<br>397.1 [M + Na]$^+$<br>413.1 [M + K]$^+$ | B |
| 38 | 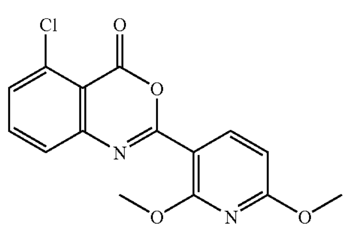 | 319.1 [M + H]$^+$<br>321.1 [M + H]$^+$<br>341.0 [M + Na]$^+$ | A |
| 39 | 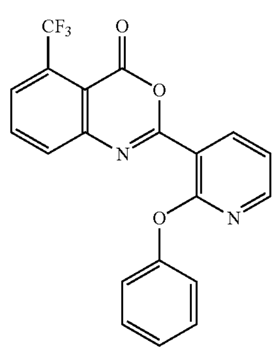 | 385.1 [M + H]$^+$<br>407.1 [M + Na]$^+$<br>423.0 [M + K]$^+$ | A |

TABLE 1-continued

Exemplary compounds and their activity

| Compound | Structure | Electrospray mass spectrometry characterization data | HNE IC$_{50}$ (nM) |
|---|---|---|---|
| 40 | 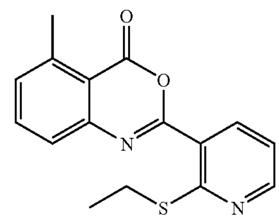 | 299.1 [M + H]$^+$ | D |
| 41 | 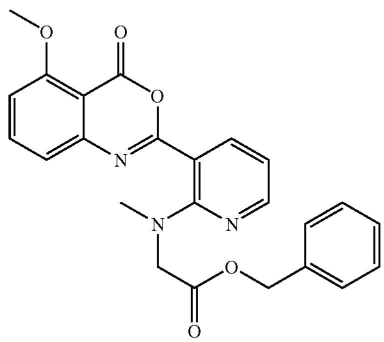 | 432.0 [M + H]$^+$<br>453.9 [M + Na]$^+$<br>469.9 [M + K]$^+$ | D |
| 42 | 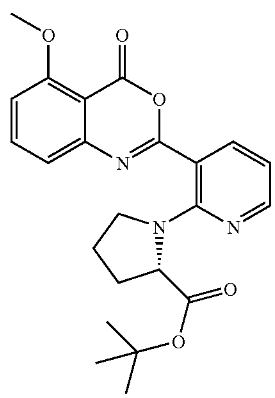 | 424.0 [M + H]$^+$<br>446.0 [M + Na]$^+$<br>461.9 [M + K]$^+$ | D |
| 43 | 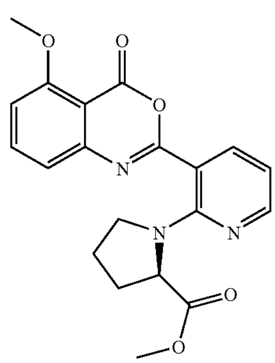 | 382.0 [M + H]$^+$<br>403.9 [M + Na]$^+$<br>419.9 [M + K]$^+$ | D |

TABLE 1-continued

Exemplary compounds and their activity

| Compound | Structure | Electrospray mass spectrometry characterization data | HNE IC$_{50}$ (nM) |
|---|---|---|---|
| 44 | 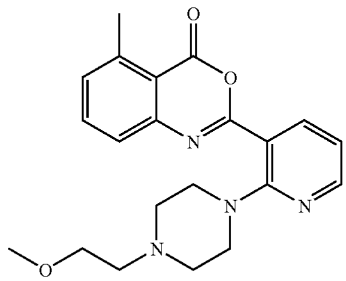 | 381.0 [M + H]$^+$<br>402.9 [M + Na]$^+$ | B |
| 45 | 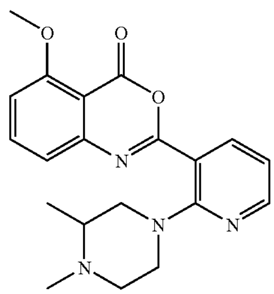 | 367.0 [M + H]$^+$<br>388.9 [M + Na]$^+$ | D |
| 46 | 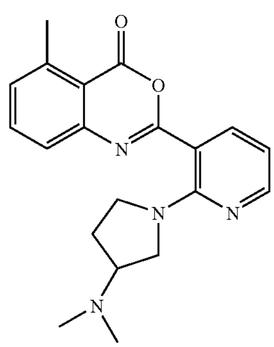 | 351.1 [M + H]$^+$ | C |
| 47 | 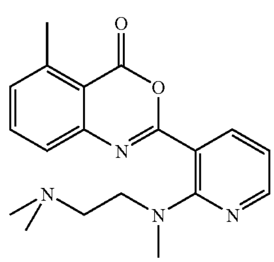 | 339.1 [M + H]$^+$ | C |
| 48 | 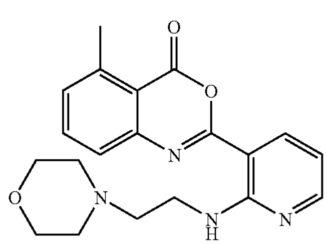 | 367.0 [M + H]$^+$ | D |

TABLE 1-continued
Exemplary compounds and their activity
| Compound | Structure | Electrospray mass spectrometry characterization data | HNE IC$_{50}$ (nM) |
|---|---|---|---|
| 49 | 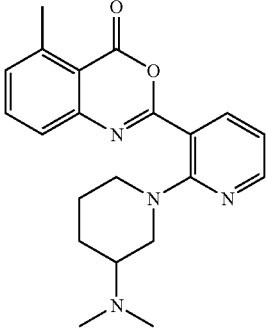 | 365.1 [M + H]$^+$ | C |
| 50 | 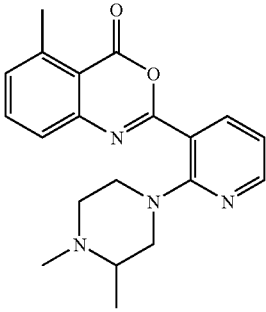 | 351.0 [M + H]$^+$ | D |
| 51 | 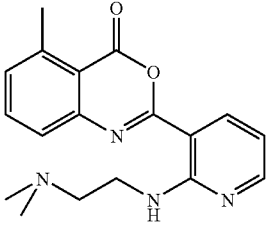 | 325.0 [M + H]$^+$ | D |
| 52 | 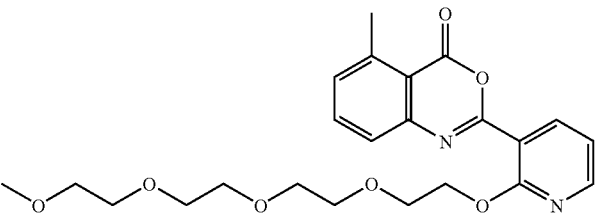 | 445.0 [M + H]$^+$<br>467.0 [M + Na]$^+$<br>482.9 [M + K]$^+$ | B |
| 53 | 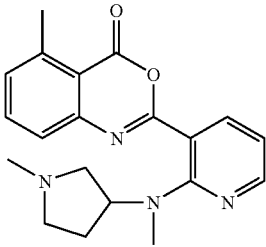 | 351.0 [M + H]$^+$ | C |

TABLE 1-continued

Exemplary compounds and their activity

| Compound | Structure | Electrospray mass spectrometry characterization data | HNE IC$_{50}$ (nM) |
|---|---|---|---|
| 54 | 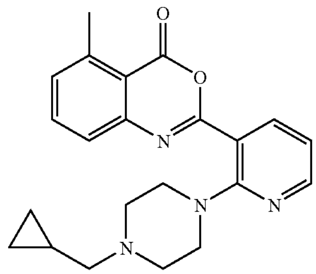 | 377.0 [M + H]$^+$ | D |
| 55 | 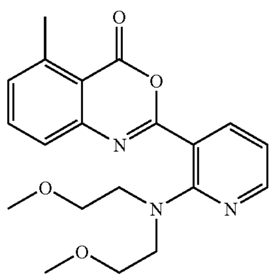 | 370.1 [M + H]$^+$<br>392.0 [M + Na]$^+$ | D |
| 56 | 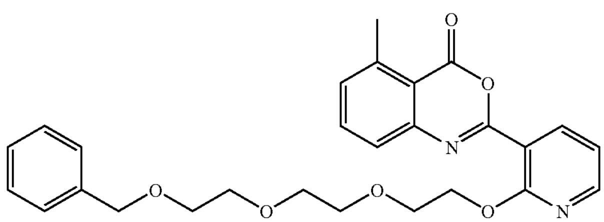 | 477.0 [M + H]$^+$<br>499.0 [M + Na]$^+$ | D |
| 57 | 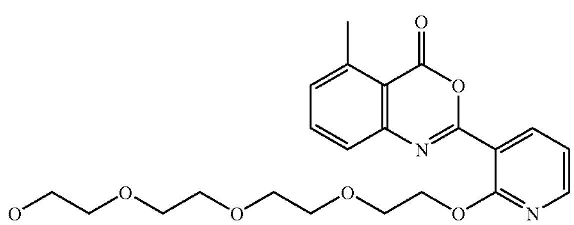 | 431.0 [M + H]$^+$<br>453.0 [M + Na]$^+$<br>470.0 [M + K]$^+$ | C |
| 58 | 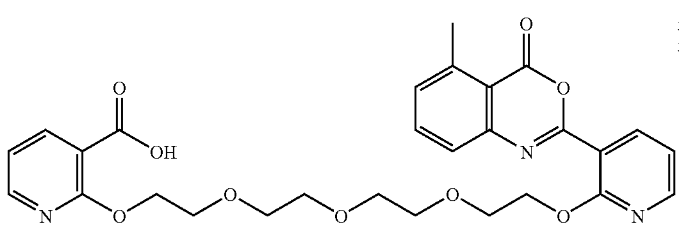 | 552.0 [M + H]$^+$<br>574.0 [M + Na]$^+$ | C |
| 59 | 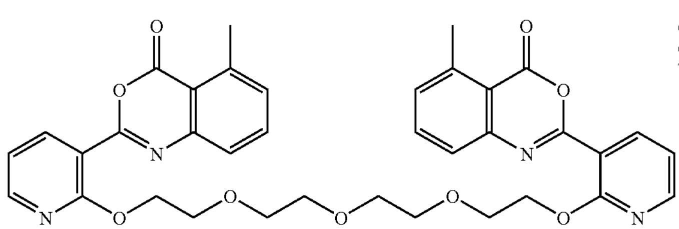 | 667.0 [M + H]$^+$<br>689.0 [M + Na]$^+$<br>705.0 [M + K]$^+$ | C |

TABLE 1-continued

Exemplary compounds and their activity

| Compound | Structure | Electrospray mass spectrometry characterization data | HNE IC$_{50}$ (nM) |
|---|---|---|---|
| 60 | 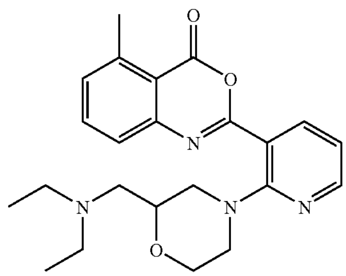 | 409.1 [M + H]$^+$ | D |
| 61 | 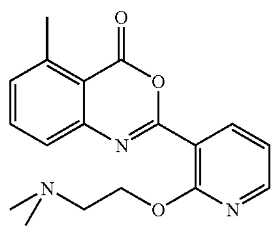 | 326.0 [M + H]$^+$ | D |
| 62 | 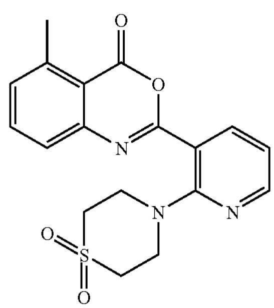 | 372.0 [M + H]$^+$<br>393.9 [M + Na]$^+$<br>409.9 [M + K]$^+$ | D |
| 63 | 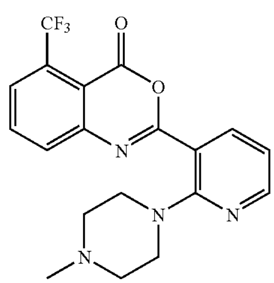 | 391.0 [M + H]$^+$ | B |
| 64 | 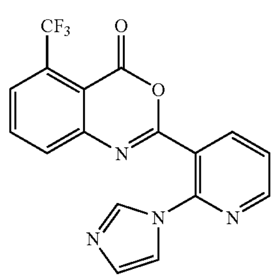 | 359.0 [M + H]$^+$<br>380.9 [M + Na]$^+$ | A |

TABLE 1-continued

Exemplary compounds and their activity

| Compound | Structure | Electrospray mass spectrometry characterization data | HNE IC$_{50}$ (nM) |
|---|---|---|---|
| 65 | 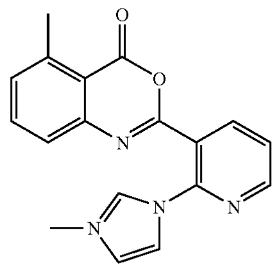 | 319.0 [M]$^+$ | D |
| 66 | 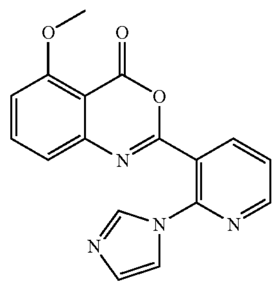 | 321.0 [M + H]$^+$<br>342.9 [M + Na]$^+$ | D |
| 67 | 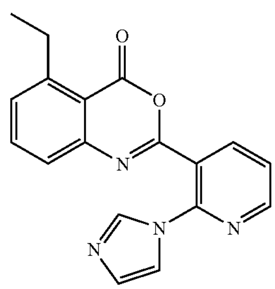 | 319.0 [M + H]$^+$<br>341.0 [M + Na]$^+$ | A |
| 68 | 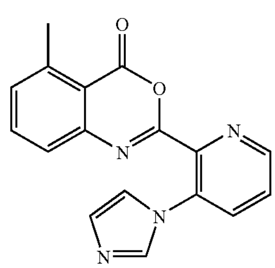 | 305.0 [M + H]$^+$ | D |
| 69 | 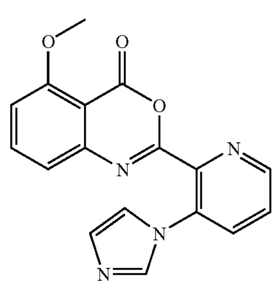 | 321.0 [M + H]$^+$ | D |

TABLE 1-continued

Exemplary compounds and their activity

| Compound | Structure | Electrospray mass spectrometry characterization data | HNE IC$_{50}$ (nM) |
|---|---|---|---|
| 70 | 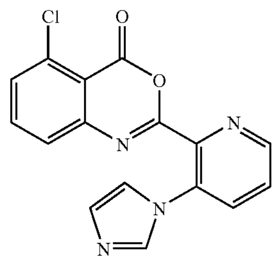 | 324.9 [M + H]$^+$<br>326.9 [M + H]$^+$ | D |
| 71 | 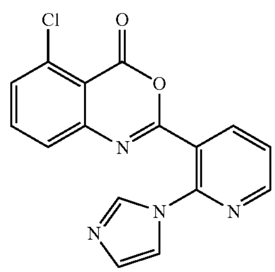 | 324.9 [M + H]$^+$<br>326.9 [M + H]$^+$<br>346.9 [M + Na]$^+$ | D |
| 72 | 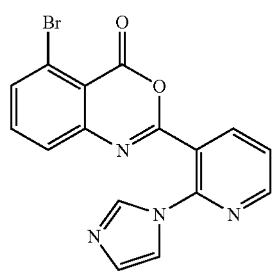 | 390.9 [M + Na]$^+$ | C |
| 73 | 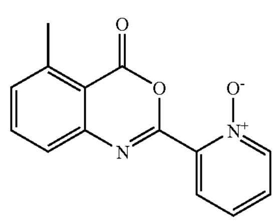 | 254.0 [M]+ | D |
| 75 | 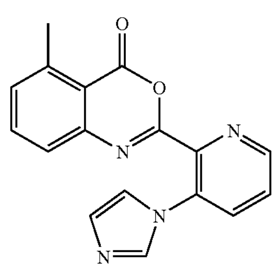 | 305.0 [M + H]+ | D |

TABLE 1-continued

Exemplary compounds and their activity

| Compound | Structure | Electrospray mass spectrometry characterization data | HNE IC$_{50}$ (nM) |
| --- | --- | --- | --- |
| 76 | 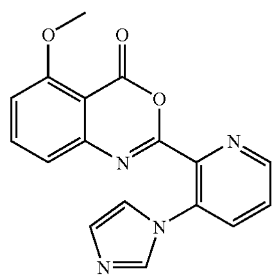 | 321.0 [M + H]+ | D |
| 83 | 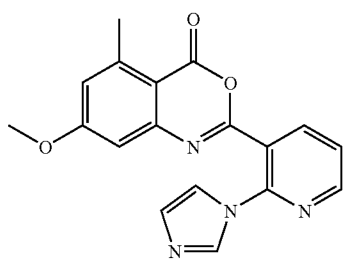 | 335.0 [M + H]+ | D |
| 84 | 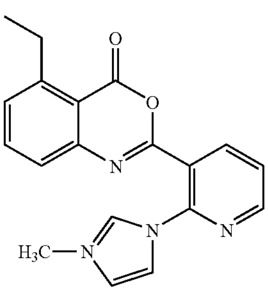 | 333.1 [M]+ | B |
| 85 | 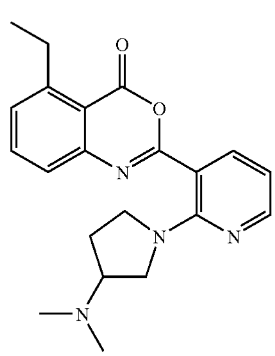 | 365.1 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 86 | 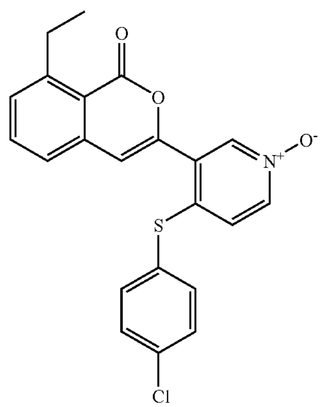 | 410.9 [M]+ | C |
| 87 | 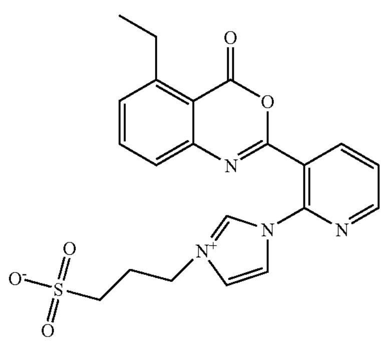 | 441.0 [M]+ | A |
| 88 | 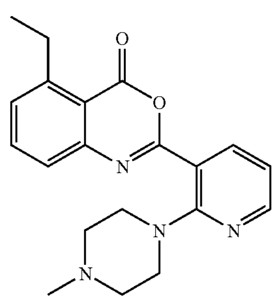 | 351.1 [M + H]+ | A |
| 89 | 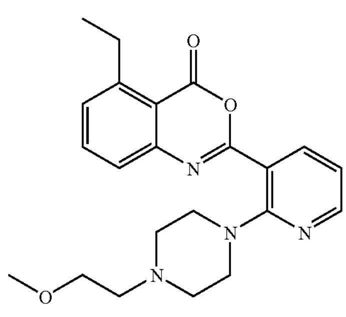 | 395.1 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 90 | 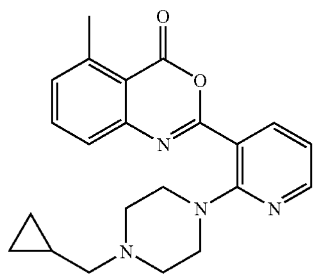 | 391.1 [M + H]+ | A |
| 91 | 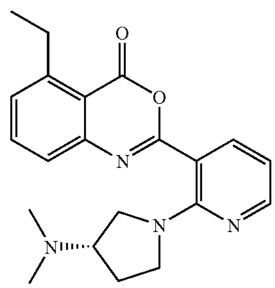 | 365.1 [M + H]+ | A |
| 92 | 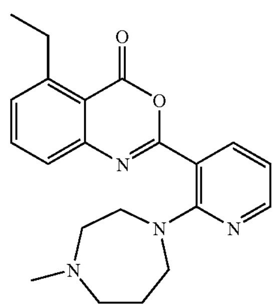 | 365.1 [M + H]+ | A |
| 93 | 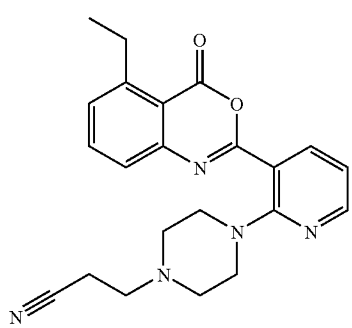 | 390.1 [M + H]+ | A |

TABLE 1-continued
Exemplary compounds and their activity
| Compound | Structure | Electrospray mass spectrometry characterization data | HNE IC$_{50}$ (nM) |
|---|---|---|---|
| 94 | 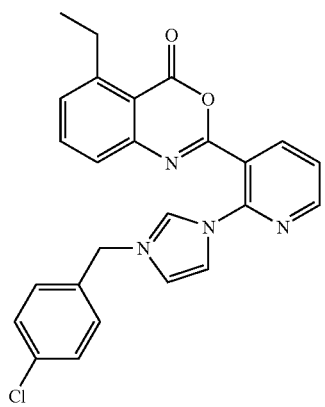 | 442.9 [M]+ | B |
| 95 | 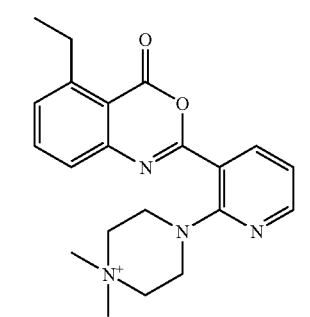 | 365.1 [M]+ | A |
| 96 | 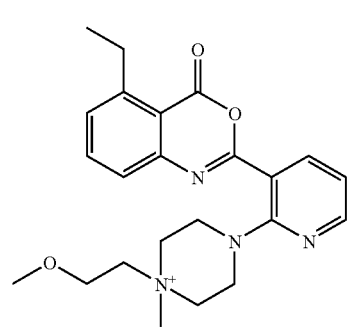 | 409.1 [M]+ | A |
| 97 | 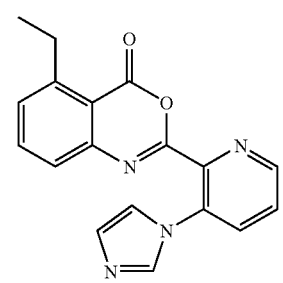 | 319.3 [M + H]+<br>341.0 [M + Na]+ | A |

TABLE 1-continued

Exemplary compounds and their activity

| Compound | Structure | Electrospray mass spectrometry characterization data | HNE IC$_{50}$ (nM) |
|---|---|---|---|
| 98 | 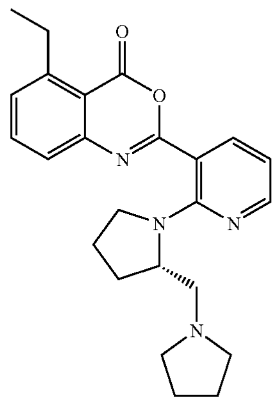 | 405.1 [M + H]+ | A |
| 99 | 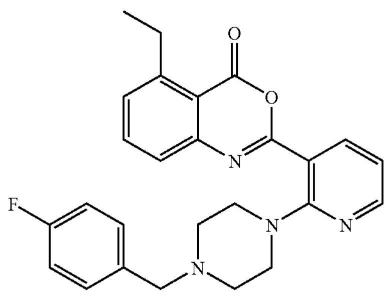 | 445.1 [M + H]+ | A |
| 100 | 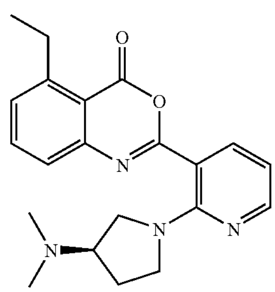 | 365.1 [M + H]+ | A |
| 101 | 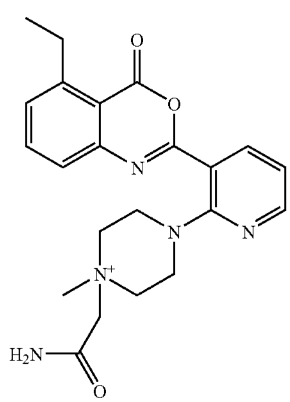 | 351.1 [M − CH$_2$CONH$_2$]+ <br> 409.1 [M]+ | A |

TABLE 1-continued
Exemplary compounds and their activity
| Compound | Structure | Electrospray mass spectrometry characterization data | HNE IC$_{50}$ (nM) |
|---|---|---|---|
| 102 | 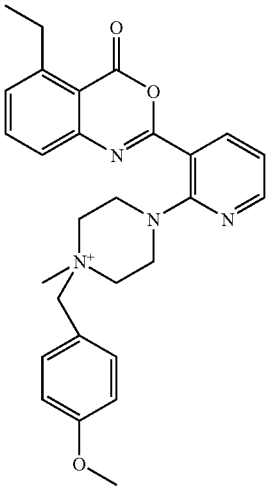 | 471.1 [M]+ | A |
| 103 | 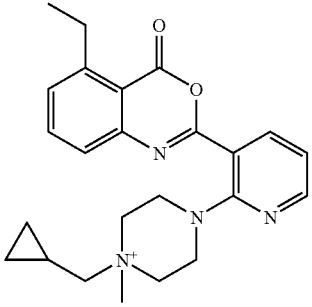 | 405.1 [M]+ | A |
| 104 | 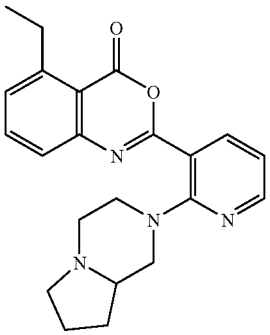 | 377.1 [M + H]+ | A |
| 105 | 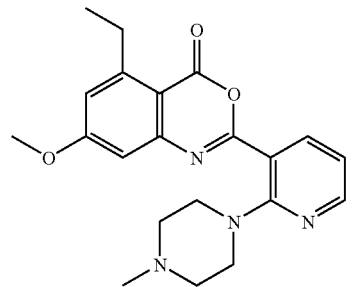 | 381.1 [M + H]+ | B |

TABLE 1-continued

Exemplary compounds and their activity

| Compound | Structure | Electrospray mass spectrometry characterization data | HNE IC$_{50}$ (nM) |
|---|---|---|---|
| 106 | 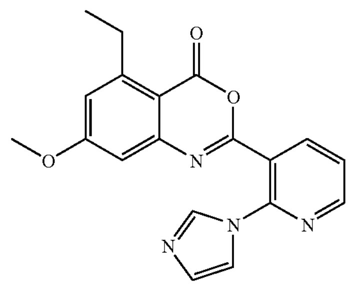 | 349.0 [M + H]+ | A |
| 107 | 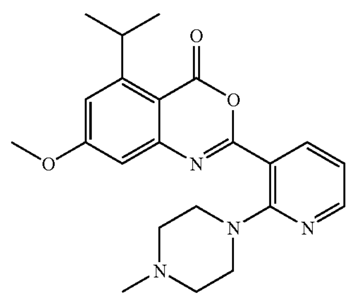 | 395.1 [M + H]+ | D |
| 108 | 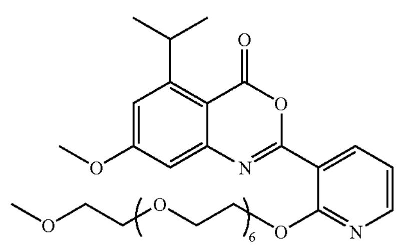 | 635.1 [M + H]+ | D |
| 109 | 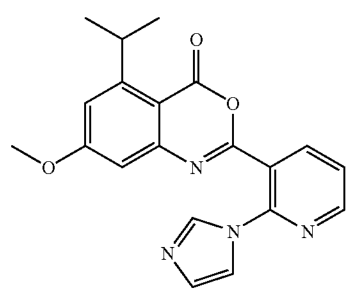 | 363.1 [M + H]+ | B |
| 110 | 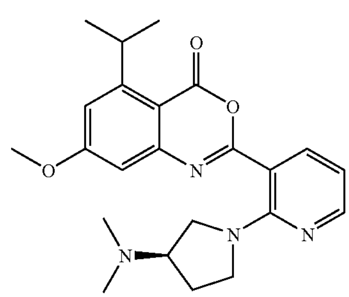 | 409.1.1 [M + H]+ | C |

TABLE 1-continued
Exemplary compounds and their activity
| Compound | Structure | Electrospray mass spectrometry characterization data | HNE IC$_{50}$ (nM) |
|---|---|---|---|
| 111 | 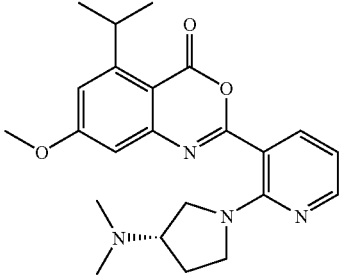 | 409.1.1 [M + H]+ | C |
| 112 | 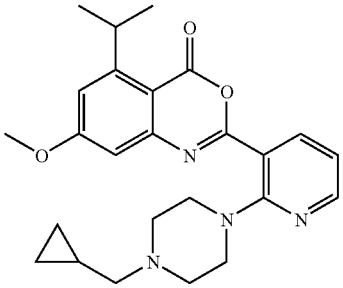 | 435.1 [M + H]+ | C |
| 113 | 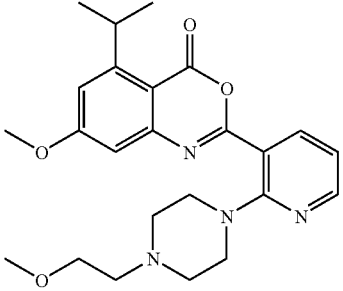 | 439.1 [M + H]+ | C |
| 114 | 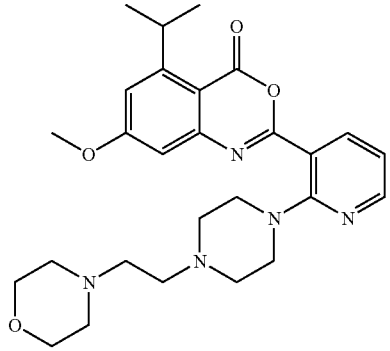 | 494.1 [M + H]+ | C |

TABLE 1-continued

Exemplary compounds and their activity

| Compound | Structure | Electrospray mass spectrometry characterization data | HNE IC$_{50}$ (nM) |
|---|---|---|---|
| 115 | 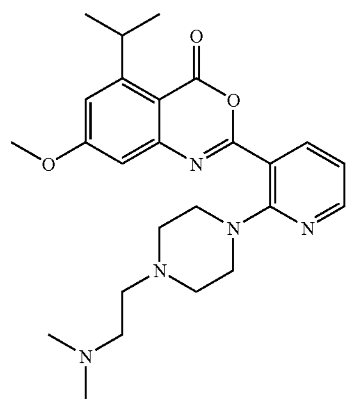 | 452.1 [M + H]+ | C |
| 116 | 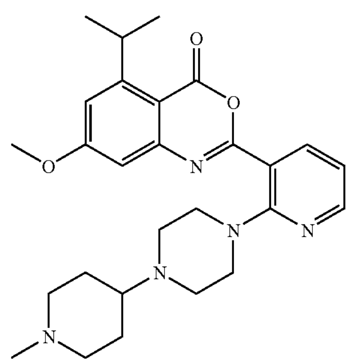 | 478.1 [M + H]+ | C |
| 117 | 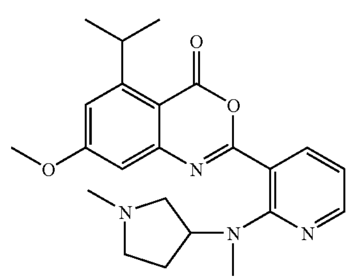 | 409.1 [M + H]+ | C |
| 118 | 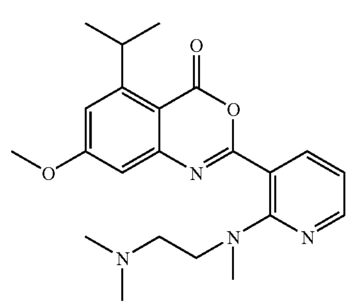 | 397.1 [M + H]+ | C |

TABLE 1-continued
Exemplary compounds and their activity
| Compound | Structure | Electrospray mass spectrometry characterization data | HNE IC$_{50}$ (nM) |
|---|---|---|---|
| 119 | 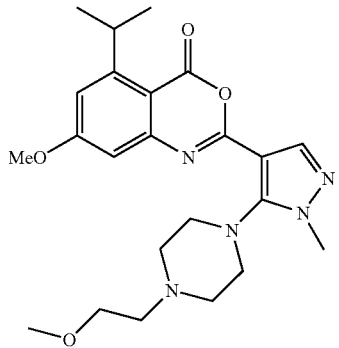 | 442.1 [M + H]+ | D |
| 120 | 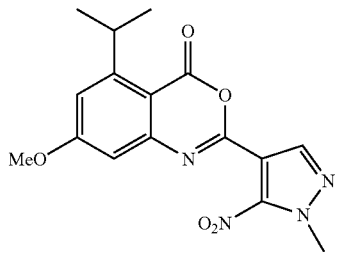 | 345.0 [M + H]+ | B |
| 121 | 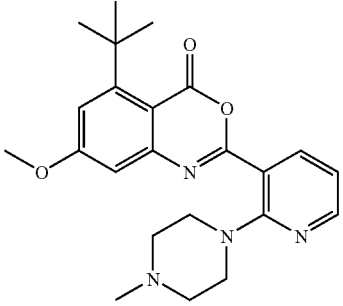 | 409.0 [M + H]+ | D |
| 122 | 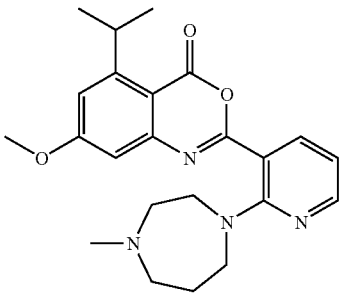 | 409.1 [M + H]+ | C |

TABLE 1-continued

Exemplary compounds and their activity

| Compound | Structure | Electrospray mass spectrometry characterization data | HNE IC$_{50}$ (nM) |
|---|---|---|---|
| 123 | 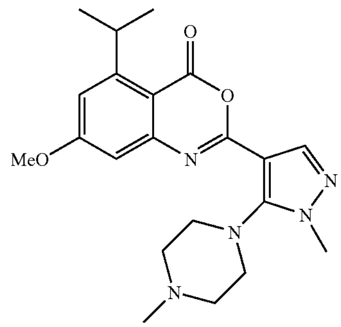 | 398.1 [M + H]+ | D |
| 124 | 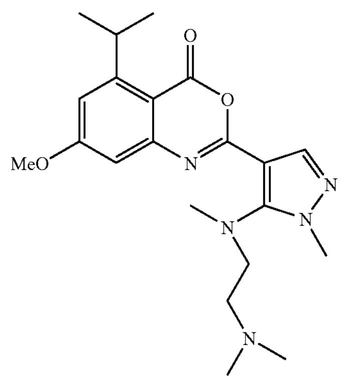 | 400.1 [M + H]+ | D |
| 125 | 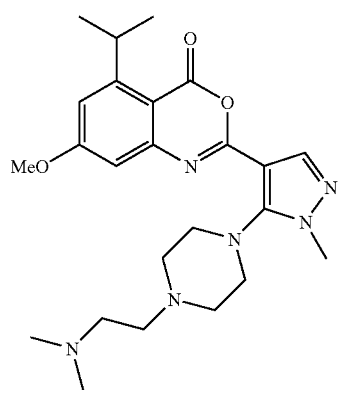 | 455.1 [M + H]+ | D |
| 126 | 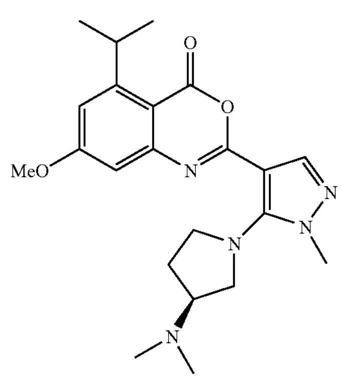 | 412.1 [M + H]+ | D |

TABLE 1-continued

Exemplary compounds and their activity

| Compound | Structure | Electrospray mass spectrometry characterization data | HNE IC$_{50}$ (nM) |
|---|---|---|---|
| 127 | 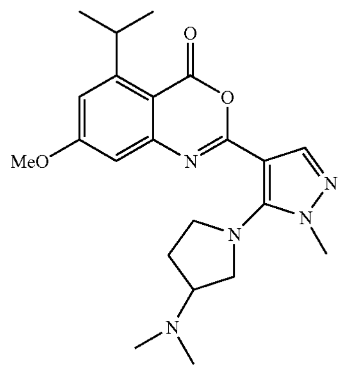 | 412.1 [M + H]+ | D |
| 128 | 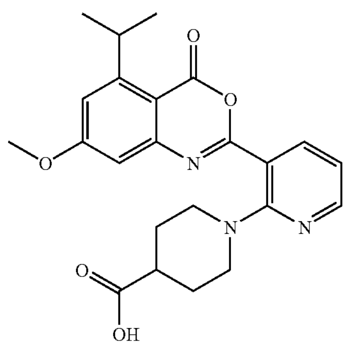 | 424.0 [M + H]+ | D |
| 129 | 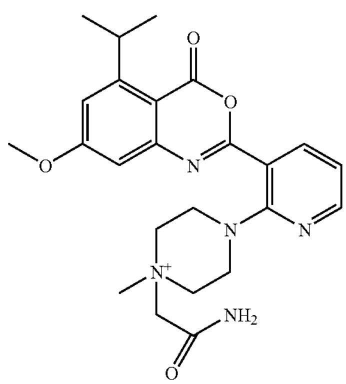 | 452.0 [M]+ | C |
| 130 | 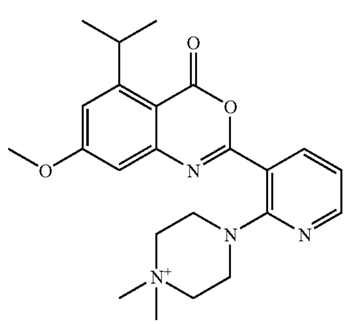 | 409.0 [M + H]+ | C |

TABLE 1-continued

Exemplary compounds and their activity

| Compound | Structure | Electrospray mass spectrometry characterization data | HNE IC$_{50}$ (nM) |
|---|---|---|---|
| 131 | 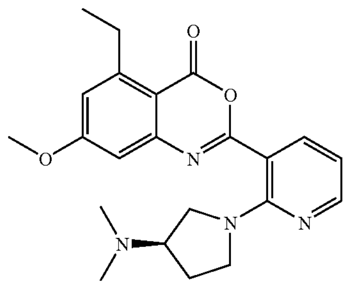 | 395.1 [M + H]+ | A |
| 132 | 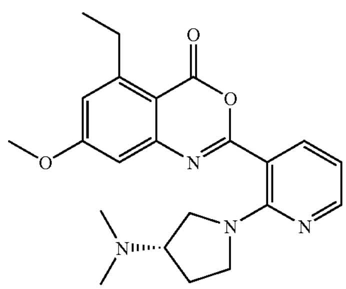 | 395.1 [M + H]+ | A |
| 133 | 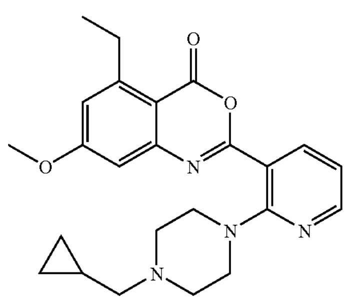 | 421.1 [M + H]+ | B |
| 134 | 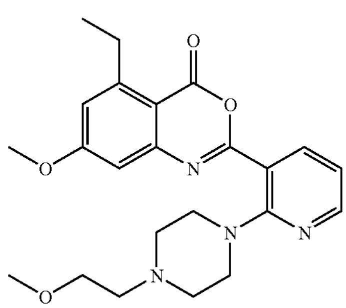 | 425.1 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 135 | 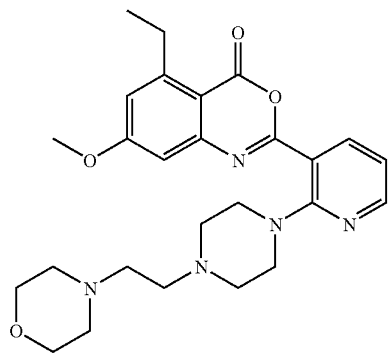 | 480.1 [M + H]+ | B |
| 136 | 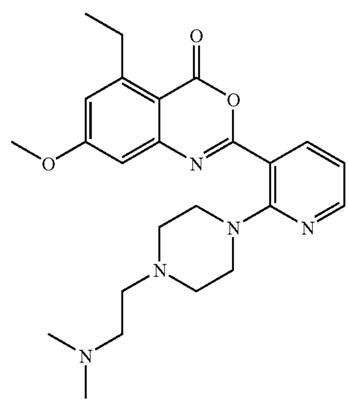 | 438.1 [M + H]+ | B |
| 138 | 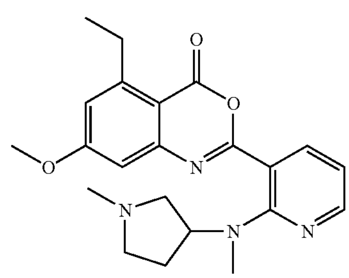 | 395.1 [M + H]+ | B |
| 139 | 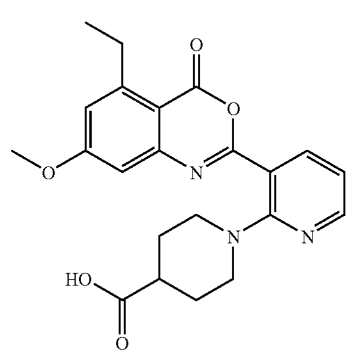 | 410.1 [M + H]+ | B |

TABLE 1-continued

Exemplary compounds and their activity

| Compound | Structure | Electrospray mass spectrometry characterization data | HNE IC$_{50}$ (nM) |
|---|---|---|---|
| 140 | 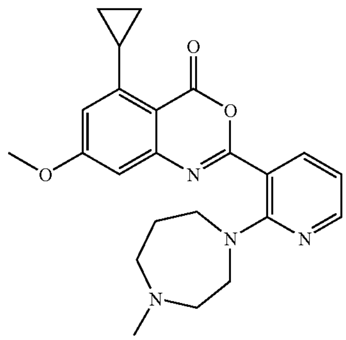 | 407.1 [M + H]+ | C |
| 141 | 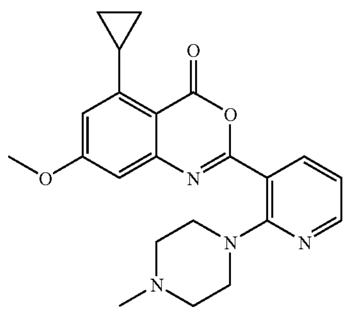 | 393.1 [M + H]+ | D |
| 142 | 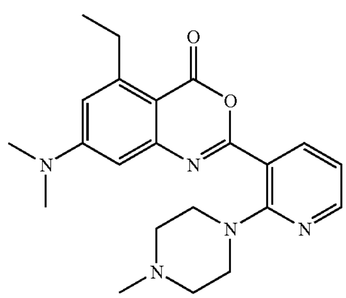 | 394.1 [M + H]+ | D |
| 143 | 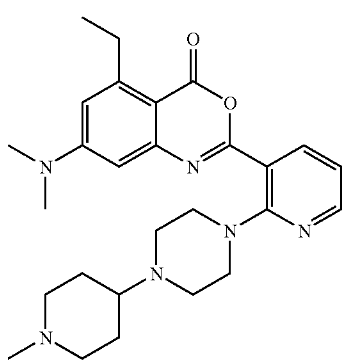 | 477.1 [M + H]+ | D |

TABLE 1-continued

Exemplary compounds and their activity

| Compound | Structure | Electrospray mass spectrometry characterization data | HNE IC$_{50}$ (nM) |
|---|---|---|---|
| 144 | 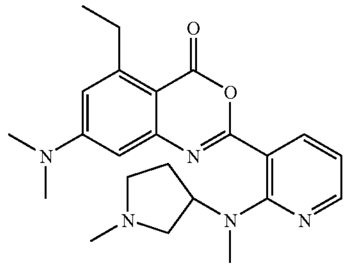 | 408.1 [M + H]+ | D |
| 145 | 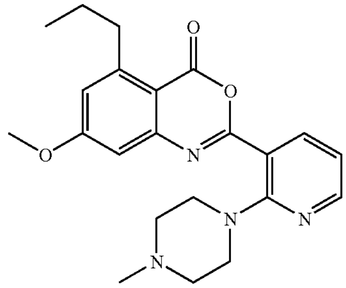 | 395.1 [M + H]+ | D |
| 146 | 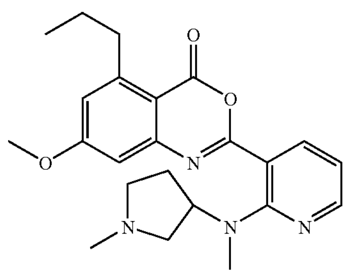 | 409.1 [M + H]+ | D |
| 147 | 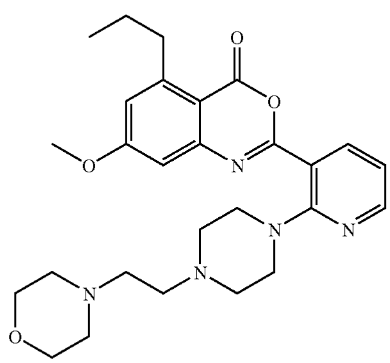 | 494.1 [M + H]+ | C |
| 148 | 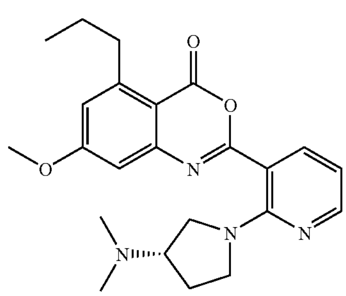 | 409.1 [M + H]+ | B |

TABLE 1-continued

Exemplary compounds and their activity

| Compound | Structure | Electrospray mass spectrometry characterization data | HNE IC$_{50}$ (nM) |
|---|---|---|---|
| 149 | 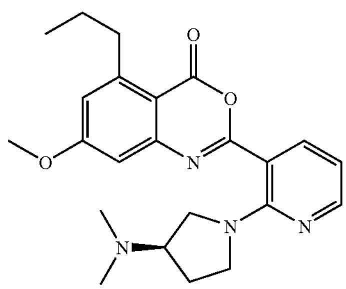 | 409.1 [M + H]+ | C |
| 150 | 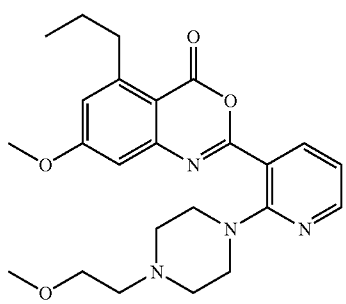 | 439.1 [M + H]+ | C |
| 151 | 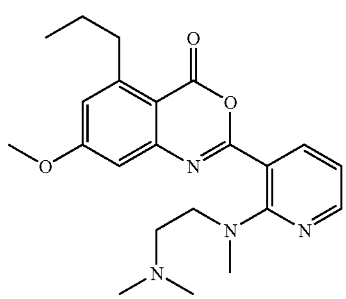 | 397.1 [M + H]+ | B |
| 152 | 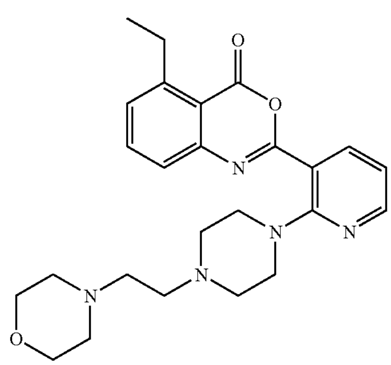 | 450.0 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 153 | 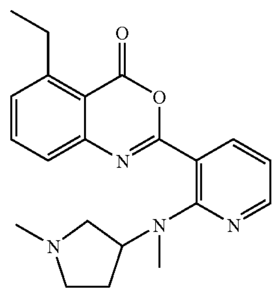 | 365.1 [M + H]+ | B |
| 154 | 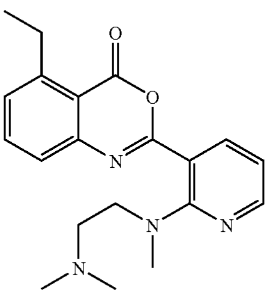 | 353.1 [M + H]+ | A |
| 155 | 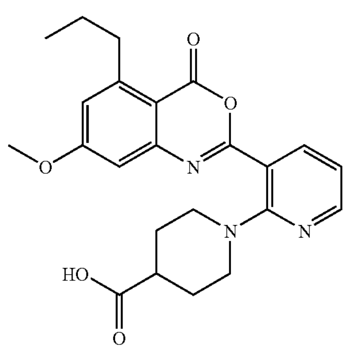 | 424.1 [M + H]+ | C |
| 156 | 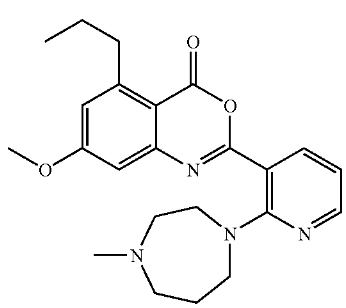 | 409.1 [M + H]+ | C |

TABLE 1-continued

Exemplary compounds and their activity

| Compound | Structure | Electrospray mass spectrometry characterization data | HNE IC$_{50}$ (nM) |
|---|---|---|---|
| 157 | 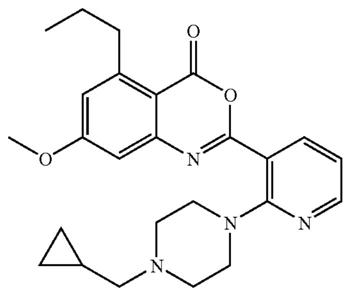 | 435.1 [M + H]+ | C |
| 158 | 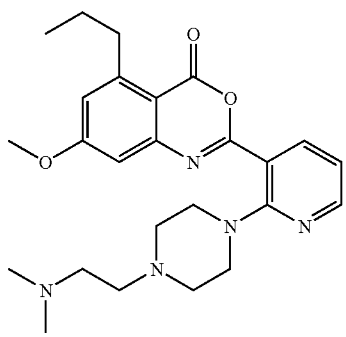 | 452.1 [M + H]+ | B |
| 159 | 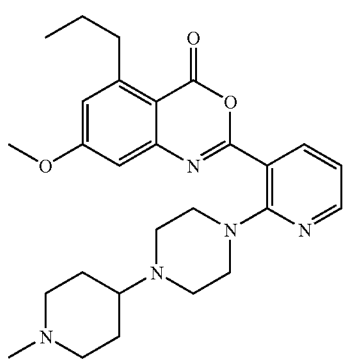 | 478.1 [M + H]+ | B |
| 161 | 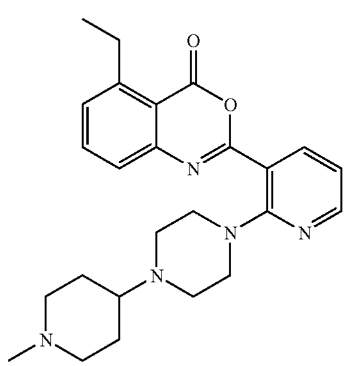 | 434.1 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 162 | 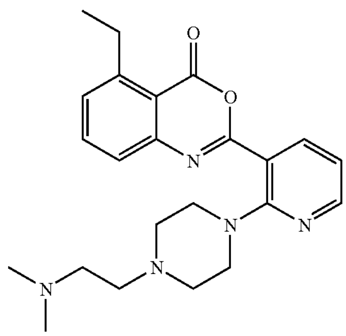 | 408.1 [M + H]+ | A |
| 163 | 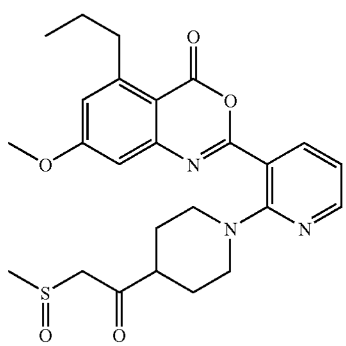 | 484.1 [M + H]+ | C |
| 164 | 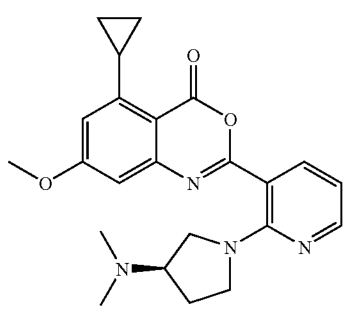 | 407.1 [M + H]+ | C |
| 165 | 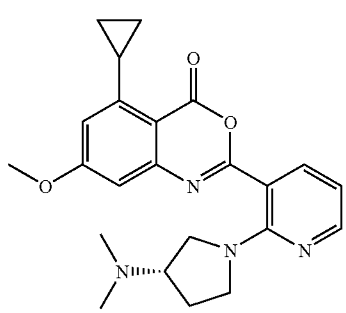 | 407.1 [M + H]+ | C |

TABLE 1-continued

Exemplary compounds and their activity

| Compound | Structure | Electrospray mass spectrometry characterization data | HNE IC$_{50}$ (nM) |
|---|---|---|---|
| 166 | 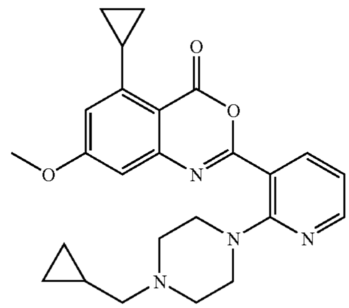 | 433.1 [M + H]+ | C |
| 167 | 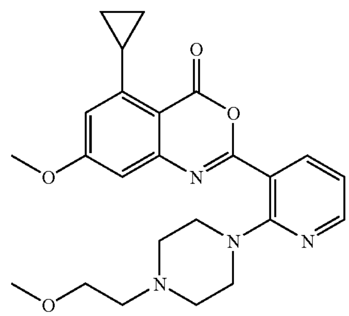 | 437.1 [M + H]+ | C |
| 168 | 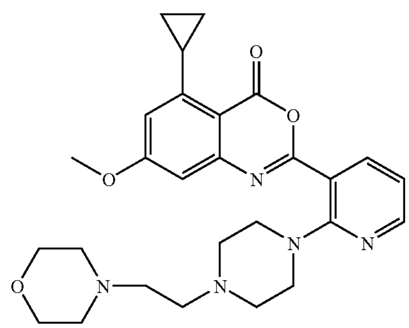 | 492.1 [M + H]+ | C |
| 169 | 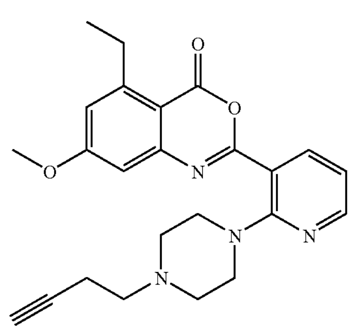 | 389.1 [M + H]+<br>411.0 [M + Na]+ | A |

TABLE 1-continued

Exemplary compounds and their activity

| Compound | Structure | Electrospray mass spectrometry characterization data | HNE IC$_{50}$ (nM) |
|---|---|---|---|
| 170 | 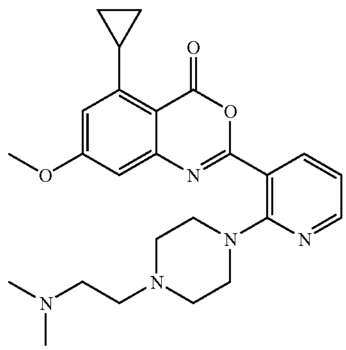 | 450.1 [M + H]+ | C |
| 171 | 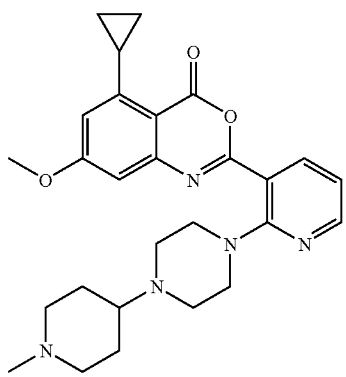 | 476.1 [M + H]+ | C |
| 172 | 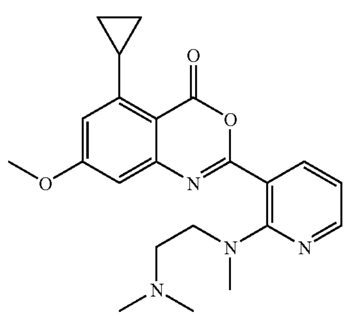 | 395.1 [M + H]+ | C |
| 173 | 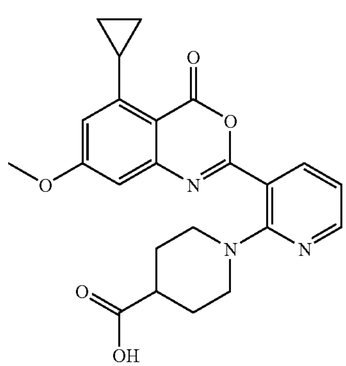 | 422.1 [M + H]+ | D |

TABLE 1-continued
Exemplary compounds and their activity
| Compound | Structure | Electrospray mass spectrometry characterization data | HNE IC$_{50}$ (nM) |
|---|---|---|---|
| 174 | 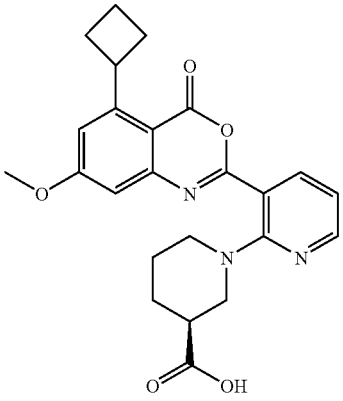 | 436.1 [M + H]+ | D |
| 175 | 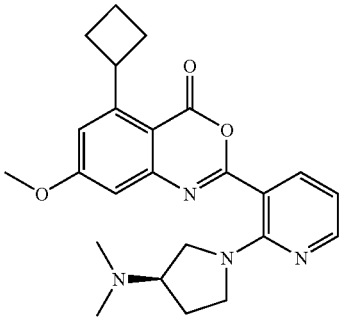 | 421.1 [M + H]+ | D |
| 176 | 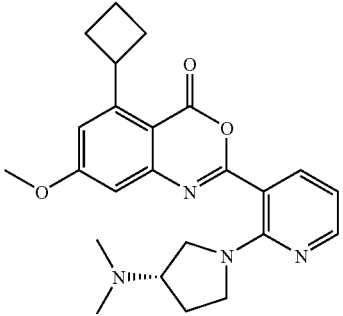 | 421.1 [M + H]+ | C |
| 177 | 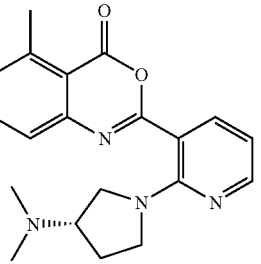 | 351.0 [M + H]+<br>373.0 [M + Na]+ | B |

TABLE 1-continued

Exemplary compounds and their activity

| Compound | Structure | Electrospray mass spectrometry characterization data | HNE IC$_{50}$ (nM) |
|---|---|---|---|
| 178 | 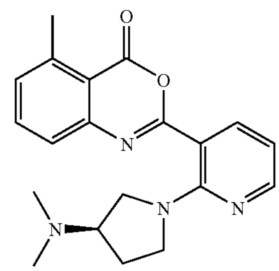 | 351.1 [M + H]+<br>373.0 [M + Na]+ | B |
| 179 | 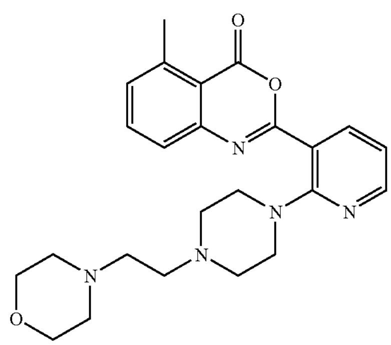 | 436.1 [M + H]+<br>458.0 [M + Na]+ | B |
| 180 | 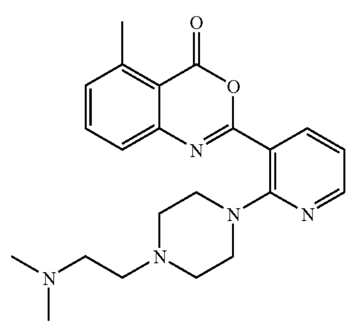 | 394.1 [M + H]+ | B |
| 181 | 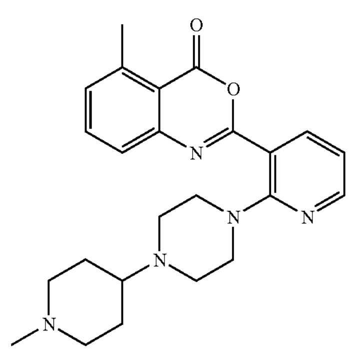 | 420.0 [M + H]+ | B |

TABLE 1-continued

Exemplary compounds and their activity

| Compound | Structure | Electrospray mass spectrometry characterization data | HNE IC$_{50}$ (nM) |
|---|---|---|---|
| 183 | 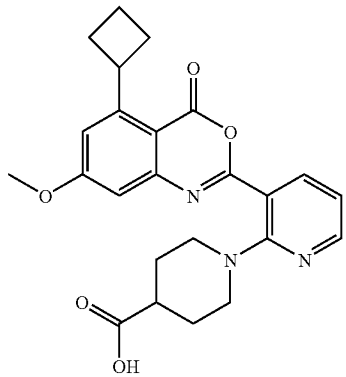 | 436.1 [M + H]+ | D |
| 184 | 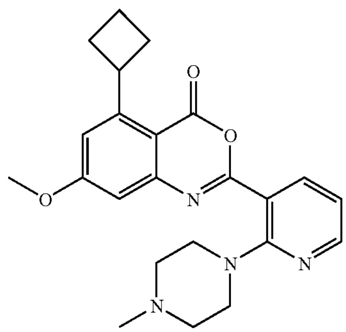 | 407.1 [M + H]+ | B |
| 185 | 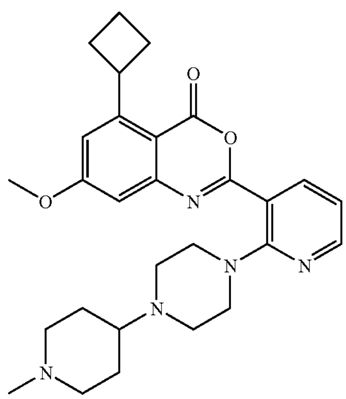 | 490.1 [M + H]+ | D |
| 186 | 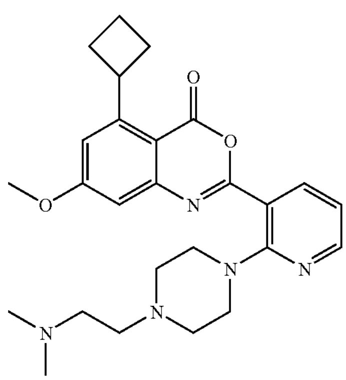 | 464.1 [M + H] | C |

TABLE 1-continued

Exemplary compounds and their activity

| Compound | Structure | Electrospray mass spectrometry characterization data | HNE IC$_{50}$ (nM) |
|---|---|---|---|
| 187 | 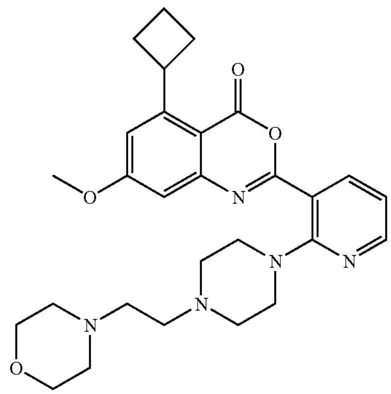 | 506.1 [M + H]+ | D |
| 188 | 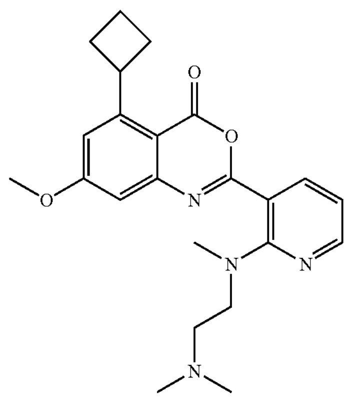 | 409.1 [M + H]+ | B |
| 189 | 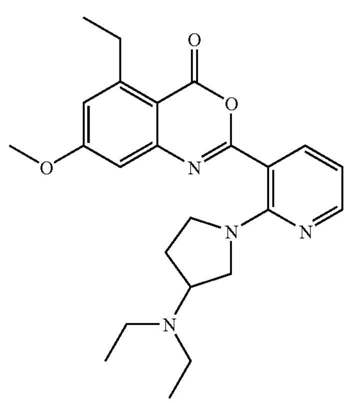 | 423.1 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 190 | 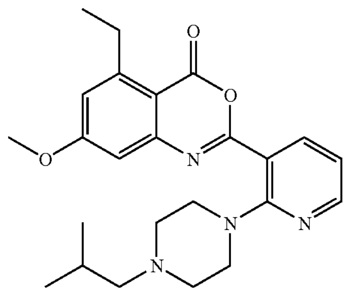 | 423.1 [M + H]+ | A |
| 191 | 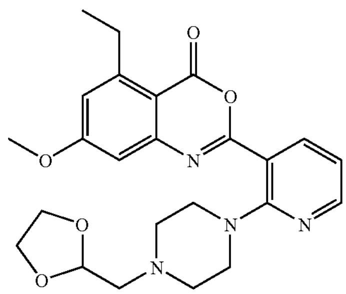 | 453.1 [M + H]+ | A |
| 192 | 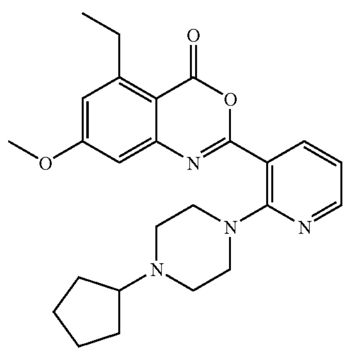 | 435.1 [M + H]+ | A |
| 193 | 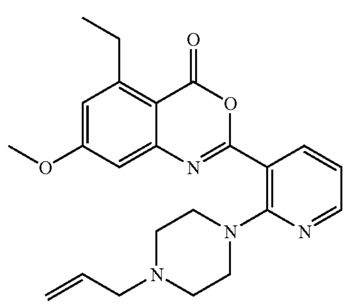 | 407.1 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 194 | 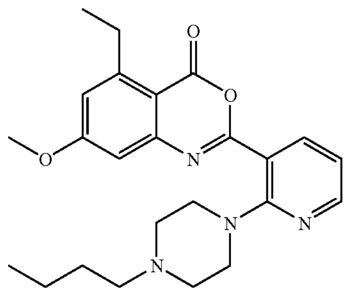 | 423.1 [M + H]+ | A |
| 195 | 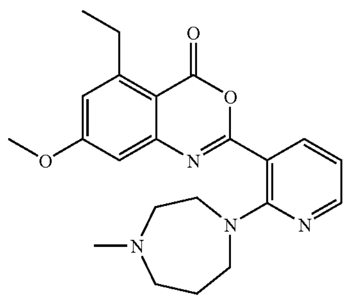 | 395.1 [M + H]+ | A |
| 196 | 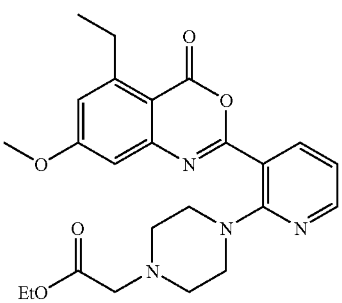 | 453.1 [M + H]+ | A |
| 197 | 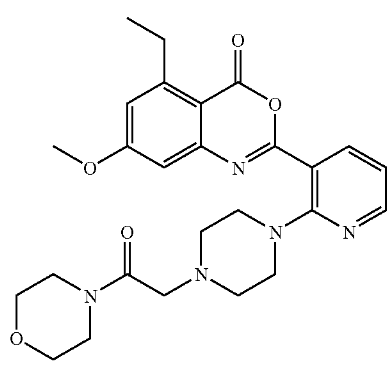 | 494.1 [M + H]+ | A |

TABLE 1-continued
Exemplary compounds and their activity
| Compound | Structure | Electrospray mass spectrometry characterization data | HNE IC$_{50}$ (nM) |
|---|---|---|---|
| 198 | 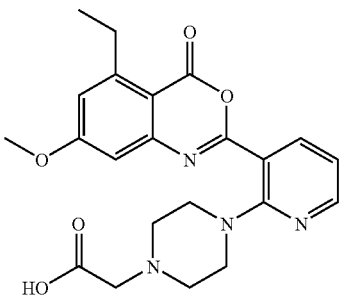 | 425.1 [M + H]+ | B |
| 199 | 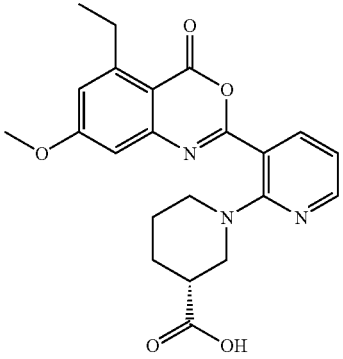 | 410.1 [M + H]+ | B |
| 200 | 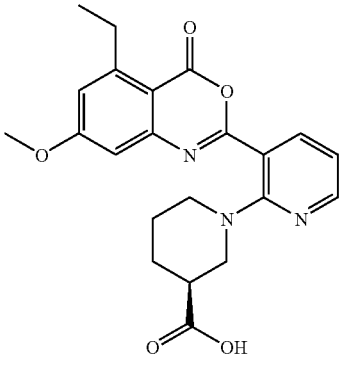 | 410.1 [M + H]+ | B |
| 201 | 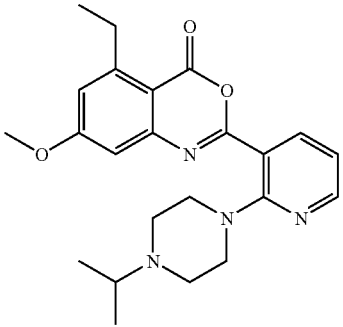 | 409.1 [M + H]+ | B |

TABLE 1-continued

Exemplary compounds and their activity

| Compound | Structure | Electrospray mass spectrometry characterization data | HNE IC$_{50}$ (nM) |
|---|---|---|---|
| 202 | 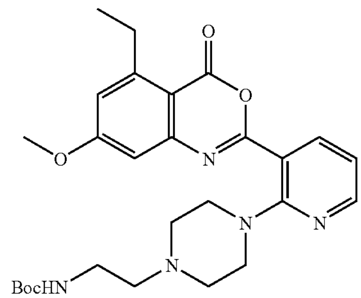 | 510.1 [M + H]+ | B |
| 203 | 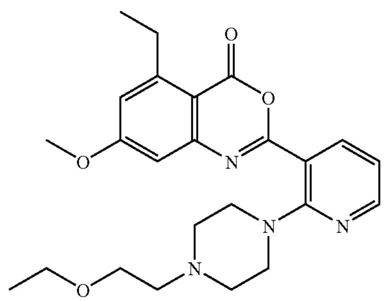 | 439.1 [M + H]+ | A |
| 204 | 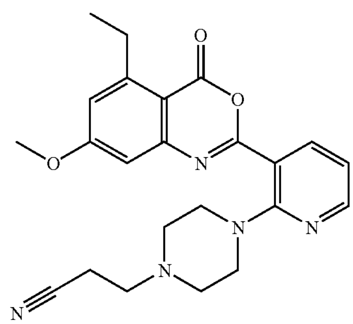 | 420.1 [M + H]+ | B |
| 205 | 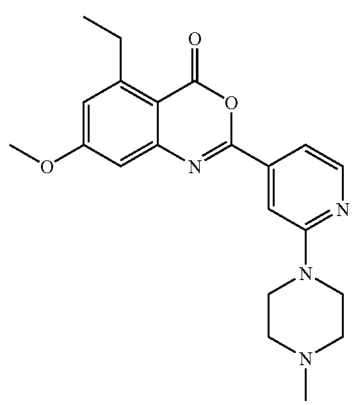 | 381.1 [M + H]+ | D |

TABLE 1-continued

Exemplary compounds and their activity

| Compound | Structure | Electrospray mass spectrometry characterization data | HNE IC$_{50}$ (nM) |
|---|---|---|---|
| 206 | 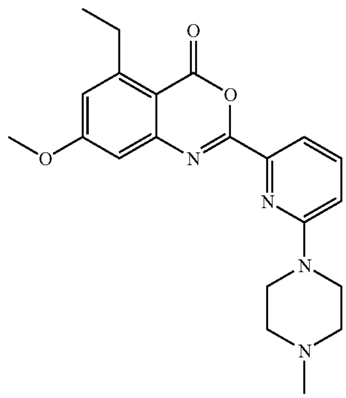 | 381.1 [M + H]+ | B |
| 207 | 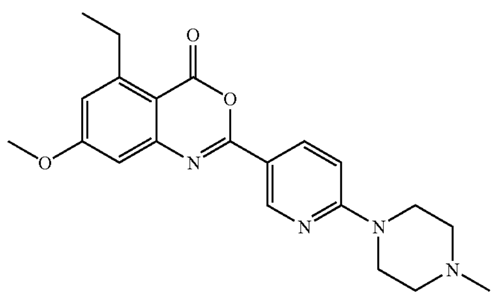 | 381.1 [M + H]+ | B |
| 208 | 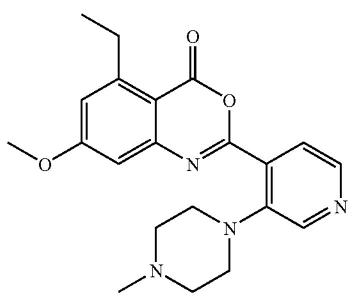 | 381.1 [M + H]+ | A |
| 209 | 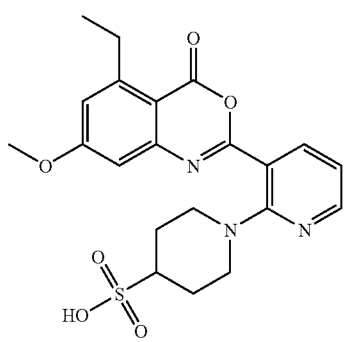 | 446.1 [M + H]+ | B |

TABLE 1-continued

Exemplary compounds and their activity

| Compound | Structure | Electrospray mass spectrometry characterization data | HNE IC$_{50}$ (nM) |
|---|---|---|---|
| 210 | 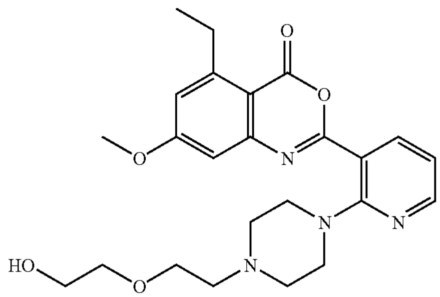 | 455.1 [M + H]+ | B |
| 211 | 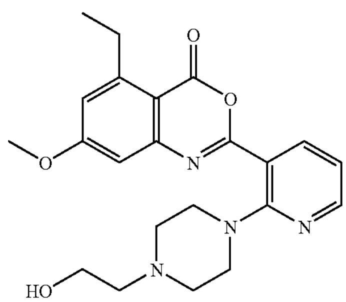 | 411.1 [M + H]+ | A |
| 212 | 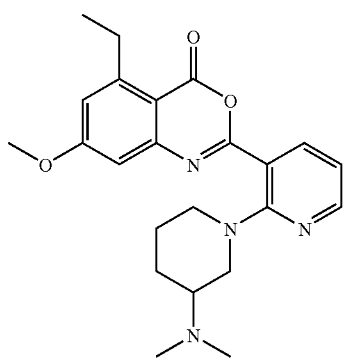 | 409.1 [M + H]+ | B |
| 213 | 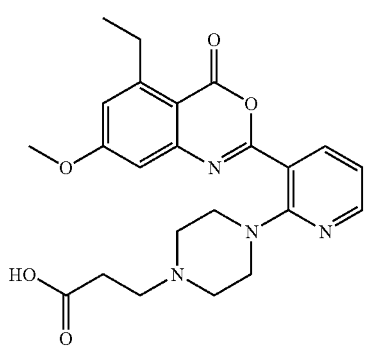 | 439.1 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 214 | 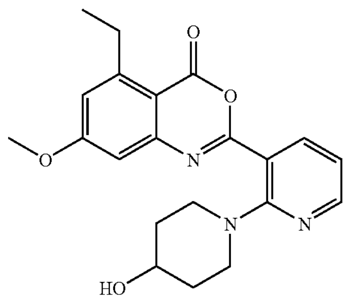 | 382.1 [M + H]+ | A |
| 215 | 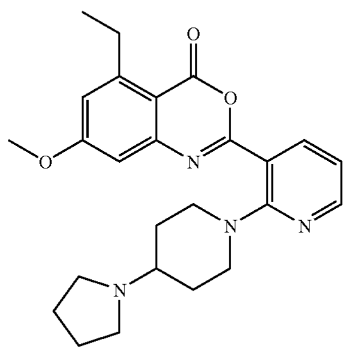 | 435.1 [M + H]+ | A |
| 216 | 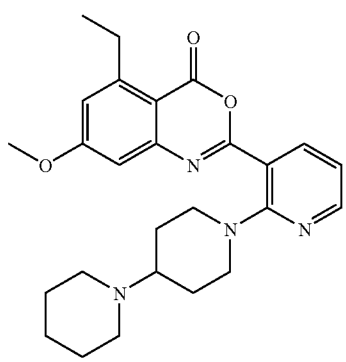 | 449.1 [M + H]+ | A |
| 217 | 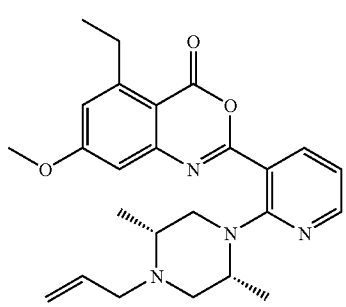 | 435.1 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 218 | 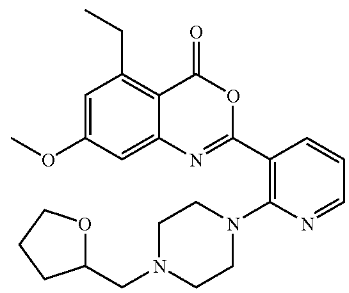 | 451.1 [M + H]+ | A |
| 219 | 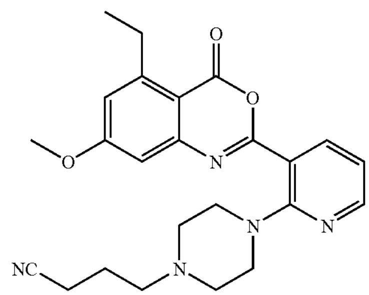 | 434.1 [M + H]+ | B |
| 220 | 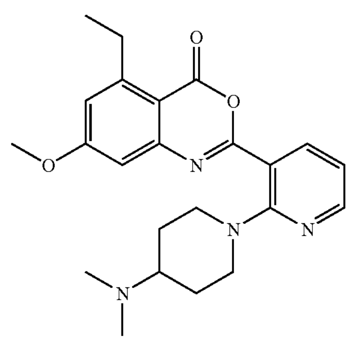 | 409.1 [M + H]+ | B |
| 221 | 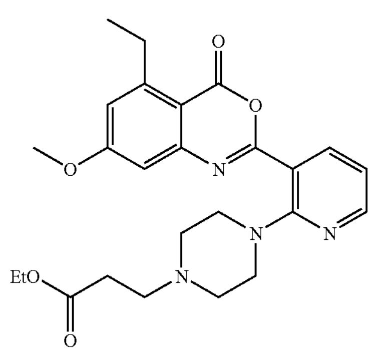 | 467.1 [M + H]+ | B |

TABLE 1-continued

Exemplary compounds and their activity

| Compound | Structure | Electrospray mass spectrometry characterization data | HNE IC$_{50}$ (nM) |
|---|---|---|---|
| 222 | 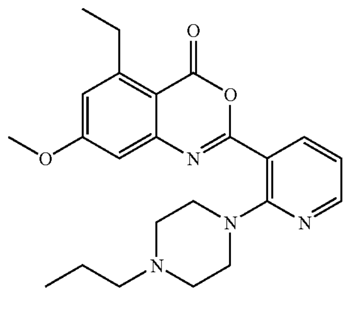 | 409.1 [M + H]+ | B |
| 223 | 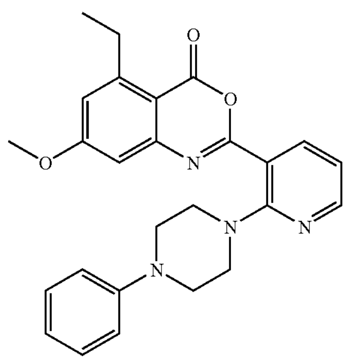 | 443.1 [M + H]+ | C |
| 224 | 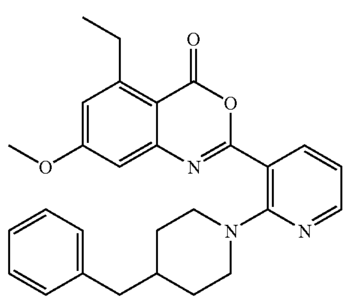 | 456.1 [M + H]+ | C |
| 225 | 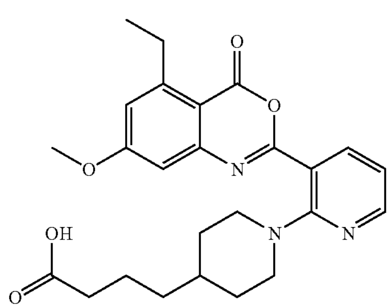 | 452.1 [M + H]+ | B |

TABLE 1-continued

Exemplary compounds and their activity

| Compound | Structure | Electrospray mass spectrometry characterization data | HNE IC$_{50}$ (nM) |
|---|---|---|---|
| 226 | 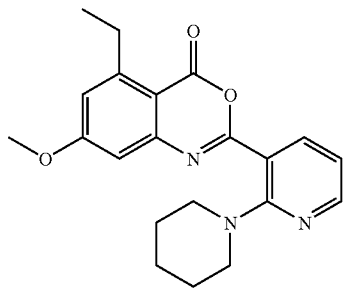 | 366.1 [M + H]+ | B |
| 227 | 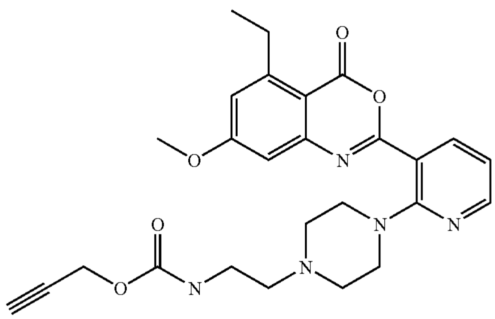 | 492.1 [M + H]+ | B |
| 228 | 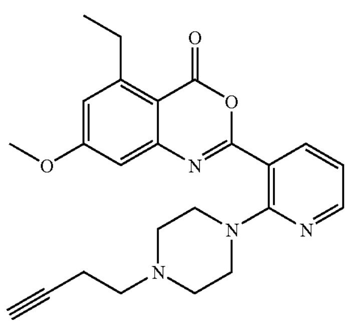 | 419.1 [M + H]+ | A |
| 229 | 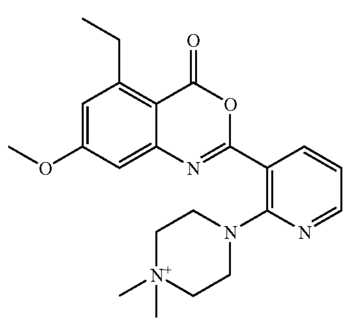 | 395.0 [M]+ | A |

TABLE 1-continued

Exemplary compounds and their activity

| Compound | Structure | Electrospray mass spectrometry characterization data | HNE IC$_{50}$ (nM) |
|---|---|---|---|
| 230 | 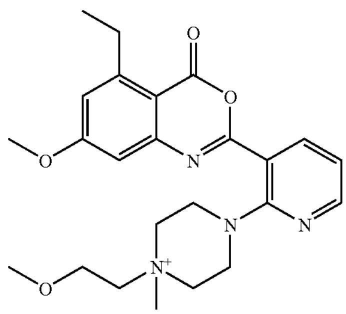 | 439.0 [M]+ | A |
| 231 | 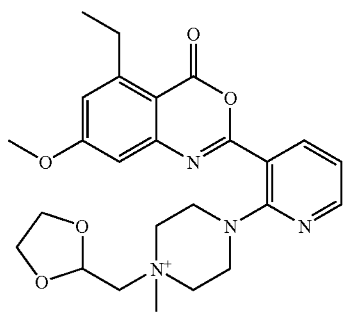 | 467.1 [M]+ | A |
| 232 | 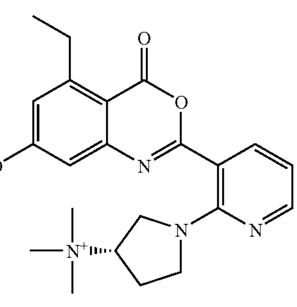 | 409.1 [M]+ | A |
| 233 | 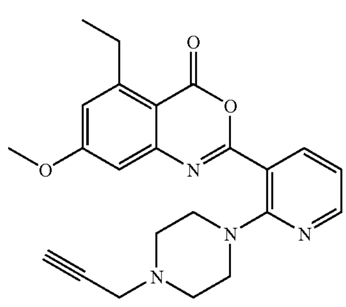 | 405.0 [M + H]+<br>427.0 [M + Na]+ | B |

TABLE 1-continued

Exemplary compounds and their activity

| Compound | Structure | Electrospray mass spectrometry characterization data | HNE IC$_{50}$ (nM) |
|---|---|---|---|
| 234 | 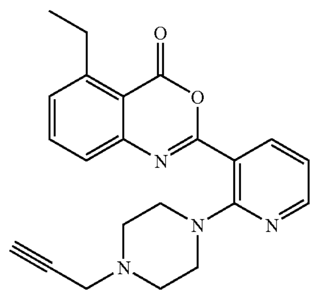 | 375.1 [M + H]+ | A |
| 235 | 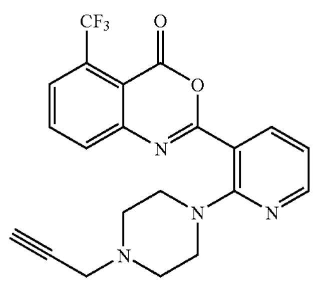 | 415.1 [M + H]+ | A |
| 236 | 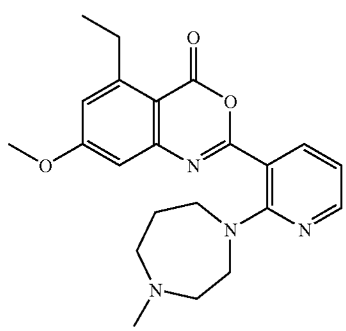 | 395.1 [M + H]+ | A |
| 237 | 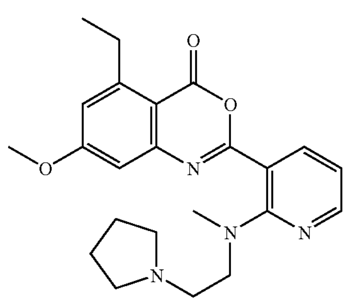 | 409.2 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 238 | 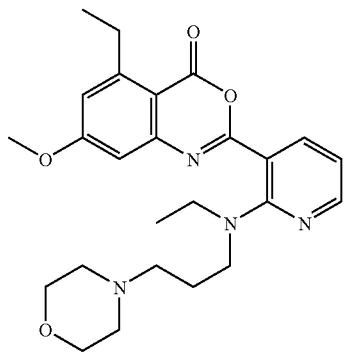 | 453.2 [M + H]+ | A |
| 239 | 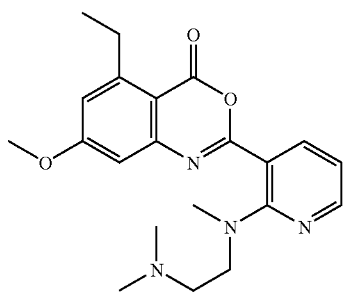 | 383.2 [M + H]+ | A |
| 240 | 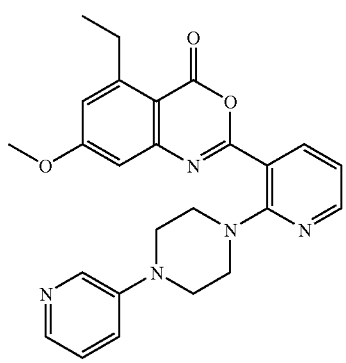 | 444.2 [M + H]+<br>466.1 [M + Na]+ | A |
| 241 | 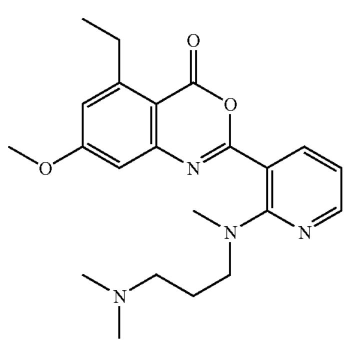 | 397.2 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 242 | 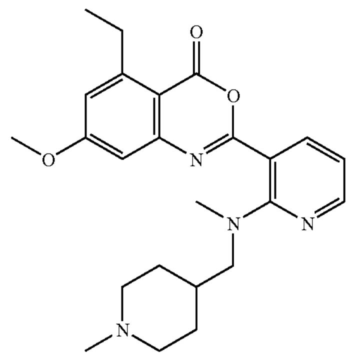 | 423.2 [M + H]+ | A |
| 243 | 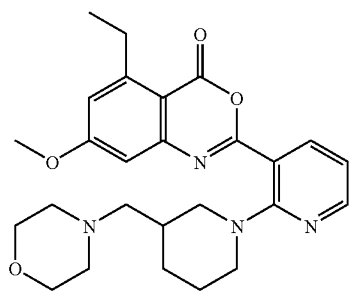 | 465.2 [M + H]+ | B |
| 244 | 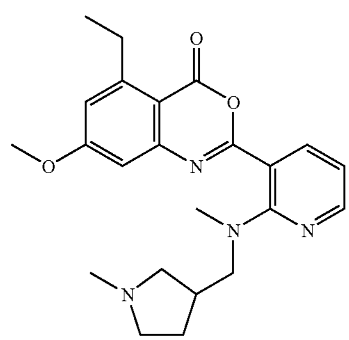 | 409.2 [M + H]+ | A |
| 245 | 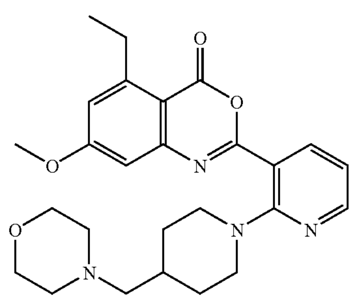 | 465.2 [M + H]+<br>487.2 [M + Na]+ | A |

TABLE 1-continued

Exemplary compounds and their activity

| Compound | Structure | Electrospray mass spectrometry characterization data | HNE IC$_{50}$ (nM) |
|---|---|---|---|
| 246 | 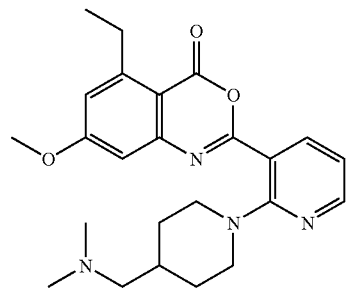 | 423.2 [M + H]+<br>445.2 [M + Na]+ | B |
| 247 | 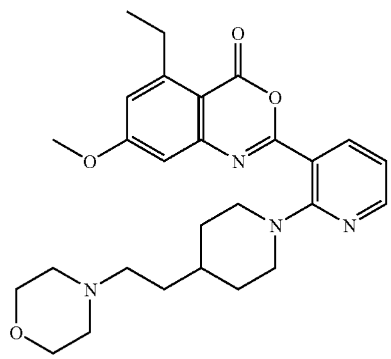 | 479.2 [M + H]+ | A |
| 248 | 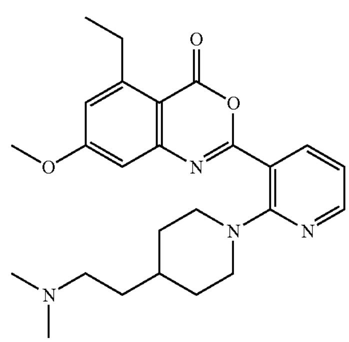 | 437.2 [M + H]+<br>459.2 [M + Na]+ | A |
| 250 | 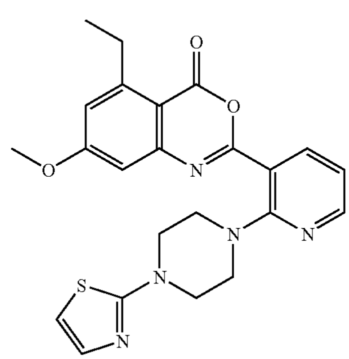 | 450.1 [M + H]+<br>472.1 [M + Na]+ | A |

TABLE 1-continued

Exemplary compounds and their activity

| Compound | Structure | Electrospray mass spectrometry characterization data | HNE IC$_{50}$ (nM) |
|---|---|---|---|
| 251 | 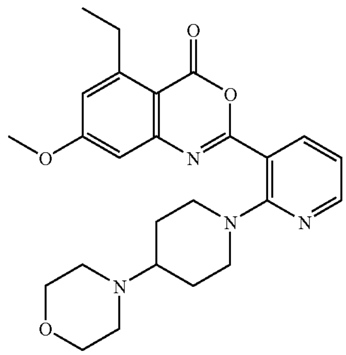 | 451.2 [M + H]+<br>473.2 [M + Na]+ | A |
| 252 | 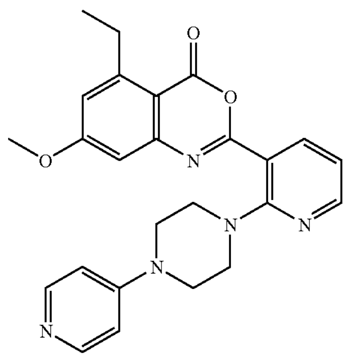 | 444.2 [M + H]+ | A |
| 253 | 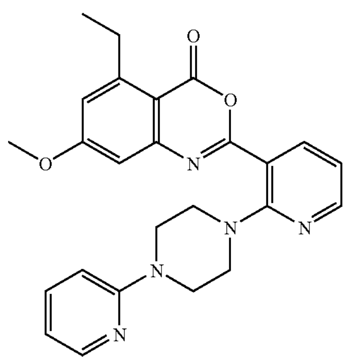 | 444.2 [M + H]+<br>466.2 [M + Na]+ | A |
| 254 | 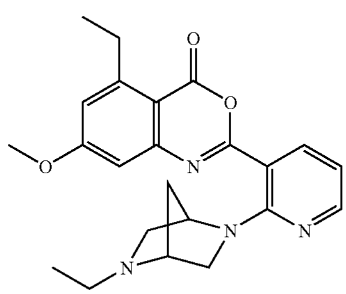 | 407.2 [M + H]+ | B |

TABLE 1-continued

Exemplary compounds and their activity

| Compound | Structure | Electrospray mass spectrometry characterization data | HNE IC$_{50}$ (nM) |
|---|---|---|---|
| 255 | 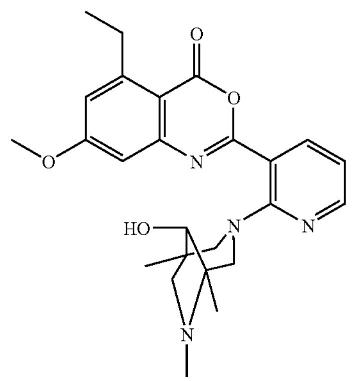 | 465.2 [M + H]+ | A |
| 257 | 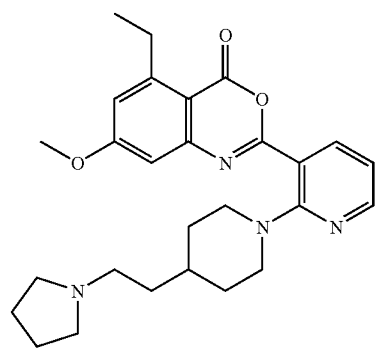 | 463.2 [M + H]+ | A |
| 258 | 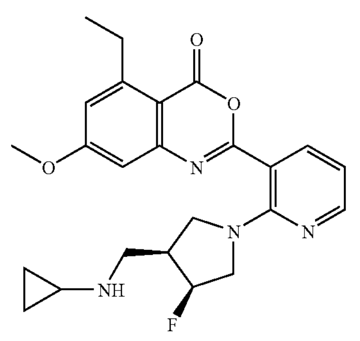 | 439.2 [M + H]+<br>461.2 [M + Na]+ | B |
| 259 | 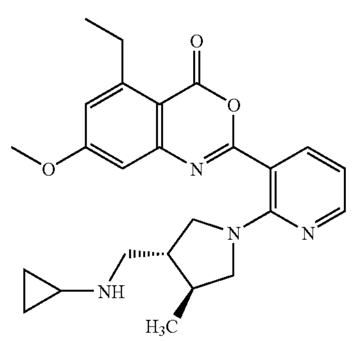 | 435.2 [M + H]+<br>457.2 [M + Na]+ | B |

TABLE 1-continued

Exemplary compounds and their activity

| Compound | Structure | Electrospray mass spectrometry characterization data | HNE IC$_{50}$ (nM) |
|---|---|---|---|
| 260 | 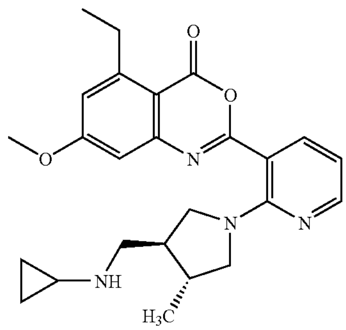 | 435.2 [M + H]+ | B |
| 261 | 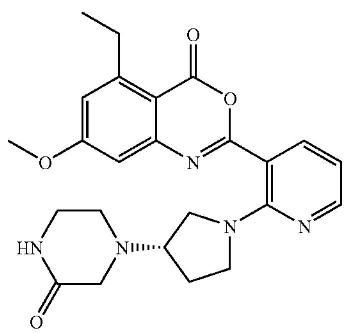 | 450.2 [M + H]+ | A |
| 262 | 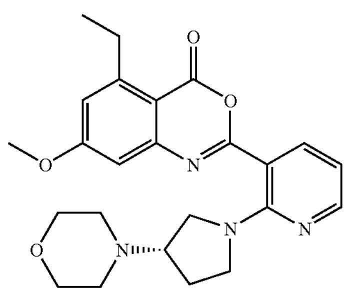 | 437.2 [M + H]+<br>459.2 [M + Na]+ | A |
| 263 | 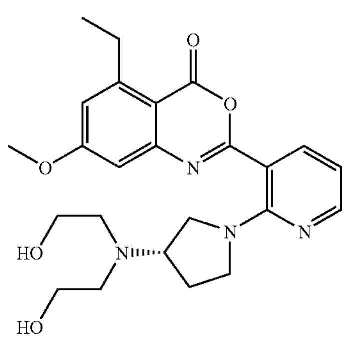 | 455.2 [M + H]+<br>477.2 [M + Na]+ | A |

TABLE 1-continued

Exemplary compounds and their activity

| Compound | Structure | Electrospray mass spectrometry characterization data | HNE IC$_{50}$ (nM) |
|---|---|---|---|
| 264 | 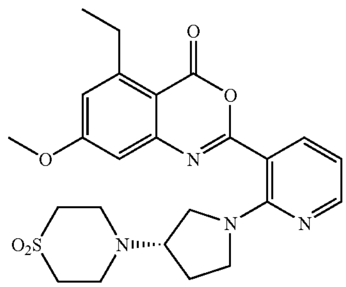 | 485.2 [M + H]+ | A |
| 265 | 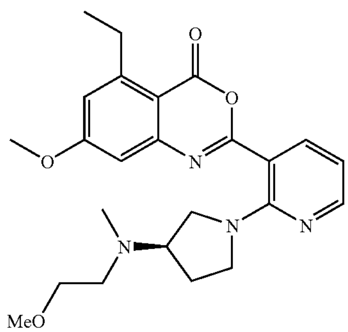 | 439.2 [M + H]+<br>461.2 [M + Na]+ | A |
| 266 | 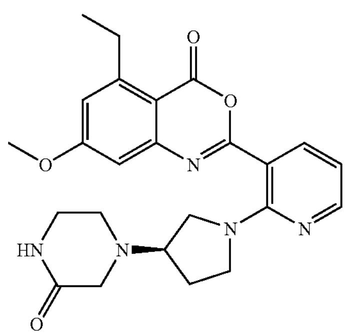 | 450.2 [M + H]+ | A |
| 267 | 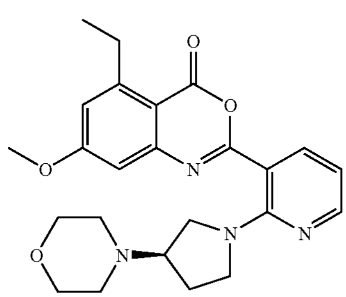 | 437.2 [M + H]+<br>459.2 [M + Na]+ | A |

US 7,879,846 B2

TABLE 1-continued

Exemplary compounds and their activity

| Compound | Structure | Electrospray mass spectrometry characterization data | HNE IC$_{50}$ (nM) |
|---|---|---|---|
| 268 | 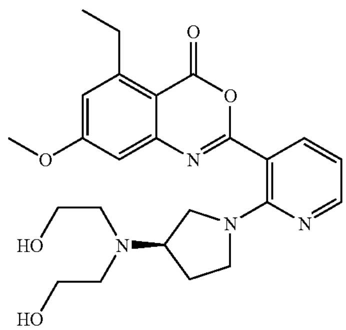 | 455.2 [M + H]+<br>477.2 [M + Na]+ | A |
| 269 | 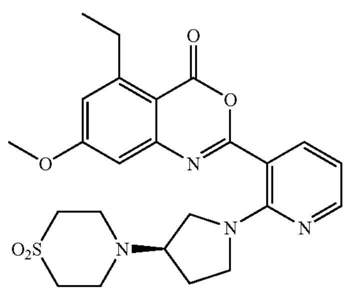 | 485.2 [M + H]+<br>507.1 [M + Na]+ | A |
| 270 | 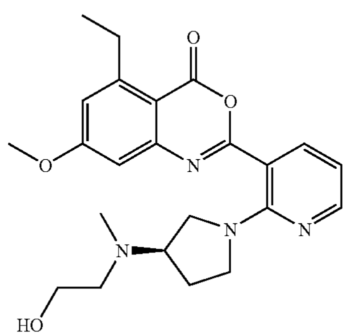 | 425.2 [M + H]+<br>447.2 [M + Na]+ | A |
| 271 | 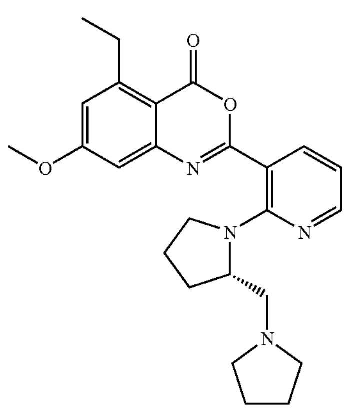 | 435.2 [M + H]+ | A |

TABLE 1-continued

Exemplary compounds and their activity

| Compound | Structure | Electrospray mass spectrometry characterization data | HNE IC$_{50}$ (nM) |
|---|---|---|---|
| 272 | 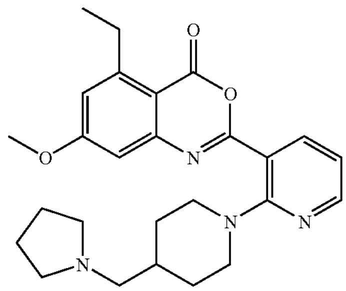 | 449.2 [M + H]+ | A |
| 273 | 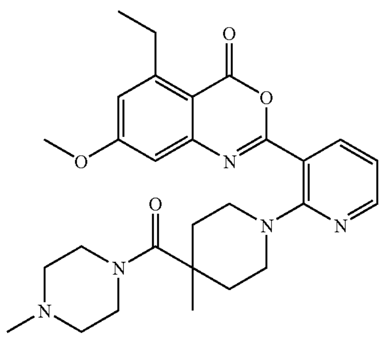 | 506.2 [M + H]+ | B |
| 274 | 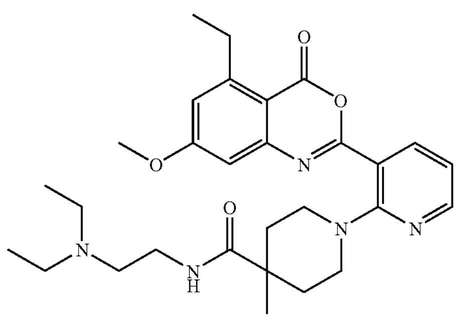 | 522.3 [M + H]+ | A |
| 275 | 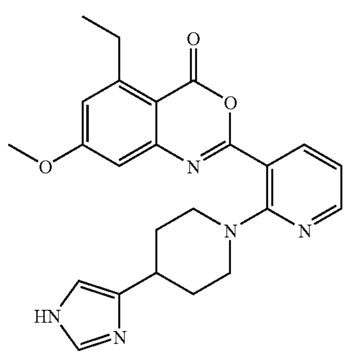 | 432.2 [M + H]+<br>454.2 [M + H]+ | A |

In Table 1, the IC$_{50}$ (nM) for human neutrophil elastase are represented as follows: A≦15; B=16-60; C=61-150; D>150 and ND=no data.

Example 14

Neutrophil Elastase-Induced Lung Hemorrhagic Assay

This in vivo assay is based on estimating the amount of hemorrhage in the lung following intratracheal administration of human neutrophil elastase (HNE). Hemorrhage is quantified by measuring the concentration of hemoglobin in the bronchoalveolar lavage fluid (BALF).

Compounds were dissolved in DMSO or saline and administered intravenously to male balb/c mice (22-30 g) at a fixed volume of 0.01 mL/10 g or 0.1 mL/10 g body weight, respectively. DMSO or saline served as vehicle controls. Mice were anesthetized with halothane and the trachea exposed by a small incision in the neck. Ten minutes after compound administration, mice received 7.5 units/animal of HNE (Elastin Products Co.) dissolved in 25 mL saline. Three hours after HNE instillation, the animals were euthanized with an overdose of urethane. The thorax was opened and the lungs were lavaged via tracheal cannula with 1 mL solution consisting of 0.4% trisodium citrate and 0.85% sodium chloride. Triton X-100 was added to the collected BALF at a final concentration of 0.2% (v/v) to ensure cell disruption. The hemoglobin concentration in the BALF was determined by measuring the absorbance at 405 nm. Results are reported in Table 2 as % inhibition of HNE-induced hemorrhage with respect to vehicle-treated controls.

TABLE 2

In vivo activity of compounds

| Compound | Structure | % Inhibition in Murine Lung Hemorrhage Model @ 10 mg/kg |
|---|---|---|
| 2 | (structure) | C |
| 4 | (structure) | C |
| 12 | (structure) | NI |

TABLE 2-continued
In vivo activity of compounds
| Compound | Structure | % Inhibition in Murine Lung Hemorrhage Model @ 10 mg/kg |
|---|---|---|
| 13 | 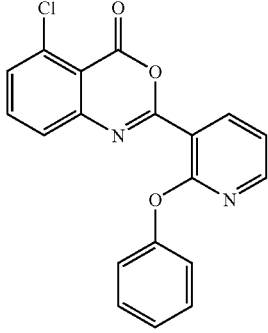 | NI |
| 16 | 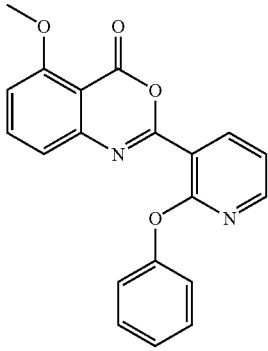 | C |
| 18 | 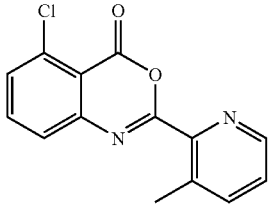 | A |
| 21 | 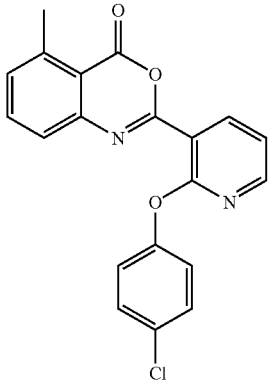 | A |

TABLE 2-continued
In vivo activity of compounds
| Compound | Structure | % Inhibition in Murine Lung Hemorrhage Model @ 10 mg/kg |
|---|---|---|
| 25 | 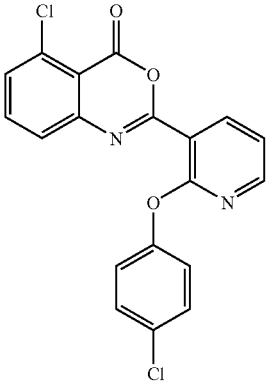 | NI |
| 26 | 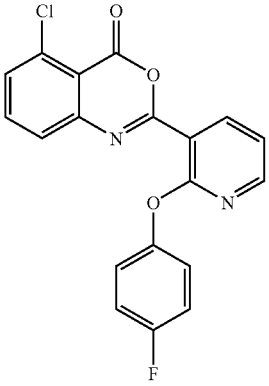 | B |
| 31 | 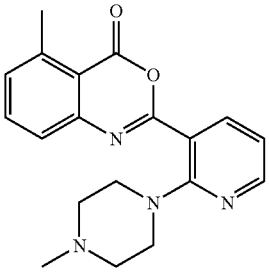 | C |
| 35 | 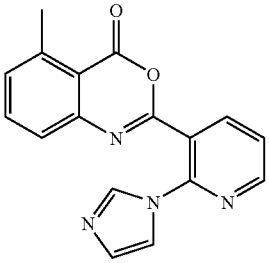 | B |

TABLE 2-continued

In vivo activity of compounds

| Compound | Structure | % Inhibition in Murine Lung Hemorrhage Model @ 10 mg/kg |
|---|---|---|
| 36 | 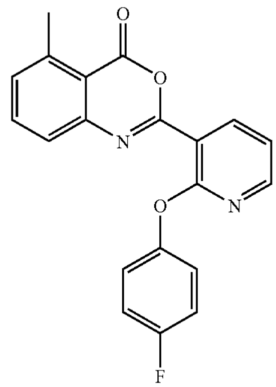 | C |
| 39 | 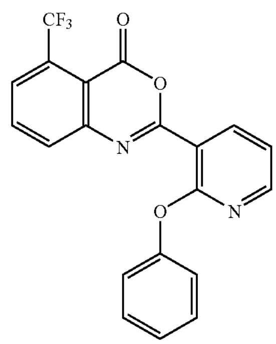 | C |
| 41 | 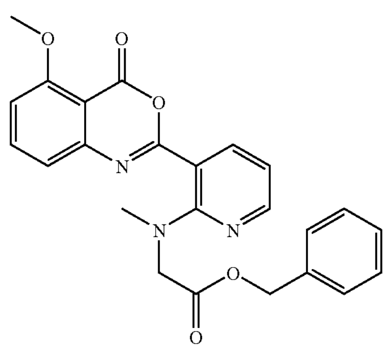 | NI |
| 44 | 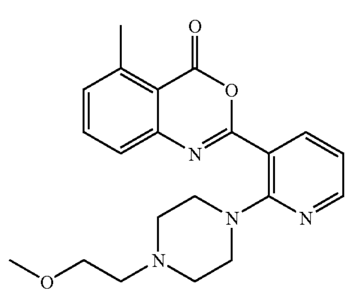 | B |

TABLE 2-continued

In vivo activity of compounds

| Compound | Structure | % Inhibition in Murine Lung Hemorrhage Model @ 10 mg/kg |
|---|---|---|
| 46 | 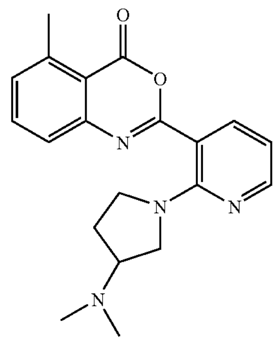 | C |
| 49 | 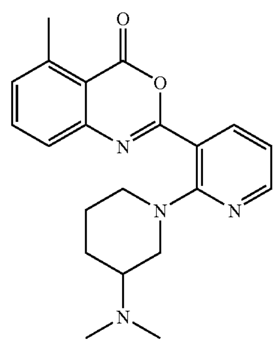 | A |
| 50 | 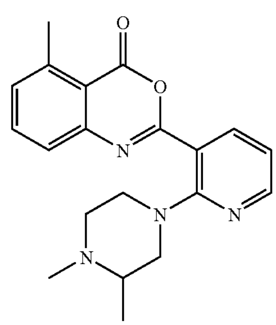 | B |
| 52 | 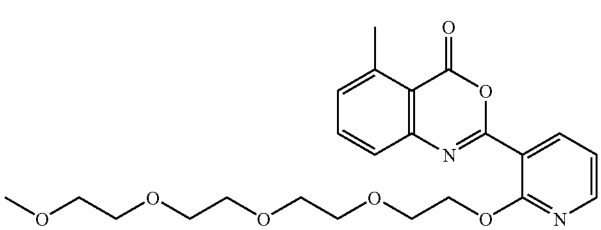 | B |

TABLE 2-continued

In vivo activity of compounds

| Compound | Structure | % Inhibition in Murine Lung Hemorrhage Model @ 10 mg/kg |
|---|---|---|
| 53 | 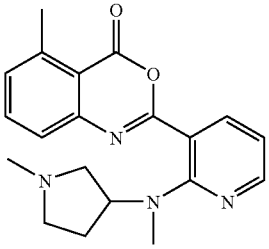 | B |
| 54 | 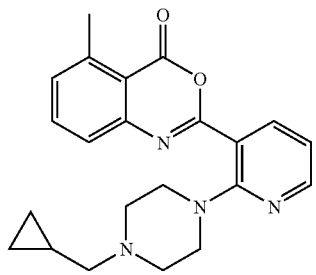 | C |

In Table 2, the % inhibition values are represented as follows: A≦10; B=11-30 and C>30 and NI=no inhibition.

Example 15

Acute Lung Injury Model (Lung Permeability Assay)

Adult male Wistar rats (200-250 g) were anesthetized with an intraperitoneal of pentobarbital (30 mg/kg). Under the anesthesia, lipopolysaccharide (LPS) (100 μL/100 μL/animal) or physiological saline (100 μL/animal) was intratracheally injected. Increase of lung permeability after LPS instillation was measured by Evan's blue dye (EBD) leakage from blood. EBD (40 mg/5 mL/kg) was administered via tail vein 5 hours after the LPS challenge. At 6 hours, animals were exsanguinated by cardiac puncture under deep anesthesia and the pulmonary vessels were perfused with 20 mL saline to ensure the removal of EBD from the vascular spaces. Lungs were removed and EBD was extracted in 6 mL formamide at 65° C. overnight. EBD content was determined by measuring absorbance at 620 nm using a spectrophotometer. The test compound was dissolved in saline with a small amount of 1 N HCl and continuously infused intravenously at a rate of 10 mg/kg/hr over 6 hours starting just after LPS challenge. Results are reported in Table 3.

TABLE 3

In vivo activity of compounds (ALI model)

| Compound | Structure | % Inhibition in the ALI model |
|---|---|---|
| 208 | 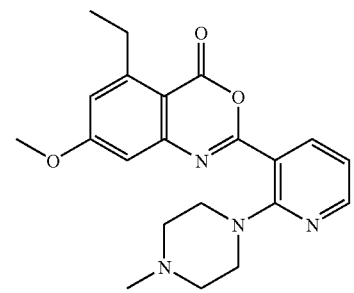 | C |
| 132 | 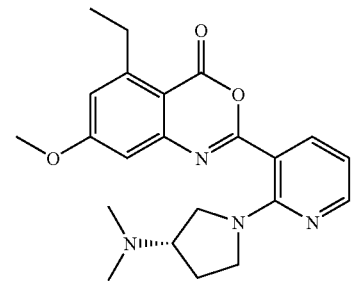 | C |

TABLE 3-continued

In vivo activity of compounds (ALI model)

| Compound | Structure | % Inhibition in the ALI model |
|---|---|---|
| 134 | 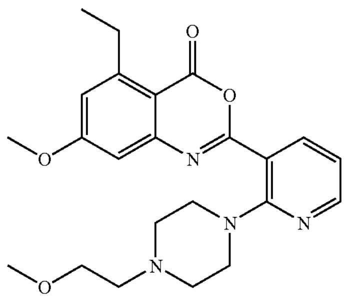 | B |

In Table 3, the % inhibition values are represented as follows: B=11-30 and C>30.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of formula I:

or a pharmaceutically acceptable derivative thereof,
wherein A is pyridinyl connected to the benzoxazine core by a carbon atom;
$R^2$ is halo, cyano, thiocyano, selenocyano, azide, alkyl, alkenyl, alkynyl, haloalkyl, cycloalkyl, $NR^aR^b$, $—OR^c$, $—C(O)R^c$ or $—S(O)_mR^c$;
$R^a$, $R^b$ and $R^c$ are each independently selected from hydrogen, alkyl, alkenyl, alkynyl, haloalkyl, cycloalkyl, aryl, heterocyclyl and heteroaryl;
$R^1$ is $—OR^3$, $—SR^3$; $—NO_2$ or $—NR^4R^5$;
each $R^3$ is independently selected from alkyl, alkenyl, alkynyl, haloalkyl, heteroalkyl, cycloalkyl, aryl, heterocyclyl and heteroaryl;
$R^4$ and $R^5$ are selected as follows:
i) $R^4$ and $R^5$ are each independently selected from hydrogen, alkyl, alkenyl, alkynyl, haloalkyl, cycloalkyl, aryl, heterocyclyl and heteroaryl, provided that at least one of $R^4$ or $R^5$ is not hydrogen; or
ii) $R^4$ and $R^5$ together with the nitrogen atom on which they are substituted form a 5-10 membered substituted or unsubstituted heterocyclyl or heteroaryl ring, wherein the substituents when present are selected from one or more $Q^1$;
m is 0-2;
each n is independently 0 to 6;
with a proviso that when A is 3-pyridinyl and $R^2$ is halo or methyl, then $R^1$ is not 2-phenoxy;
$R^1$, $R^2$, $R^3$, $R^4$ and $R^5$ are optionally substituted with 1, 2, 3 or 4 substituents, each independently selected from $Q^1$, where $Q^1$ is halo, cyano, thiocyano, selenocyano, azide, hydroxy, oxo, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, heteroalkyl, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, heterocyclylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{51}R^{52}R^{53}$, $P(R^{50})_2$, $P(=O)(R^{50})_2$, $OP(=O)(R^{50})_2$, $—NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1, 2 or 1, 3 arrangement, together form —O—(CH$_2$)$_y$—O—, —S—(CH$_2$)$_y$—O— or —S—(CH$_2$)$_y$—S—, where y is 1 or 2; or two $Q^1$ groups, which substitute the same atom, together form alkylene; and each $Q^1$ is independently unsubstituted or substituted with one, two or three substituents, each independently selected from $Q^2$;

each $Q^2$ is independently halo, cyano, thiocyano, selenocyano, azide, hydroxy, oxo, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, heteroalkyl, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, heterocyclylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylaminocarbonyloxy, diarylaminocarbonyloxy, alkynylalkoxycarbonyl, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N', N'-dialkylureido, N,N'-diaryl-N'-alkylureido, N,N', N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{51}$R$^{52}$R$^{53}$, P(R$^{50}$)$_2$, P(=O)(R$^{50}$)$_2$, OP(=O)(R$^{50}$)$_2$, —NR$^{60}$C(=O)R$^{63}$, dialkylphosphonyl, alkylarylphosphonyl, diarylphosphonyl, hydroxyphosphonyl, alkylthio, arylthio, perfluoroalkylthio, hydroxycarbonylalkylthio, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1, 2 or 1, 3 arrangement, together form —O—(CH$_2$)$_y$—O—, —S—(CH$_2$)$_y$—O— or —S—(CH$_2$)$_y$—S—, where y is 1 or 2; or two $Q^2$ groups, which substitute the same atom, together form alkylene;

each $Q^3$ is independently selected from halo, cyano, thiocyano, selenocyano, azide, hydroxy, oxo, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, heteroalkyl, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, heterocyclylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, alkynoxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{51}$R$^{52}$R$^{53}$, P(R$^{50}$)$_2$, P(=O)(R$^{50}$)$_2$, OP(=O)(R$^{50}$)$_2$, —NR$^{60}$C(=O)R$^{63}$, dialkylphosphonyl, alkylarylphosphonyl, diarylphosphonyl, hydroxyphosphonyl, alkylthio, arylthio, perfluoroalkylthio, hydroxycarbonylalkylthio, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1, 2 or 1, 3 arrangement, together form —O—

(CH$_2$)$_y$—O—, —S—(CH$_2$)$_y$—O— or —S—(CH$_2$)$_y$—S—, where y is 1 or 2; or two Q$^3$ groups, which substitute the same atom, together form alkylene; and each Q$^3$ is independently unsubstituted or substituted with one, two or three substituents, each independently selected from Q$^2$;

R$^{50}$ is hydroxy, alkoxy, aralkoxy, alkyl, heteroaryl, heterocyclyl, aryl or —NR$^{70}$R$^{71}$, where R$^{70}$ and R$^{71}$ are each independently hydrogen, alkyl, aralkyl, aryl, heteroaryl, heteroaralkyl or heterocyclyl, or R$^{70}$ and R$^{71}$ together form alkylene, azaalkylene, oxaalkylene or thiaalkylene;

R$^{51}$, R$^{52}$ and R$^{53}$ are each independently hydrogen, alkyl, aryl, aralkyl, heteroaryl, heteroaralkyl, heterocyclyl or heterocyclylalkyl;

R$^{60}$ is hydrogen, alkyl, aryl, aralkyl, heteroaryl, heteroaralkyl, heterocyclyl or heterocyclylalkyl; and R$^{63}$ is alkoxy, aralkoxy, alkyl, heteroaryl, heterocyclyl, aryl or —NR$^{70}$R$^{71}$.

2. The compound of claim 1, wherein R$^1$ is —OR$^3$, —SR$^3$ or —NR$^4$R$^5$.

3. The compound of claim 1, wherein A is 3-pyridinyl.

4. The compound of claim 1, wherein A is 2-pyridinyl.

5. The compound of claim 1, wherein A is 4-pyridinyl.

6. The compound of claim 1, wherein R$^2$ is halo, alkyl, haloalkyl or alkoxy.

7. The compound of claim 1, wherein R$^2$ is chloro, bromo, methyl, ethyl, trifluoromethyl or methoxy.

8. The compound of claim 1, wherein R$^1$ is —OR$^3$ or —NR$^4$R$^5$.

9. The compound of claim 1, wherein R$^1$ is —NR$^4$R$^5$.

10. The compound of claim 1, wherein R$^3$ is alkyl, haloalkyl, heteroalkyl, aryl, haloaryl, alkoxyalkyl, alkylaryl or arylsulfonylalkyl.

11. The compound of claim 1, wherein R$^3$ is methyl, ethyl, phenyl, 4-chlorophenyl, 4-fluorophenyl, 4-tolyl, phenylsulfonylethyl, 3,4-methylenedioxybenzyl or dimethoxyaminoethyl.

12. The compound of claim 1, wherein R$^4$ is hydrogen, lower alkyl or alkoxyalkyl.

13. The compound of claim 1, wherein R$^4$ is hydrogen, methyl or methoxyethyl.

14. The compound of claim 1, wherein R$^5$ is aralkyloxycarbonylalkyl, dialkylaminoalkyl, heterocyclylalkyl, alkylheterocyclyl or alkoxyalkyl.

15. The compound of claim 1, wherein R$^5$ is benzyloxycarbonylmethyl, dimethylaminoethyl, 4-morpholinoethyl, N-methylpyrrolidin-3-yl or methoxyethyl.

16. The compound of claim 1, wherein R$^4$ and R$^5$ together with the nitrogen atom on which they are substituted form a 5 or 6 membered heterocyclyl or heteroaryl ring.

17. The compound of claim 1, wherein R$^4$ and R$^5$ together with the nitrogen atom on which they are substituted form a 5 or 6 membered heterocyclyl ring.

18. The compound of claim 1, wherein R$^1$ is

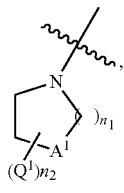

wherein A$^1$ is CR$^6$R$^7$ or NR$^6$;

R$^6$ is hydrogen, alkyl, alkenyl, alkynyl, phenyl, heteroaryl, alkoxyalkyl, cycloalkylalkyl, hydroxyalkyl, cyanoalkyl, aralkyl, heteroarylalkyl, heterocyclylalkyl, aminocarbonylalkyl, dialkylaminoalkyl, alkoxycarbonylalkyl, hydroxycarbonylalkyl, heterocyclylcarbonylalkyl, hydroxyalkoxyalkyl, alkoxycarbonylaminoalkyl, alkynoxycarbonylaminoalkyl, or imidamidyl; R$^7$ is hydrogen or alkyl;

R$^7$ is hydrogen or alkyl;

Q$^1$ is alkyl, alkoxycarbonyl, phenyl, dialkylamino, alkoxycarbonyl, dialkylaminoalkyl, aralkyl, hydroxycarbonyl, hydroxyalkyl, hydroxyalkoxyalkyl, hydroxycarbonylalkyl, heterocyclyl, heterocyclylalkyl, —N$^+$R$^{51}$R$^{52}$R$^{53}$, alkylsulfinylalkylcarbonyl, cycloalkylaminoalkyl, halo, di(hydroxyalkyl)amino, dialkylaminoalkylcarbonyl, heterocyclylcarbonyl, —SO$_3$H or alkylsulfonate;

n$_1$ is 1 or 2; and n$_2$ is 0-5.

19. The compound of claim 18, wherein R$^6$ is hydrogen, methyl, ethyl, isopropyl, 2-propenyl, 2-propynyl, 3-butynyl, phenyl, cyclopropylmethyl, 2-hydroxyethyl, hydroxycarbonylethyl, hydroxycarbonylpropyl, ethoxycarbonylethyl, methoxymethyl, ethoxymethyl, cyanoethyl, 3-cyanopropyl, dimethylaminomethyl, dimethylaminoethyl, 4-morpholinoethyl, 2-pyrimidinyl, 3-pyrimidinyl, 4-pyrimidinyl, 2-thiazolyl, 4-fluorophenylmethyl, 4-methoxyphenylmethyl, pyrrolidin-1-ylmethyl, tetrahydrofuran-2-ylmethyl, 1,3-dioxolan-2-ylmethyl, N-methylpiperidin-4-yl, ethoxycarbonylmethyl, hydroxycarbonylmethyl, morpholin-4-ylcarbonylmethyl, t-butlyoxycarbonylaminoethyl, hydroxyethoxyethyl, aminocarbonylmethyl, 2-propynyloxycarbonylaminoethyl, or —C(NH)NH$_2$.

20. The compound of claim 18, wherein Q$^1$ is methyl, ethyl, propyl, isopropyl, phenyl, dimethylamino, diethylamino, dimethylaminomethyl, dimethylaminoethyl, diethylaminomethyl, hydroxy, hydroxycarbonyl, methoxycarbonyl, ethoxycarbonyl, phenylmethyl, hydroxycarbonylpropyl, hydroxyalkyl, hydroxyalkoxyalkyl, 1-imidazolyl, 4-morpholino, morpholin-4-ylmethyl, morpholin-4-ylethyl, —N(CH$_3$)$_3^+$, methylsulfinylmethylcarbonyl, cycloalkylaminoalkyl, fluoro, di(hydroxyethyl)amino, dialkylaminoalkylcarbonyl, pyrrolidin-1-ylmethyl, pyrrolidin-1-ylethyl, cyclopropylaminomethyl, 2-oxo-piperazin-4-yl, 1,1-dioxothiomorpholin-4-yl, N-methyl-N-(methoxyethyl)amino, N-methyl-piperazin-4-ylcarbonyl, N,N-dimethylaminoethylamino(methyl)carbonyl, —SO$_3$H or —(CH$_2$)$_3$SO$_3$H.

21. The compound of claim 18, wherein R$^6$ is hydrogen, methyl, methoxymethyl or cyclopropylmethyl;

R$^7$ is hydrogen;

Q$^1$ is methyl, dimethylamino, tert-butyloxycarbonyl or methoxycarbonyl;

n$_1$ is 1 or 2; and n$_2$ is 1 or 2.

22. The compound of claim 1, wherein R$^1$ is

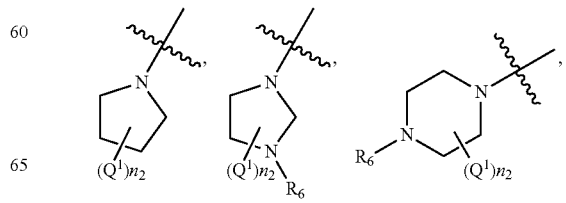

-continued

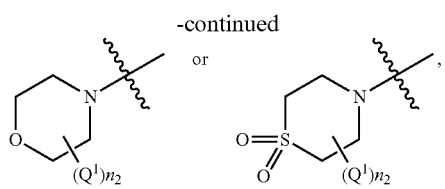

wherein R⁶ is hydrogen, alkyl, alkoxyalkyl or cycloalkylalkyl;
Q¹ is alkyl, dialkylamino or alkoxycarbonyl; and
n₂ is 0-5.

23. The compound of claim 22, wherein R⁶ is hydrogen, methyl, methoxyethyl or cyclopropylmethyl.

24. The compound of claim 22, wherein n₂ is 1 and Q¹ is methyl, dimethylamino, tert-butyloxycarbonyl or methoxycarbonyl.

25. The compound of claim 1, wherein R¹ is

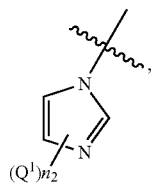

wherein Q¹ is alkyl, dialkylamino or alkoxycarbonyl; and
n₂ is 0-3.

26. The compound of claim 1, having formula:

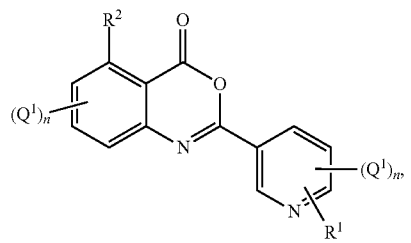

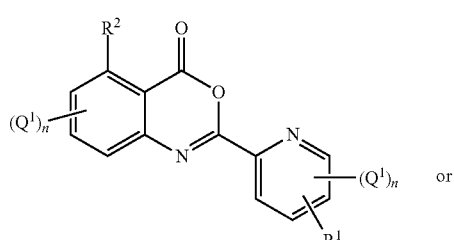

or

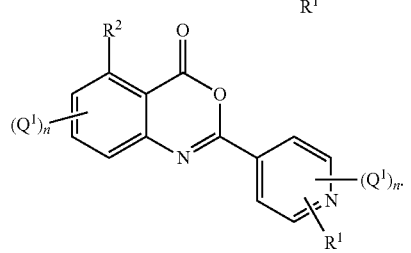

27. The compound of claim 1, having formula:

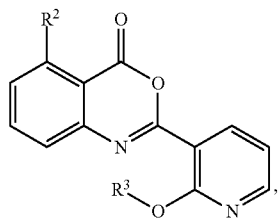

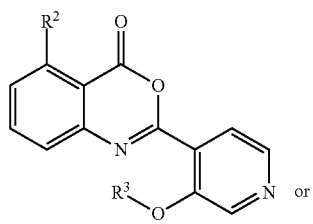

or

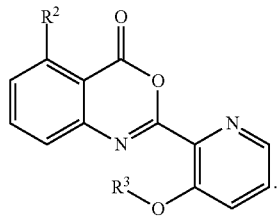

28. The compound of claim 1, having formula:

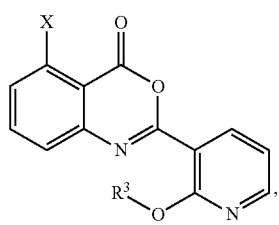

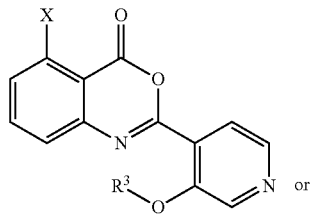

or

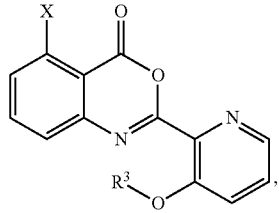

wherein X is fluoro or chloro.

29. The compound of claim 1, having formula:
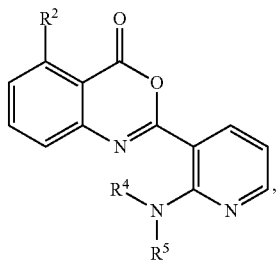
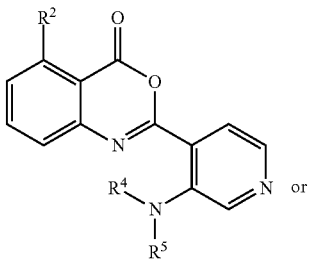 or
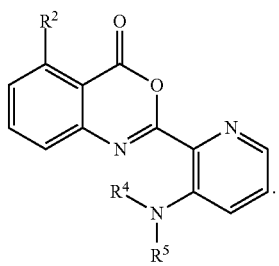
30. The compound of claim 18 having formula:
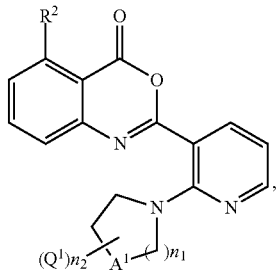
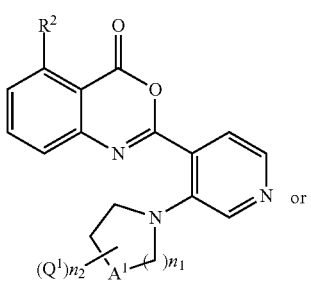 or
-continued
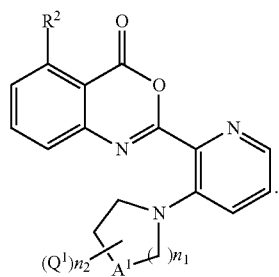
31. The compound of claim 30 having formula:
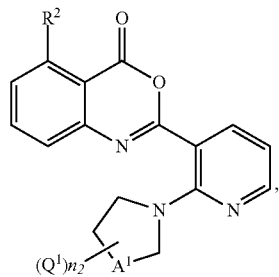
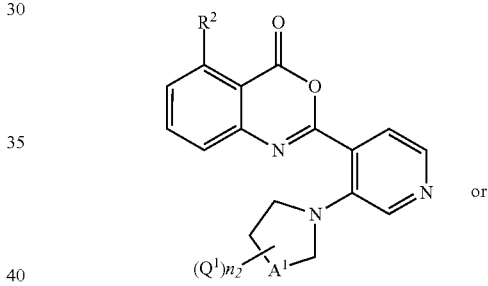 or
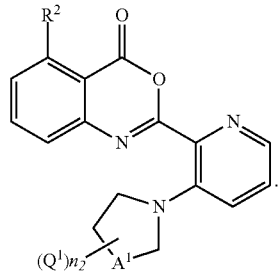
32. The compound of claim 30 having formula:
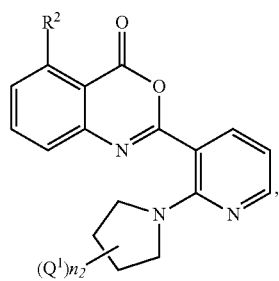

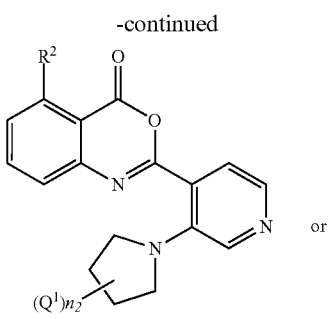

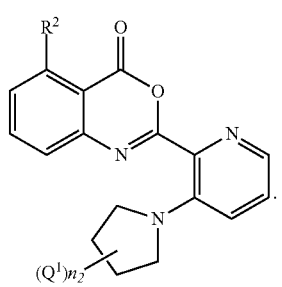

33. The compound of claim 25 having formula:

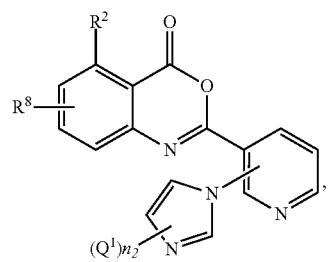

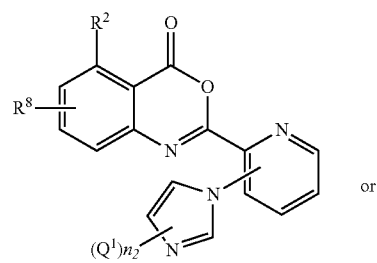

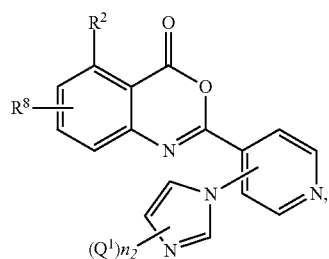

wherein $R^8$ is selected from hydrogen, alkoxy, heterocyclyl and heteroaryl.

34. The compound of claim 33 having formula:

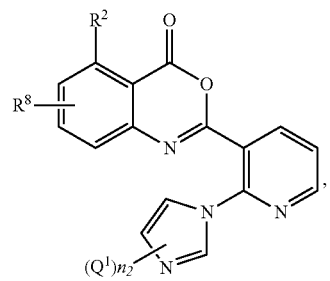

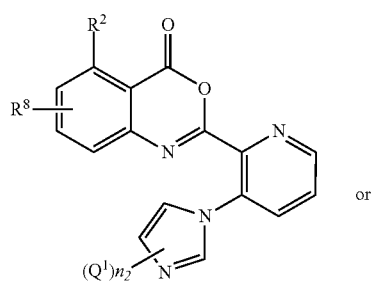

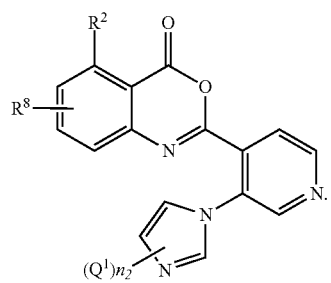

35. The compound of claim 34 having formula:

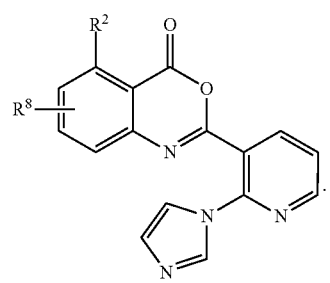

36. The compound of claims 34, wherein $R^2$ is alkyl, haloalkyl, alkoxy, amino, halo, alkylcarbonyl or alkylsulfenyl.

37. The compound of any of claims 31-33, wherein $R^2$ is methyl, ethyl, isopropyl, trifluoromethyl, methoxy, hydroxy, amino, chloro, acyl or methylsulfenyl.

38. The compound of claim 35, wherein $R^8$ is alkoxy, pyrrolyl, pyrrolidinyl, pyrazolyl, imidazolyl, triazolyl or tetrazolyl.

39. The compound of claim 1, having formula:

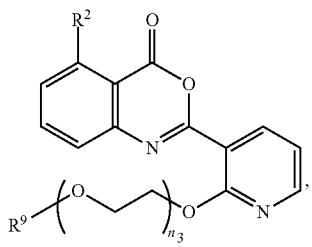

wherein R⁹ is hydrogen or unsubstituted or substituted alkyl, alkenyl, alkynyl, haloalkyl, cycloalkyl, aryl, heterocyclyl or heteroaryl and n₃ is 1-20.

40. The compound of claim 39, wherein n₃ is 3 or 4.

41. The compound of claim 39, wherein R⁹ is hydrogen, methyl, phenyl or 3-carboxypyridin-2-yl.

42. The compound of claim 1, having formula:

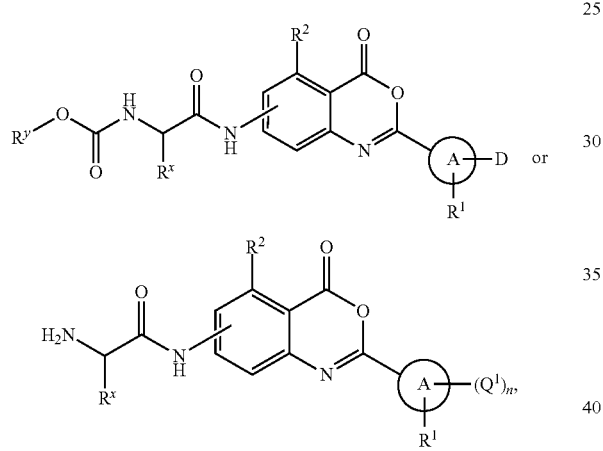

wherein R$^x$ and R$^y$ are each independently selected from hydrogen or alkyl.

43. The compound of claim 42 having formula:

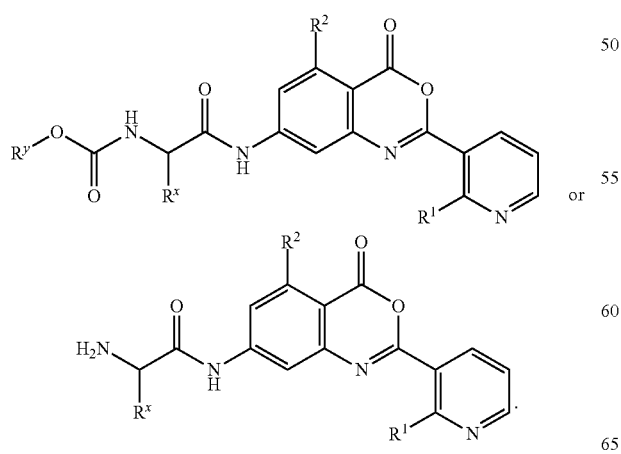

44. A compound of claim 1, selected from:

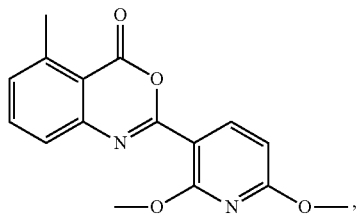

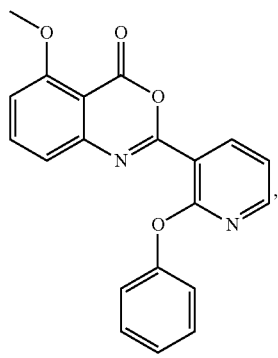

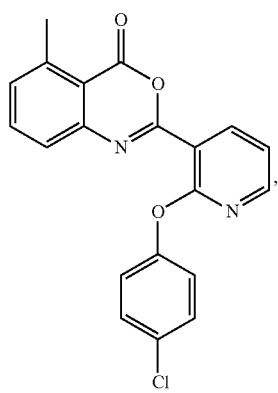

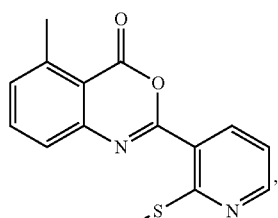

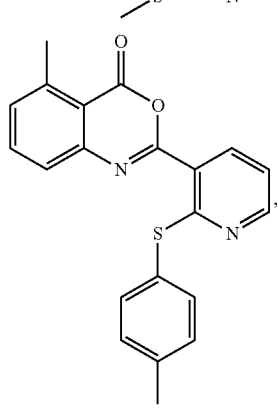

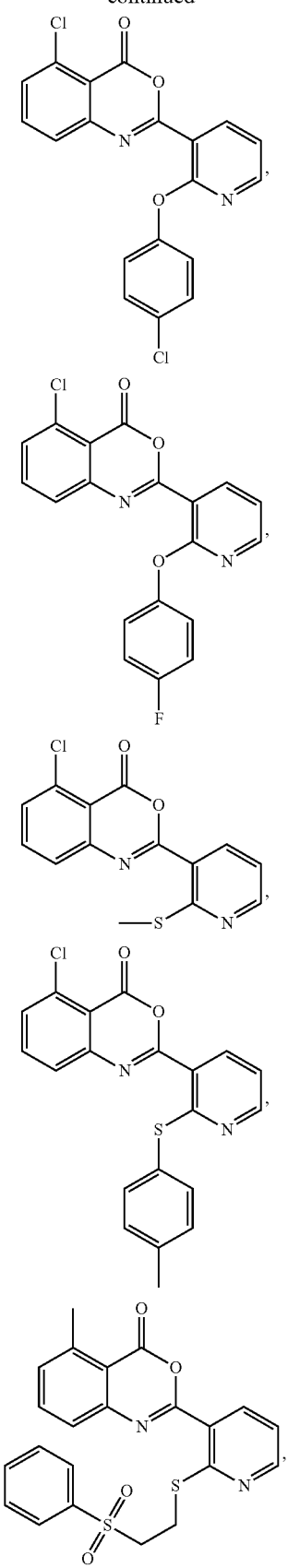
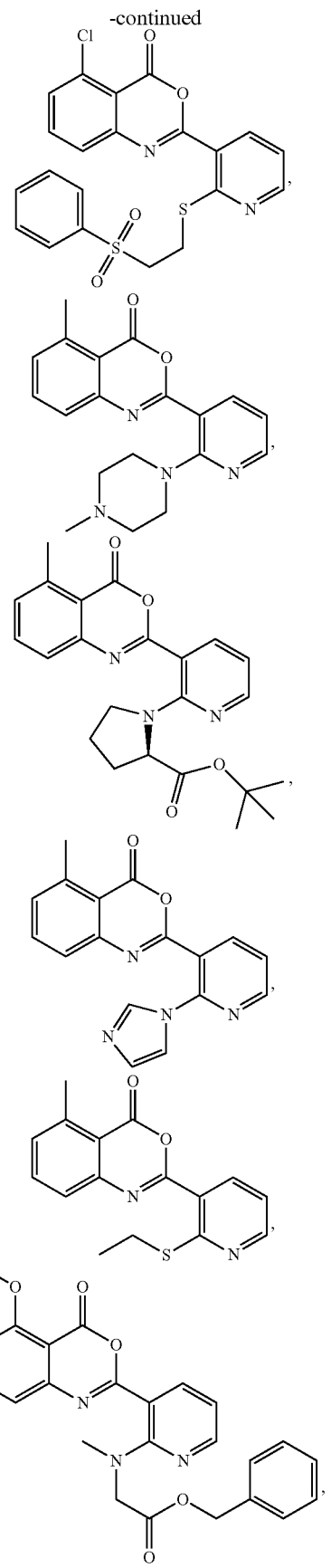

-continued
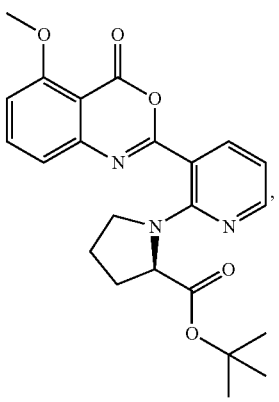
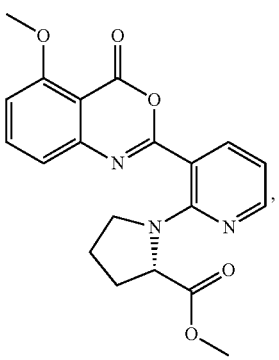
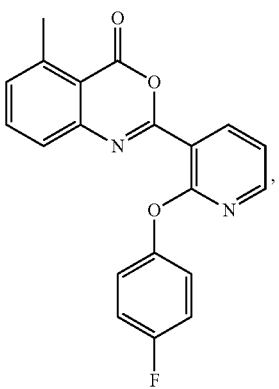
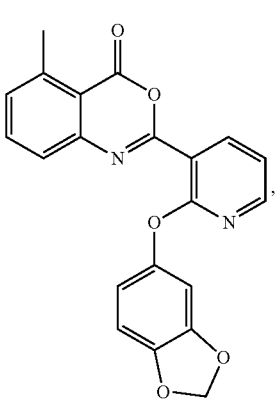
-continued
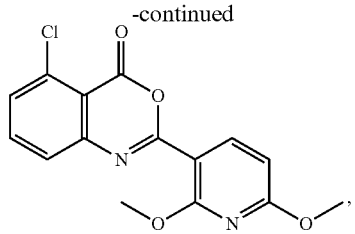
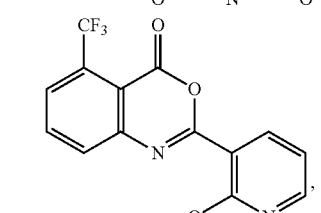
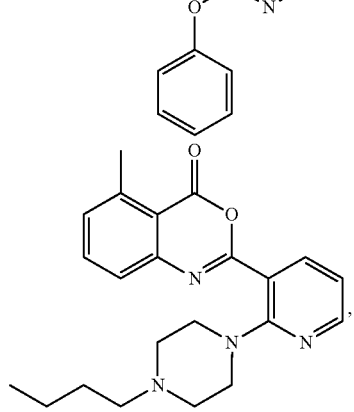
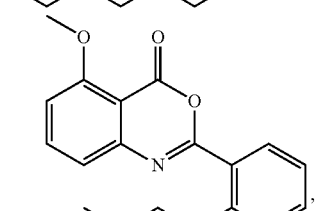
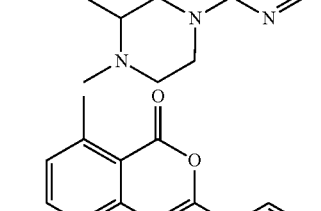
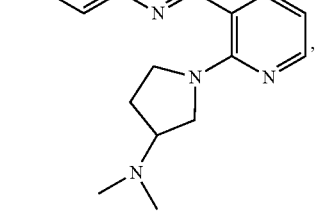
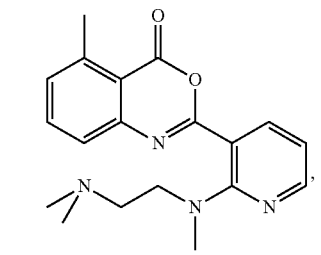

-continued
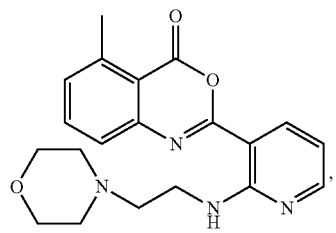,
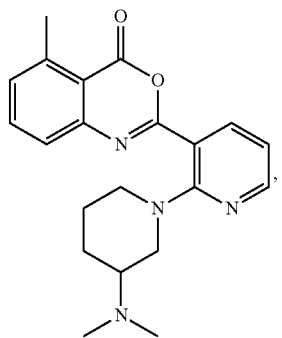,
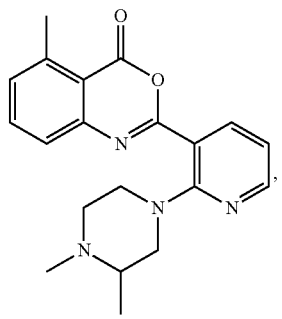,
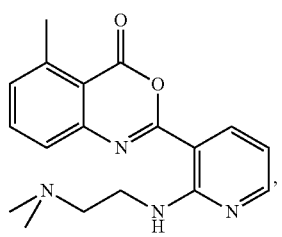,
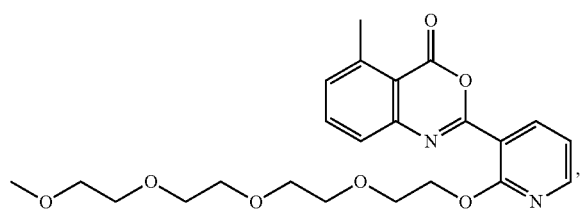,
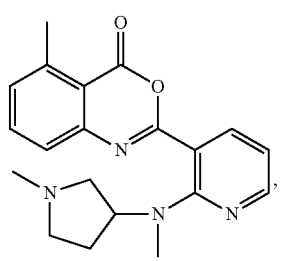,
-continued
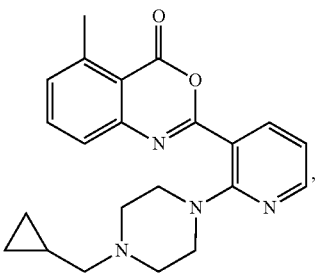,
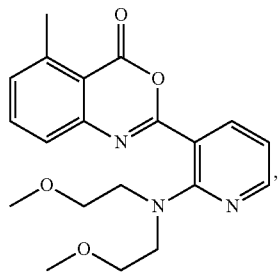,
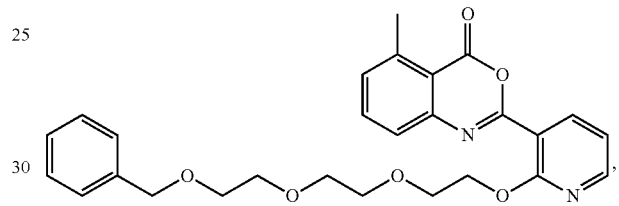,
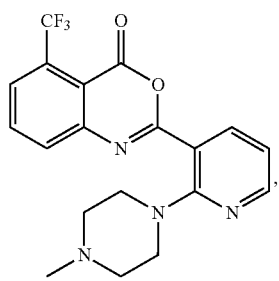,
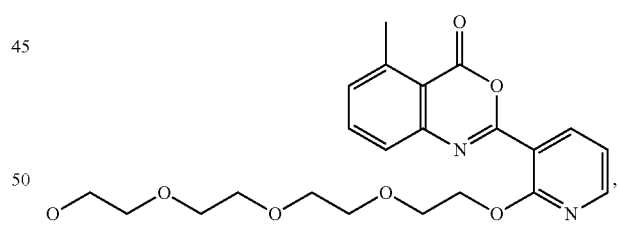,
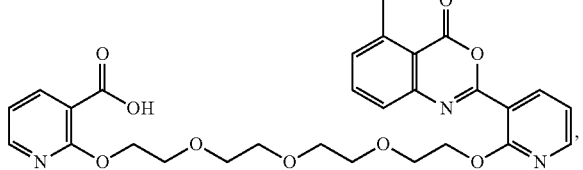,
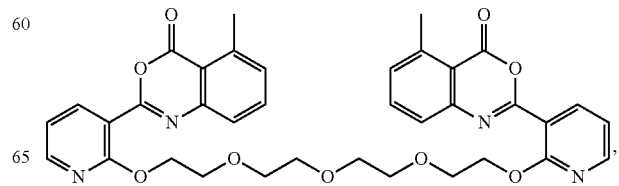, -continued
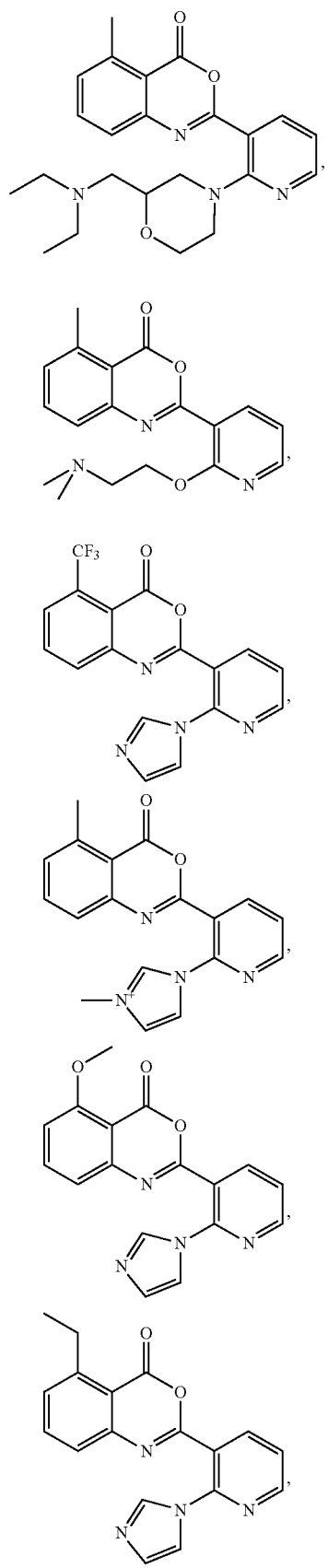
-continued
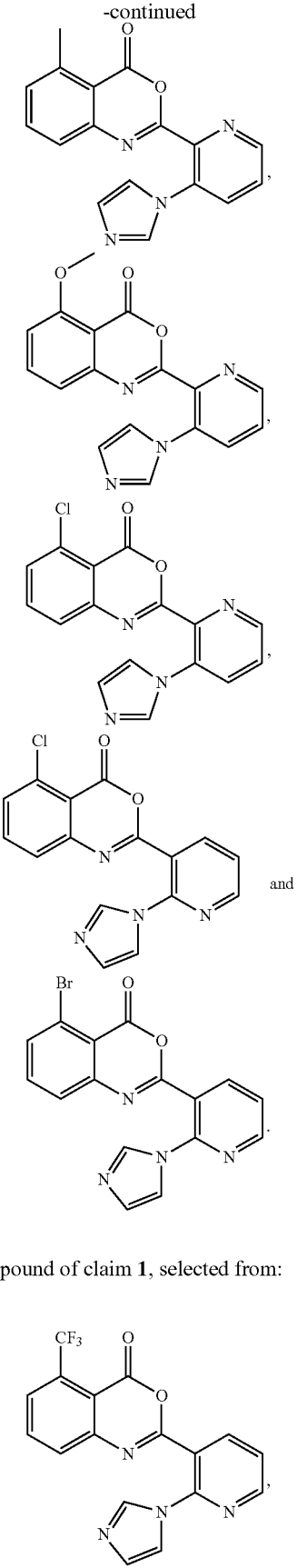
45. A compound of claim 1, selected from:
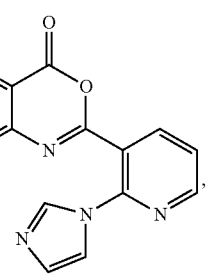

-continued
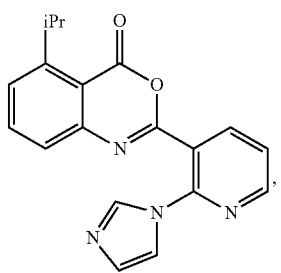
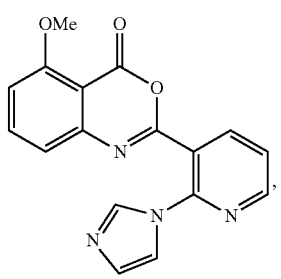
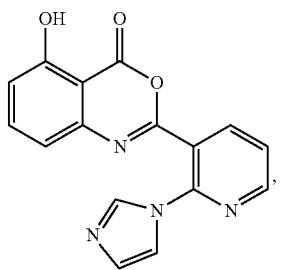
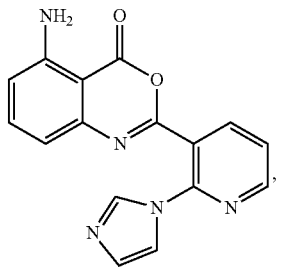
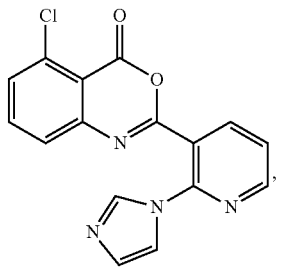
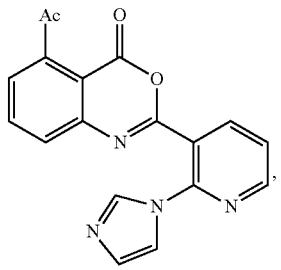
-continued
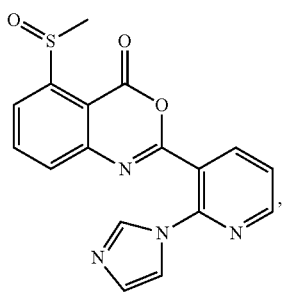
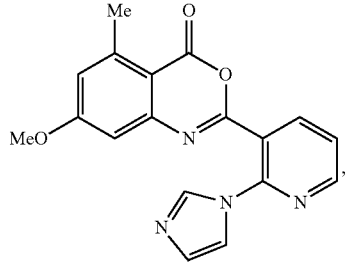
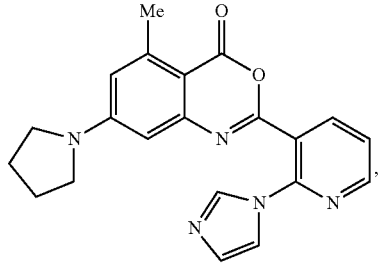
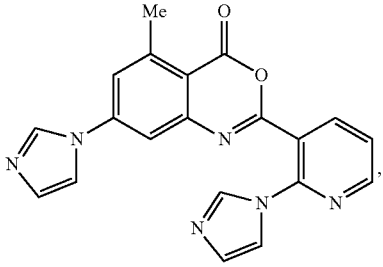
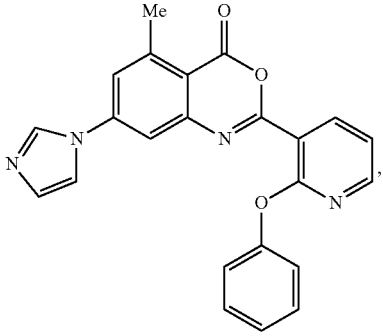
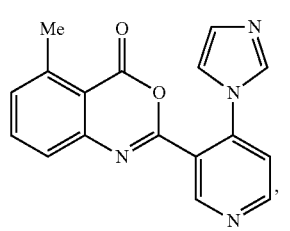

-continued

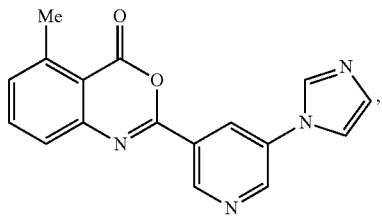

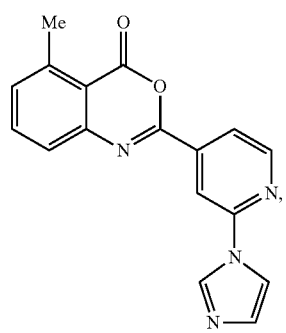

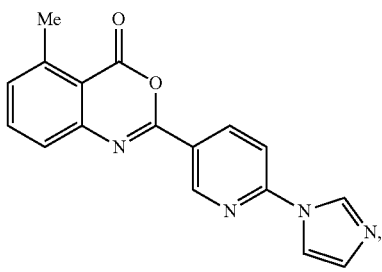

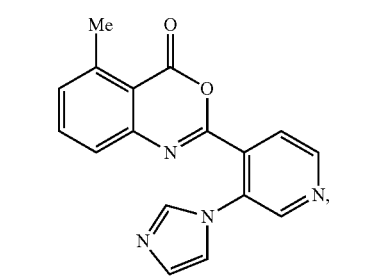

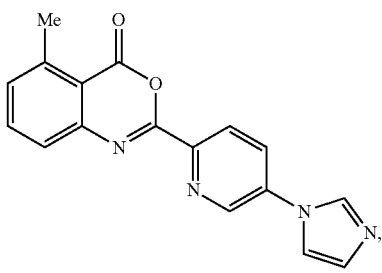

-continued

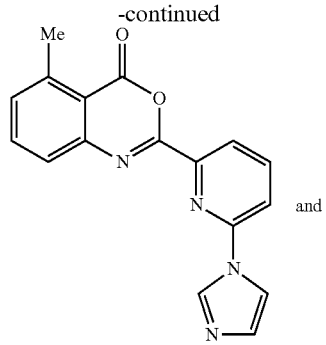

and

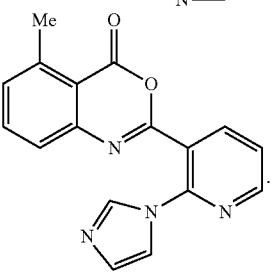

46. A pharmaceutical composition comprising a compound of claim 1, and a pharmaceutically acceptable carrier.

47. A method for the treatment of a serine hydrolase-mediated disease comprising administering a compound of claim 1 to a patient in need thereof, wherein the disease is selected from pulmonary emphysema, acute respiratory distress syndrome, adult respiratory distress syndrome, idiopathic interstitial pneumonia, cystic pulmonary fibrosis, chronic interstitial pneumonia, chronic bronchitis, chronic sinopulmonary infection, diffuse panbronchiolitis, bronchiectasis, asthma, pancreatitis, nephritis, hepatic failure, chronic rheumatoid arthritis, joint scleroma, osteoarthritis, psoriasis, periodontitis, atherosclerosis, rejection against organ transplant, premature amniorrhexis, bullous dermatosis, shock, sepsis, systemic lupus erythematosus, Crohn's disease, disseminated intracapillary coagulation, tissue injury after ischemia-reperfusion, formation of cornea cicatricial tissue and myelitis.

48. An article of manufacture, comprising a packaging material, the compound of claim 1, or pharmaceutically acceptable derivative thereof contained within packaging material, which is used for treatment, prevention or amelioration a serine hydrolase-mediated disease, and a label that indicates that the compound or the pharmaceutically acceptable derivative thereof is used for treatment, prevention or amelioration of a serine hydrolase-mediated disease selected from pulmonary emphysema, acute respiratory distress syndrome, adult respiratory distress syndrome, idiopathic interstitial pneumonia, cystic pulmonary fibrosis, chronic interstitial pneumonia, chronic bronchitis, chronic sinopulmonary infection, diffuse panbronchiolitis, bronchiectasis, asthma, pancreatitis, nephritis, hepatic failure, chronic rheumatoid arthritis, joint scleroma, osteoarthritis, psoriasis, periodontitis, atherosclerosis, rejection against organ transplant, premature amniorrhexis, bullous dermatosis, shock, sepsis, systemic lupus erythematosus, Crohn's disease, disseminated intracapillary coagulation, tissue injury after ischemia-reperfusion, formation of cornea cicatricial tissue and myelitis.

49. The compound of claim 1 selected from
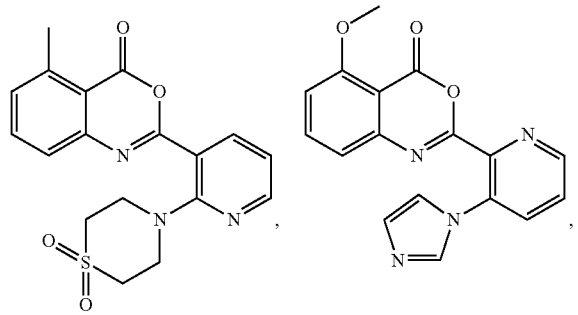
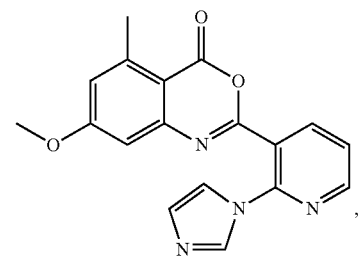
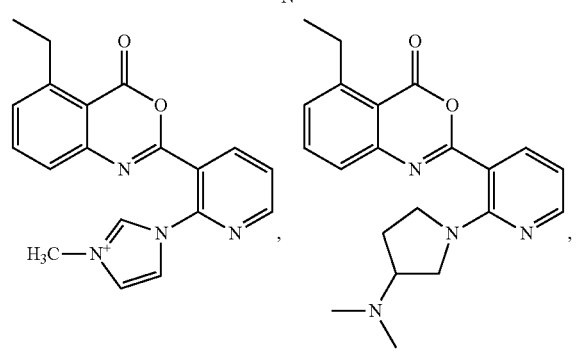
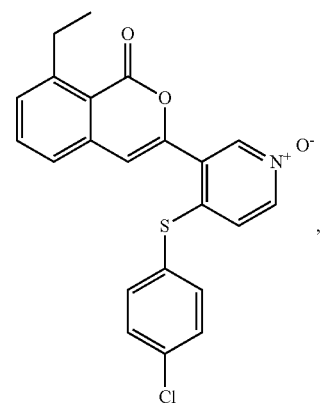
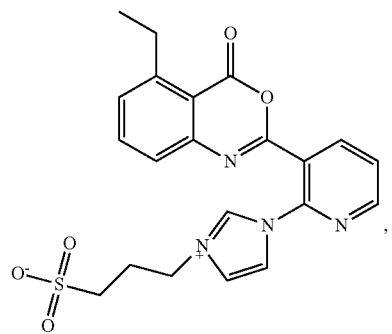
-continued
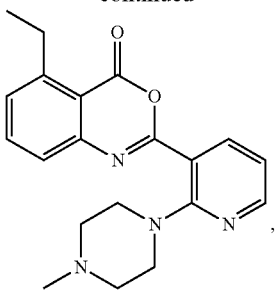
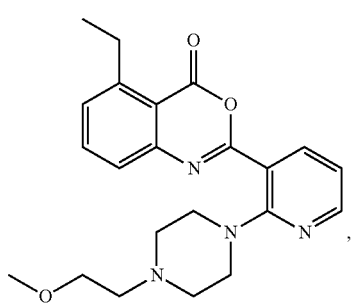
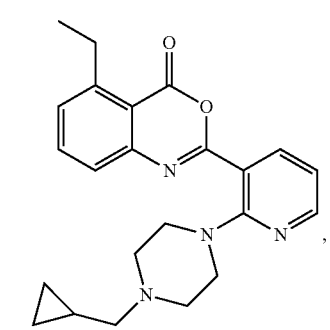
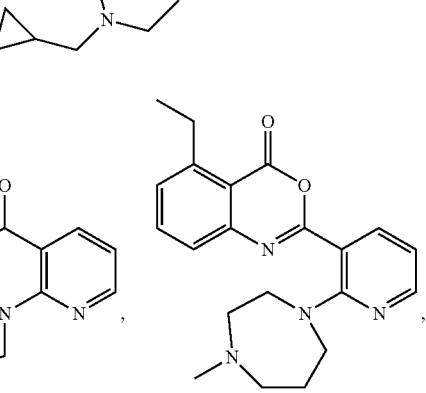
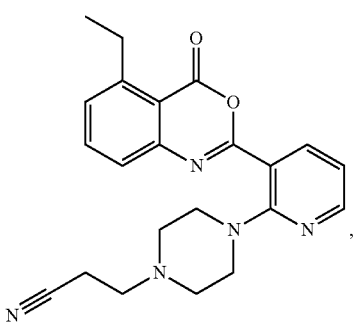

247
-continued
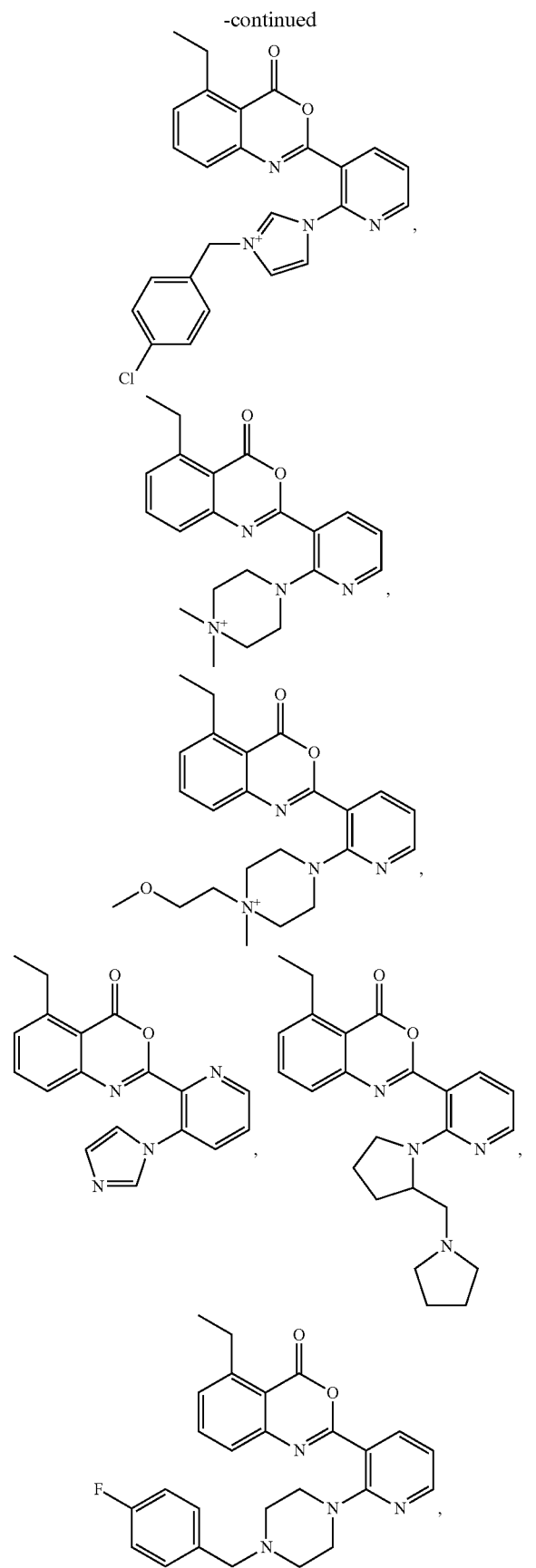
248
-continued
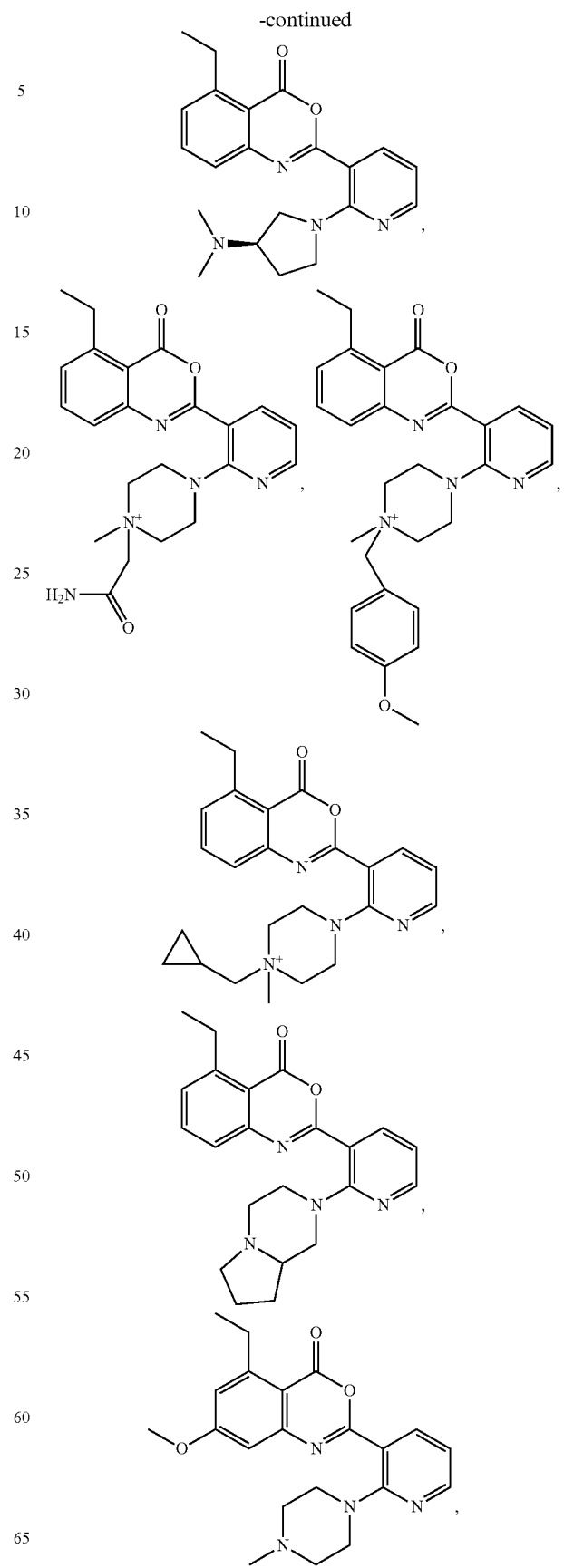

249
-continued
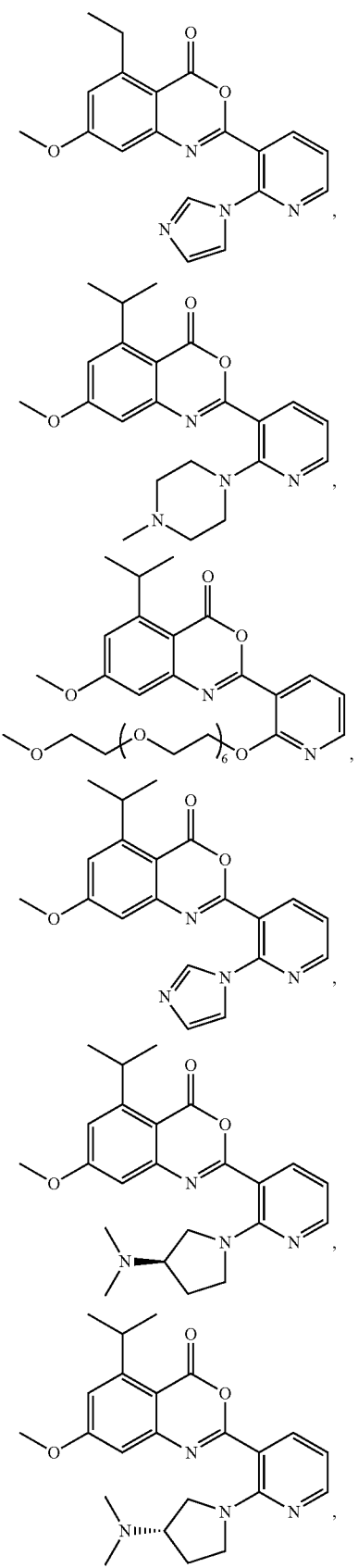
250
-continued
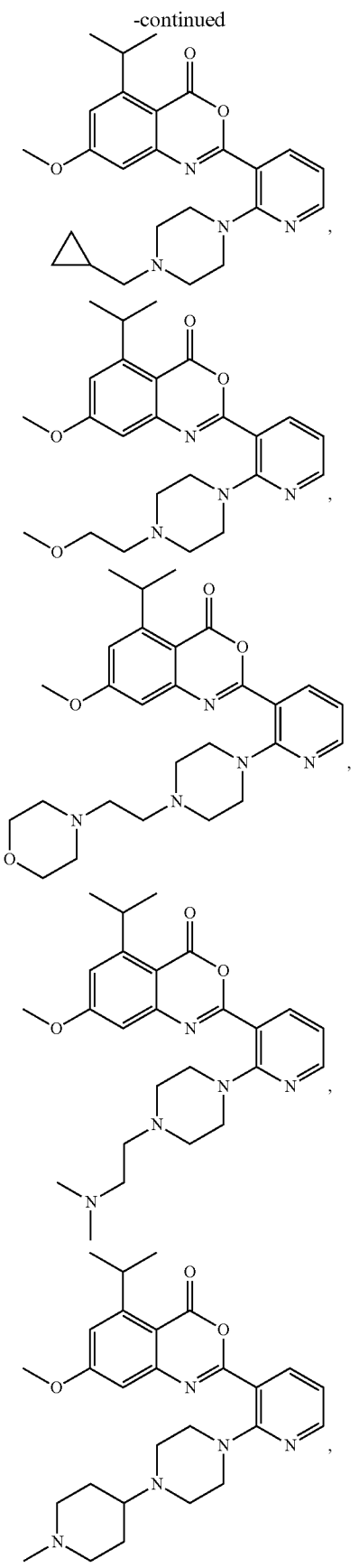

251
-continued
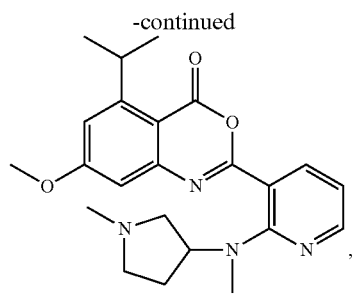
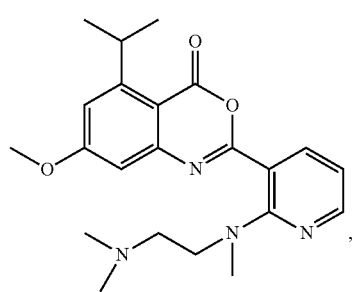
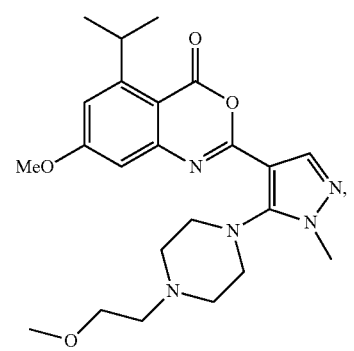
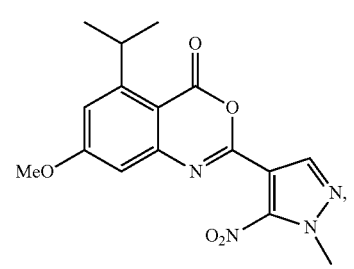
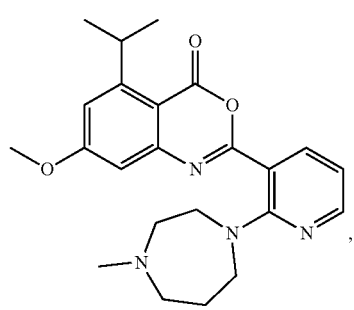
252
-continued
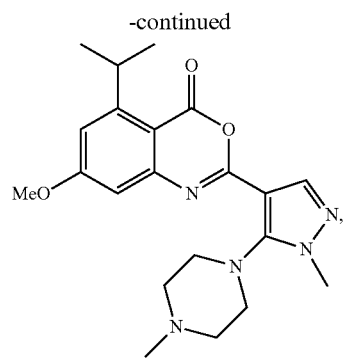
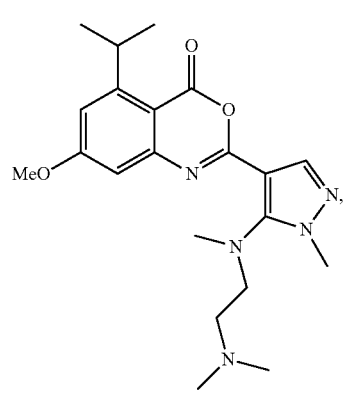
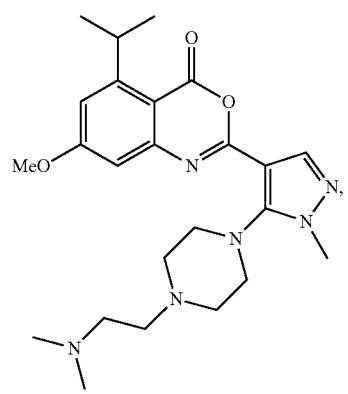
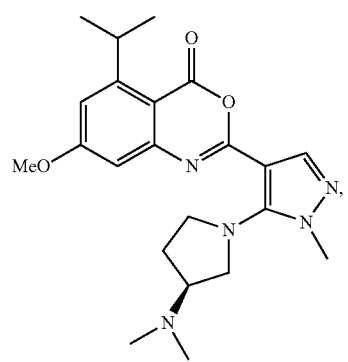

253
-continued
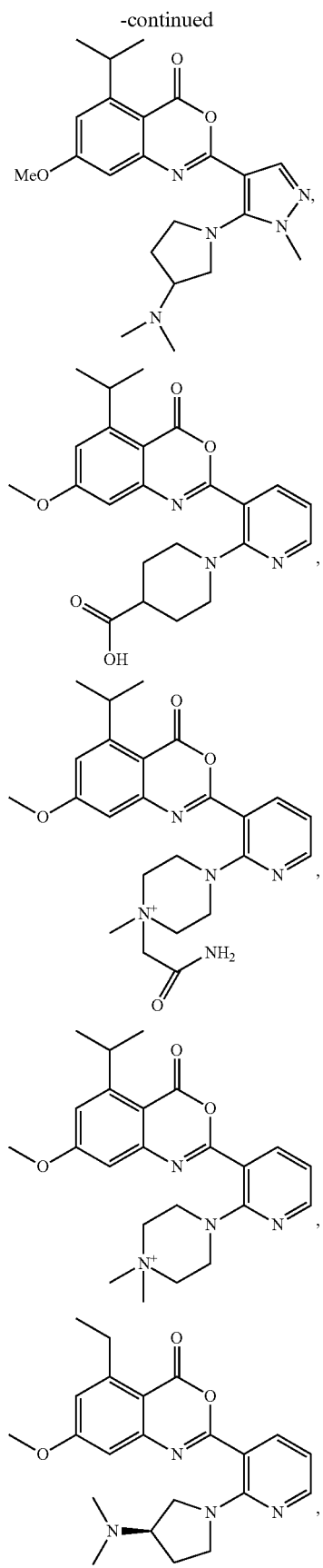
254
-continued
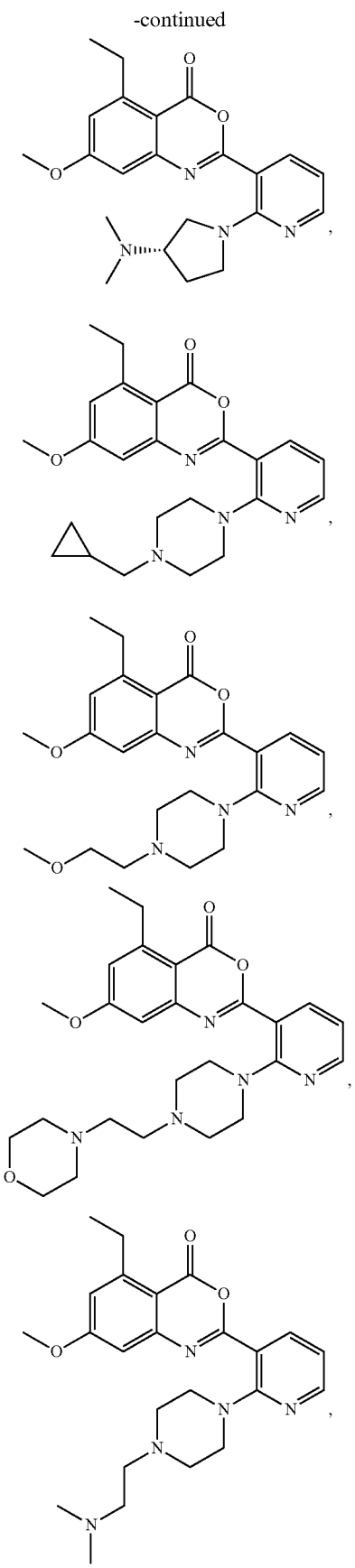

255                                          256
-continued                                -continued
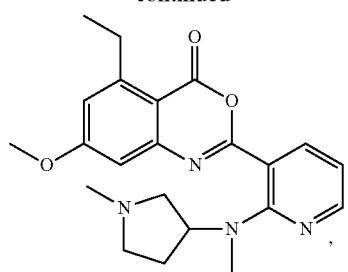
,
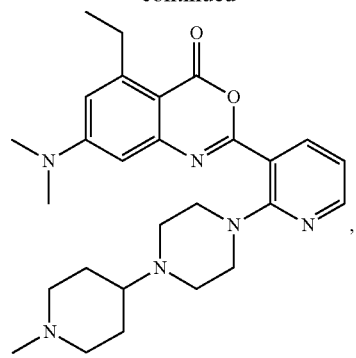
,
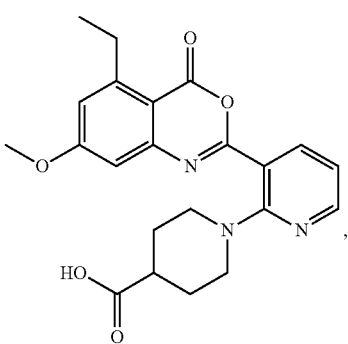
,
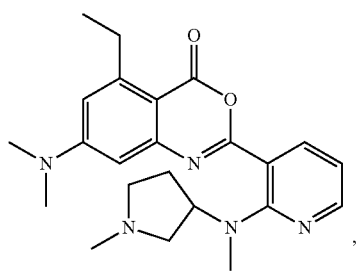
,
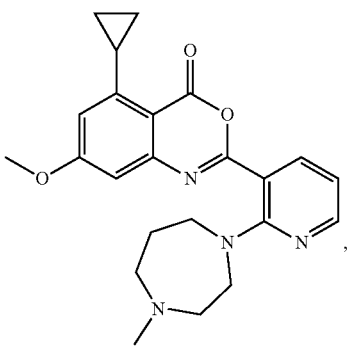
,
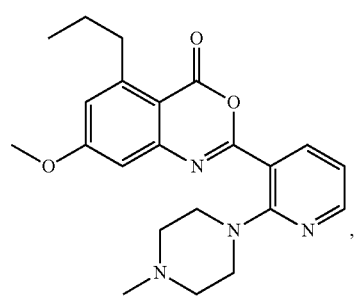
,
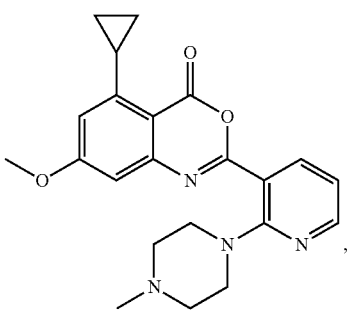
,
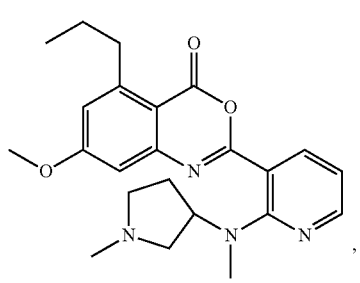
,
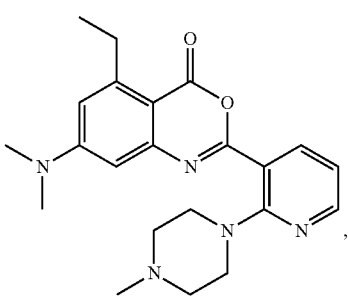
,
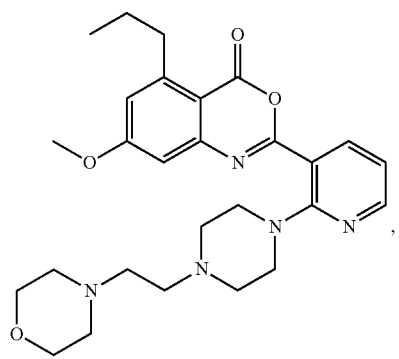
, 257
-continued
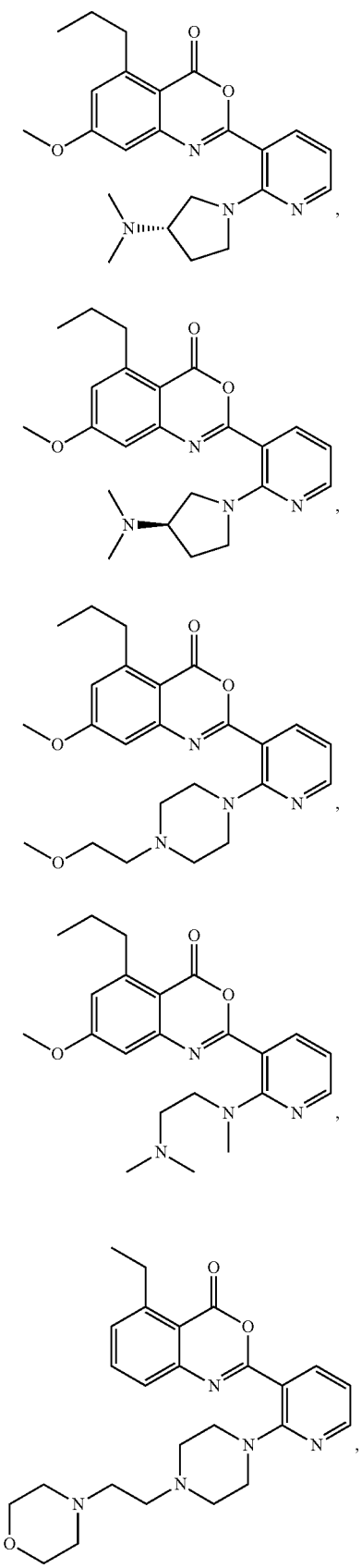
258
-continued
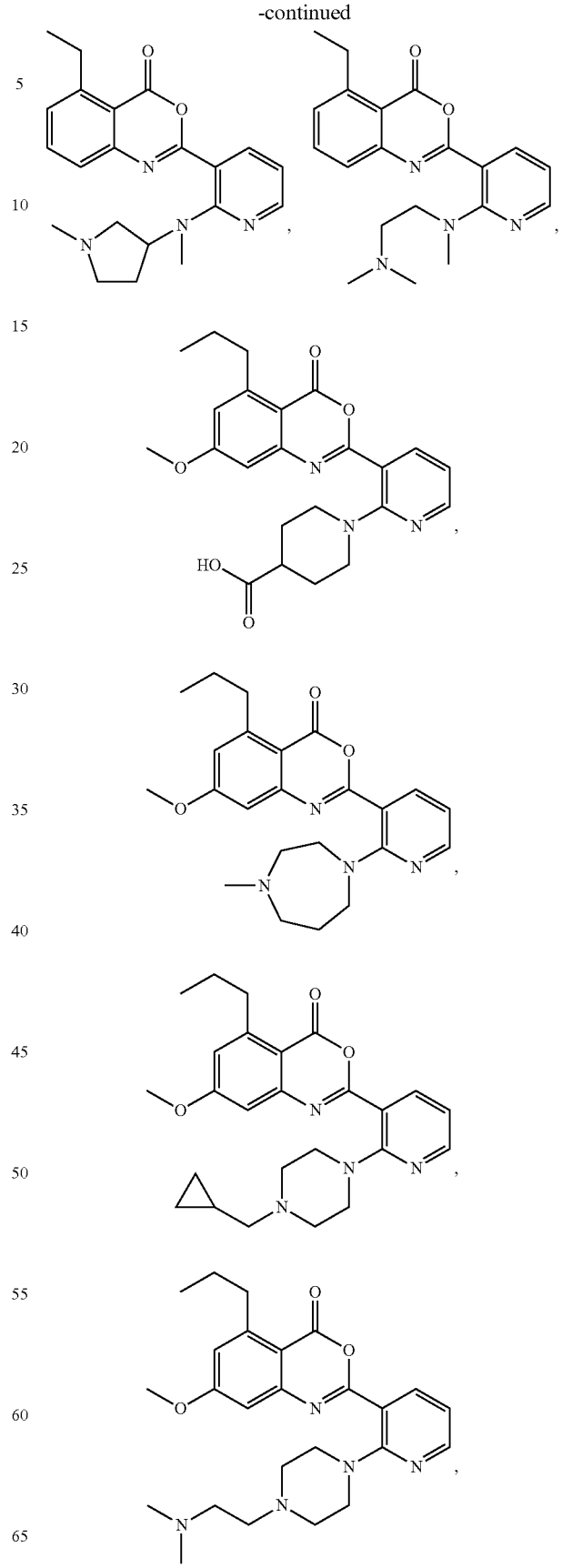

259
-continued
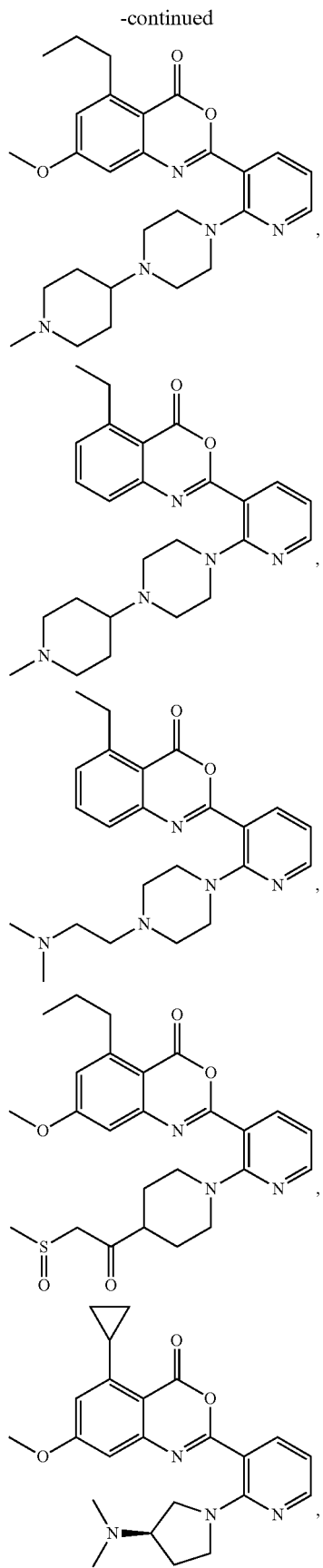
260
-continued
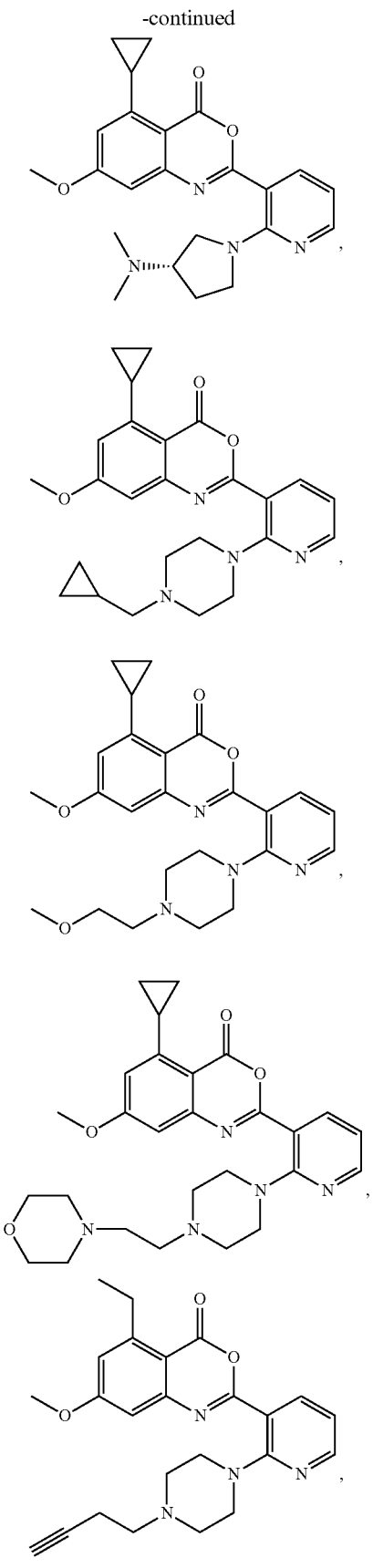

-continued
261
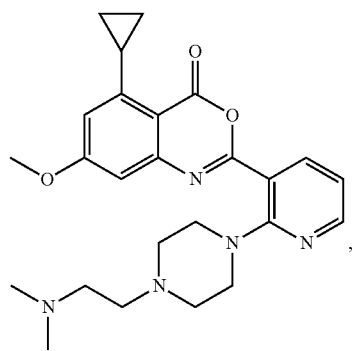
262
-continued
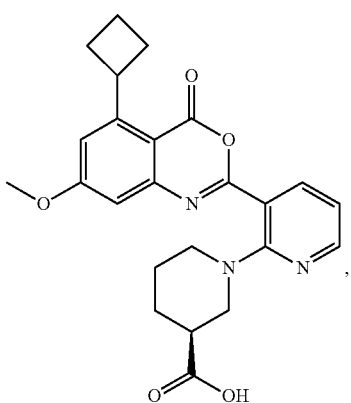
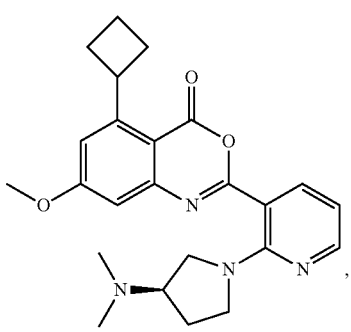
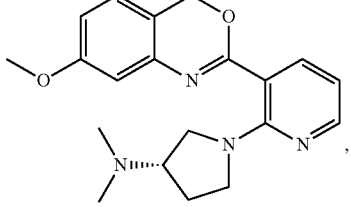
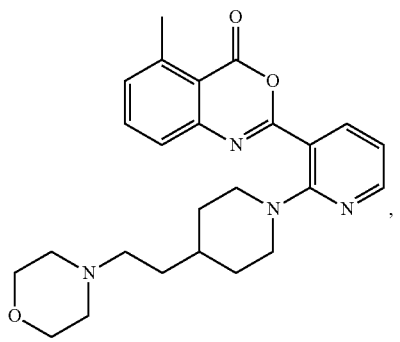

263
-continued
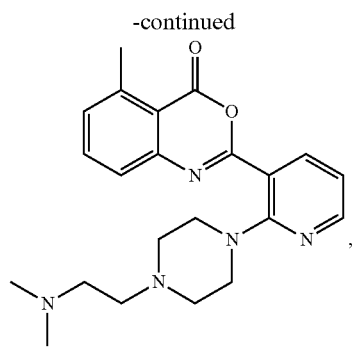
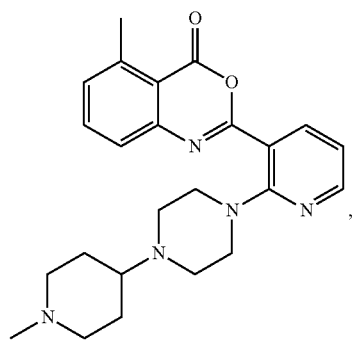
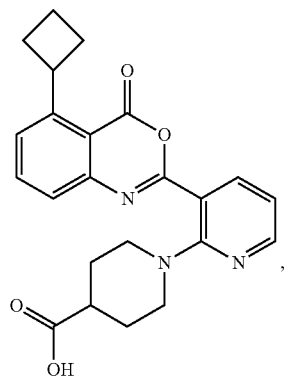
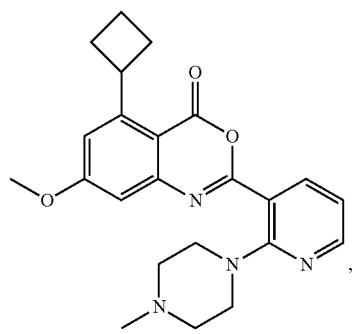
264
-continued
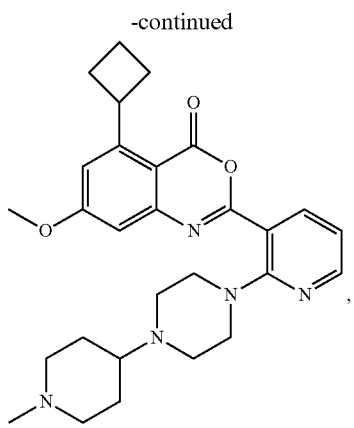
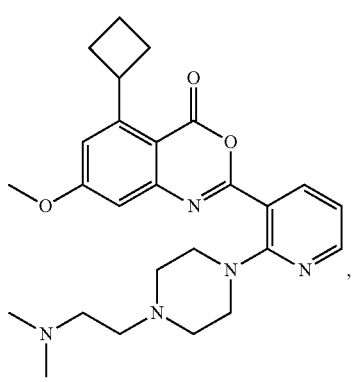
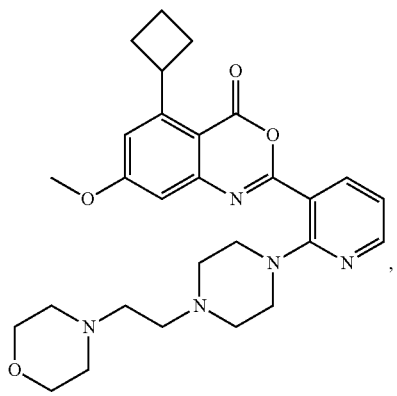
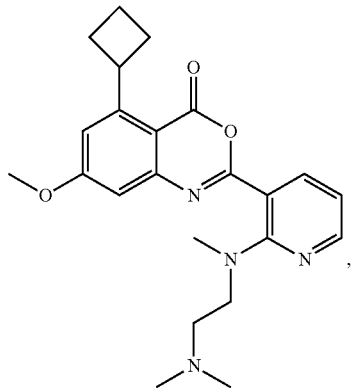

265
-continued
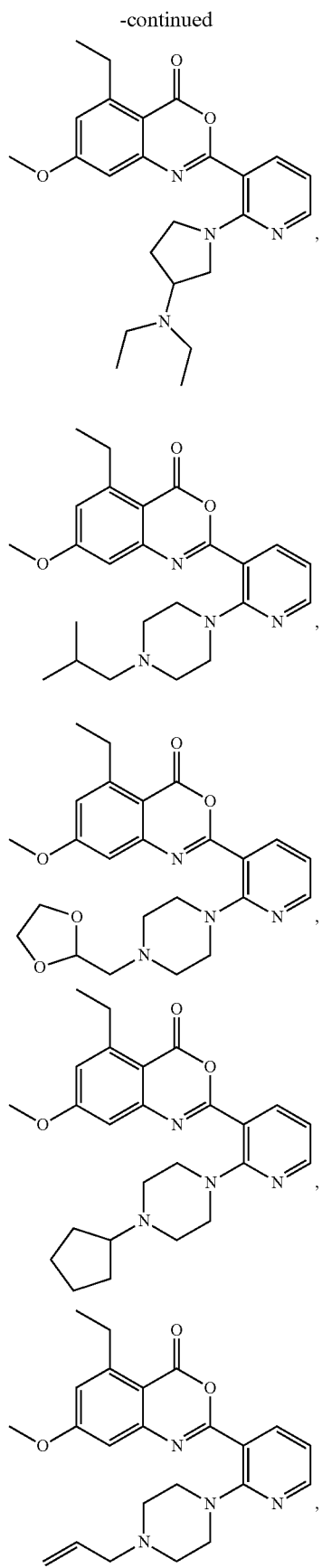
266
-continued
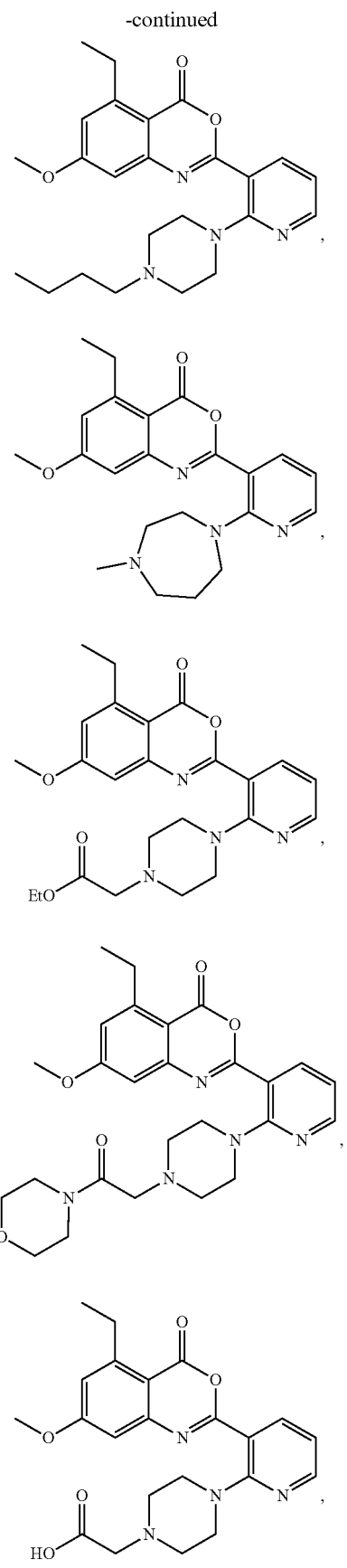

267 -continued
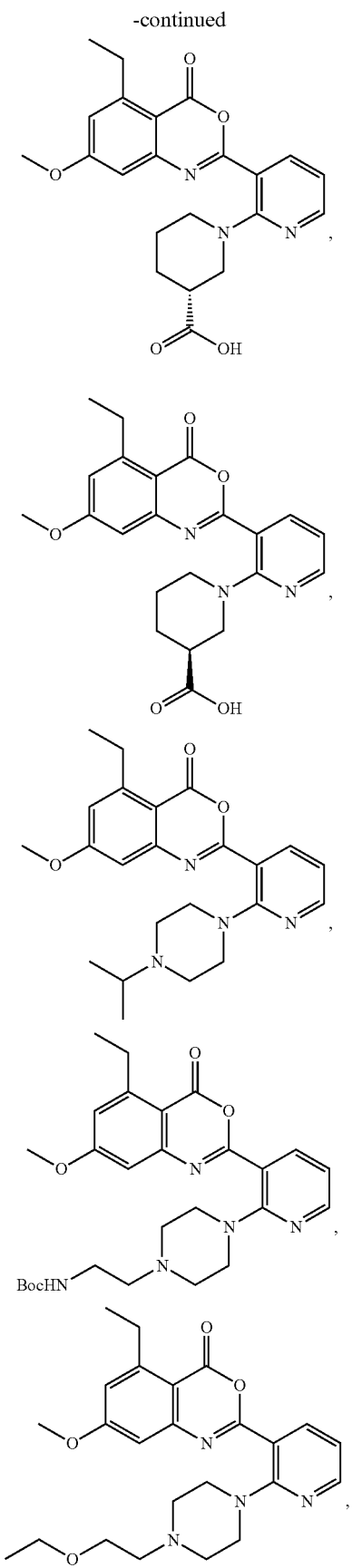
268 -continued
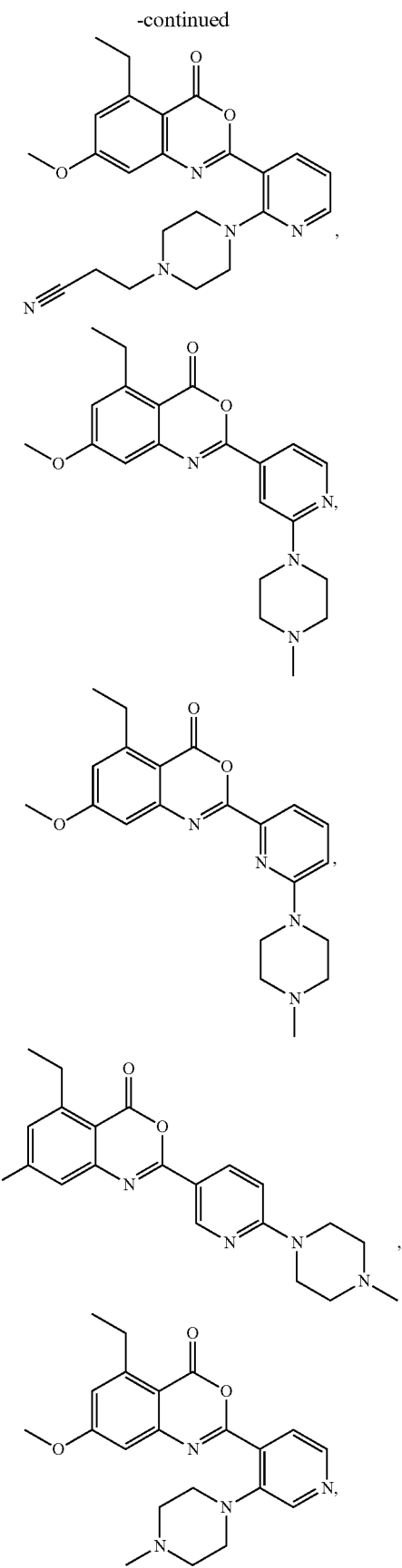

269
-continued
270
-continued
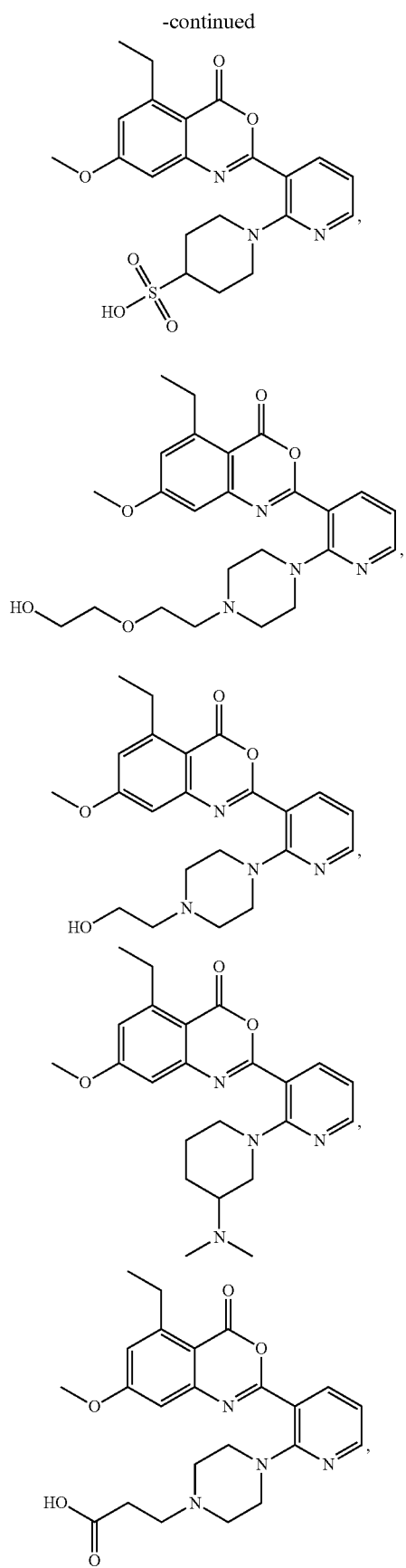
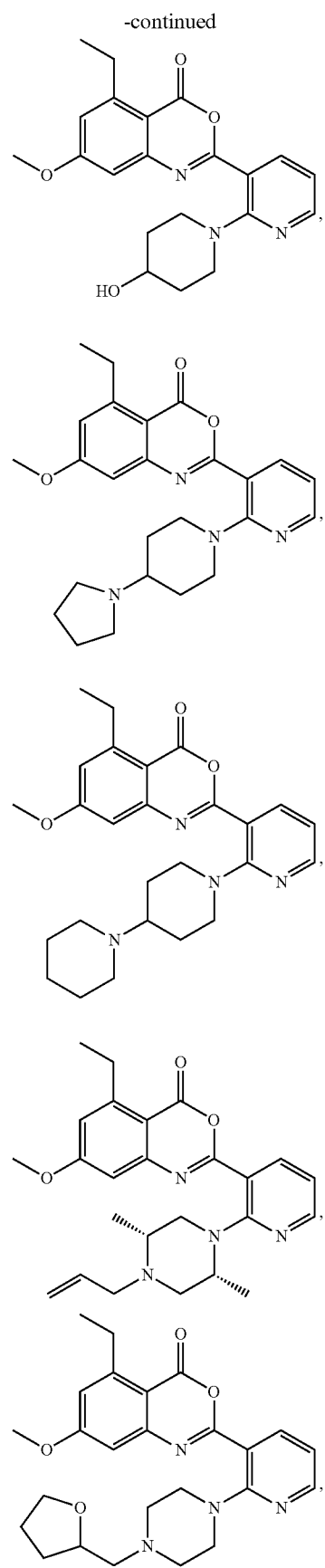

271
-continued
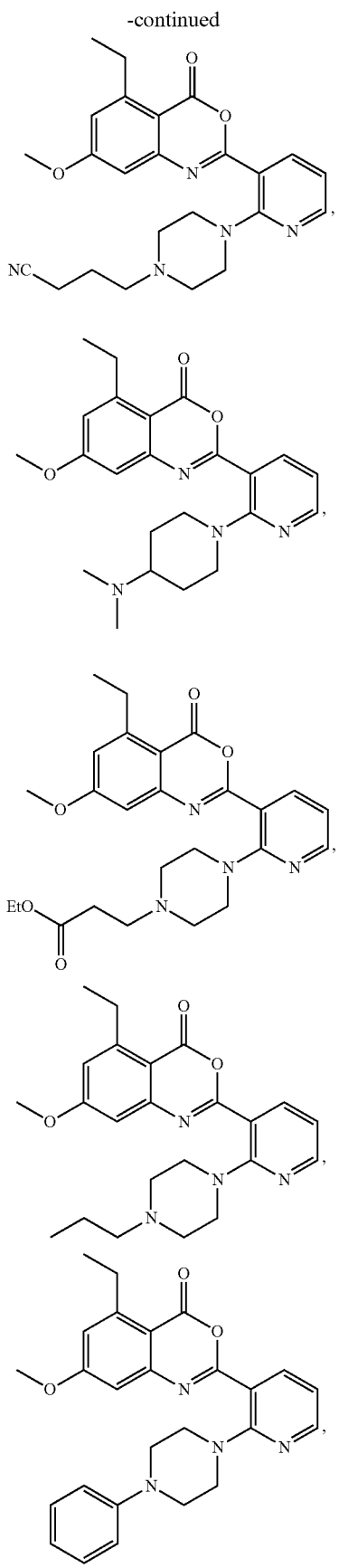
272
-continued
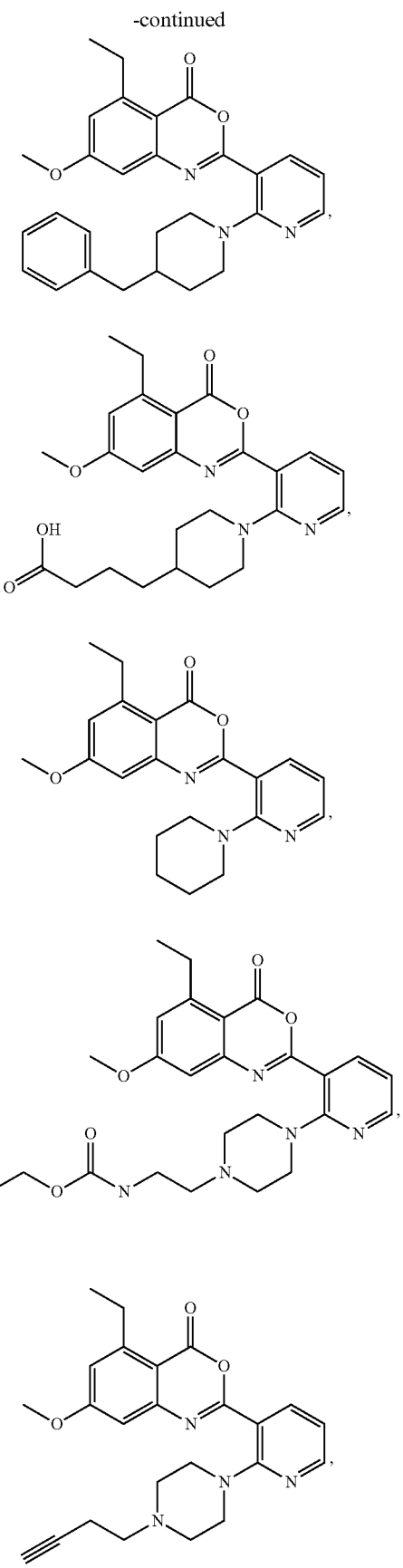

273
-continued
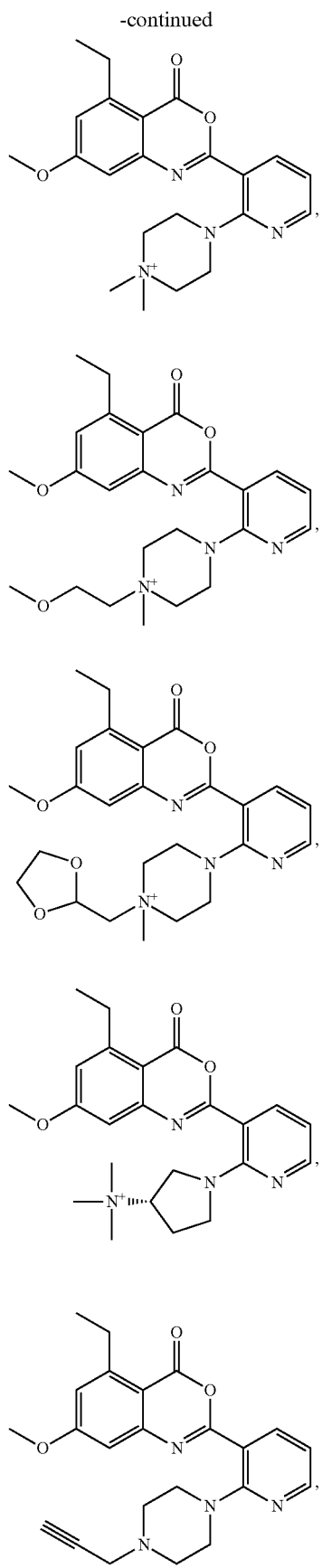
274
-continued
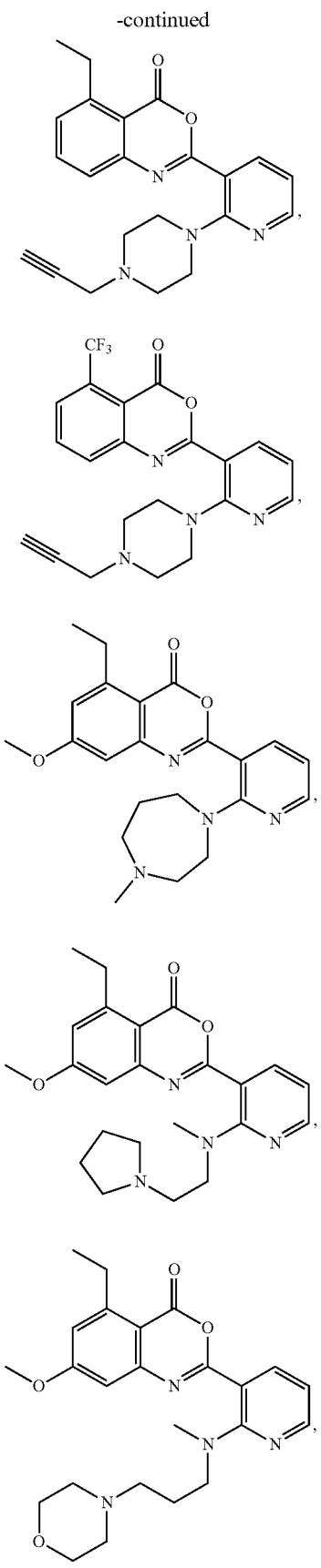

275
-continued
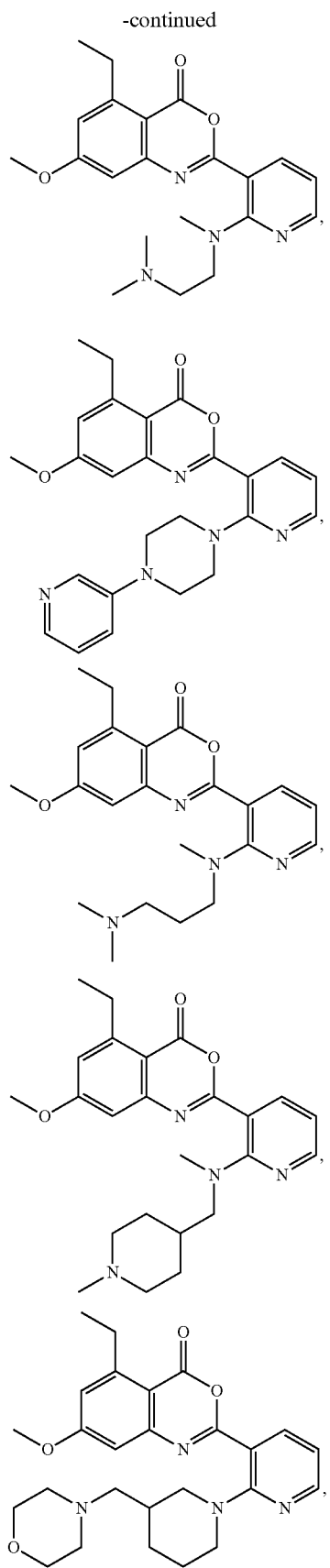
276
-continued
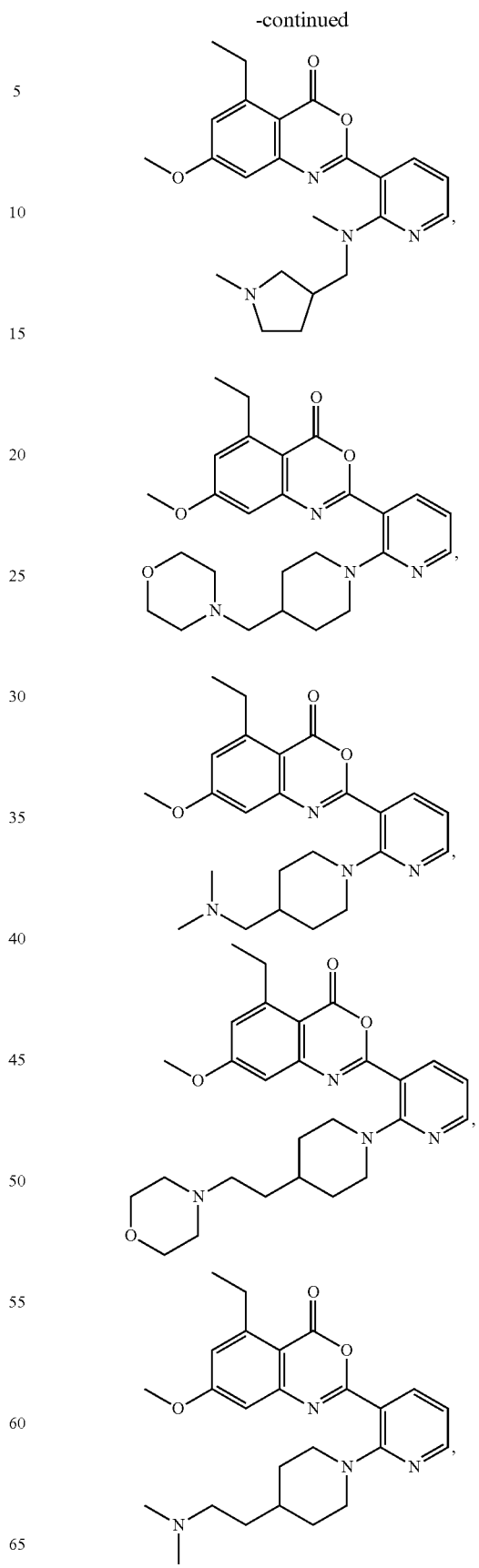

-continued
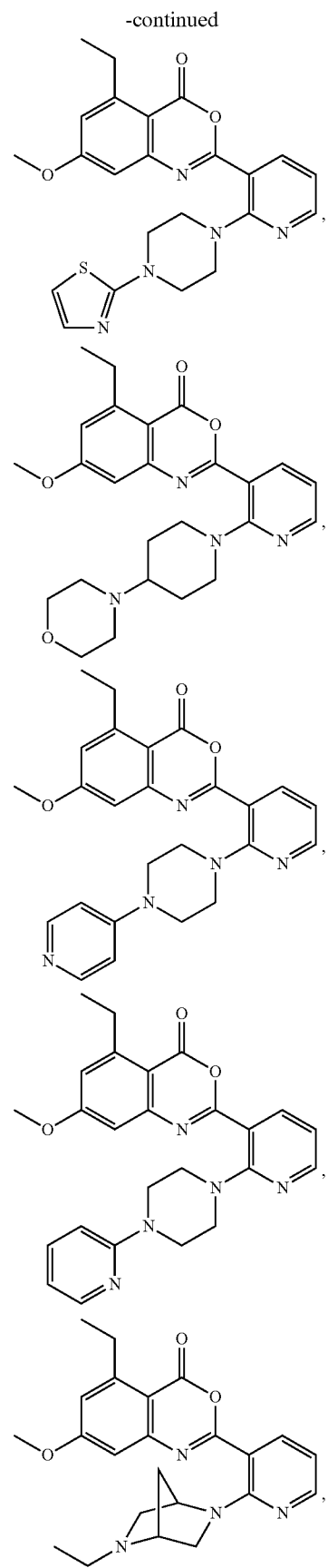
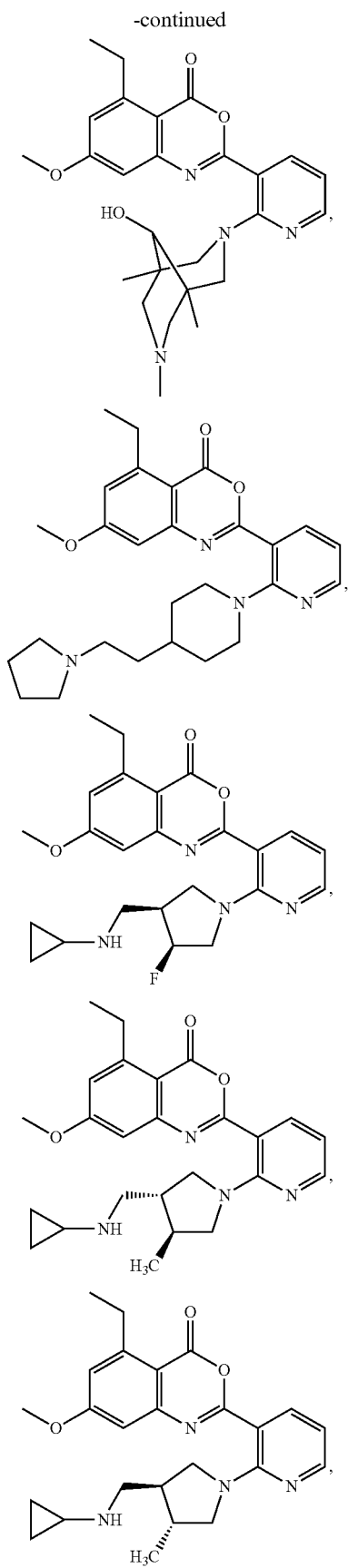

| 279 | 280 |
|---|---|
| -continued | -continued |
| 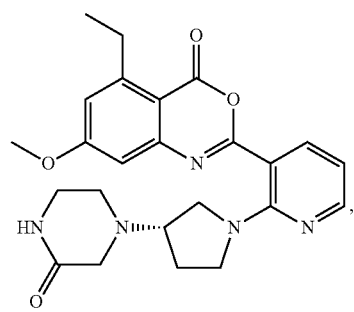 | 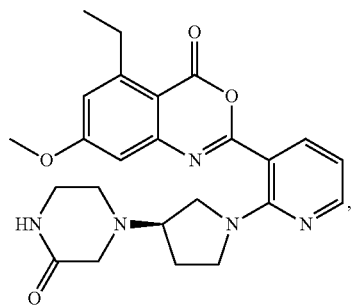 |
| 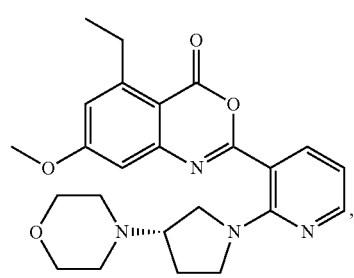 | 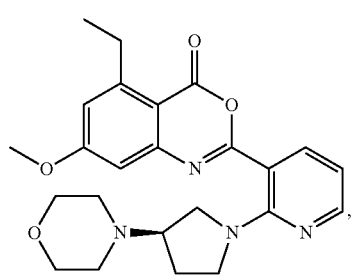 |
| 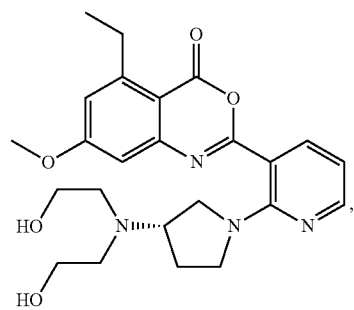 | 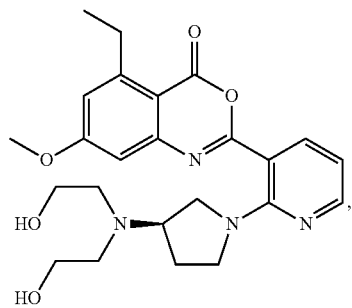 |
| 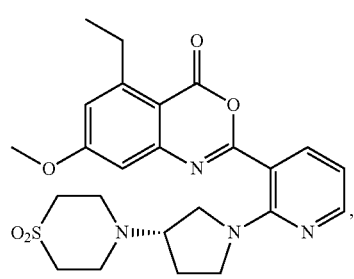 | 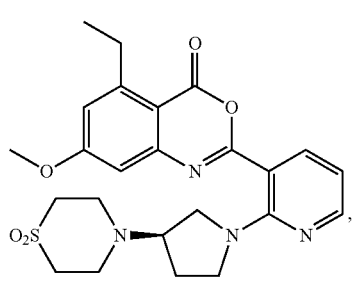 |
| 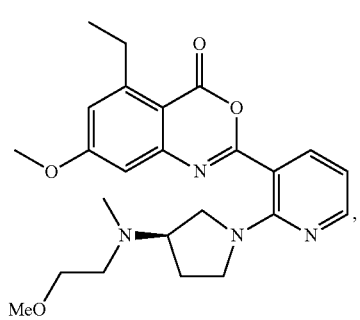 | 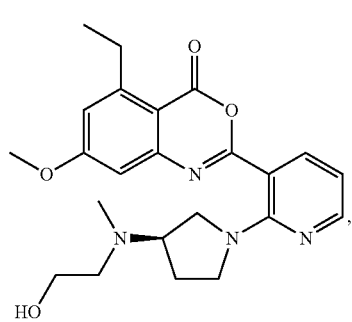 |

-continued
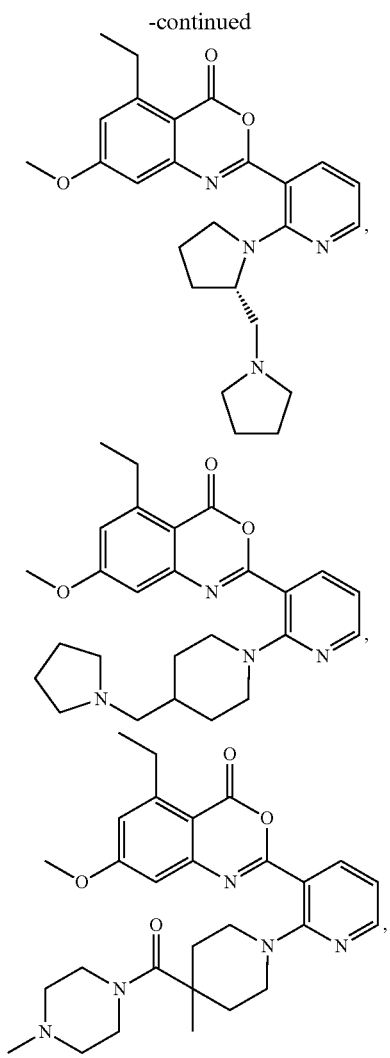
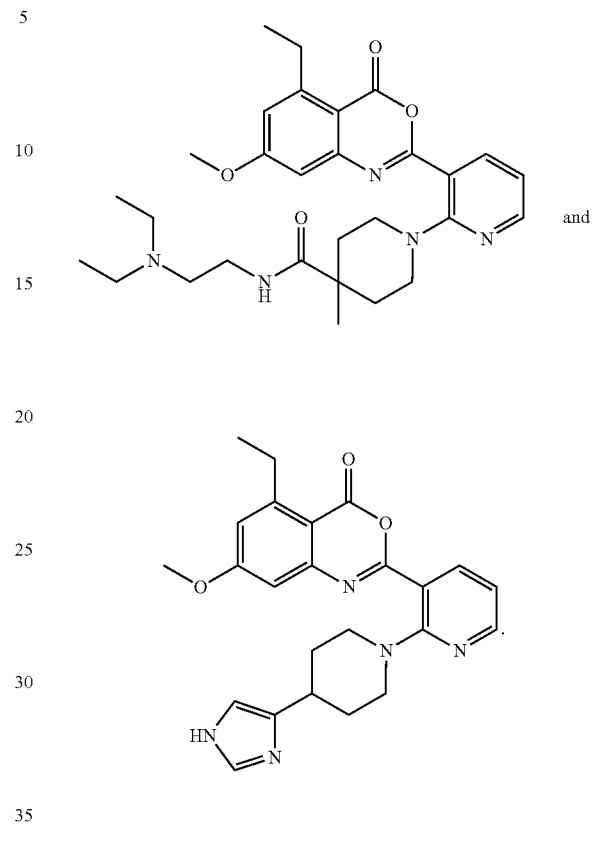
50. A pharmaceutical composition comprising the compound of claim 49 and a pharmaceutically acceptable carrier.
* * * * *